(12) United States Patent
Manabe et al.

(10) Patent No.: US 10,774,061 B2
(45) Date of Patent: *Sep. 15, 2020

(54) LIQUID-CRYSTALLINE MEDIUM AND LIQUID-CRYSTAL DISPLAY COMPRISING THE SAME

(71) Applicant: Merck Patent GmbH, Darmstadt (DE)

(72) Inventors: Atsutaka Manabe, Bensheim (DE); Constanze Brocke, Gross-Gerau (DE); Brigitte Schuler, Grossostheim (DE); Ramin Tavakoli, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/021,657

(22) Filed: Jun. 28, 2018

(65) Prior Publication Data

US 2019/0002430 A1    Jan. 3, 2019

(30) Foreign Application Priority Data

Jun. 30, 2017 (EP) .................................... 17001126
Nov. 10, 2017 (EP) .................................... 17201168

(51) Int. Cl.

| | |
|---|---|
| *G02F 1/1333* | (2006.01) |
| *C07D 333/76* | (2006.01) |
| *C09K 19/34* | (2006.01) |
| *C09K 19/30* | (2006.01) |
| *C09K 19/20* | (2006.01) |
| *C09K 19/44* | (2006.01) |
| *G02F 1/1343* | (2006.01) |
| *G02F 1/137* | (2006.01) |
| *C09K 19/12* | (2006.01) |
| *C09K 19/04* | (2006.01) |

(52) U.S. Cl.
CPC ............ *C07D 333/76* (2013.01); *C09K 19/20* (2013.01); *C09K 19/3098* (2013.01); *C09K 19/3402* (2013.01); *C09K 19/3491* (2013.01); *C09K 19/44* (2013.01); *G02F 1/137* (2013.01); *G02F 1/134363* (2013.01); *C09K 2019/0466* (2013.01); *C09K 2019/122* (2013.01); *C09K 2019/123* (2013.01); *C09K 2019/124* (2013.01); *C09K 2019/301* (2013.01); *C09K 2019/3004* (2013.01); *C09K 2019/3054* (2013.01); *C09K 2019/3422* (2013.01); *G02F 2001/13706* (2013.01); *G02F 2001/13712* (2013.01); *G02F 2001/134372* (2013.01)

(58) Field of Classification Search
CPC ............... C09K 19/20; C09K 19/3098; C09K 19/3402; C09K 19/3491; C09K 19/44; C09K 2019/0466; C09K 2019/122–124; C09K 2019/3004; C09K 2019/301; C09K 2019/3054; C09K 2019/3422; G02F 1/1333; G02F 1/137; G02F 1/134363; G02F 2001/134372; G02F 2001/13706; G02F 2001/13712; C07D 333/76
USPC ..................................................... 252/299.61
See application file for complete search history.

(56) References Cited

U.S. PATENT DOCUMENTS

| | | | |
|---|---|---|---|
| 4,813,770 | A | 3/1989 | Clerc |
| 7,018,685 | B2 | 3/2006 | Schmidt |
| 2004/0124399 | A1 | 7/2004 | Schmidt |

(Continued)

FOREIGN PATENT DOCUMENTS

| | | |
|---|---|---|
| CN | 104232105 A | 12/2014 |
| DE | 102016003902 A1 | 10/2016 |

(Continued)

OTHER PUBLICATIONS

EP application No. 2016194162A (unpublished).

(Continued)

*Primary Examiner* — Geraldina Visconti
(74) *Attorney, Agent, or Firm* — Millen White Zelano and Branigan, PC; Csaba Henter

(57) ABSTRACT

The invention relates to a liquid-crystalline medium, preferably having a nematic phase and dielectric anisotropy of 0.5 or more, which comprises one or more compounds of formula S

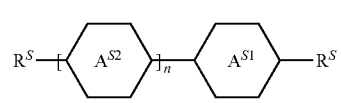

in which

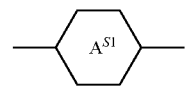

denotes

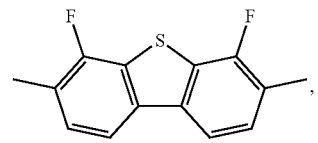

and to the use thereof in an electro-optical display, particularly in an active-matrix display based on the IPS or FFS effect, to displays of this type which contain a liquid-crystalline medium of this type, and to the use of the compounds of formula S for the improvement of the trans- (Continued)

mission and/or response times of a liquid-crystalline medium which comprises one or more additional mesogenic compounds.

20 Claims, No Drawings

(56) References Cited

U.S. PATENT DOCUMENTS

| | | | |
|---|---|---|---|
| 2013/0207038 A1 | 8/2013 | Haensel | |
| 2015/0299161 A1 | 10/2015 | Reiffenrath | |
| 2016/0046865 A1 | 2/2016 | Xie | |
| 2016/0090532 A1 | 3/2016 | Saito | |
| 2016/0298034 A1 | 10/2016 | Lietzau | |
| 2016/0319194 A1 | 11/2016 | Hirschmann | |
| 2018/0086980 A1 | 3/2018 | Manabe | |
| 2019/0093013 A1* | 3/2019 | Manabe | C09K 19/3491 |

FOREIGN PATENT DOCUMENTS

| | | |
|---|---|---|
| EP | 240379 A1 | 10/1987 |
| EP | 3081620 A2 | 10/2016 |
| EP | 3095834 A2 | 11/2016 |
| EP | 2937401 B1 | 4/2017 |
| EP | 3228681 A1 | 10/2017 |
| WO | 2002055463 A1 | 7/2002 |
| WO | 2014192390 A1 | 12/2014 |
| WO | 2015007173 A1 | 1/2015 |

OTHER PUBLICATIONS

EP application No. 2016197206A (unpublished).
EP application No. 2016199580A (unpublished).
Search Report in corresponding EP18179989 dated Sep. 25, 2018 (pp. 1-11).

* cited by examiner

LIQUID-CRYSTALLINE MEDIUM AND LIQUID-CRYSTAL DISPLAY COMPRISING THE SAME

The present invention relates to novel liquid crystalline media, in particular for use in liquid crystal displays, and to these liquid-crystal displays, particularly to liquid-crystal displays which use the IPS (in-plane switching) or, preferably, the FFS (fringe field switching) effect using dielectrically positive liquid crystals. The last one is also called SB-FFS (super brightness FFS) effect occasionally. For this effect dielectrically positive liquid crystals are used, which comprise one or more compounds having at the same time a high dielectric constant parallel to the molecular director and perpendicular to the molecular director, leading to a large average dielectric constant and a high dielectric ratio and, preferably, to a relatively small dielectric anisotropy at the same time. The liquid crystalline media optionally additionally comprise dielectrically negative, dielectrically neutral compounds or both. The liquid crystalline media are used in a homogeneous (i.e. planar) initial alignment. The liquid-crystal media according to the invention have a positive dielectric anisotropy and comprise compounds having at the same time large dielectric constants parallel and perpendicular to the molecular director.

The media are distinguished by a particularly high transmission and reduced response time in respective displays, which is brought about by their unique combination of physical properties, especially by their dielectric properties and in particular by their high ratio of $(\varepsilon_\perp/\varepsilon_{av.})$ respectively of the high values of their dielectric ratio $(\varepsilon_\perp/\Delta\varepsilon)$. This also leads to their excellent performance in the displays according to the invention.

IPS and FFS displays using dielectrically positive liquid crystals are well known in the field and have been widely adopted for various types of displays like e.g. desk top monitors and TV sets, but also for mobile applications.

However, recently, IPS and in particular FFS displays using dielectrically negative liquid crystals are widely adopted. The latter ones are sometimes also called UB-FFS (ultra bright FFS). Such displays are disclosed e.g. in US 2013/0207038 A1. These displays are characterized by a markedly increased transmission compared to the previously used IPS- and FFS displays, which have been dielectrically positive liquid crystals. These displays using dielectrically negative liquid crystals, however, have the severe disadvantage of requiring a higher operation voltage than the respective displays using dielectrically positive liquid crystals. Liquid crystalline media used for UB-FFS have a dielectric anisotropy of −0.5 or less and preferably of −1.5 or less.

Liquid crystalline media used for HB-FFS (high brightness FFS) have a dielectric anisotropy of 0.5 or more and preferably of 1.5 or more. Respective media comprising both dielectrically negative and dielectrically positive liquid crystalline compounds, respectively mesogenic compounds are disclosed e.g. in US 2013/0207038 A1. These media feature rather large values of $\varepsilon_\perp$ and of $\varepsilon_{av.}$ already, however, their ratio of $(\varepsilon_\perp/\Delta\varepsilon)$ is relatively small.

According to the present application, however, the IPS or the FFS effect with dielectrically positive liquid crystalline media in a homogeneous alignment are preferred.

Industrial application of this effect in electro-optical display elements requires LC phases which have to meet a multiplicity of requirements. Particularly important here are chemical resistance to moisture, air and physical influences, such as heat, radiation in the infrared, visible and ultraviolet regions, and direct (DC) and alternating (AC) electric fields.

Furthermore, LC phases which can be used industrially are required to have a liquid-crystalline mesophase in a suitable temperature range and low viscosity.

None of the series of compounds having a liquid-crystalline mesophase that have been disclosed hitherto includes a single compound which meets all these requirements. Mixtures of two to 25, preferably three to 18, compounds are therefore generally prepared in order to obtain substances which can be used as LC phases.

Matrix liquid-crystal displays (MLC displays) are known. Non-linear elements which can be used for individual switching of the individual pixels are, for example, active elements (i.e. transistors). The term "active matrix" is then used, where in general use is made of thin-film transistors (TFTs), which are generally arranged on a glass plate as substrate.

A distinction is made between two technologies: TFTs comprising compound semiconductors, such as, for example, CdSe, or metal oxides like ZnO or TFTs based on polycrystalline and, inter alia, amorphous silicon. The latter technology currently has the greatest commercial importance worldwide.

The TFT matrix is applied to the inside of one glass plate of the display, while the other glass plate carries the transparent counter electrode on its inside. Compared with the size of the pixel electrode, the TFT is very small and has virtually no adverse effect on the image. This technology can also be extended to fully colour-capable displays, in which a mosaic of red, green and blue filters is arranged in such a way that a filter element is located opposite each switchable pixel.

The TFT displays most used hitherto usually operate with crossed polarisers in transmission and are backlit. For TV applications, ECB (or VAN) cells or FFS cells are used, whereas monitors usually use IPS cells or TN (twisted nematic) cells, and notebooks, laptops and mobile applications usually use TN, VA or FFS cells.

The term MLC displays here encompasses any matrix display having integrated non-linear elements, i.e., besides the active matrix, also displays with passive elements, such as varistors or diodes (MIM=metal-insulator-metal).

MLC displays of this type are particularly suitable for TV applications, monitors and notebooks or for displays with a high information density, for example in automobile manufacture or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210-288 Matrix LCD Controlled by Double Stage Diode Rings, pp. 141 ff., Paris; STROMER, M., Proc. Eurodisplay 84, September 1984: Design of Thin Film Transistors for Matrix Addressing of Television Liquid Crystal Displays, pp. 145 ff., Paris]. With decreasing resistance, the contrast of an MLC display deteriorates. Since the specific resistance of the liquid-crystal mixture generally drops over the life of an MLC display owing to interaction with the inside surfaces of the display, a high (initial) resistance is very important for displays that have to have acceptable resistance values over a long operating period.

Displays which use the ECB effect have become established as so-called VAN (vertically aligned nematic) displays, besides IPS displays (for example: Yeo, S. D., Paper 15.3: "An LC Display for the TV Application", SID 2004 International Symposium, Digest of Technical Papers, XXXV, Book II, pp. 758 and 759) and the long-known TN displays, as one of the three more recent types of liquid-crystal display that are currently the most important, in particular for television applications.

The most important designs may be mentioned here: MVA (multidomain vertical alignment, for example: Yoshide, H. et al., Paper 3.1: "MVA LCD for Notebook or Mobile PCs . . . ", SID 2004 International Symposium, Digest of Technical Papers, XXXV, Book I, pp. 6 to 9, and Liu, C. T. et al., Paper 15.1: "A 46-inch TFT-LCD HDTV Technology . . . ", SID 2004 International Symposium, Digest of Technical Papers, XXXV, Book II, pp. 750 to 753), PVA (patterned vertical alignment, for example: Kim, Sang Soo, Paper 15.4: "Super PVA Sets New State-of-the-Art for LCD-TV", SID 2004 International Symposium, Digest of Technical Papers, XXXV, Book II, pp. 760 to 763) and ASV (advanced super view, for example: Shigeta, Mitzuhiro and Fukuoka, Hirofumi, Paper 15.2: "Development of High Quality LCDTV", SID 2004 International Symposium, Digest of Technical Papers, XXXV, Book II, pp. 754 to 757). More modern versions of the VA effect, are the so called PAVA (photo-alignment VA) and PSVA (polymer-stabilized VA).

In general form, the technologies are compared, for example, in Souk, Jun, SID Seminar 2004, Seminar M-6: "Recent Advances in LCD Technology", Seminar Lecture Notes, M-6/1 to M-6/26, and Miller, Ian, SID Seminar 2004, Seminar M-7: "LCD-Television", Seminar Lecture Notes, M-7/1 to M-7/32. Although the response times of modern ECB displays have already been significantly improved by addressing methods with overdrive, for example: Kim, Hyeon Kyeong et al., Paper 9.1: "A 57-in. Wide UXGA TFT-LCD for HDTV Application", SID 2004 International Symposium, Digest of Technical Papers, XXXV, Book I, pp. 106 to 109, the achievement of video-compatible response times, in particular in the switching of grey shades, is still a problem which has not yet been solved to a satisfactory extent.

ECB displays, like ASV displays, use liquid-crystalline media having negative dielectric anisotropy ($\Delta\varepsilon$), whereas TN and to date all conventional IPS displays use liquid-crystalline media having positive dielectric anisotropy. However, presently there is an increasing demand for IPS and FFS displays utilizing dielectrically negative liquid crystalline media.

In liquid-crystal displays of this type, the liquid crystals are used as dielectrics, whose optical properties change reversibly on application of an electrical voltage.

Since in displays in general, i.e. also in displays in accordance with these mentioned effects, the operating voltage should be as low as possible, use is made of liquid-crystal media which are generally predominantly composed of liquid-crystal compounds, all of which have the same sign of the dielectric anisotropy and have the highest possible value of the dielectric anisotropy. In general, at most relatively small proportions of neutral compounds and if possible no compounds having a sign of the dielectric anisotropy which is opposite to that of the medium are employed. In the case of liquid-crystal media having negative dielectric anisotropy e.g. for ECB or UB-FFS displays, predominantly compounds having negative dielectric anisotropy are thus employed. The respective liquid-crystalline media employed generally consist predominantly and usually even essentially of liquid-crystal compounds having negative dielectric anisotropy.

In the media used in accordance with the present application, significant amounts of dielectrically positive liquid-crystal compounds and generally only very small amounts of dielectrically compounds or even none at all are typically employed, since in general the liquid-crystal displays are intended to have the lowest possible addressing voltages. At the same time small amounts of dielectrically neutral compounds may be beneficially used in some cases.

US 2013/0207038 A1 discloses liquid crystalline media for HB-FFS displays proposing to improve the performance of the FFS displays using liquid crystals having a positive dielectric anisotropy by the additional incorporation of dielectrically negative liquid crystals. This, however, leads to the necessity of a compensation of the negative contribution of these compounds to the overall dielectric anisotropy of the resultant media. To this end, either the concentration of the dielectrically positive materials has to be increased, which, in turn, leaves less room for the use of dielectrically neutral compounds as diluters in the mixtures, or, alternatively, compounds with a stronger positive dielectric anisotropy have to be used. Both of these alternatives have the strong drawback of increasing the response time of the liquid crystals in the displays.

Liquid crystalline media having a positive dielectric anisotropy for IPS and FFS displays have already been disclosed. In the following some examples will be given.

CN 104232105 A discloses liquid crystalline media with a positive dielectric anisotropy having dielectric ratios ($\varepsilon_\perp/\Delta\varepsilon$) of up to 0.7.

WO 2014/192390 also discloses liquid crystalline media with a positive dielectric anisotropy having rather high values of $\varepsilon_\parallel$, but having dielectric ratios ($\varepsilon_\perp/\Delta\varepsilon$) of only about 0.5.

WO 2015/007173 discloses liquid crystalline media with a positive dielectric anisotropy, some of which have a dielectric ratio ($\varepsilon_\perp/\Delta\varepsilon$) of about 0.7 and slightly above, up to 0.88.

Laid open DE 102016003902.3, EP 3 081 620 and EP 3 095 834 are related to liquid crystal compounds respectively liquid crystalline media for application in respective displays.

Pending, not yet published Applications EP 17164891.8, EP 16190393.5, EP 16194162.0, EP 16197206.2 and EP 16199580.8 of the applicant of the instant application are also related to liquid crystal compounds respectively liquid crystalline media for application in respective displays.

Obviously, the range of the nematic phase of the liquid-crystal mixture must be sufficiently broad for the intended application of the display.

The response times of the liquid-crystal media in the displays also have to be improved, i.e. reduced. This is particularly important for displays for television or multimedia applications. In order to improve the response times, it has repeatedly been proposed in the past to optimise the rotational viscosity of the liquid-crystal media ($\gamma_1$), i.e. to achieve media having the lowest possible rotational viscosity. However, the results achieved here are inadequate for many applications and therefore make it appear desirable to find further optimisation approaches.

Adequate stability of the media to extreme loads, in particular to UV exposure and heating, is very particularly important. In particular in the case of applications in displays in mobile equipment, such as, for example, mobile telephones, this may be crucial.

Besides their relatively poor transmission and their relatively long response times, the MLC displays disclosed hitherto, have further disadvantages. These are e.g. their comparatively low contrast, their relatively high viewing-angle dependence and the difficulty in the reproduction of grey scales in these displays, especially when observed from an oblique viewing angle, as well as their inadequate VHR and their inadequate lifetime. The desired improvements of the transmission of the displays and of their response times are required in order to improve their energy efficiency, respectively their capacity to render rapidly moving pictures.

There thus continues to be a great demand for MLC displays having very high specific resistance at the same time as a large working-temperature range, short response times and a low threshold voltage, with the aid of which various grey shades can be produced and which have, in particular, a good and stable VHR.

The invention has the object of providing MLC displays, not only for monitor and TV applications, but also for mobile applications such as e.g. telephones and navigation systems, which are based on the ECB, IPS or FFS effect, do not have the disadvantages indicated above, or only do so to a lesser extent, and at the same time have very high specific resistance values. In particular, it must be ensured for mobile telephones and navigation systems that they also work at extremely high and extremely low temperatures.

Surprisingly, it has been found that it is possible to achieve liquid-crystal displays which have, in particular in IPS and FFS displays, a low threshold voltage with short response times, a sufficiently broad nematic phase, favourable, relatively low birefringence (Δn) and, at the same time, a high transmission, good stability to decomposition by heating and by UV exposure, and a stable, high VHR if use is made in these display elements of nematic liquid-crystal mixtures which comprise at least one compound, preferably two or more compounds of formula S, preferably selected from the group of the compounds of the sub-formulae S-1 and S-2 and optionally of formulae S, preferably selected from S0-1 and S0-2, and I, preferably selected from I-1, I-2, I-3 and I-4, particularly preferably of these of the sub-formulate I-2 and/or I-3 and/or I-4, more preferably I-2 and/or I-4, and preferably additionally at least one compound, preferably two or more compounds, selected from the group of the compounds of the formulae II and III, the former preferably of formula II-1 and/or II-2, and/or at least one compound, preferably two or more compounds selected from the group of formulae IV and/or V and, preferably, one or more compounds selected from the group of formulae VII to IX (all formulae as defined herein below).

Media of this type can be used, in particular, for electro-optical displays having active-matrix addressing for IPS- or FFS displays.

The media according to the present invention preferably additionally comprise a one or more compounds selected from the group of compounds of formulae II and III, preferably one or more compounds of formula II, more preferably in addition one or more compounds of formula III and, most preferably, additionally one or more compounds selected from the group of the compounds of formulae IV and V and, again preferably, one or more compounds selected from the group of compounds of formulae VI to IX (all formulae as defined below).

The mixtures according to the invention exhibit very broad nematic phase ranges with clearing points ≥70° C., very favourable values for the capacitive threshold, relatively high values for the holding ratio and at the same time good low-temperature stabilities at −20° C. and −30° C., as well as very low rotational viscosities. The mixtures according to the invention are furthermore distinguished by a good ratio of clearing point and rotational viscosity and by a relatively high positive dielectric anisotropy.

Now, it has been found surprisingly that LCs of the FFS type using liquid crystals with positive dielectric anisotropy may be realised using specially selected liquid crystalline media. These media are characterised by a particular combination of physical properties. Most decisive amongst these are their dielectric properties and here a high average dielectric constant ($\varepsilon_{av.}$), a high dielectric constant perpendicular to the director of the liquid crystal molecules ($\varepsilon_\perp$), a high value of the dielectric anisotropy ($\Delta\varepsilon$), and, in particular, the relatively high ratio of these latter two values: ($\varepsilon_\perp/\Delta\varepsilon$).

The liquid crystalline media according to the present invention preferably have a positive dielectric anisotropy, preferably in the range from 1.5 or more to 20.0 or less, more preferably in the range from 3.0 or more to 8.0 or less and, most preferably in the range from 4.0 or more to 7.0. or less.

The liquid crystalline media according to the present invention preferably have a dielectric constant perpendicular to the director of the liquid crystal molecules ($\varepsilon_\perp$) of 5.0 or more, more preferably of 6.0 or more, more preferably of 7.0 or more, more preferably of 8.0 or more, more preferably of 9 or more and, most preferably, of 10.0 or more.

The liquid crystalline media according to the present invention preferably have a dielectric ratio ($\varepsilon_\perp/\Delta\varepsilon$) of 0.65 or more, more preferably of 0.75 or more and, most preferably, of 1.0 or more.

In a preferred embodiment of the present invention the liquid crystalline medium, preferably having a dielectric anisotropy ($\Delta\varepsilon$) of 0.5 or more, preferably comprises a) one or more compounds of formula S, having both a high dielectric constant perpendicular to the director and parallel to the director, preferably in a concentration in the range from 1% to 60%, more preferably in the range from 5% to 40%, particularly preferably in the range from 8% to 35%,

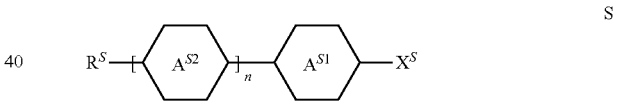

S in which

denotes

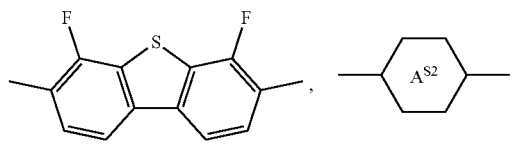

denotes

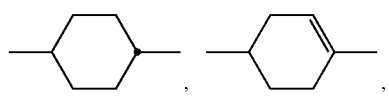

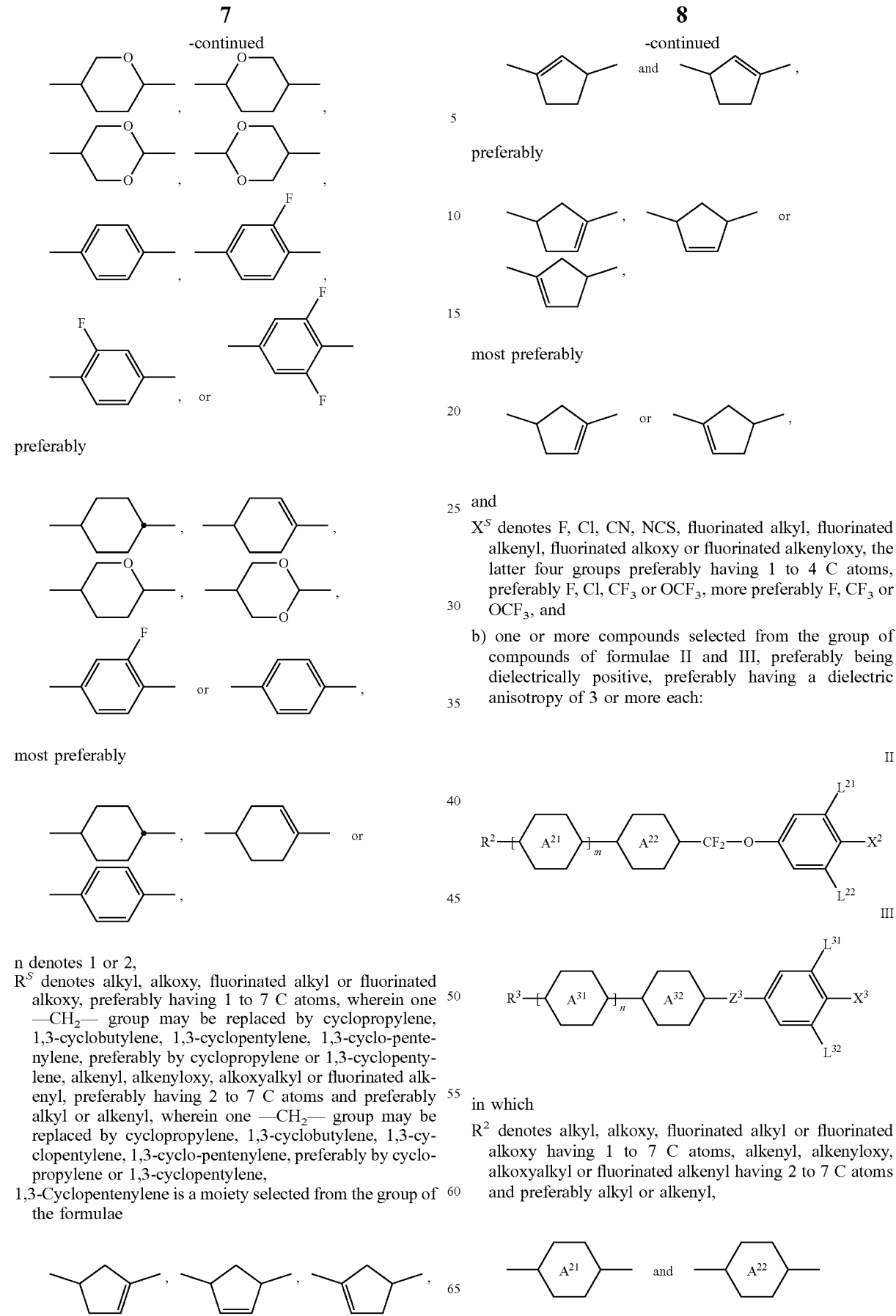

n denotes 1 or 2, $R^S$ denotes alkyl, alkoxy, fluorinated alkyl or fluorinated alkoxy, preferably having 1 to 7 C atoms, wherein one —CH$_2$— group may be replaced by cyclopropylene, 1,3-cyclobutylene, 1,3-cyclopentylene, 1,3-cyclo-pentenylene, preferably by cyclopropylene or 1,3-cyclopentylene, alkenyl, alkenyloxy, alkoxyalkyl or fluorinated alkenyl, preferably having 2 to 7 C atoms and preferably alkyl or alkenyl, wherein one —CH$_2$— group may be replaced by cyclopropylene, 1,3-cyclobutylene, 1,3-cyclopentylene, 1,3-cyclo-pentenylene, preferably by cyclopropylene or 1,3-cyclopentylene, 1,3-Cyclopentenylene is a moiety selected from the group of the formulae $X^S$ denotes F, Cl, CN, NCS, fluorinated alkyl, fluorinated alkenyl, fluorinated alkoxy or fluorinated alkenyloxy, the latter four groups preferably having 1 to 4 C atoms, preferably F, Cl, CF$_3$ or OCF$_3$, more preferably F, CF$_3$ or OCF$_3$, and b) one or more compounds selected from the group of compounds of formulae II and III, preferably being dielectrically positive, preferably having a dielectric anisotropy of 3 or more each:

in which $R^2$ denotes alkyl, alkoxy, fluorinated alkyl or fluorinated alkoxy having 1 to 7 C atoms, alkenyl, alkenyloxy, alkoxyalkyl or fluorinated alkenyl having 2 to 7 C atoms and preferably alkyl or alkenyl, on each appearance, independently of one another, denote

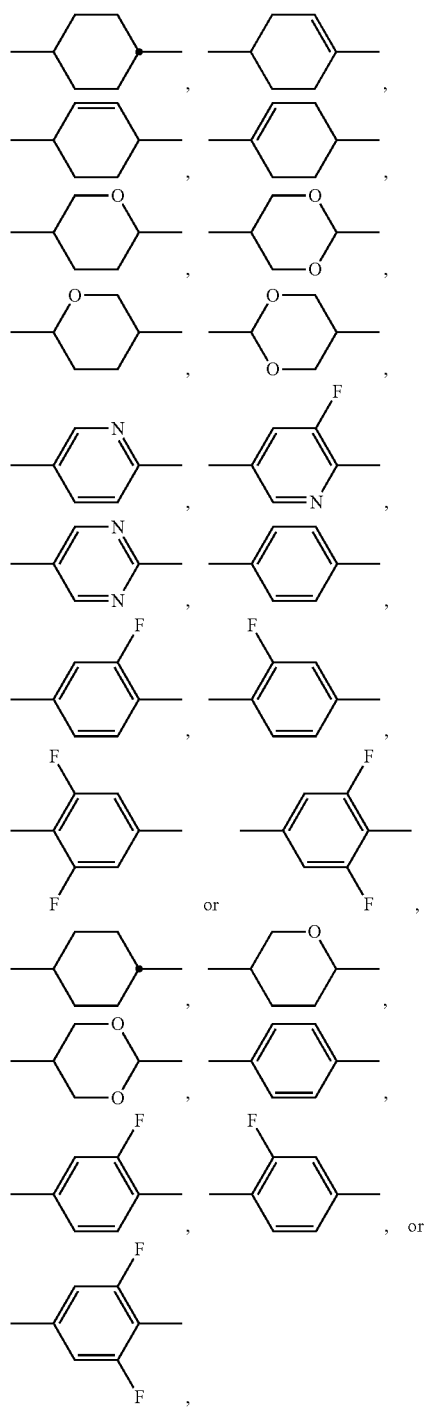

, preferably

, or $L^{21}$ and $L^{22}$ denote independently of each other H or F, preferably $L^{21}$ denotes F, $X^2$ denotes halogen, halogenated alkyl or alkoxy having 1 to 3 C atoms or halogenated alkenyl or alkenyloxy having 2 or 3 C atoms, preferably F, Cl, —OCF$_3$, —O—CH$_2$CF$_3$, —O—CH=CH$_2$, —O—CH=CF$_2$ or —CF$_3$, very preferably F, Cl, —O—CH=CF$_2$ or —OCF$_3$, m denotes 0, 1, 2 or 3, preferably 1 or 2 and particularly preferably 1, $R^3$ denotes alkyl, alkoxy, fluorinated alkyl or fluorinated alkoxy having 1 to 7 C atoms, alkenyl, alkenyloxy, alkoxyalkyl or fluorinated alkenyl having 2 to 7 C atoms and preferably alkyl or alkenyl,

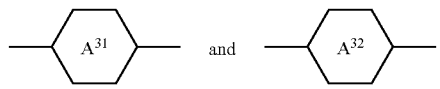

on each appearance, independently of one another, are

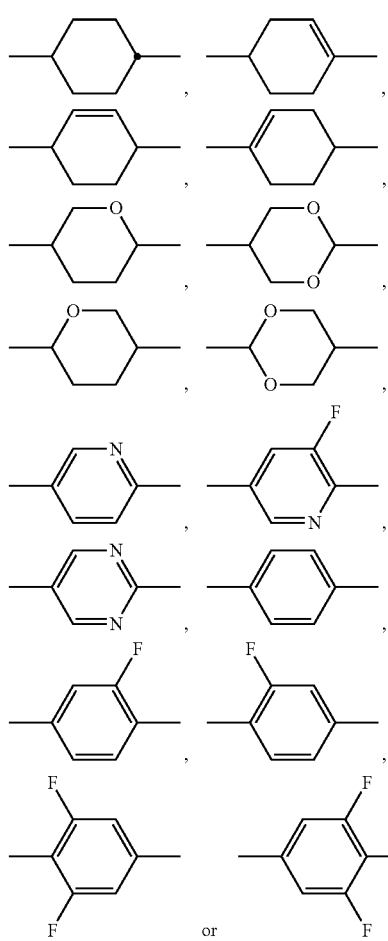

, or preferably

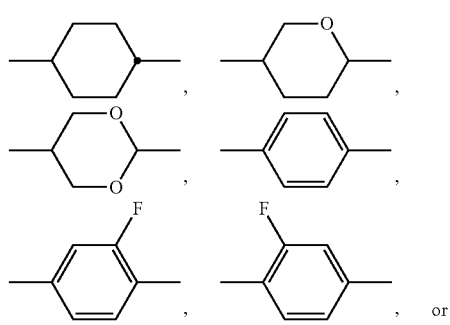

, or

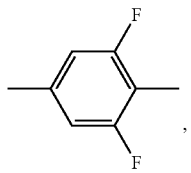

$L^{31}$ and $L^{32}$, independently of one another, denote H or F, preferably $L^{31}$ denotes F, $X^3$ denotes halogen, halogenated alkyl or alkoxy having 1 to 3 C atoms or halogenated alkenyl or alkenyloxy having 2 or 3 C atoms, F, Cl, —OCF$_3$, —OCHF$_2$, —O—CH$_2$CF$_3$, —O—CH=CF$_2$, —O—CH=CH$_2$ or —CF$_3$, very preferably F, Cl, —O—CH=CF$_2$, —OCHF$_2$ or —OCF$_3$, $Z^3$ denotes —CH$_2$CH$_2$—, —CF$_2$CF$_2$—, —COO—, trans-CH=CH—, trans-CF=CF—, —CH$_2$O— or a single bond, preferably —CH$_2$CH$_2$—, —COO—, trans-CH=CH— or a single bond and very preferably —COO—, trans-CH=CH— or a single bond, and n denotes 0, 1, 2 or 3, preferably 1, 2 or 3 and particularly preferably 1, and c) optionally one or more compounds selected from the group of formulae IV and V, preferably being dielectrically neutral:

IV

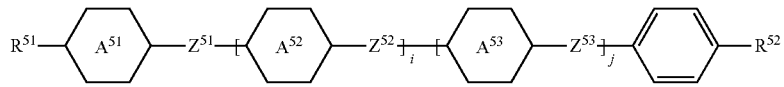

V in which $R^{41}$ and $R^{42}$, independently of one another, have the meaning indicated above for $R^2$ under formula II, preferably $R^{41}$ denotes alkyl and $R^{42}$ denotes alkyl or alkoxy or $R^{41}$ denotes alkenyl and $R^{42}$ denotes alkyl,

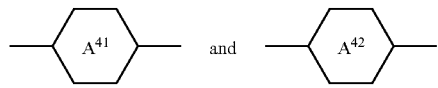

independently of one another and, if

occurs twice, also these independently of one another, denote

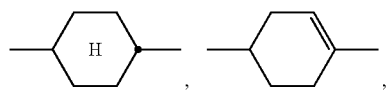

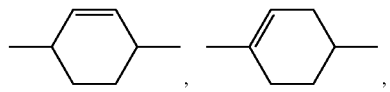

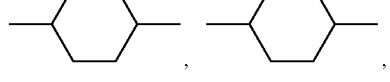

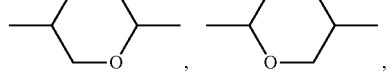

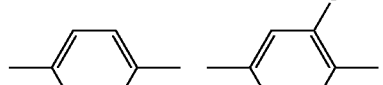

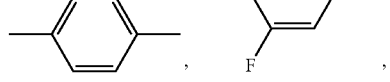

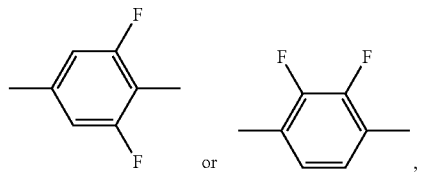

preferably one or more of

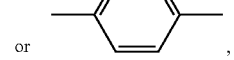

denotes or denote,

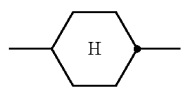

$Z^{41}$ and $Z^{42}$, independently of one another and, if $Z^{41}$ occurs twice, also these independently of one another, denote —CH$_2$CH$_2$—, —COO—, trans-CH=CH—, trans- CF=CF—, —CH$_2$O—, —CF$_2$O—, —C≡C— or a single bond, preferably one or more thereof denotes/denote a single bond, and p denotes 0, 1 or 2, preferably 0 or 1, and R$^{51}$ and R$^{52}$, independently of one another, have one of the meanings given for R$^{41}$ and R$^{42}$ and preferably denote alkyl having 1 to 7 C atoms, preferably n-alkyl, particularly preferably n-alkyl having 1 to 5 C atoms, alkoxy having 1 to 7 C atoms, preferably n-alkoxy, particularly preferably n-alkoxy having 2 to 5 C atoms, alkoxyalkyl, alkenyl or alkenyloxy having 2 to 7 C atoms, preferably having 2 to 4 C atoms, preferably alkenyloxy,

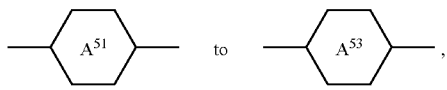

if present, each, independently of one another, denote

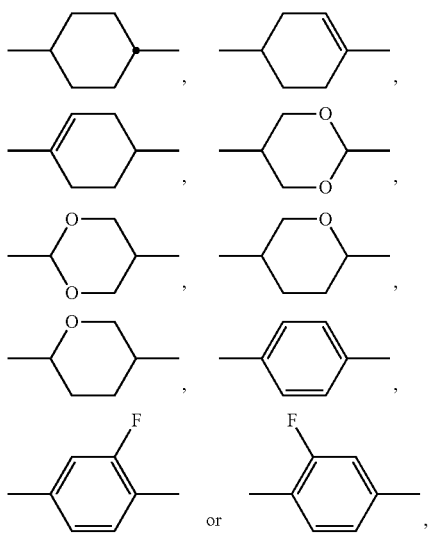

preferably

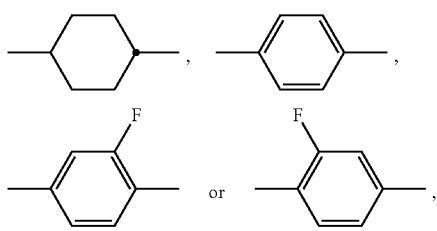

preferably

denotes

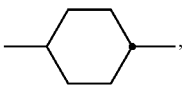

and, if present,

preferably denotes

Z$^{51}$ to Z$^{53}$ each, independently of one another, denote —CH$_2$—CH$_2$—, —CH$_2$—O—, —CH=CH—, —C≡C—, —COO— or a single bond, preferably —CH$_2$—CH$_2$—, —CH$_2$—O— or a single bond and particularly preferably a single bond, i and j each, independently of one another, denote 0 or 1, (i+j) preferably denotes 0, 1 or 2, more preferably 0 or 1 and, most preferably, 1, d) again optionally, either alternatively or additionally, one or more compounds selected from the group of formulae VI to IX, preferably being dielectrically negative:

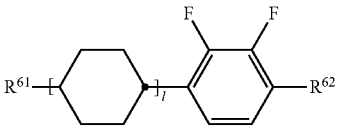

VI

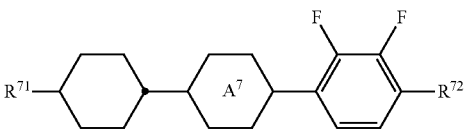

VII

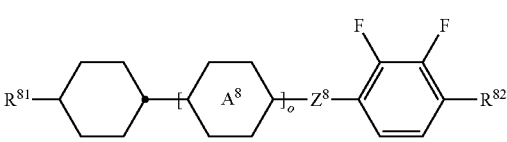

VIII

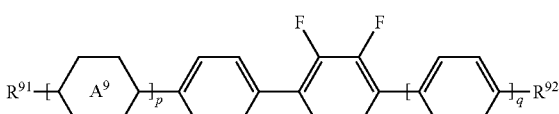

IX wherein

R$^{61}$ denotes an unsubstituted alkyl radical having 1 to 7 C atoms, preferably a straight-chain alkyl radical, more preferably an n-alkyl radical, most preferably propyl or pentyl, an unsubstituted alkenyl radical having 2 to 7 C atoms, preferably a straight-chain alkenyl radical, particularly preferably having 2 to 5 C atoms, an unsubstituted alkoxy radical having 1 to 6 C atoms or an unsubstituted alkenyloxy radical having 2 to 6 C atoms, $R^{62}$ denotes an unsubstituted alkyl radical having 1 to 7 C atoms, an unsubstituted alkoxy radical having 1 to 6 C atoms or an unsubstituted alkenyloxy radical having 2 to 6 C atoms, and l denotes 0 or 1, $R^{71}$ denotes an unsubstituted alkyl radical having 1 to 7 C atoms, preferably a straight-chain alkyl radical, more preferably an n-alkyl radical, most preferably propyl or pentyl, or an unsubstituted alkenyl radical having 2 to 7 C atoms, preferably a straight-chain alkenyl radical, particularly preferably having 2 to 5 C atoms, $R^{72}$ denotes an unsubstituted alkyl radical having 1 to 7 C atoms, preferably having 2 to 5 C atoms, an unsubstituted alkoxy radical having 1 to 6 C atoms, preferably having 1, 2, 3 or 4 C atoms, or an unsubstituted alkenyloxy radical having 2 to 6 C atoms, preferably having 2, 3 or 4 C atoms, and

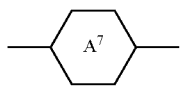

denotes

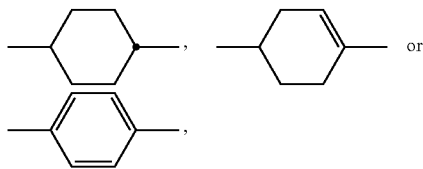

$R^{81}$ denotes an unsubstituted alkyl radical having 1 to 7 C atoms, preferably a straight-chain alkyl radical, more preferably an n-alkyl radical, most preferably propyl or pentyl, or an unsubstituted alkenyl radical having 2 to 7 C atoms, preferably a straight-chain alkenyl radical, particularly preferably having 2 to 5 C atoms, $R^{82}$ denotes an unsubstituted alkyl radical having 1 to 7 C atoms, preferably having 2 to 5 C atoms, an unsubstituted alkoxy radical having 1 to 6 C atoms, preferably having 1, 2, 3 or 4 C atoms, or an unsubstituted alkenyloxy radical having 2 to 6 C atoms, preferably having 2, 3 or 4 C atoms,

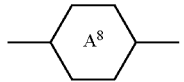

denotes

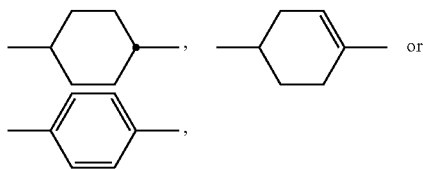

preferably

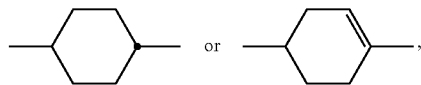

more preferably

$Z^8$ denotes —(C=O)—O—, —CH$_2$—O—, —CF$_2$—O— or —CH$_2$—CH$_2$—, preferably —(C=O)—O— or —CH$_2$—O—, and o denotes 0 or 1, $R^{91}$ and $R^{92}$ independently of one another have the meaning given for $R^{72}$ above, $R^{91}$ preferably denotes an alkyl radical having 2 to 5 C atoms, preferably having 3 to 5 C atoms, $R^{92}$ preferably denotes an alkyl or alkoxy radical having 2 to 5 C atoms, more preferably an alkoxy radical having 2 to 4 C atoms, or an alkenyloxy radical having 2 to 4 C atoms.

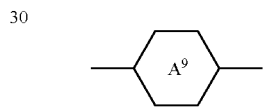

denotes

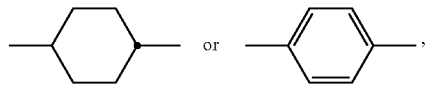

p and q independently of each other denote 0 or 1, and (p+q) preferably denotes 0 or 1, and in case

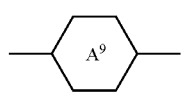

denotes

alternatively, preferably p=q=1, e) again optionally, one or more compounds of formula I, having both a high dielectric constant perpendicular to the director and parallel to the director, preferably in a concentration in the range from 1% to 60%, more preferably in the range from 5% to 40%, particularly preferably in the range from 8% to 35%,

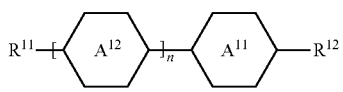

in which

denotes

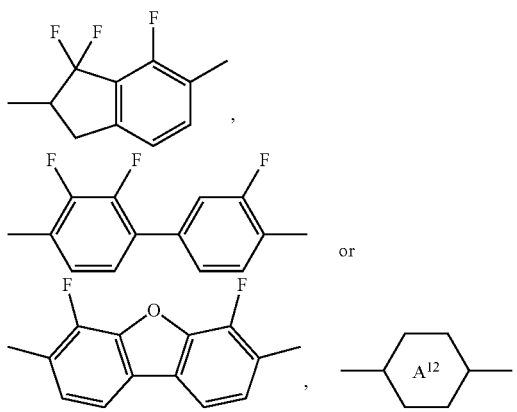

denotes

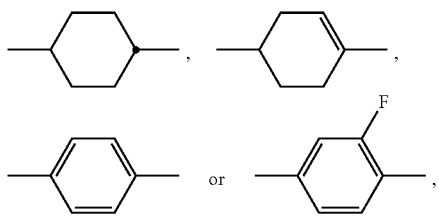

n denotes 0 or 1,
R$^{11}$ and R$^{12}$ independently of each other denote alkyl, alkoxy, fluorinated alkyl or fluorinated alkoxy, preferably having 1 to 7 C atoms, alkenyl, alkenyloxy, alkoxyalkyl or fluorinated alkenyl having 2 to 7 C atoms and preferably alkyl, alkoxy, alkenyl or alkenyloxy, most preferably alkyl, alkoxy or alkenyloxy, and R$^{11}$ alternatively denotes R$^1$ and R$^{12}$ alternatively denotes X$^1$,
R$^1$ denotes alkyl, alkoxy, fluorinated alkyl or fluorinated alkoxy, preferably having 1 to 7 C atoms, wherein one —CH$_2$— group may be replaced by cyclopropylene, 1,3-cyclobutylene, 1,3-cyclopentylene, 1,3-cyclo-pentenylene, preferably by cyclopropylene or 1,3-cyclopentylene, alkenyl, alkenyloxy, alkoxyalkyl or fluorinated alkenyl having 2 to 7 C atoms wherein one —CH$_2$— group may be replaced by cyclo-propylene, 1,3-cyclobutylene, 1,3-cyclopentylene, 1,3-cyclo-pentenylene, preferably by cyclo-propylene or 1,3-cyclopentylene, and preferably alkyl or alkenyl,
1,3-Cyclopentenylene is a moiety selected from the group of the formulae

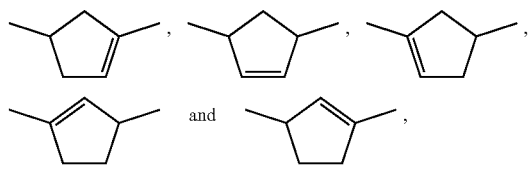

preferably

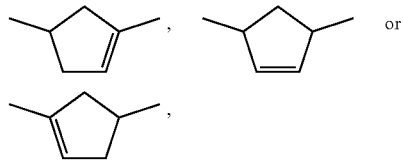

most preferably

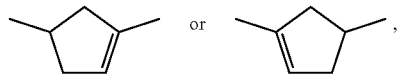

and

X$^1$ denotes F, Cl, fluorinated alkyl, fluorinated alkenyl, fluorinated alkoxy or fluorinated alkenyoxy, the latter four groups preferably having 1 to 4 C atoms, preferably F, Cl, CF$_3$ or OCF$_3$, in particular for formulae I-1 and I-2 preferably F and for formula I-4 preferably OCF$_3$ and f) again optionally, one or more compounds of formula S0, having both a high dielectric constant perpendicular to the director and parallel to the director, preferably in a concentration in the range from 1% to 60%, more preferably in the range from 5% to 40%, particularly preferably in the range from 8% to 35%,

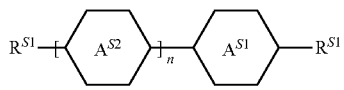

in which

denotes

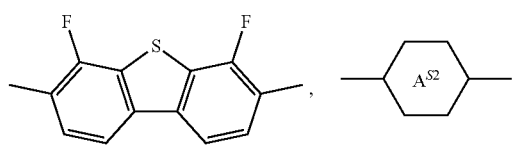

denotes

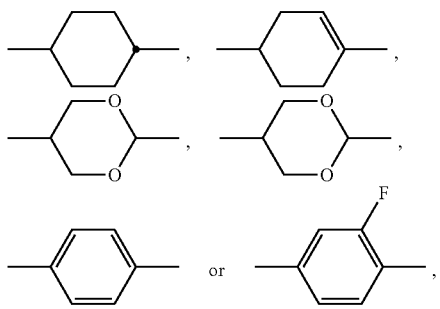

$R^{S1}$ and $R^{S2}$ independently of each other denote alkyl, alkoxy, fluorinated alkyl or fluorinated alkoxy, preferably having 1 to 7 C atoms, wherein one —CH$_2$— group may be replaced by cyclopropylene, 1,3-cyclobutylene, 1,3-cyclopentylene, 1,3-cyclo-pentenylene, preferably by cyclopropylene or 1,3-cyclopentylene, alkenyl, alkenyloxy, alkoxyalkyl or fluorinated alkenyl having 2 to 7 C atoms, wherein one —CH$_2$— group may be replaced by cyclopropylene, 1,3-cyclobutylene, 1,3-cyclopentylene, 1,3-cyclo-pentenylene, preferably by cyclopropylene or 1,3-cyclopentylene, and preferably alkyl, alkoxy, alkenyl or alkenyloxy, most preferably alkyl, alkoxy or alkenyloxy, and $R^{S1}$ alternatively denotes $R^S$ and $R^{S2}$ alternatively denotes $X^S$, $R^S$ and $X^S$ have the meanings given under formula S above n denotes 0, and in case $R^{S2}$ denotes $X^S$, alternatively may denote 1.

The liquid-crystalline media in accordance with the present application preferably have a nematic phase.

Preferably the compounds of formula S are selected from the group of compounds of formulae S-1 and S-2:

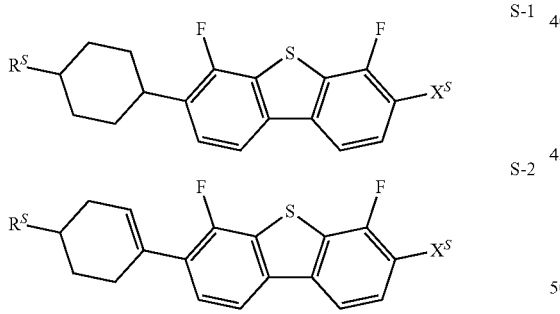

in which
$R^S$ denotes alkyl, alkoxy, fluorinated alkyl or fluorinated alkoxy, preferably having 1 to 7 C atoms, wherein one —CH$_2$— group may be replaced by cyclopropylene, 1,3-cyclobutylene, 1,3-cyclopentylene, 1,3-cyclopentenylene, preferably by cyclopropylene or 1,3-cyclopentylene, alkenyl, alkenyloxy, alkoxyalkyl or fluorinated alkenyl having 2 to 7 C atoms, wherein one —CH$_2$— group may be replaced by cyclopropylene, 1,3-cyclobutylene, 1,3-cyclopentylene, 1,3-cyclopentenylene, preferably by cyclopropylene or 1,3-cyclopentylene and preferably alkyl, alkoxy, alkenyl or alkenyloxy, most preferably alkoxy or alkenyloxy, $X^S$ denotes F, Cl, CN, NCS, fluorinated alkyl, fluorinated alkenyl, fluorinated alkoxy or fluorinated alkenyloxy, the latter four groups preferably having 1 to 4 C atoms, preferably F, Cl, CF$_3$ or OCF$_3$, more preferably CF$_3$ or OCF$_3$.

The compounds of formula S, and in particular of formulae S-1 and S-2, may be prepared via various synthetic route. The essential step is in all cases the formation of the S-heterocyclic ring system via successive Migita coupling and closure of the ring induced by a base. These reactions optionally, and in many cases beneficially, may be performed as a "one pot" (or "single pot") reaction.

The compounds of formula S-1 are prepared similar to the synthesis of compounds of formula I-3 according to WO 02/055463 and compounds of the formula S-1 containing two alkoxy groups: (Scheme 1)

Scheme 1.
General Synthetic Scheme

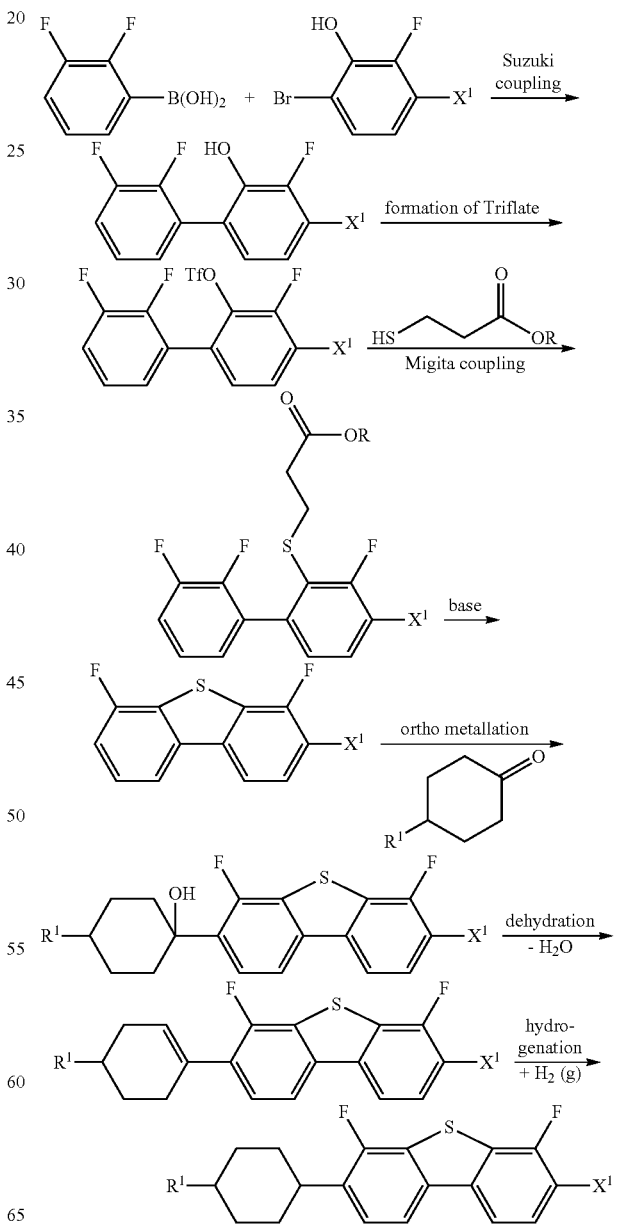

Remarks:
X¹=F, CF₃ or OCF₃; R=ethyl or 2-ethylhexyl, R¹=alkyl or, in case of 1,4-cyclohexenylene compound, alternatively also alkenyl.

Obviously, instead of the cyclohexanone compound also a respective cyclohexylcyclohexanone derivative may be used.

An alternative synthetic route is exemplified for the following propyl homologue of formula S-1.

Scheme 2.
Alternative General Synthetic Scheme

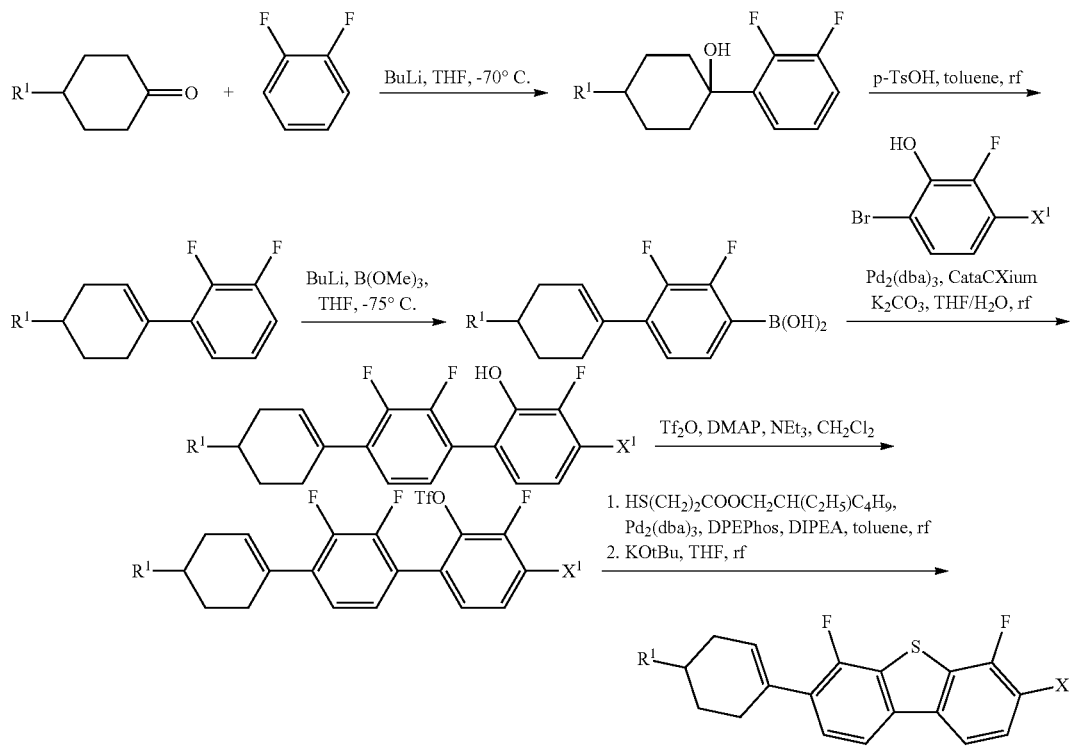

Remarks:
X¹=F, CF₃ or OCF₃; R=ethyl or 2-ethylhexyl, R¹=alkyl or alkenyl. (Tf=trifluoromethanesulfonyl=—SO₂—CF₃

Also here the product may be hydrogenated, leading to the corresponding 1,4-cyclohexylene compound and instead of the cyclohexanone compound also a respective cyclohexyl-cyclohexanone derivative may be used.

Particularly suitable synthetic routes to the compounds of formulae S-1 and S-2 used according to the invention are explained below with reference to Scheme 3.

Scheme 3. Synthesis of the compounds of formula S. The radicals R, A, Z, X¹, X², Y and the index m have the respective meanings meaning indicated for ring $A^{S1}$, $R^S$, $X^S$ under formula S.

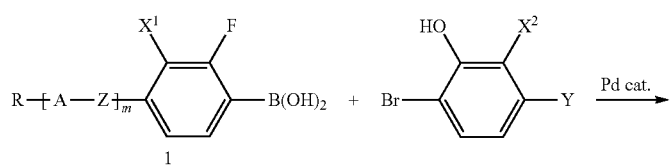

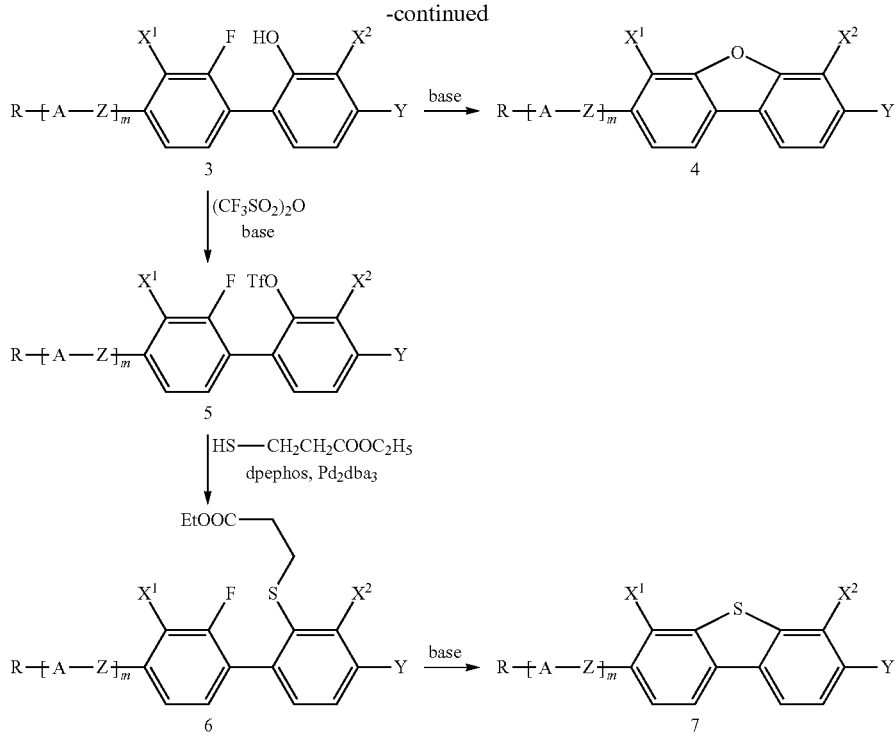

Scheme 3 should only be regarded as illustrative. The person skilled in the art will be able to carry out corresponding variations of the syntheses presented, and also follow other suitable synthetic routes, in order to obtain compounds of the formulae S-1 and S-2.

In accordance with the synthesis depicted above and below, the present invention in an embodiment also encompasses one or more processes for the preparation of compounds of the formulae S-1 and S-2.

The invention thus encompasses a process for the preparation of compounds of the formula S which is characterised in that it comprises a process step in which a compound of the formula II is converted into compounds of the formulae S-1 and S-2 in the presence of a base, as shown in Scheme 4 and in which R, A, Z, $X^1$, $X^2$, W and m have the meaning indicated above and G denotes —OH, —SH or SG' and G' denotes a base-labile protecting group for thiols. Preferred protecting groups are acetyl, dimethylaminocarbonyl, 2-tetrahydropyranyl, ethoxycarbonylethyl, tert-butyl, methyl and 2-ethylhexyloxycarbonyl-ethyl, particularly preferably ethoxycarbonylethyl or 2-ethylhexyloxy-carbonylethyl.

Scheme 4. Process for the preparation of the compounds of the formulae S-1 and S-2.

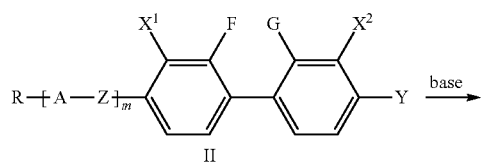

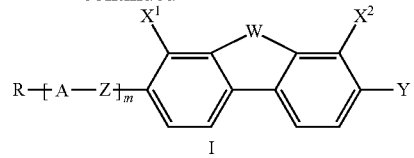

The process and the subsequent work-up of the reaction mixture can basically be carried out as a batch reaction or in a continuous reaction procedure. The continuous reaction procedure encompasses, for example, reaction in a continuous stirred-tank reactor, a stirred-reactor cascade, a loop or cross-flow reactor, a flow tube or in a micro reactor. The reaction mixtures are optionally worked up, as necessary, by filtration via solid phases, chromatography, separation between immiscible phases (for example extraction), adsorption onto solid supports, removal of solvents and/or azeotropic mixtures by distillation, selective distillation, sublimation, crystallisation, co-crystallisation or by nanofiltration on membranes.

The invention furthermore relates to the use of liquid-crystal mixtures and liquid-crystalline media according to the invention in IPS and FFS displays, in particular the use in SG-FFS displays containing a liquid-crystalline medium, for improving the response times and/or the transmission.

The invention furthermore relates to a liquid-crystal display containing a liquid-crystalline medium according to the invention, in particular an IPS or FFS display, particularly preferably a FFS or SG-FFS display.

The invention furthermore relates to a liquid-crystal display of the IPS or FFS type comprising a liquid-crystal cell consisting of two substrates, where at least one substrate is transparent to light and at least one substrate has an electrode layer, and a layer, located between the substrates, of a liquid-crystalline medium comprising a polymerised component and a low-molecular-weight component, where the polymerised component is obtainable by polymerisation of one or more polymerisable compounds in the liquid-crystalline medium between the substrates of the liquid-crystal cell, preferably with application of an electrical voltage and where the low-molecular-weight component is a liquid-crystal mixture according to the invention as described above and below.

The displays in accordance with the present invention are preferably addressed by an active matrix (active matrix LCDs, AMDs for short), preferably by a matrix of thin-film transistors (TFTs). However, the liquid crystals according to the invention can also be used in an advantageous manner in displays having other known addressing means.

The invention furthermore relates to a process for the preparation of a liquid-crystalline medium according to the invention by mixing one or more compounds of formula S, preferably selected from the group of compounds of formulae S-1 and S-2 with one or more low-molecular-weight liquid-crystalline compounds, or a liquid-crystal mixture and optionally with further liquid-crystalline compounds and/or additives.

The following meanings apply above and below:

The term "FFS" is, unless indicated otherwise, used to represent FFS and SG-FFS displays.

The term "mesogenic group" is known to the person skilled in the art and is described in the literature, and denotes a group which, due to the anisotropy of its attracting and repelling interactions, essentially contributes to causing a liquid-crystalline (LC) phase in low-molecular-weight or polymeric substances. Compounds containing mesogenic groups (mesogenic compounds) do not necessarily have to have a liquid-crystalline phase themselves. It is also possible for mesogenic compounds to exhibit liquid-crystalline phase behaviour only after mixing with other compounds and/or after polymerisation. Typical mesogenic groups are, for example, rigid rod- or disc-shaped units. An overview of the terms and definitions used in connection with mesogenic or liquid-crystalline compounds is given in Pure Appl. Chem. 73(5), 888 (2001) and C. Tschierske, G. Pelzl, S. Diele, Angew. Chem. 2004, 116, 6340-6368.

The term "spacer group" or "spacer" for short, also referred to as "Sp" above and below, is known to the person skilled in the art and is described in the literature, see, for example, Pure Appl. Chem. 73(5), 888 (2001) and C. Tschierske, G. Pelzl, S. Diele, Angew. Chem. 2004, 116, 6340-6368. Unless indicated otherwise, the term "spacer group" or "spacer" above and below denotes a flexible group which connects the mesogenic group and the polymerisable group(s) to one another in a polymerisable mesogenic compound.

For the purposes of this invention, the term "liquid-crystalline medium" is intended to denote a medium which comprises a liquid-crystal mixture and one or more polymerisable compounds (such as, for example, reactive mesogens). The term "liquid-crystal mixture" (or "host mixture") is intended to denote a liquid-crystalline mixture which consists exclusively of unpolymerisable, low-molecular-weight compounds, preferably of two or more liquid-crystalline compounds and optionally further additives, such as, for example, chiral dopants or stabilisers.

Particular preference is given to liquid-crystal mixtures and liquid-crystalline media which have a nematic phase, in particular at room temperature.

In a preferred embodiment of the present invention, the liquid-crystal medium comprises one or more compounds of formula I, preferably selected from the group of compounds of formulae I-1 to I-4

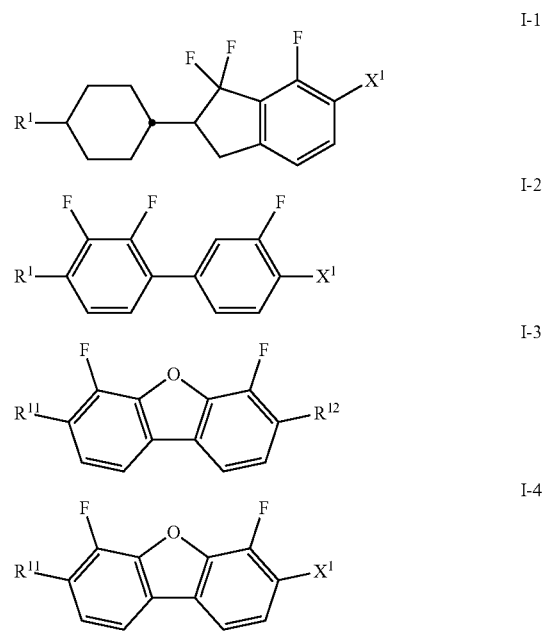

in which the parameters have the meanings given above and preferably $R^{11}$ and $R^{12}$ independently of each other denote alkyl, alkoxy, fluorinated alkyl or fluorinated alkoxy, preferably having 1 to 7 C atoms, wherein one —$CH_2$— group may be replaced by cyclo-propylene, 1,3-cyclobutylene, 1,3-cyclopentylene, 1,3-cyclo-pentenylene, preferably by cyclopropylene or 1,3-cyclopentylene, alkenyl, alkenyloxy, alkoxyalkyl or fluorinated alkenyl having 2 to 7 C atoms, wherein one —$CH_2$— group may be replaced by cyclo-propylene, 1,3-cyclobutylene, 1,3-cyclopentylene, 1,3-cyclo-pentenylene, preferably by cyclopropylene or 1,3-cyclopentylene and preferably alkyl, alkoxy, alkenyl or alkenyloxy, most preferably alkoxy or alkenyloxy, $R^1$ denotes alkyl, alkoxy, fluorinated alkyl or fluorinated alkoxy preferably having 1 to 7 C atoms, wherein one —$CH_2$— group may be replaced by cyclo-propylene, 1,3-cyclobutylene, 1,3-cyclopentylene, 1,3-cyclopentenylene, preferably by cyclopropylene or 1,3-cyclopentylene, alkenyl, alkenyloxy, alkoxyalkyl or fluorinated alkenyl having 2 to 7 C atoms, wherein one —$CH_2$— group may be replaced by cyclopropylene, 1,3-cyclobutylene, 1,3-cyclopentylene, 1,3-cyclo-pentenylene, preferably by cyclopropylene or 1,3-cyclopentylene and preferably alkyl or alkenyl, and $X^1$ denotes F, Cl, CN, NCS, fluorinated alkyl, fluorinated alkenyl, fluorinated alkoxy or fluorinated alkenyoxy, the latter four groups preferably having 1 to 4 C atoms, preferably F, Cl, $CF_3$ or $OCF_3$, in particular for formulae I-1 and I-2 preferably F and for formula I-4 preferably $OCF_3$.

In a preferred embodiment of the present invention, the liquid-crystal medium comprises one or more compounds of formula S0, preferably selected from the group of compounds of formulae S0-1 and S0-2

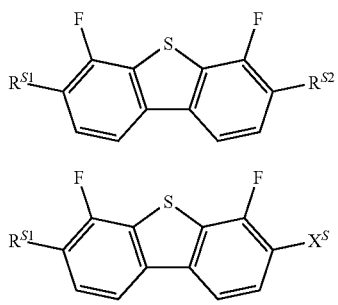
S0-1

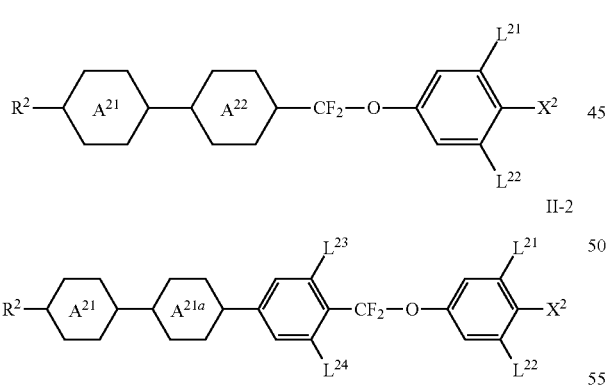
S0-2 in which the parameters have the meanings given above and preferably $R^{S1}$ and $R^{S2}$ independently of each other denote alkyl, alkoxy, fluorinated alkyl or fluorinated alkoxy, preferably having 1 to 7 C atoms, wherein one —CH$_2$— group may be replaced by cyclopropylene, 1,3-cyclobutylene, 1,3-cyclopentylene, 1,3-cyclo-pentenylene, preferably by cyclopropylene or 1,3-cyclopentylene, alkenyl, alkenyloxy, alkoxyalkyl or fluorinated alkenyl having 2 to 7 C atoms, wherein one —CH$_2$— group may be replaced by cyclopropylene, 1,3-cyclobutylene, 1,3-cyclopentylene, 1,3-cyclo-pentenylene, preferably by cyclopropylene or 1,3-cyclopentylene and preferably alkyl, alkoxy, alkenyl or alkenyloxy, most preferably alkoxy or alkenyloxy, $X^S$ denotes F, Cl, CN, NCS, fluorinated alkyl, fluorinated alkenyl, fluorinated alkoxy or fluorinated alkenyoxy, the latter four groups preferably having 1 to 4 C atoms, preferably F, Cl, CF$_3$ or OCF$_3$, more preferably CF$_3$ or OCF$_3$.

In a preferred embodiment of the present invention, the liquid-crystal medium comprises one or more, preferably dielectrically positive, compounds preferably having a dielectric anisotropy of 3 or more, selected from the group of the compounds of the formulae II-1 and II-2:

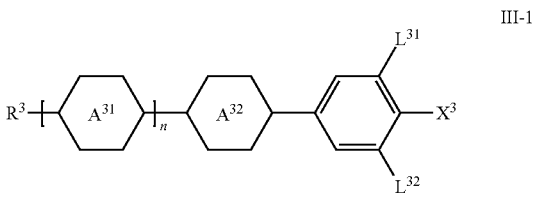
II-1

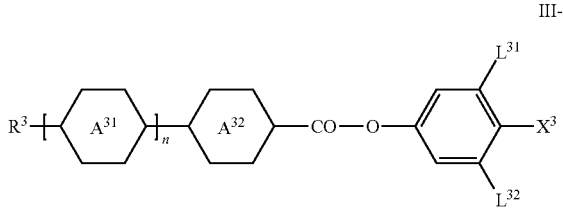
II-2 in which the parameters have the respective meanings indicated above under formula II, and $L^{23}$ and $L^{24}$, independently of one another, denote H or F, preferably $L^{23}$ denotes F, and

has one of the meanings given for

and, in the case of formulae II-1 and II-2, $X^2$ preferably denotes F or OCF$_3$, particularly preferably F, and, in the case of formula II-2,

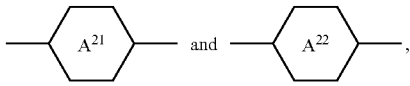

independently of one another, preferably denote

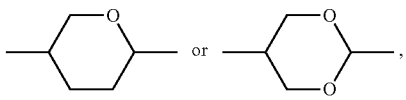

and/or selected from the group of the compounds of the formulae III-1 and III-2:

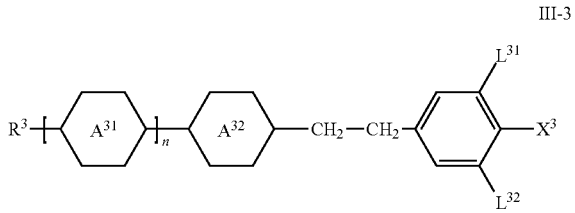
III-1

III-2 in which the parameters have the meanings given under formula III,
and the media in accordance with the present invention may comprise, alternatively or in addition to the compounds of the formulae III-1 and/or III-2, one or more compounds of the formula III-3

III-3 in which the parameters have the respective meanings indicated above, and the parameters $L^{31}$ and $L^{32}$, independently of one another and of the other parameters, denote H or F.

The liquid-crystal medium preferably comprises compounds selected from the group of the compounds of the formulae II-1 and II-2 in which $L^{21}$ and $L^{22}$ and/or $L^{23}$ and $L^{24}$ both denote F.

In a preferred embodiment, the liquid-crystal medium comprises compounds selected from the group of the compounds of the formulae II-1 and II-2 in which $L^{21}$, $L^{22}$, $L^{23}$ and $L^{24}$ all denote F.

The liquid-crystal medium preferably comprises one or more compounds of the formula II-1. The compounds of the formula II-1 are preferably selected from the group of the compounds of the formulae II-1a to II-1e, preferably one or more compounds of formulae II-1a and/or II-1b and/or II-1d, preferably of formula II-1a and/or II-1d or II-1b and/or II-1d, most preferably of formula II-1d:

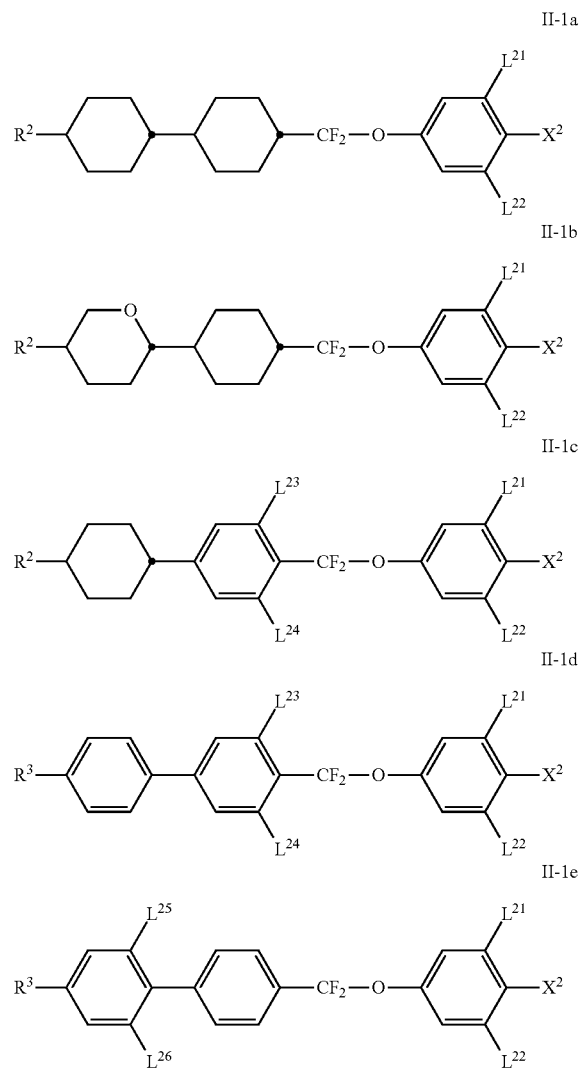

in which the parameters have the respective meanings indicated above, and $L^{25}$ and $L^{26}$, independently of one another and of the other parameters, denote H or F, and preferably
in the formulae II-1a and II-1b,
$L^{21}$ and $L^{22}$ both denote F,
in the formulae II-1c and II-1d,
$L^{21}$ and $L^{22}$ both denote F and/or $L^{23}$ and $L^{24}$ both denote F,
and in formula II-1e,
$L^{21}$, $L^{22}$ and $L^{23}$ denote F.

The liquid-crystal medium preferably comprises one or more compounds of the formula II-2, which are preferably selected from the group of the compounds of the formulae II-2a to II-2k, preferably one or more compounds each of formulae II-2a and/or II-2h and/or II-2j:

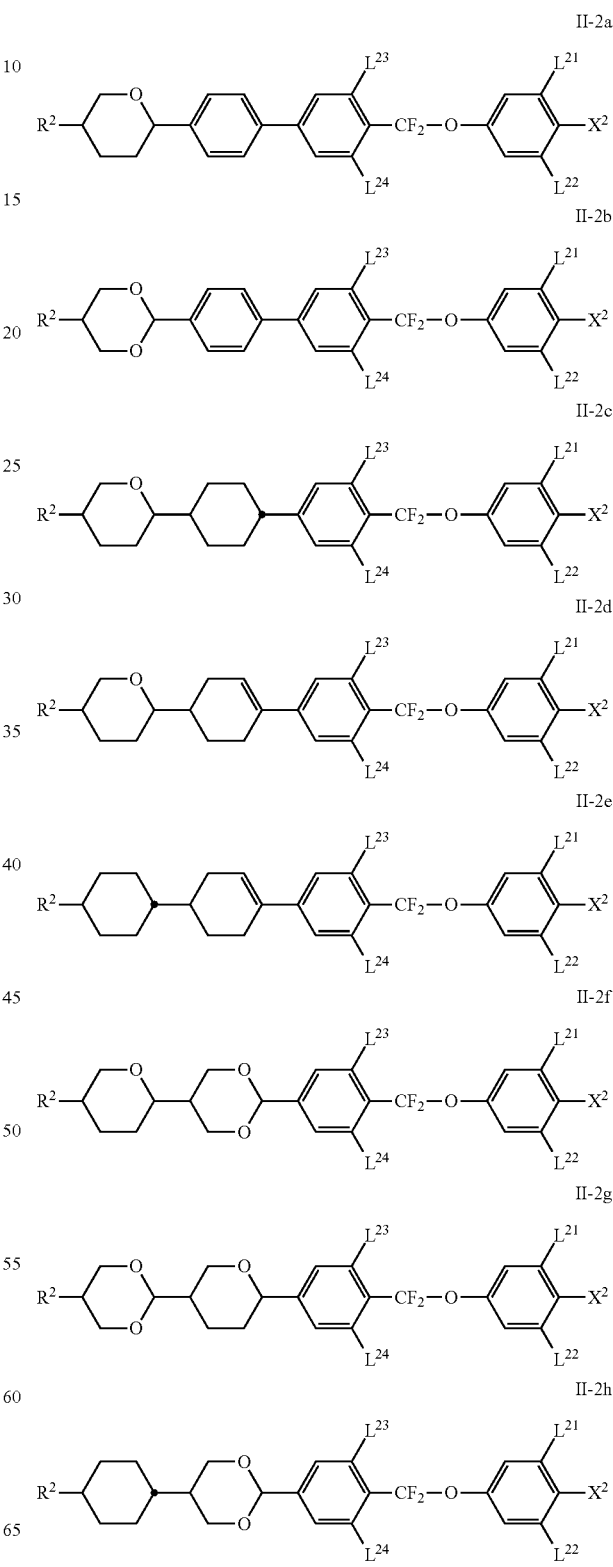

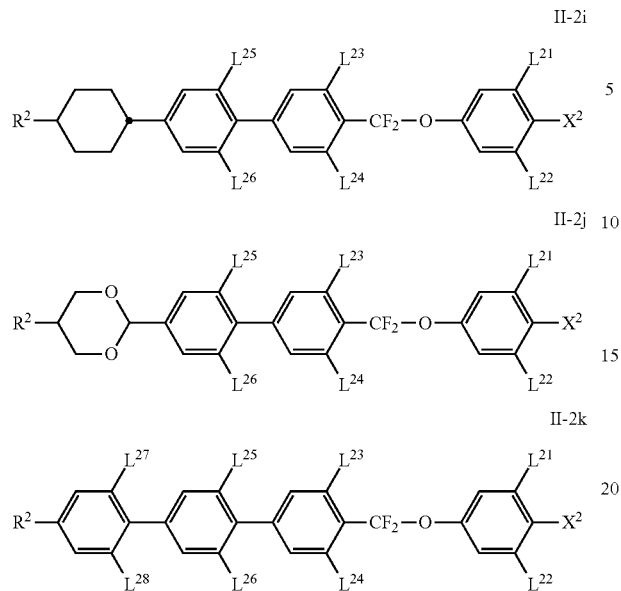

in which the parameters have the respective meanings indicated above, and $L^{25}$ to $L^{28}$, independently of one another, denote H or F, preferably $L^{27}$ and $L^{28}$ both denote H, particularly preferably $L^{26}$ denotes H.

The liquid-crystal medium preferably comprises compounds selected from the group of the compounds of the formulae II-1a to II-1e in which $L^{21}$ and $L^{22}$ both denote F and/or $L^{23}$ and $L^{24}$ both denote F.

In a preferred embodiment, the liquid-crystal medium comprises compounds selected from the group of the compounds of the formulae II-2a to II-2k in which $L^{21}$, $L^{22}$, $L^{23}$ and $L^{24}$ all denote F.

Especially preferred compounds of the formula II-2 are the compounds of the following formulae, particularly preferred of formulae II-2a-1 and/or II-2h-1 and/or II-2k-2:

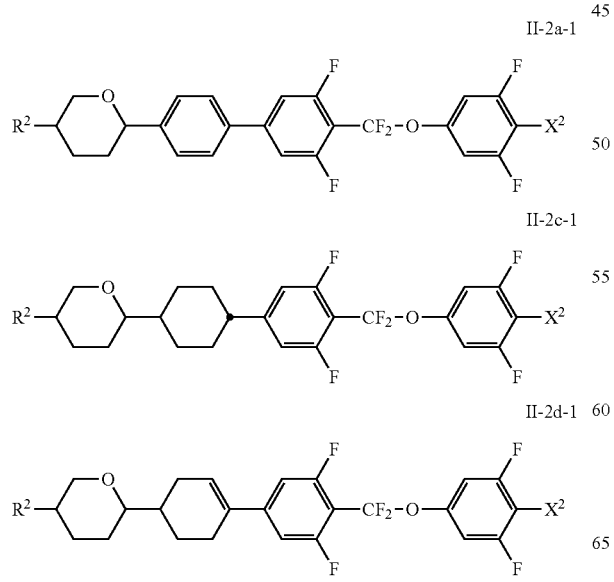

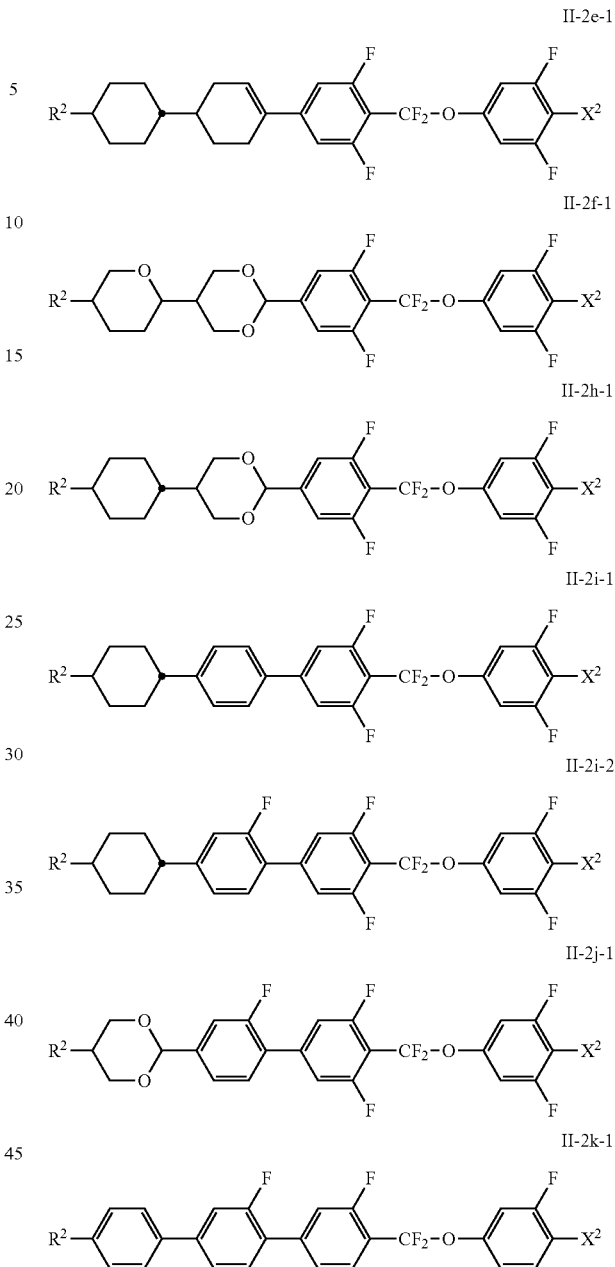

in which $R^2$ and $X^2$ have the meanings indicated above, and $X^2$ preferably denotes F.

The liquid-crystal medium preferably comprises one or more compounds of the formula III-1. The compounds of the formula III-1 are preferably selected from the group of the compounds of the formulae III-1a to III-1j, preferably from formulae III-1c, III-1f, III-1g and III-1j:

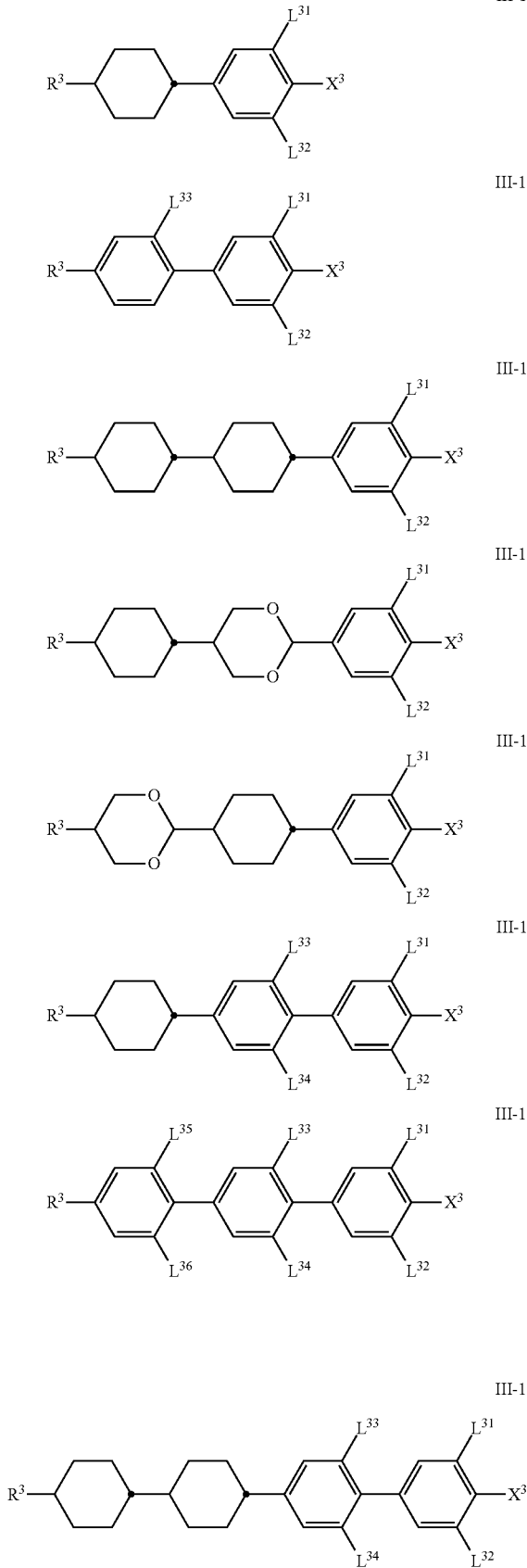

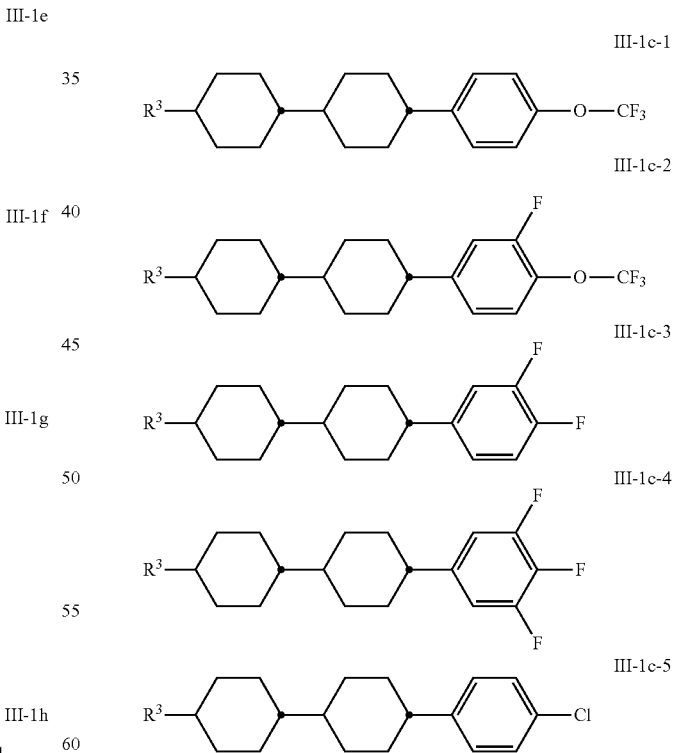

in which the parameters have the meanings given above and preferably in which the parameters have the respective meanings indicated above, the parameters $L^{35}$ and $L^{36}$, independently of one another and of the other parameters, denote H or F, and the parameters $L^{35}$ and $L^{36}$, independently of one another and of the other parameters, denote H or F.

The liquid-crystal medium preferably comprises one or more compounds of the formula III-1c, which are preferably selected from the group of the compounds of the formulae III-1c-1 to III-1c-5, preferably of formulae III-1c-1 and/or III-1c-2, most preferably of formula III-1c-1:

in which $R^3$ has the meaning indicated above.

The liquid-crystal medium preferably comprises one or more compounds of the formula III-1f, which are preferably selected from the group of the compounds of the formulae III-1f-1 to III-1f-6, preferably of formulae III-1f-1 and/or III-1f-2 and/or III-1f-3 and/or III-1f-6, more preferably of formula III-1f-3 and/or III-1f-6, more preferably of formula III-1f-6:

III-1f-1
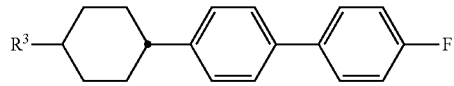

III-1f-2
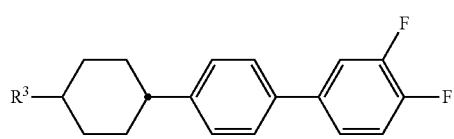

III-1f-3
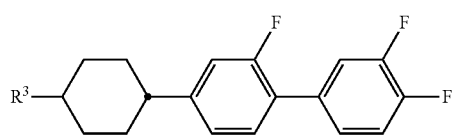

III-1f-4
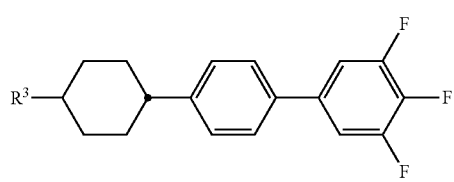

III-1f-5
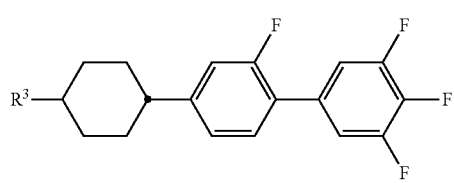

III-1f-6
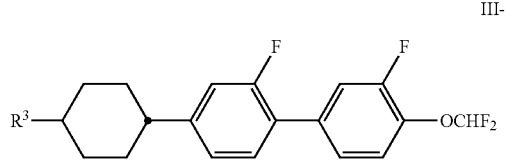

in which $R^3$ has the meaning indicated above.

The liquid-crystal medium preferably comprises one or more compounds of the formula III-1g, which are preferably selected from the group of the compounds of the formulae III-1g-1 to III-1g-5, preferably of formula III-1g-3:

III-1g-1
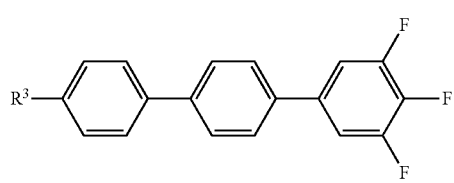

III-1g-2
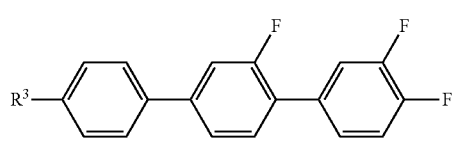

III-1g-3
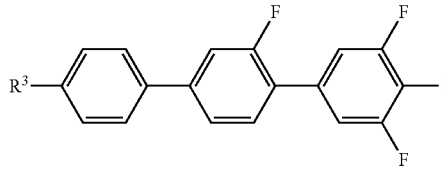

III-1g-4
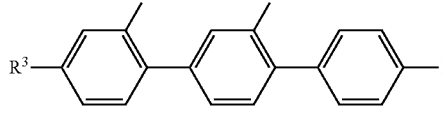

III-1g-5
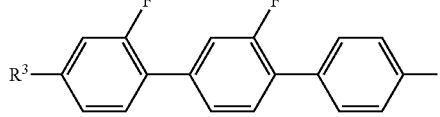

in which $R^3$ has the meaning indicated above.

The liquid-crystal medium preferably comprises one or more compounds of the formula III-1h, which are preferably selected from the group of the compounds of the formulae III-1h-1 to III-1h-3, preferably of the formula III-1h-3:

III-1h-1
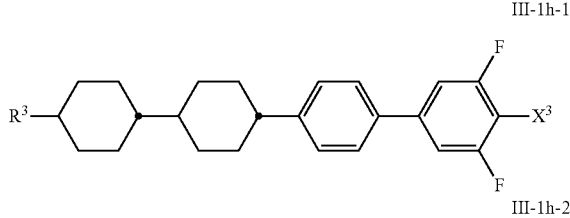

III-1h-2
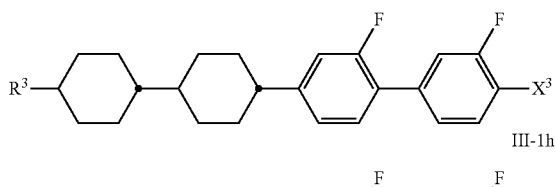

III-1h-3
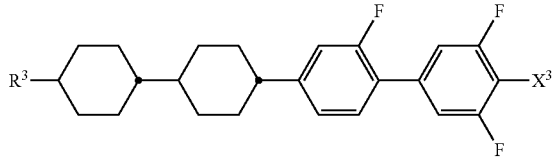

in which the parameters have the meanings given above, and $X^3$ preferably denotes F.

The liquid-crystal medium preferably comprises one or more compounds of the formula III-1i, which are preferably selected from the group of the compounds of the formulae III-1i-1 and III-1i-2, preferably of the formula III-1i-2:

III-1i-1
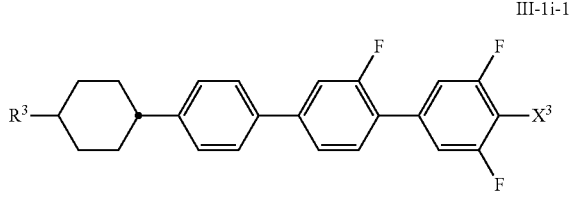

-continued

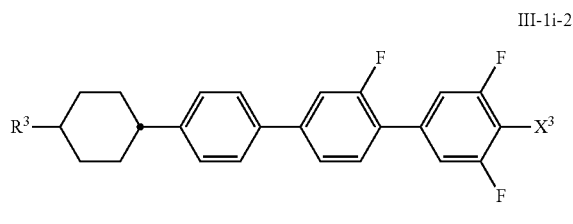

III-1i-2 in which the parameters have the meanings given above, and $X^3$ preferably denotes F.

The liquid-crystal medium preferably comprises one or more compounds of the formula III-1j, which are preferably selected from the group of the compounds of the formulae III-1j-1 and III-1j-2, preferably of the formula III-1j-1:

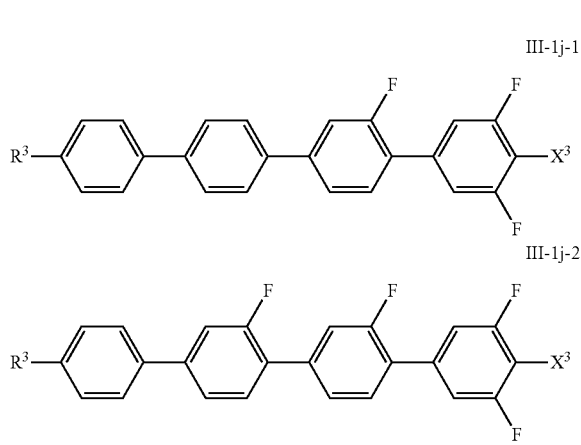

III-1j-1

III-1j-2 in which the parameters have the meanings given above.

The liquid-crystal medium preferably comprises one or more compounds of the formula III-2. The compounds of the formula III-2 are preferably selected from the group of the compounds of the formulae III-2a and III-2b, preferably of formula III-2b:

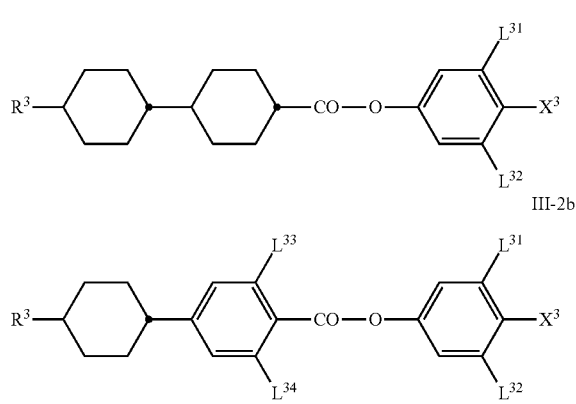

III-2a

III-2b in which the parameters have the respective meanings indicated above, and the parameters $L^{33}$ and $L^{34}$, independently of one another and of the other parameters, denote H or F.

The liquid-crystal medium preferably comprises one or more compounds of the formula III-2a, which are preferably selected from the group of the compounds of the formulae III-2a-1 to III-2a-6:

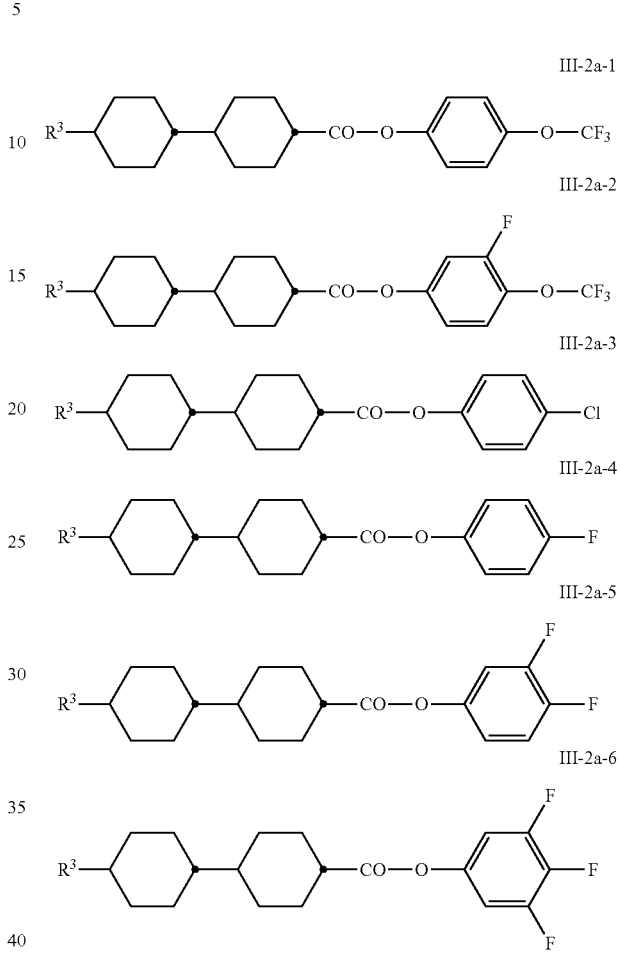

III-2a-1

III-2a-2

III-2a-3

III-2a-4

III-2a-5

III-2a-6 in which $R^3$ has the meaning indicated above.

The liquid-crystal medium preferably comprises one or more compounds of the formula III-2b, which are preferably selected from the group of the compounds of the formulae III-2b-1 to III-2b-4, preferably III-2b-4:

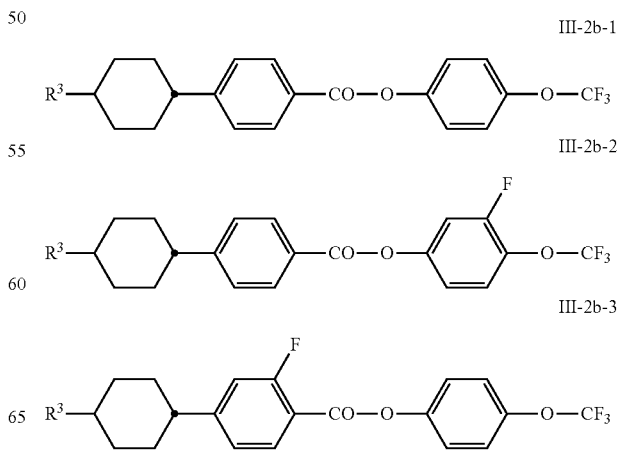

III-2b-1

III-2b-2

III-2b-3

-continued

III-2b-4

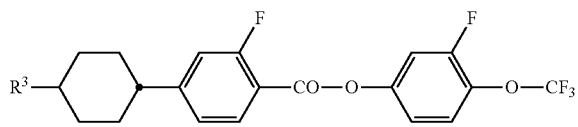

in which R³ has the meaning indicated above.

Alternatively or in addition to the compounds of the formulae III-1 and/or III-2, the media in accordance with the present invention may comprise one or more compounds of the formula III-3

III-3

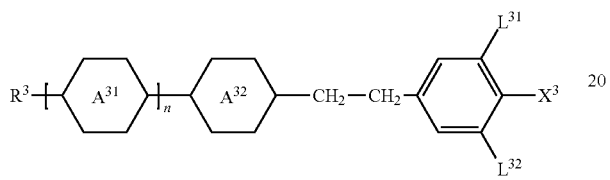

in which the parameters have the respective meanings indicated above under formula III.

These compounds are preferably selected from the group of the formulae III-3a and III-3b:

III-3a
III-3b

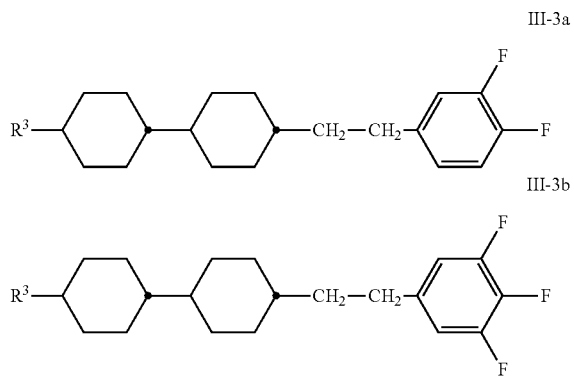

in which R³ has the meaning indicated above.

The liquid-crystalline media in accordance with the present invention preferably comprise one or more dielectrically neutral compounds, preferably having a dielectric anisotropy in the range from −1.5 to 3, preferably selected from the group of the compounds of the formulae VI, VII, VIII and IX.

In the present application, the elements all include their respective isotopes. In particular, one or more H in the compounds may be replaced by D, and this is also particularly preferred in some embodiments. A correspondingly high degree of deuteration of the corresponding compounds enables, for example, detection and recognition of the compounds. This is very helpful in some cases, in particular in the case of the compounds of formula I.

In the present application, alkyl particularly preferably denotes straight-chain alkyl, in particular $CH_3-$, $C_2H_5-$, $n-C_3H_7-$, $n-C_4H_9-$ or $n-C_5H_{11}-$, and alkenyl particularly preferably denotes $CH_2=CH-$, $E-CH_3-CH=CH-$,

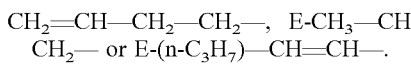

In a preferred embodiment of the present invention, the media according to the invention in each case comprise one or more compounds of formula VI selected from the group of the compounds of the formulae VI-1 and VI-2, preferably one or more compounds each of formulae VI-1 and one or more compounds of formula VI-2,

VI-1

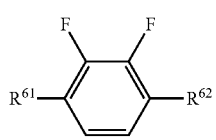

VI-2

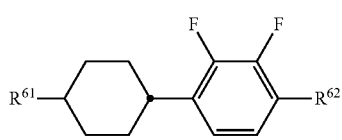

in which the parameters have the respective meanings given above under formula VI, and preferably in formula VI-1

$R^{61}$ and $R^{62}$ independently of each other denote methoxy, ethoxy, propoxy, butoxy (also or pentoxy, preferably ethoxy, butoxy or pentoxy, more preferably ethoxy or butoxy and, most preferably butoxy.

in formula VI-2

$R^{61}$ preferably denotes vinyl, 1-E-propenyl, but-4-en-1-yl, pent-1-en-1-yl or pent-3-en-1-yl and n-propyl or n-pentyl and $R^{62}$ denotes an unsubstituted alkyl radical having 1 to 7 C atoms, preferably having 2 to 5 C atoms, or, preferably, an unsubstituted alkoxy radical having 1 to 6 C atoms, particularly preferably having 2 or 4 C atoms and, most preferably, ethoxy, and In a preferred embodiment of the present invention, the media according to the invention in each case comprise one or more compounds of formula VII selected from the group of the compounds of the formulae VII-1 to VII-3, preferably one or more compounds each of the formulae VII-1 and one or more compounds of formula VII-2,

VII-1

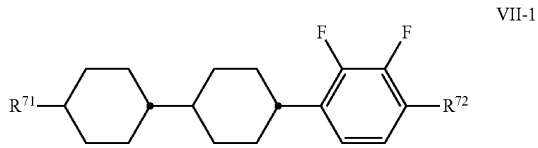

VII-2

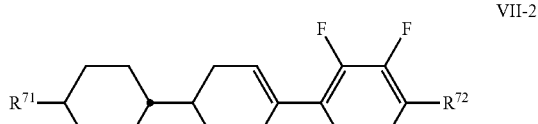

VII-3

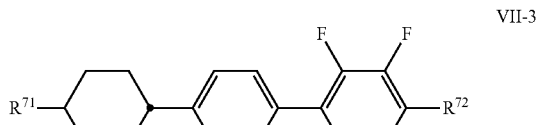

in which the parameters have the respective meanings given above under formula VII, and preferably $R^{71}$ denotes vinyl, 1-E-propenyl, but-4-en-1-yl, pent-1-en-1-yl or pent-3-en-1-yl, n-propyl or n-pentyl and $R^{72}$ denotes an unsubstituted alkyl radical having 1 to 7 C atoms, preferably having 2 to 5 C atoms, or, preferably, an unsubstituted alkoxy radical having 1 to 6 C atoms, particularly preferably having 2 or 4 C atoms and, most preferably, ethoxy.

In a preferred embodiment of the present invention, the media according to the invention in each case comprise one or more compounds of formula VI-1 selected from the group of the following compounds:

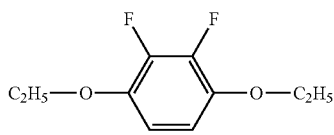

VI-1a

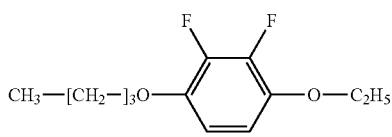

VI-1b

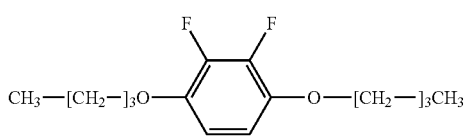

VI-1c

In a preferred embodiment of the present invention, the media according to the invention in each case comprise one or more compounds of formula VI-2 selected from the group of the following compounds:

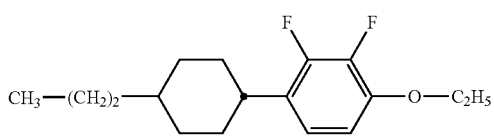

VI-2a

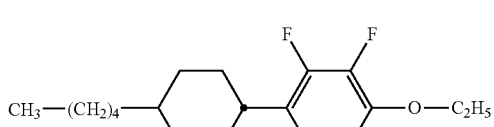

VI-2b

In a preferred embodiment of the present invention, the media according to the invention in each case comprise one or more compounds of formula VII-1 selected from the group of the following compounds:

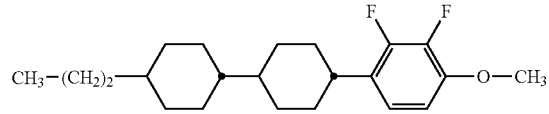

VII-1a

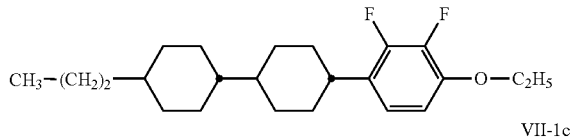

VII-1b

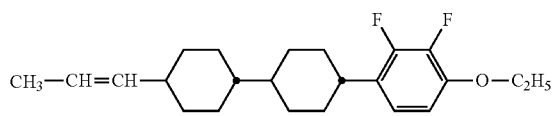

VII-1c

In a preferred embodiment of the present invention, the media according to the invention in each case comprise one or more compounds of formula VII-2 selected from the group of the following compounds:

VII-2a

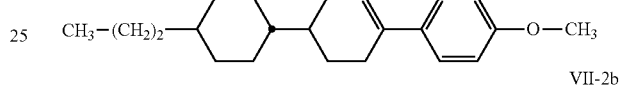

VII-2b

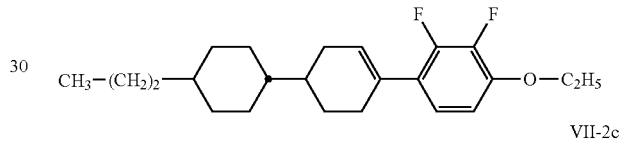

VII-2c

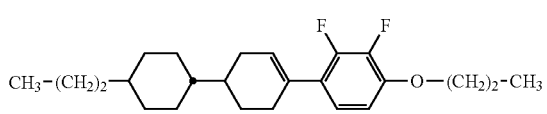

In addition to the compounds of formula I or the preferred sub-formulae thereof, the media in accordance with the present invention preferably comprise one or more, preferably dielectrically neutral, compounds selected from the group of compounds of the formulae VI and VII, preferably in a total concentration in the range from 5% or more to 90% or less, preferably from 10% or more to 80% or less, particularly preferably from 20% or more to 70% or less.

In a preferred embodiment of the present invention, the media according to the invention in each case comprise one or more compounds of formula VIII selected from the group of the compounds of the formulae VIII-1 to VIII-3, preferably one or more compounds each of the formulae VIII-1 and/or one or more compounds of formula VIII-3,

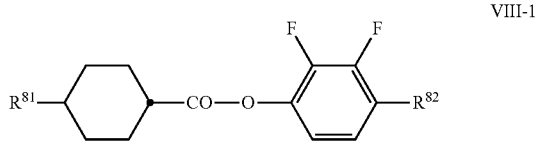

VIII-1

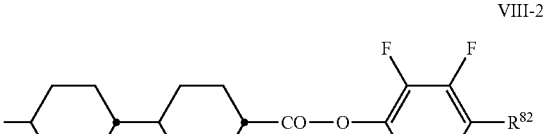

VIII-2

VIII-3

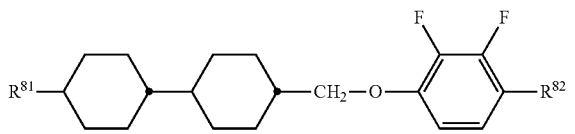

in which the parameters have the respective meanings given above under formula VIII, and preferably
$R^{81}$ denotes vinyl, 1-E-propenyl, but-4-en-1-yl, pent-1-en-1-yl or pent-3-en-1-yl, ethyl, n-propyl or n-pentyl, alkyl, preferably ethyl, n-propyl or n-pentyl and
$R^{82}$ denotes an unsubstituted alkyl radical having 1 to 7 C atoms, preferably having 1 to 5 C atoms or an unsubstituted alkoxy radical having 1 to 6 C atoms.

In formulae VIII-1 and VIII-2 $R^{82}$ denotes preferably alkoxy having 2 or 4 C atoms and, most preferably, ethoxy and in formula VIII-3 it denotes preferably alkyl, preferably methyl, ethyl or n-propyl, most preferably methyl.

In a further preferred embodiment, the medium comprises one or more compounds of formula IV
one or more compounds of formula IV

IV

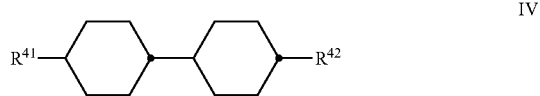

in which
$R^{41}$ denotes an unsubstituted alkyl radical having 1 to 7 C atoms or an unsubstituted alkenyl radical having 2 to 7 C atoms, preferably an n-alkyl radical, particularly preferably having 2, 3, 4 or 5 C atoms, and
$R^{42}$ denotes an unsubstituted alkyl radical having 1 to 7 C atoms, an unsubstituted alkenyl radical having 2 to 7 C atoms, or an unsubstituted alkoxy radical having 1 to 6 C atoms, both preferably having 2 to 5 C atoms, an unsubstituted alkenyl radical having 2 to 7 C atoms, preferably having 2, 3 or 4 C atoms, more preferably a vinyl radical or 1-propenyl radical and in particular a vinyl radical.

In a particularly preferred embodiment, the medium comprises one or more compounds of formula IV selected from the group of the compounds of the formulae IV-1 to IV-4, preferably of formula IV-1,

IV-1

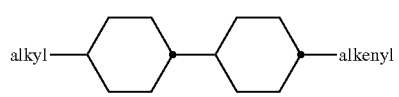

IV-2

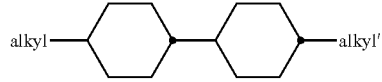

IV-3

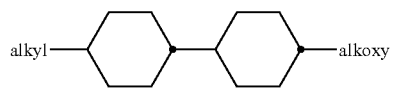

IV-4

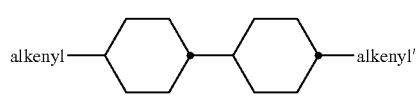

in which
alkyl and alkyl', independently of one another, denote alkyl having 1 to 7 C atoms, preferably having 2 to 5 C atoms,
alkenyl and alkenyl' independently of one another, denote an alkenyl radical having 2 to 5 C atoms, preferably having 2 to 4 C atoms, particularly preferably 2 C atoms,
alkenyl' denotes an alkenyl radical having 2 to 5 C atoms, preferably having 2 to 4 C atoms, particularly preferably having 2 to 3 C atoms, and
alkoxy denotes alkoxy having 1 to 5 C atoms, preferably having 2 to 4 C atoms.

In a particularly preferred embodiment, the media according to the invention comprise one or more compounds of formula IV-1 and/or one or more compounds of formula IV-2.

In a further preferred embodiment, the medium comprises one or more compounds of formula V.

The media according to the invention preferably comprise the following compounds in the total concentrations indicated:
   1-60% by weight of one or more compounds selected from the group of the compounds of formula S and
   0-60% preferably 1-by 60% weight of one or more compounds selected from the group of the compounds of formula I and/or
   5-60% by weight of one or more compounds of formula II, preferably selected from the group of the compounds of the formulae II-1 and II-2 and/or
   5-25% by weight of one or more compounds of formula III, and/or
   5-45% by weight of one or more compounds of formula IV and/or
   5-25% by weight of one or more compounds of formula V, and/or
   5-25% by weight of one or more compounds of formula VI, and/or
   5-20% by weight of one or more compounds of formula VII, and/or
   5-30% by weight of one or more compounds of formula VIII, preferably selected from the group of the compounds of the formulae VIII-1 and VIII-2 and/or
   0-60% by weight of one or more compounds of formula IX,
   where the total content of all compounds of formulae S and I to IX, which are present, in the medium preferably is 95% or more and, more preferably 100%.

The latter condition is preferred for all media according to the present application.

In a further preferred embodiment, the media in accordance with the present invention in addition to the compounds of formula S or the preferred sub-formulae thereof, and/or of formula I or the preferred sub-formulae thereof and to the compounds of formulae VI and/or VII and/or VIII and/or IX, preferably comprise one or more, preferably dielectrically neutral, compounds selected from the group of compounds of formulae IV and V preferably in a total concentration in the range from 5% or more to 90% or less, preferably from 10% or more to 80% or less, particularly preferably from 20% or more to 70% or less.

The medium according to the invention in a particularly preferred embodiment comprises
   one or more compounds of formula II in a total concentration in the range from 5% or more to 50% or less, preferably in the range from 10% or more to 40% or less, and/or one or more compounds of formula VII-1 in a total concentration in the range from 5% or more to 30% or less, and/or one or more compounds of formula VII-2 in a total concentration in the range from 3% or more to 30% or less.

Preferably the concentration of the compounds of formula S in the media according to the invention is in the range from 1% or more to 60% or less, more preferably from 5% or more to 40% or less, most preferably from 8% or more to 35% or less Preferably the concentration of the compounds of formula I, if present, in the media according to the invention is in the range from 1% or more to 60% or less, more preferably from 5% or more to 40% or less, most preferably from 8% or more to 35% or less In a preferred embodiment of the present invention the media comprise one or more compounds of formula S, preferably selected from the group of formulae S-1 and S-2 and one or more compounds of formula I, preferably selected from the group of formulae I-1 to I-4, preferably of formulae I-3 and/or I-4.

In a preferred embodiment of the present invention the concentration of the compounds of formula II in the media is in the range from 3% or more to 60% or less, more preferably from 5% or more to 55% or less, more preferably from 10% or more to 50% or less and, most preferably, from 15% or more to 45% or less.

In a preferred embodiment of the present invention the concentration of the compounds of formula VII in the media is in the range from 2% or more to 50% or less, more preferably from 5% or more to 40% or less, more preferably from 10% or more to 35% or less and, most preferably, from 15% or more to 30% or less.

In a preferred embodiment of the present invention the concentration of the compounds of formula VII-1 in the media is in the range from 1% or more to 40% or less, more preferably either from 2% or more to 35% or less, or, alternatively, from 15% or more to 25% or less.

In a preferred embodiment of the present invention the concentration of the compounds of formula VII-2 in the media, if present, is in the range from 1% or more to 40% or less, more preferably from 5% or more to 35% or less and, most preferably, from 10% or more to 30% or less.

The present invention also relates to electro-optical displays or electro-optical components which contain liquid-crystalline media according to the invention. Preference is given to electro-optical displays which are based on the VA, ECB, IPS or FFS effect, preferably on the VA; IPS or FFS effect, and in particular those which are addressed by means of an active-matrix addressing device.

Accordingly, the present invention likewise relates to the use of a liquid-crystalline medium according to the invention in an electro-optical display or in an electro-optical component, and to a process for the preparation of the liquid-crystalline media according to the invention, characterised in that one or more compounds of formula I are mixed with one or more compounds of formula II, preferably with one or more compounds of the sub-formulae II-1 and/or II-2 and/or with one or more compounds of formula VII, preferably with one or more compounds of the sub-formulae VII-1 and/or VII-2, particularly preferably one or more compounds from two or more, preferably from three or more, different formulae thereof and very particularly preferably from all four of these formulae II-1, II-2, VII-1 and VII-2 and one or more further compounds, preferably selected from the group of the compounds of the formulae IV and V, more preferably with one or more compounds both of formula IV and of formula V.

In a further preferred embodiment, the medium comprises one or more compounds of formula IV, selected from the group of the compounds of the formulae IV-2 and IV-3,

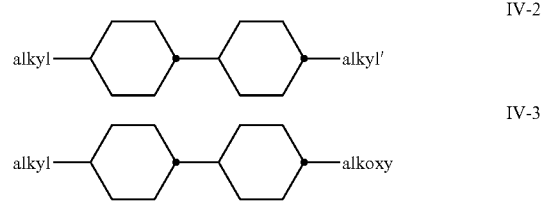

in which
alkyl and alkyl', independently of one another, denote alkyl having 1 to 7 C atoms, preferably having 2 to 5 C atoms,
alkoxy denotes alkoxy having 1 to 5 C atoms, preferably having 2 to 4 C atoms.

In a further preferred embodiment, the medium comprises one or more compounds of formula V selected from the group of the compounds of the formulae V-1 and V-2, preferably of formulae V-1,

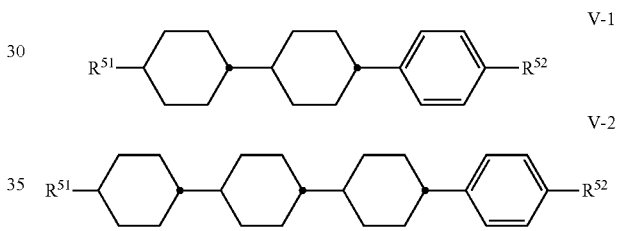

in which the parameters have the meanings given above under formula V, and preferably
$R^{51}$ denotes alkyl having 1 to 7 C atoms or alkenyl having 2 to 7 C atoms, and
$R^{52}$ denotes alkyl having 1 to 7 C atoms, alkenyl having 2 to 7 C atoms or alkoxy having 1 to 6 C atoms, preferably alkyl or alkenyl, particularly preferably alkyl.

In a further preferred embodiment, the medium comprises one or more compounds of formula V-1 selected from the group of the compounds of the formulae V-1a and V-1b,

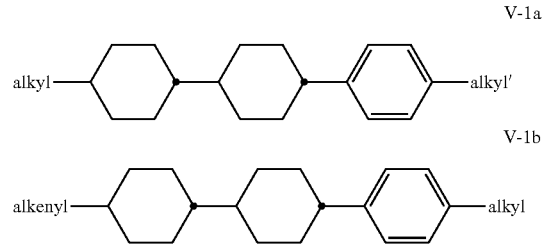

in which
alkyl and alkyl', independently of one another, denote alkyl having 1 to 7 C atoms, preferably having 2 to 5 C atoms, and
alkenyl denotes alkenyl having 2 to 7 C atoms, preferably having 2 to 5 C atoms.

In addition, the present invention relates to a method for the reduction of the wavelength dispersion of the birefringence of a liquid-crystalline medium which comprises one or more compounds of formula II, optionally one or more compounds selected from the group of the compounds of the formulae VII-1 and VII-2 and/or one or more compounds of formula IV and/or one or more compounds of formula V, characterised in that one or more compounds of formula I are used in the medium.

Besides compounds of the formulae I to V, other constituents may also be present, for example in an amount of up to 45%, but preferably up to 35%, in particular up to 10%, of the mixture as a whole.

The media according to the invention may optionally also comprise a dielectrically positive component, whose total concentration is preferably 20% or less, more preferably 10% or less, based on the entire medium.

In a preferred embodiment, the liquid-crystal media according to the invention comprise in total, based on the mixture as a whole,
1% or more to 50% or less, preferably 2% or more to 35% or less, particularly preferably 3% or more to 25% or less, of the compound of formula S,
1% or more to 20% or less, preferably 2% or more to 15% or less, particularly preferably 3% or more to 12% or less, of the compound of formula I.
20% or more to 50% or less, preferably 25% or more to 45% or less, particularly preferably 30% or more to 40% or less, of compounds of formulae II and/or III, and
0% or more to 35% or less, preferably 2% or more to 30% or less, particularly preferably 3% or more to 25% or less, of compounds of formulae IV and/or V, and
5% or more to 50% or less 10% or more to 45% or less, preferably 15% or more to 40% or less of compounds of the formulae VI and/or VII and/or VIII and/or IX.

The liquid-crystal media in accordance with the present invention may comprise one or more chiral compounds.

Particularly preferred embodiments of the present invention meet one or more of the following conditions, where the acronyms (abbreviations) are explained in Tables A to C and illustrated by examples in Table D.

Preferably the media according to the present invention fulfil one or more of the following conditions:
i. The liquid-crystalline medium has a birefringence of 0.060 or more, particularly preferably 0.070 or more.
ii. The liquid-crystalline medium has a birefringence of 0.200 or less, particularly preferably 0.180 or less.
iii. The liquid-crystalline medium has a birefringence in the range from 0.090 or more to 0.120 or less.
iv. The liquid-crystalline medium comprises one or more particularly preferred compounds of formula I-4.
v. The total concentration of the compounds of formula IV in the mixture as a whole is 25% or more, preferably 30% or more, and is preferably in the range from 25% or more to 49% or less, particularly preferably in the range from 29% or more to 47% or less, and very particularly preferably in the range from 37% or more to 44% or less.
vi. The liquid-crystalline medium comprises one or more compounds of formula IV selected from the group of the compounds of the following formulae: CC-n-V and/or CC-n-Vm and/or CC-V-V and/or CC-V-Vn and/or CC-nV-Vn, particularly preferably CC-3-V, preferably in a concentration of up to 60% or less, particularly preferably up to 50% or less, and optionally additionally CC-3-V1, preferably in a concentration of up to 15% or less, and/or CC-4-V, preferably in a concentration of up to 24% or less, particularly preferably up to 30% or less.
vii. The media comprise the compound of formula CC-n-V, preferably CC-3-V, preferably in a concentration of 1% or more to 60% or less, more preferably in a concentration of 3% or more to 35% or less.

The total concentration of the compounds of formula CC-3-V in the mixture as a whole preferably either is 15% or less, preferably 10% or less or 20% or more, preferably 25% or more.

viii. The total concentration of the compounds of formula Y-nO-Om in the mixture as a whole is 2% or more to 30% or less, preferably 5% or more to 15% or less.
ix. The total concentration of the compounds of formula CY-n-Om in the mixture as a whole is 5% or more to 60% or less, preferably 15% or more to 45% or less.
x. The total concentration of the compounds of formula CCY-n-Om and/or CCY-n-m, preferably of CCY-n-Om, in the mixture as a whole is 5% or more to 40% or less, preferably 1% or more to 25% or less.
xi. The total concentration of the compounds of formula CLY-n-Om in the mixture as a whole is 5% or more to 40% or less, preferably 10% or more to 30% or less.
xii. The liquid-crystalline medium comprises one or more compounds of formula IV, preferably of the formulae IV-1 and/or IV-2, preferably in a total concentration of 1% or more, in particular 2% or more, and very particularly preferably 3% or more to 50% or less, preferably 35% or less.
xiii. The liquid-crystalline medium comprises one or more compounds of formula V, preferably of the formulae V-1 and/or V-2, preferably in a total concentration of 1% or more, in particular 2% or more, and very particularly preferably 15% or more to 35% or less, preferably to 30% or less.
xiv. The total concentration of the compounds of formula CCP-V-n, preferably CCP-V-1, in the mixture as a whole preferably is 5% or more to 30% or less, preferably 15% or more to 25% or less.
xv. The total concentration of the compounds of formula CCP-V2-n, preferably CCP-V2-1, in the mixture as a whole preferably is 1% or more to 15% or less, preferably 2% or more to 10% or less.

The invention furthermore relates to an electro-optical display having active-matrix addressing based on the VA, ECB, IPS, FFS or UB-FFS effect, characterised in that it contains, as dielectric, a liquid-crystalline medium in accordance with the present invention.

The liquid-crystal mixture preferably has a nematic phase range having a width of at least 70 degrees.

The rotational viscosity $\gamma_1$ is preferably 200 mPa·s or less, preferably 150·s or less and, in particular, 120 mPa·s or less.

The mixtures according to the invention are suitable for all IPS and FFS-TFT applications using dielectrically positive liquid crystalline media, such as, e.g. SG-FFS (Super Grip FFS).

The liquid-crystalline media according to the invention preferably virtually completely consist of 4 to 18, in particular 5 to 15, and particularly preferably 12 or less, compounds. These are preferably selected from the group of the compounds of the formulae S, I, II III, IV, V, VI, VII, VIII and IX.

The liquid-crystalline media according to the invention may optionally also comprise more than 18 compounds. In this case, they preferably comprise 18 to 25 compounds.

In a preferred embodiment, the liquid-crystal media according to the invention predominantly consist of, preferably essentially consist of and, most preferably, virtually completely consist of compounds which do not comprise a cyano group.

In a preferred embodiment, the liquid-crystal media according to the invention comprise compounds selected from the group of the compounds of the formulae S, I, II and III, IV and V and VI to IX, preferably selected from the group of the compounds of the formulae S1, S-2, S0, preferably selected from S0-1 and S0-2, I, preferably selected from I-1, I-2, I-3 and I-4, II, preferably selected from II-1 and II-2, III, preferably selected from III-1 and III-2, IV, V, VII, preferably selected from VII-1 and VII-2, VIII and IX; they preferably consist predominantly, particularly preferably essentially and very particularly preferably virtually completely of the compounds of the said formulae.

The liquid-crystal media according to the invention preferably have a nematic phase from in each case at least −10° C. or less to 70° C. or more, particularly preferably from −20° C. or less to 80° C. or more, very particularly preferably from −30° C. or less to 85° C. or more and most preferably from −40° C. or less to 90° C. or more.

The expression "have a nematic phase" here means on the one hand that no smectic phase and no crystallisation are observed at low temperatures at the corresponding temperature and on the other hand that no clearing occurs on heating out of the nematic phase. The investigation at low temperatures is carried out in a flow viscometer at the corresponding temperature and checked by storage in test cells having a cell thickness corresponding to the electro-optical application for at least 100 hours. If the storage stability at a temperature of −20° C. in a corresponding test cell is 1000 h or more, the medium is regarded as stable at this temperature. At temperatures of −30° C. and −40° C., the corresponding times are 500 h and 250 h respectively. At high temperatures, the clearing point is measured in capillaries by conventional methods.

In a preferred embodiment, the liquid-crystal media according to the invention are characterised by optical anisotropy values in the moderate to low range. The birefringence values are preferably in the range from 0.075 or more to 0.130 or less, particularly preferably in the range from 0.085 or more to 0.120 or less and very particularly preferably in the range from 0.090 or more to 0.115 or less.

In this embodiment, the liquid-crystal media according to the invention have a positive dielectric anisotropy and relatively high absolute values of the dielectric anisotropy $\Delta\varepsilon$, which preferably is in the range from 0.5 or more, preferably of 1.0 or more, more preferably of 2.0 or more to 20 or less, more preferably to 15 or less, more preferably from 3.0 or more to 10 or less, particularly preferably from 4.0 or more to 9.0 or less and very particularly preferably from 4.5 or more to 8.0 or less.

The liquid-crystal media according to the invention preferably have relatively low values for the threshold voltage ($V_0$) in the range from 1.0 V or more to 2.7 V or less, preferably from 1.2 V or more to 2.5 V or less, particularly preferably from 1.3 V or more to 2.2 V or less.

In a further preferred embodiment, the liquid-crystal media according to the invention preferably have relatively high values of the average dielectric constant ($\varepsilon_{av.} \equiv (\varepsilon_{\parallel} + 2\varepsilon_{\perp})/3$) which are preferably in the range from 4.0 or more to 25.0 or less, preferably from 5.0 or more to 20.0 or less, still more preferably from 6.0 or more to 19.0 or less, particularly preferably from 10.0 or more to 18.0 or less and very particularly preferably from 9.0 or more to 16.5 or less.

In addition, the liquid-crystal media according to the invention have high values for the VHR in liquid-crystal cells.

In freshly filled cells at 20° C. in the cells, these values of the VHR are greater than or equal to 95%, preferably greater than or equal to 97%, particularly preferably greater than or equal to 98% and very particularly preferably greater than or equal to 99%, and after 5 minutes in the oven at 100° C. in the cells, these are greater than or equal to 90%, preferably greater than or equal to 93%, particularly preferably greater than or equal to 96% and very particularly preferably greater than or equal to 98%.

In general, liquid-crystal media having a low addressing voltage or threshold voltage here have a lower VHR than those having a higher addressing voltage or threshold voltage, and vice versa.

These preferred values for the individual physical properties are preferably also in each case maintained by the media according to the invention in combination with one another.

In the present application, the term "compounds", also written as "compound(s)", means both one and also a plurality of compounds, unless explicitly indicated otherwise.

In a preferred embodiment, the liquid-crystalline media according to the invention comprise:
one or more compounds of formula S and
one or more compounds of formula I and/or
one or more compounds of formula II, preferably of the formulae PUQU-n-F, CDUQU-n-F, APUQU-n-F and PGUQU-n-F, and/or
one or more compounds of formula III, preferably of the formulae CCP-n-OT, CLP-n-T, CGG-n-F, and CGG-n-OD, and/or
one or more compounds of formula IV, preferably of the formulae CC-n-V, CC-n-Vm, CC-n-m, and CC-V-V and/or
one or more compounds of formula V, preferably of the formulae CCP-n-m, CCP-V-n, CCP-V2-n, CLP-V-n, CCVC-n-V, and CGP-n-m and/or
one or more compounds of formula VI, preferably of the formulae Y-n-Om, Y-nO-Om and/or CY-n-Om, selected from the group of the compounds of the formulae Y-3-O1, Y-4O-O4, CY-3-O2, CY-3-O4, CY-5-O2 and CY-5-O4, and/or
optionally, preferably obligatorily, one or more compounds of formula VII-1, preferably selected from the group of the compounds of the formulae CCY-n-m and CCY-n-Om, preferably of formula CCY-n-Om, preferably selected from the group of the compounds of the formulae CCY-3-O2, CCY-2-O2, CCY-3-O1, CCY-3-O3, CCY-4-O2, CCY-3-O2 and CCY-5-O2, and/or
optionally, preferably obligatorily, one or more compounds of formula VII-2, preferably of formula CLY-n-Om, preferably selected from the group of the compounds of the formulae CLY-2-O4, CLY-3-O2, CLY-3-O3, and/or
one or more compounds of formula VIII, preferably of the formulae CZY-n-On and CCOY-n-m and/or
one or more compounds of formula IX, preferably of the formula PYP-n-m and/or
optionally, preferably obligatorily, one or more compounds of formula
IV, preferably selected from the group of the compounds of the formulae CC-n-V, CC-n-Vm and CC-nV-Vm, preferably CC-3-V, CC-3-V1, CC-4-V, CC-S-V and CC-V-V, particularly preferably selected from the group of the compounds CC-3-V, CC-3-V1, CC-4-V and CC-V-V, very particularly preferably the compound CC-3-V, and optionally additionally the compound(s) CC-4-V and/or CC-3-V1 and/or CC-V-V, and/or
optionally, preferably obligatorily, one or more compounds of formula V, preferably of the formulae CCP-V-1 and/or CCP-V2-1.

In a specific preferred embodiment of the present invention, the media according to the invention comprise one or more compounds of formula IX, The compounds of formula IX, are also highly suitable as stabilisers in liquid-crystal mixtures, especially in case p=q=1 and ring $A^9$=1,4-phenylene. In particular, they stabilise the VHR of the mixtures against UV exposure.

In a preferred embodiment the media according to the invention comprise one or more compounds of formula IX selected from one or more formulae of the group of the compounds of the formulae IX-1 to IX-4, very particularly preferably of the formulae IX-1 to IX-3,

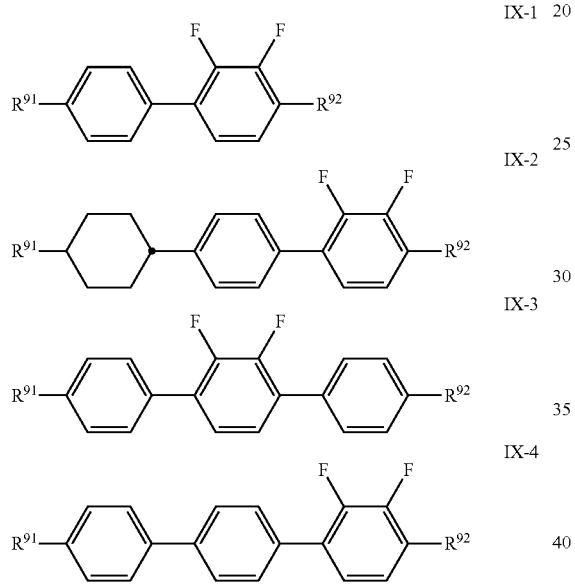

in which the parameters have the meanings given under formula IX.

In a further preferred embodiment, the medium comprises one or more compounds of formula IX-3, preferably of formula IX-3-a,

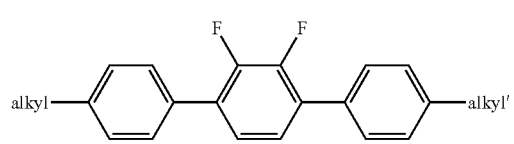

in which
alkyl and alkyl', independently of one another, denote alkyl having 1 to 7 C atoms, preferably having 2 to 5 C atoms.

In case the compounds of formula IX are used in the liquid crystalline media according to the present application, they are preferably present in a concentration of 20% or less, more preferably of 10% or less and, most preferably, of 5% or less and for the individual i.e. (homologous) compounds preferably in a concentration of 10% or less and, more preferably, of 5% or less.

For the present invention, the following definitions apply in connection with the specification of the constituents of the compositions, unless indicated otherwise in individual cases:

"comprise": the concentration of the constituents in question in the composition is preferably 5% or more, particularly preferably 10% or more, very particularly preferably 20% or more, "predominantly consist of": the concentration of the constituents in question in the composition is preferably 50% or more, particularly preferably 55% or more and very particularly preferably 60% or more, "essentially consist of": the concentration of the constituents in question in the composition is preferably 80% or more, particularly preferably 90% or more and very particularly preferably 95% or more, and "virtually completely consist of": the concentration of the constituents in question in the composition is preferably 98% or more, particularly preferably 99% or more and very particularly preferably 100.0%.

This applies both to the media as compositions with their constituents, which can be components and compounds, and also to the components with their constituents, the compounds. Only in relation to the concentration of an individual compound relative to the medium as a whole does the term comprise mean: the concentration of the compound in question is preferably 1% or more, particularly preferably 2% or more, very particularly preferably 4% or more.

For the present invention, "≤" means less than or equal to, preferably less than, and "≥" means greater than or equal to, preferably greater than.

For the present invention,

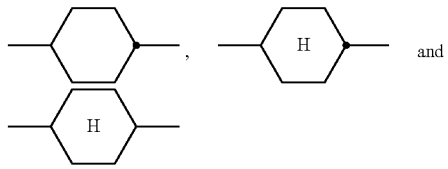

denote trans-1,4-cyclohexylene,

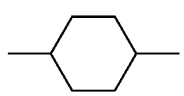

denotes 1,4-cyclohexylene, preferably trans-1,4-cyclohexylene, and

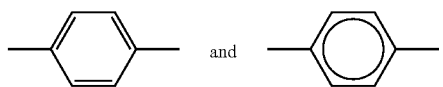

denote 1,4-phenylene.

For the present invention, the expression "dielectrically positive compounds" means compounds having a Δε of >1.5, the expression "dielectrically neutral compounds" generally means those where −1.5≤Δε≤1.5 and the expression "dielectrically negative compounds" means those where Δε<−1.5. The dielectric anisotropy of the compounds is determined here by dissolving 10% of the compounds in a liquid-crystalline host and determining the capacitance of the resultant mixture in each case in at least one test cell having a cell thickness of 20 µm with homeotropic and with homogeneous surface alignment at a temperature of 20° C. and at a frequency of 1 kHz. The measurement voltage is typically 1.0 V, but is always lower than the capacitive threshold of the respective liquid-crystal mixture investigated.

The host mixture used for dielectrically positive and dielectrically neutral compounds is ZLI-4792 and that used for dielectrically negative compounds is ZLI-2857, both from Merck KGaA, Germany. The values for the respective compounds to be investigated are obtained from the change in the dielectric constant of the host mixture after addition of the compound to be investigated and extrapolation to 100% of the compound employed. The compound to be investigated is dissolved in the host mixture in an amount of 10%. If the solubility of the substance is too low for this purpose, the concentration is halved in steps until the investigation can be carried out at the desired temperature.

The liquid-crystal media according to the invention may, if necessary, also comprise further additives, such as, for example, stabilisers and/or pleochroitic, e.g. dichroitic, dyes and/or chiral dopants in the usual amounts. The amount of these additives employed is preferably in total 0% or more to 10% or less, based on the amount of the entire mixture, particularly preferably 0.1% or more to 6% or less. The concentration of the individual compounds employed is preferably 0.1% or more to 3% or less. The concentration of these and similar additives is generally not taken into account when specifying the concentrations and concentration ranges of the liquid-crystal compounds in the liquid-crystal media.

In a preferred embodiment, the liquid-crystal media according to the invention comprise a polymer precursor which comprises one or more reactive compounds, preferably reactive mesogens, and, if necessary, also further additives, such as, for example, polymerisation initiators and/or polymerisation moderators, in the usual amounts. The amount of these additives employed is in total 0% or more to 10% or less, based on the amount of the entire mixture, preferably 0.1% or more to 2% or less. The concentration of these and similar additives is not taken into account when specifying the concentrations and concentration ranges of the liquid-crystal compounds in the liquid-crystal media.

The compositions consist of a plurality of compounds, preferably 3 or more to 30 or fewer, particularly preferably 6 or more to 20 or fewer and very particularly preferably 10 or more to 16 or fewer compounds, which are mixed in a conventional manner. In general, the desired amount of the components used in lesser amount is dissolved in the components making up the principal constituent of the mixture. This is advantageously carried out at elevated temperature. If the selected temperature is above the clearing point of the principal constituent, completion of the dissolution operation is particularly easy to observe. However, it is also possible to prepare the liquid-crystal mixtures in other conventional ways, for example using pre-mixes or from a so-called "multi-bottle system".

The mixtures according to the invention exhibit very broad nematic phase ranges having clearing points of 65° C. or more, very favourable values for the capacitive threshold, relatively high values for the voltage holding ratio (VHR) and at the same time very good low-temperature stabilities at –30° C. and –40° C. Furthermore, the mixtures according to the invention are distinguished by low rotational viscosities $\gamma_1$.

It goes without saying to the person skilled in the art that the media according to the invention for use in VA, IPS, FFS or PALC displays may also comprise compounds in which, for example, H, N, O, Cl, F have been replaced by the corresponding isotopes.

The structure of the liquid-crystal displays according to the invention corresponds to the usual geometry, as described, for example, in EP-A 0 240 379.

The liquid-crystal phases according to the invention can be modified by means of suitable additives in such a way that they can be employed in any type of, for example, IPS and FFS LCD display that has been disclosed to date.

Table E below indicates possible dopants which can be added to the mixtures according to the invention. If the mixtures comprise one or more dopants, it is (they are) employed in amounts of 0.01% to 4%, preferably 0.1% to 1.0%.

Stabilisers which can be added, for example, to the mixtures according to the invention, preferably in amounts of 0.01% to 6%, in particular 0.1% to 3%, are shown below in Table F.

For the purposes of the present invention, all concentrations are, unless explicitly noted otherwise, indicated in percent by weight and relate to the corresponding mixture as a whole or to the respective mixture component, again as a whole, unless explicitly indicated otherwise. In this context the term "the mixture" describes the liquid crystalline medium.

All temperature values indicated in the present application, such as, for example, the melting point T(C,N), the smectic (S) to nematic (N) phase transition T(S,N) and the clearing point T(N,I), are indicated in degrees Celsius (° C.) and all temperature differences are correspondingly indicated in differential degrees (° or degrees), unless explicitly indicated otherwise.

For the present invention, the term "threshold voltage" relates to the capacitive threshold ($V_0$), also known as the Freedericks threshold, unless explicitly indicated otherwise.

All physical properties are and have been determined in accordance with "Merck Liquid Crystals, Physical Properties of Liquid Crystals", status November 1997, Merck KGaA, Germany, and apply for a temperature of 20° C., and $\Delta n$ is determined at 436 nm, 589 nm and at 633 nm, and $\Delta\varepsilon$ at 1 kHz, unless explicitly indicated otherwise in each case.

The electro-optical properties, for example the threshold voltage ($V_0$) (capacitive measurement), are, as is the switching behaviour, determined in test cells produced at Merck Japan. The measurement cells have soda-lime glass substrates and are constructed in an ECB or VA configuration with polyimide alignment layers (SE-1211 with diluent **26 (mixing ratio 1:1), both from Nissan Chemicals, Japan), which have been rubbed perpendicularly to one another and effect homeotropic alignment of the liquid crystals. The surface area of the transparent, virtually square ITO electrodes is 1 cm$^2$.

Unless indicated otherwise, a chiral dopant is not added to the liquid-crystal mixtures used, but the latter are also particularly suitable for applications in which doping of this type is necessary.

The rotational viscosity is determined using the rotating permanent magnet method and the flow viscosity in a modified Ubbelohde viscometer. For liquid-crystal mixtures ZLI-2293, ZLI-4792 and MLC-6608, all products from Merck KGaA, Darmstadt, Germany, the rotational viscosity values determined at 20° C. are 161 mPa·s, 133 mPa·s and 186 mPa·s respectively, and the flow viscosity values (v) are 21 mm$^2$·s$^{-1}$, 14 mm$^2$·s$^{-1}$ and 27 mm$^2$·s$^{-1}$, respectively.

The dispersion of the refractive index of the materials may for practical purposes be conveniently characterized in the following way, which is used throughout this application unless explicitly stated otherwise. The values of the birefringence are determined at a temperature of 20° C. at several fixed wavelengths using a modified Abbé refractometer with homeotropically aligning surfaces on the sides of the prisms in contact with the material. The birefringence values are determined at the specific wavelength values of 436 nm (respective selected spectral line of a low pressure mercury lamp), 589 nm (sodium "D" line) and 633 nm (wavelength of a HE-Ne laser (used in combination with an attenuator/diffusor in order to prevent damage to the eyes of the observers. In the following table Δn is given at 589 nm and Δ(Δn) is given as Δ(Δn)=Δn(436 nm)−Δn(633 nm).

The following symbols are used, unless explicitly indicated otherwise:

$V_0$ threshold voltage, capacitive [V] at 20° C.,
$n_e$ extraordinary refractive index measured at 20° C. and 589 nm,
$n_o$ ordinary refractive index measured at 20° C. and 589 nm,
Δn optical anisotropy measured at 20° C. and 589 nm,
λ wavelength λ [nm],
Δn(λ) optical anisotropy measured at 20° C. and wavelength λ,
Δ(Δn) change in optical anisotropy defined as:

Δn(20° C., 436 nm)−Δn(20° C., 633 nm),

Δ(Δn*) "relative change in optical anisotropy" defined as:

Δ(Δn)/Δn(20° C., 589 nm), $\varepsilon_\perp$ dielectric susceptibility perpendicular to the director at 20° C. and 1 kHz,
$\varepsilon_\parallel$ dielectric susceptibility parallel to the director at 20° C. and 1 kHz,
Δε dielectric anisotropy at 20° C. and 1 kHz,
T(N,I) or cl.p. clearing point [° C.],
ν flow viscosity measured at 20° C. [mm$^2$·s$^{-1}$],
$\gamma_1$ rotational viscosity measured at 20° C. [mPa·s],
$k_{11}$ elastic constant, "splay" deformation at 20° C. [pN],
$k_{22}$ elastic constant, "twist" deformation at 20° C. [pN],
$k_{33}$ elastic constant, "bend" deformation at 20° C. [pN],
LTS low-temperature stability of the phase, determined in test cells,
VHR voltage holding ratio,
GVHR decrease in the voltage holding ratio, and
$S_{rel}$ relative stability of the VHR, The following examples explain the present invention without limiting it. However, they show the person skilled in the art preferred mixture concepts with compounds preferably to be employed and the respective concentrations thereof and combinations thereof with one another. In addition, the examples illustrate the properties and property combinations that are accessible.

For the present invention and in the following examples, the structures of the liquid-crystal compounds are indicated by means of acronyms, with the transformation into chemical formulae taking place in accordance with Tables A to C below. All radicals $C_nH_{2n+1}$, $C_mH_{2m+1}$ and $C_lH_{2l+1}$ or $C_nH_{2n}$, $C_mH_{2m}$ and $C_lH_{2l}$ are straight-chain alkyl radicals or alkylene radicals, in each case having n, m and l C atoms respectively. Preferably n, m and l are independently of each other 1, 2, 3, 4, 5, 6, or 7. Table A shows the codes for the ring elements of the nuclei of the compound, Table B lists the bridging units, and Table C lists the meanings of the symbols for the left- and right-hand end groups of the molecules. The acronyms are composed of the codes for the ring elements with optional linking groups, followed by a first hyphen and the codes for the left-hand end group, and a second hyphen and the codes for the right-hand end group. Table D shows illustrative structures of compounds together with their respective abbreviations.

TABLE A

Ring elements

C — cyclohexane

D — 1,3-dioxane

DI — 1,3-dioxane (isomer)

A — tetrahydropyran

AI — tetrahydropyran (isomer)

P — phenylene

G — 2-fluorophenylene

GI — 3-fluorophenylene

TABLE A-continued
| | | | |
|---|---|---|---|
| U | 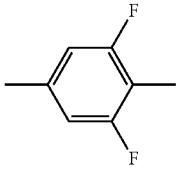 | UI | 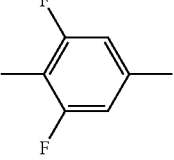 |
| Y | 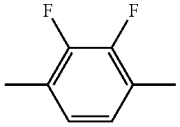 | | |
| P(F, Cl)Y | 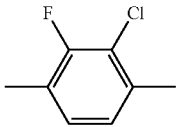 | P(Cl, F)Y | 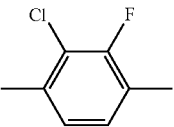 |
| np | 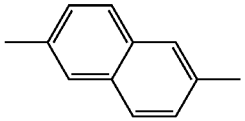 | | |
| n3f | 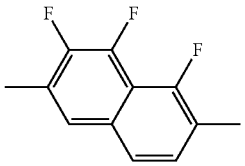 | nN3fI | 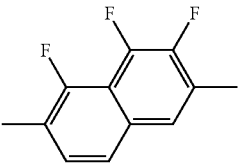 |
| th | 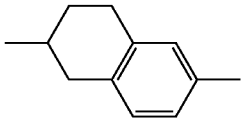 | thI | 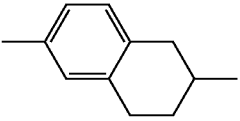 |
| tH2f | 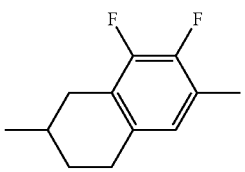 | tH2fI | 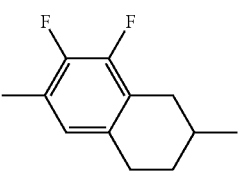 |
| o2f | 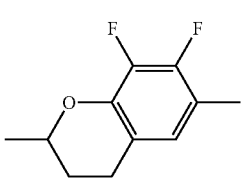 | o2fI | 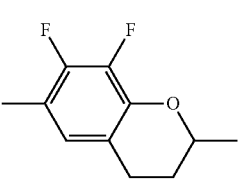 |
| dh | 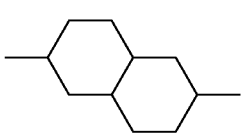 | | |
| B | 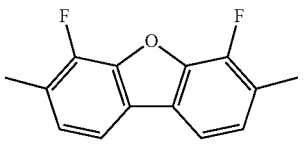 | B(S) | 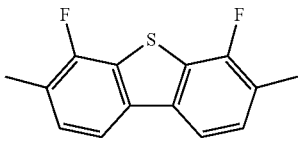 |

TABLE A-continued

Ring elements

K, KI: (indane ring structures with F substituents)

L, LI: (cyclohexene ring structures)

F, FI: (fluorinated cyclohexene ring structures)

TABLE B

Bridging units

| | | | |
|---|---|---|---|
| E | $-CH_2-CH_2-$ | | |
| V | $-CH=CH-$ | | |
| T | $-C\equiv C-$ | | |
| W | $-CF_2-CF_2-$ | | |
| B | $-CF=CF-$ | | |
| Z | $-CO-O-$ | ZI | $-O-CO-$ |
| X | $-CF=CH-$ | XI | $-CH=CF-$ |
| O | $-CH_2-O-$ | OI | $-O-CH_2-$ |
| Q | $-CF_2-O-$ | QI | $-O-CF_2-$ | in which n and m are each integers, and the three dots "..." are placeholders for other abbreviations from this table.

Besides the compounds of formula I, the mixtures according to the invention preferably comprise one or more compounds of the compounds mentioned below.

The following abbreviations are used:

(n, m and l are, independently of one another, each an integer, preferably 1 to 6, l possibly also 0 and preferably 0 or 2)

TABLE C

End groups

| On the left individually or in combination | | On the right individually or in combination | |
|---|---|---|---|
| -n- | $C_nH_{2n+1}-$ | -n | $-C_nH_{2n+1}$ |
| -nO- | $C_nH_{2n+1}-O-$ | -On | $-O-C_nH_{2n+1}$ |
| -V- | $CH_2=CH-$ | -V | $-CH=CH_2$ |
| -nV- | $C_nH_{2n+1}-CH=CH-$ | -nV | $-C_nH_{2n}-CH=CH_2$ |
| -Vn- | $CH_2=CH-C_nH_{2n}-$ | -Vn | $-CH=CH-C_nH_{2n+1}$ |
| -nVm- | $C_nH_{2n+1}-CH=CH-C_mH_{2m}-$ | -nVm | $-C_nH_{2n}-CH=CH-C_mH_{2m+1}$ |
| -N- | $N\equiv C-$ | -N | $-C\equiv N$ |
| -S- | $S=C=N-$ | -S | $-N=C=S$ |
| -F- | $F-$ | -F | $-F$ |
| -CL- | $Cl-$ | -CL | $-Cl$ |
| -M- | $CFH_2-$ | -M | $-CFH_2$ |
| -D- | $CF_2H-$ | -D | $-CF_2H$ |
| -T- | $CF_3-$ | -T | $-CF_3$ |
| -MO- | $CFH_2O-$ | -OM | $-OCFH_2$ |
| -DO- | $CF_2HO-$ | -OD | $-OCF_2H$ |
| -TO- | $CF_3O-$ | -OT | $-OCF_3$ |
| -A- | $H-C\equiv C-$ | -A | $-C\equiv C-H$ |
| -nA- | $C_nH_{2n+1}-C\equiv C-$ | -An | $-C\equiv C-C_nH_{2n+1}$ |
| -NA- | $N\equiv C-C\equiv C-$ | -AN | $-C\equiv C-C\equiv N$ |

| On the left only in combination | | On the right only in combination | |
|---|---|---|---|
| -...n...- | $-C_nH_{2n}-$ | -...n... | $-C_nH_{2n}-$ |
| -...M...- | $-CFH-$ | -...M... | $-CFH-$ |
| -...D...- | $-CF_2-$ | -...D... | $-CF_2-$ |
| -...V...- | $-CH=CH-$ | -...V... | $-CH=CH-$ |
| -...Z...- | $-CO-O-$ | -...Z... | $-CO-O-$ |
| -...ZI...- | $-O-CO-$ | -...ZI... | $-O-CO-$ |
| -...K...- | $-CO-$ | -...K... | $-CO-$ |
| -...W...- | $-CF=CF-$ | -...W... | $-CF=CF-$ |

TABLE D
Exemplary, preferred compounds of formula S having a high $\varepsilon_1$.
CB(S)-n-F
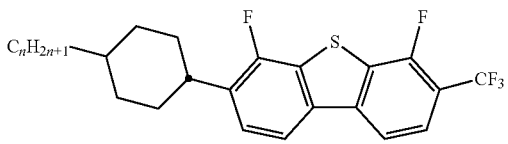
CB(S)-n-T
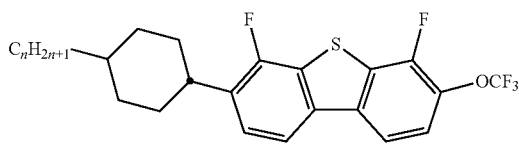
CB(S)-n-OT
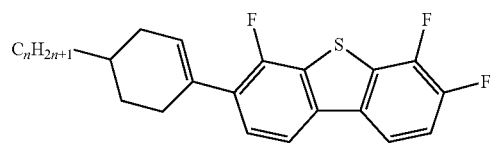
LB(S)-n-F
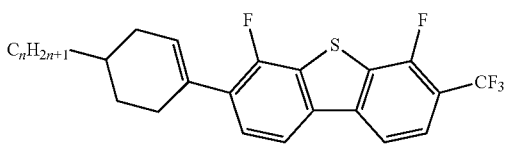
LB(S)-n-T
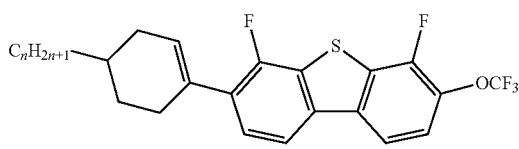
LB(S)-n-OT
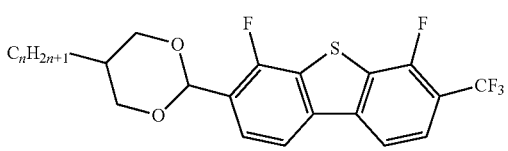
DB(S)-n-T
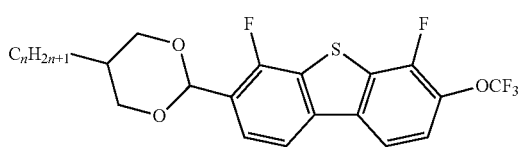
DB(S)-n-OT TABLE D-continued
Exemplary, preferred compounds of formula S-01 having a high $\varepsilon_1$:
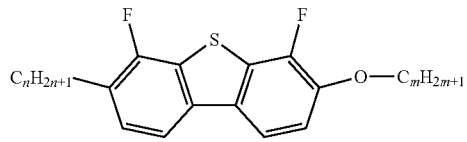
B(S)-n-Om
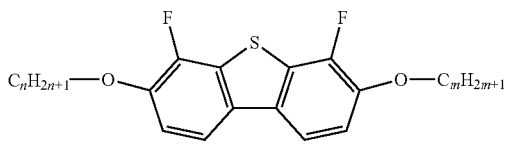
B(S)-nO-Om
Exemplary, preferred compounds of formula S-02 having a high $\varepsilon_1$:
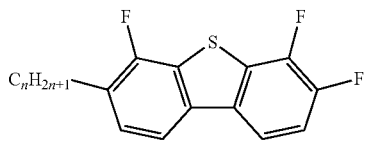
B(S)-n-F
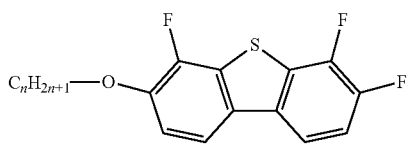
B(S)-nO-F
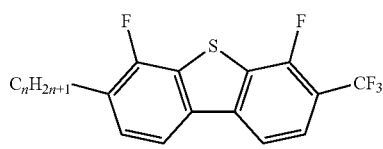
B(S)-n-T
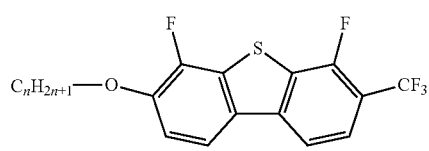
B(S)-nO-T
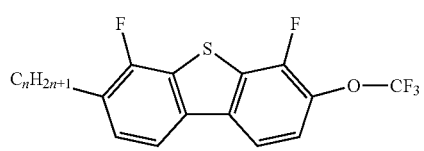
B(S)-n-OT
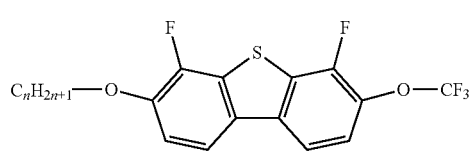
B(S)-nO-OT TABLE D-continued
Exemplary, preferred compounds of formula I having a high $\varepsilon_\perp$:
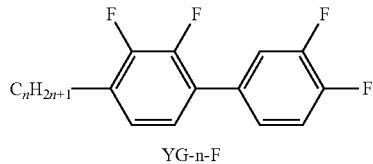
YG-n-F
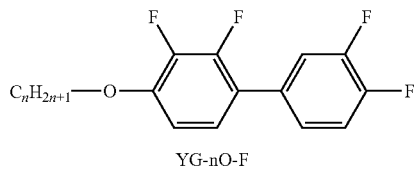
YG-nO-F
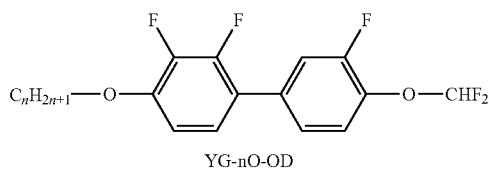
YG-nO-OD
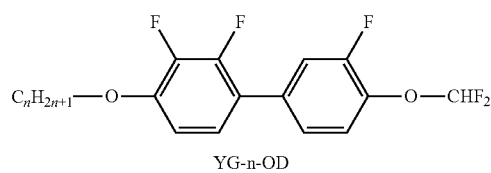
YG-n-OD
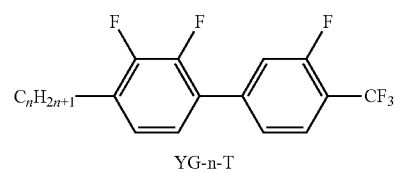
YG-n-T
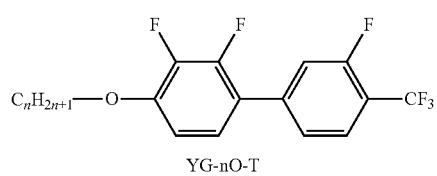
YG-nO-T
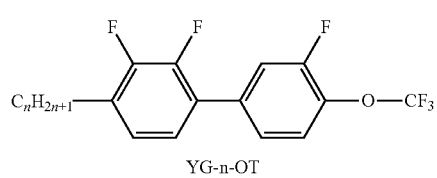
YG-n-OT
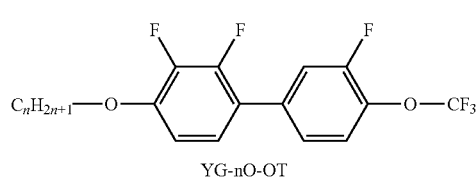
YG-nO-OT TABLE D-continued
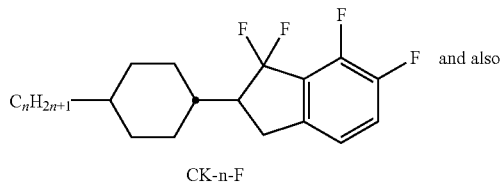
CK-n-F and also
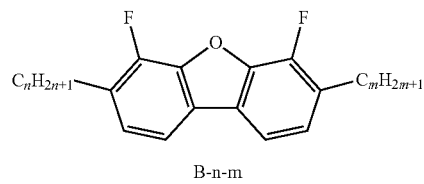
B-n-m
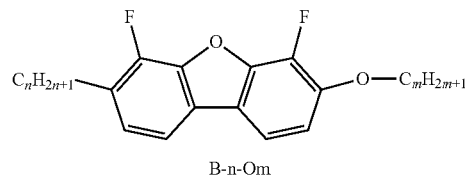
B-n-Om
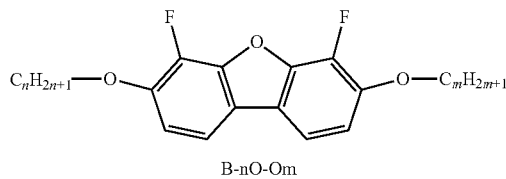
B-nO-Om
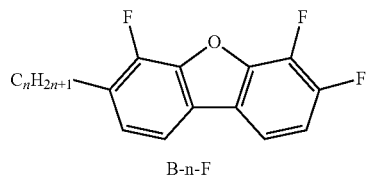
B-n-F
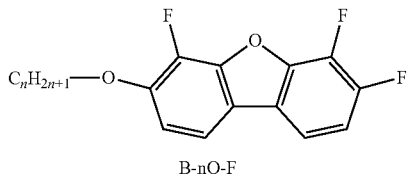
B-nO-F
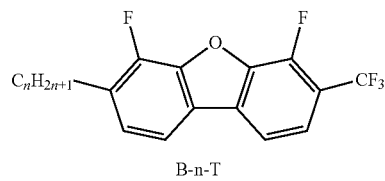
B-n-T
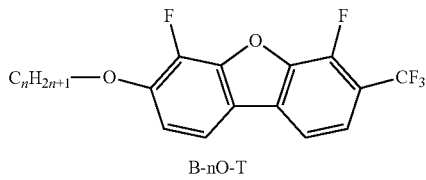
B-nO-T TABLE D-continued
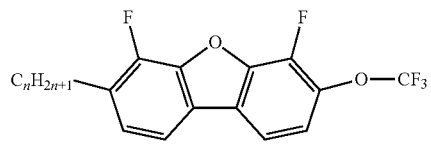
B-n-OT
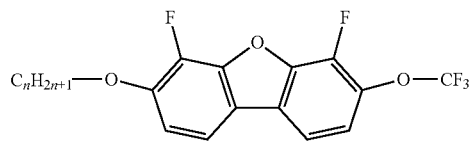
B-nO-OT
Exemplary, preferred dielectrically positive compounds
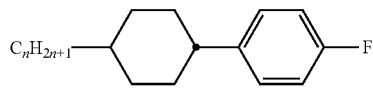
CP-n-F
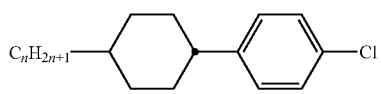
CP-n-CL
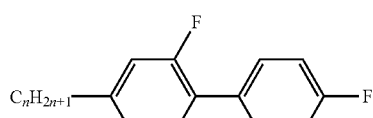
GP-n-F
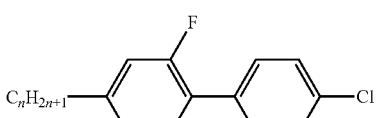
GP-n-CL
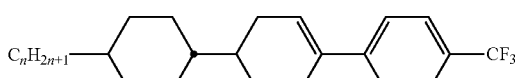
CLP-n-T
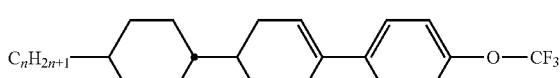
CLP-n-OT
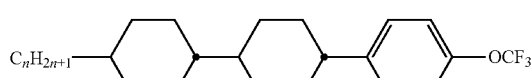
CCP-n-OT
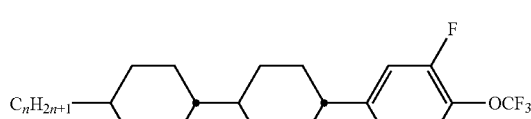
CCG-n-OT TABLE D-continued
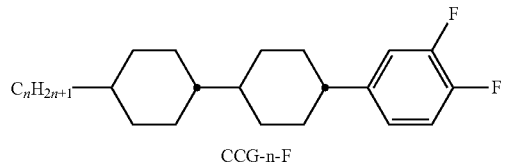
CCG-n-F
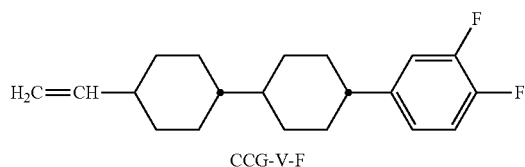
CCG-V-F
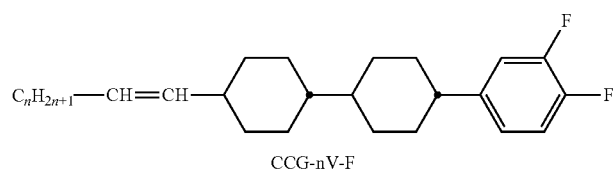
CCG-nV-F
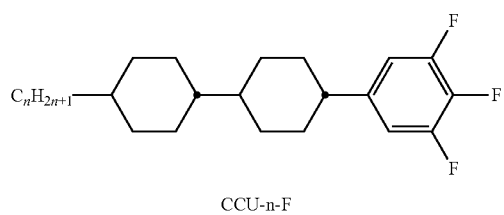
CCU-n-F
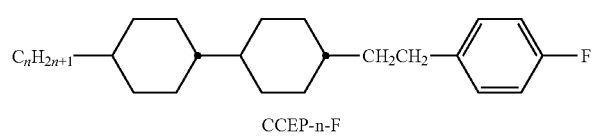
CCEP-n-F
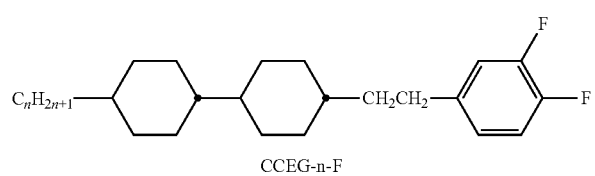
CCEG-n-F
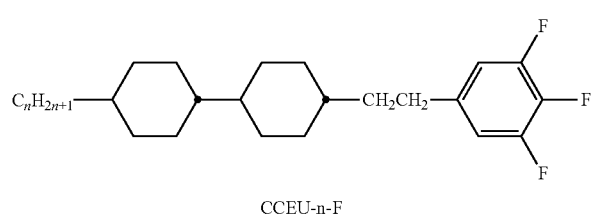
CCEU-n-F
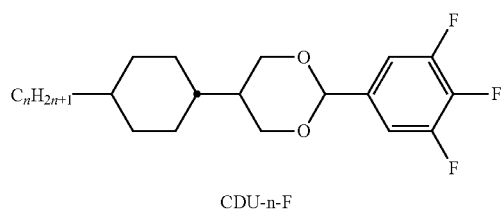
CDU-n-F TABLE D-continued
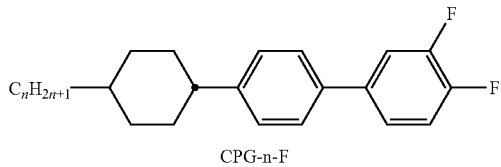
CPG-n-F
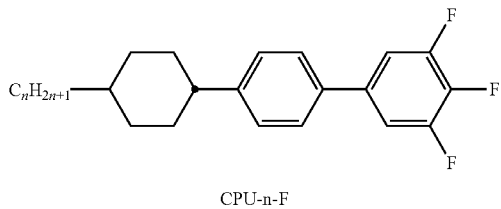
CPU-n-F
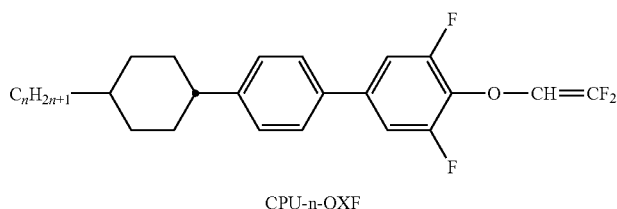
CPU-n-OXF
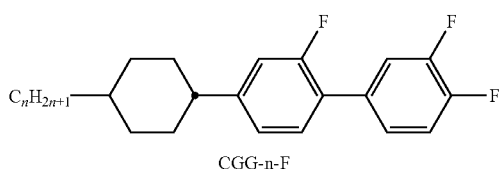
CGG-n-F
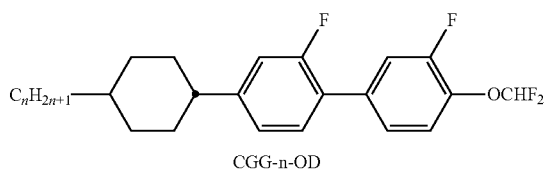
CGG-n-OD
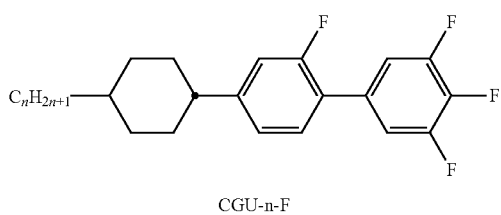
CGU-n-F
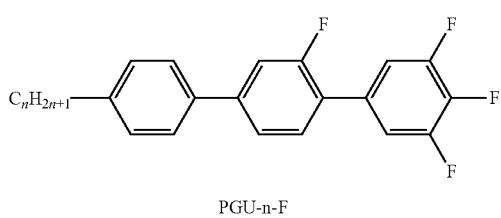
PGU-n-F
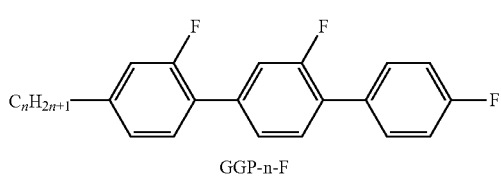
GGP-n-F TABLE D-continued
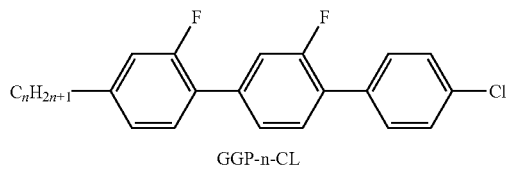
GGP-n-CL
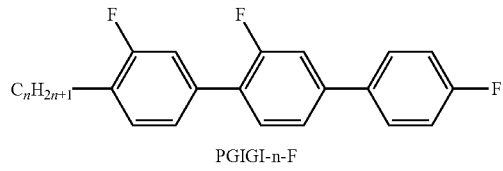
PGIGI-n-F
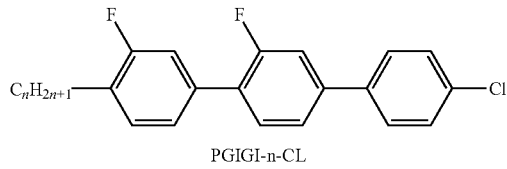
PGIGI-n-CL
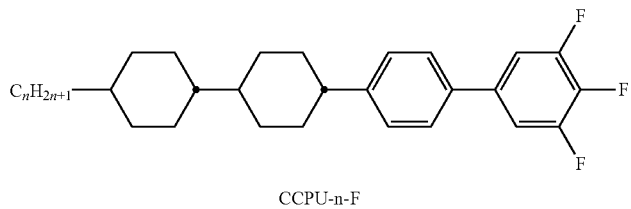
CCPU-n-F
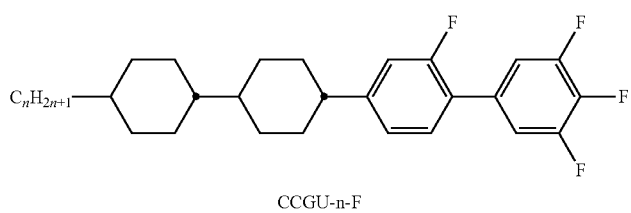
CCGU-n-F
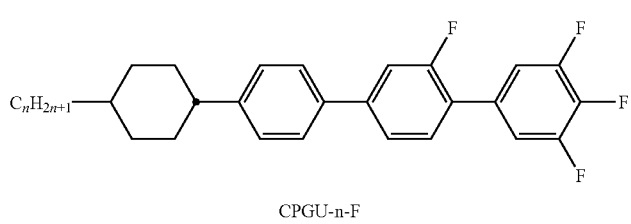
CPGU-n-F
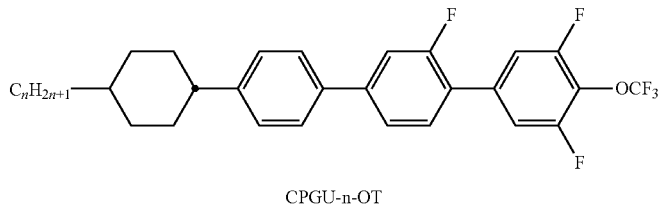
CPGU-n-OT
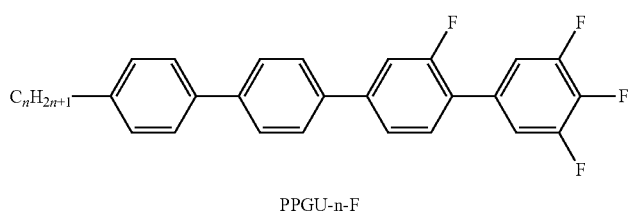
PPGU-n-F TABLE D-continued
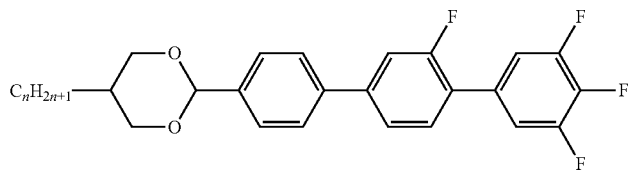
DPGU-n-F
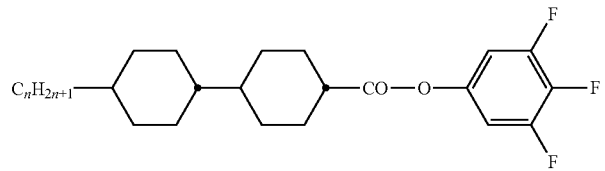
CCZU-n-F
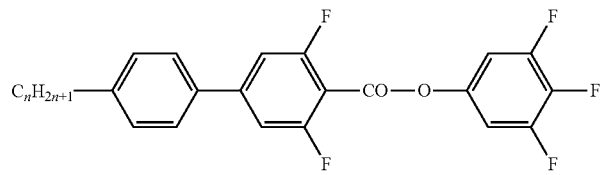
PUZU-n-F
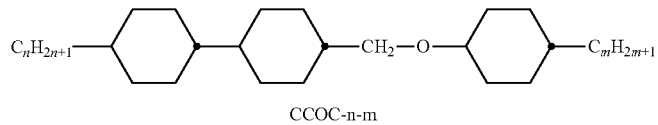
CCOC-n-m
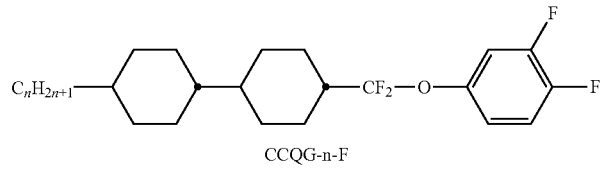
CCQG-n-F
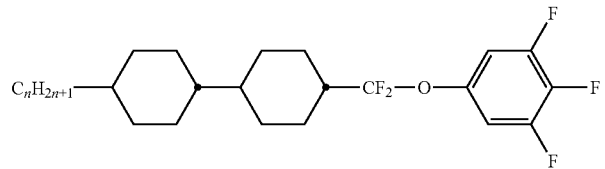
CCQU-n-F
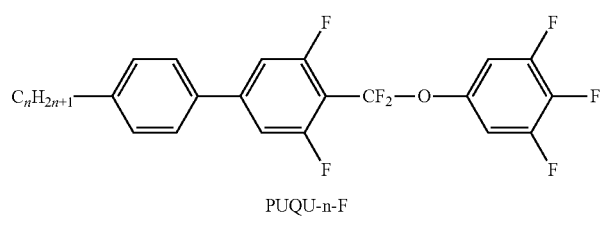
PUQU-n-F TABLE D-continued
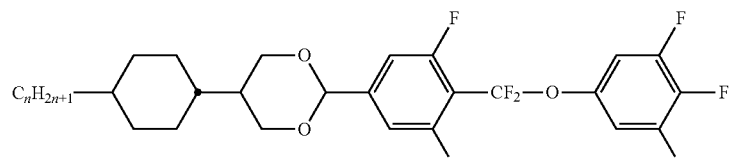
CDUQU-n-F
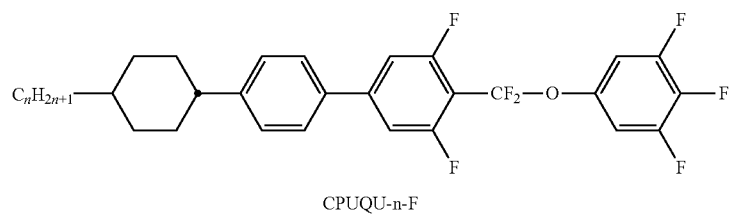
CPUQU-n-F
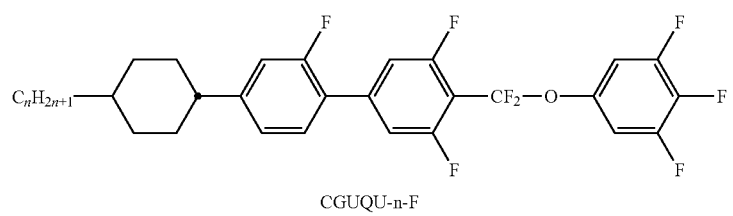
CGUQU-n-F
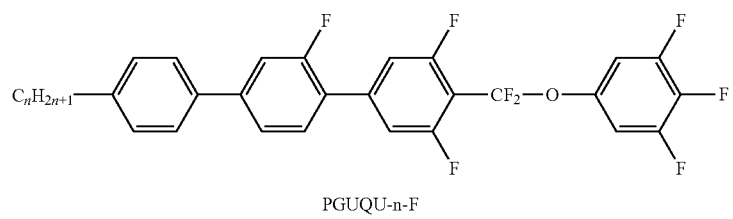
PGUQU-n-F
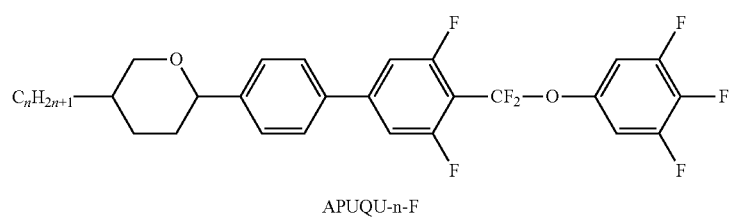
APUQU-n-F
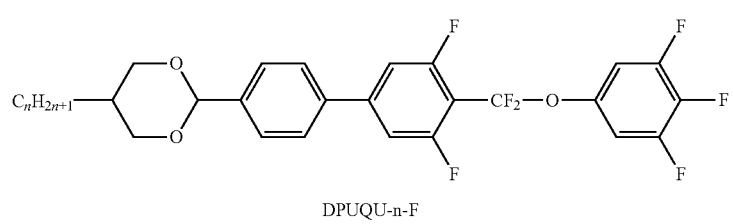
DPUQU-n-F
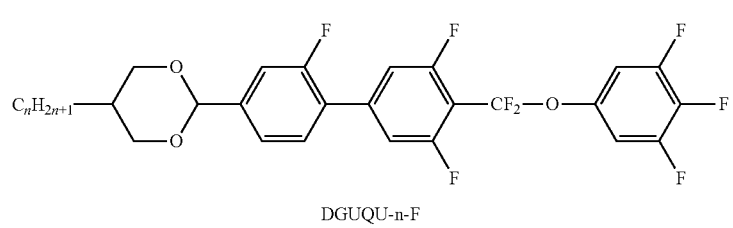
DGUQU-n-F TABLE D-continued
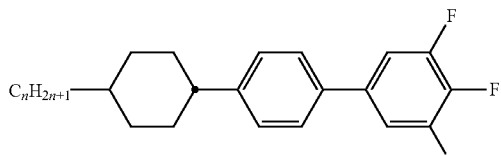
CPU-n-F
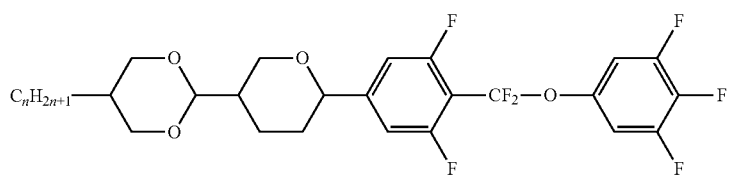
DAUQU-n-F
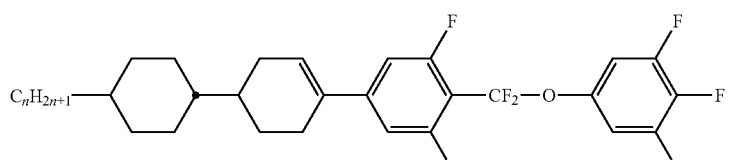
CLUQU-n-F
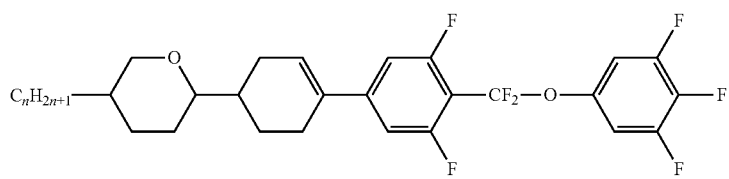
ALUQU-n-F
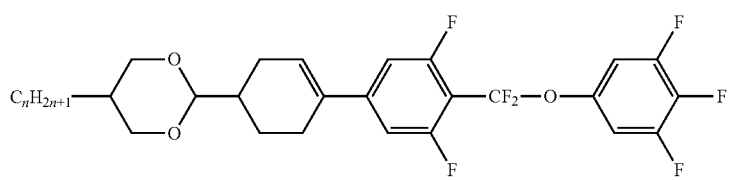
DLUQU-n-F
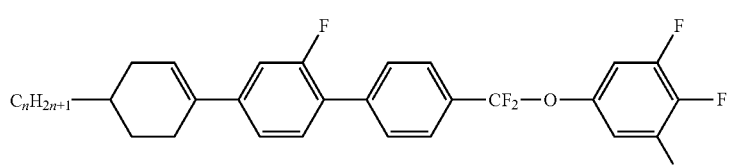
LGPQU-n-F
Exemplary, preferred dielectrically neutral compounds
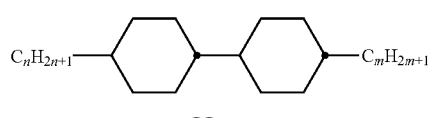
CC-n-m
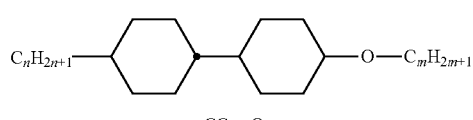
CC-n-Om TABLE D-continued
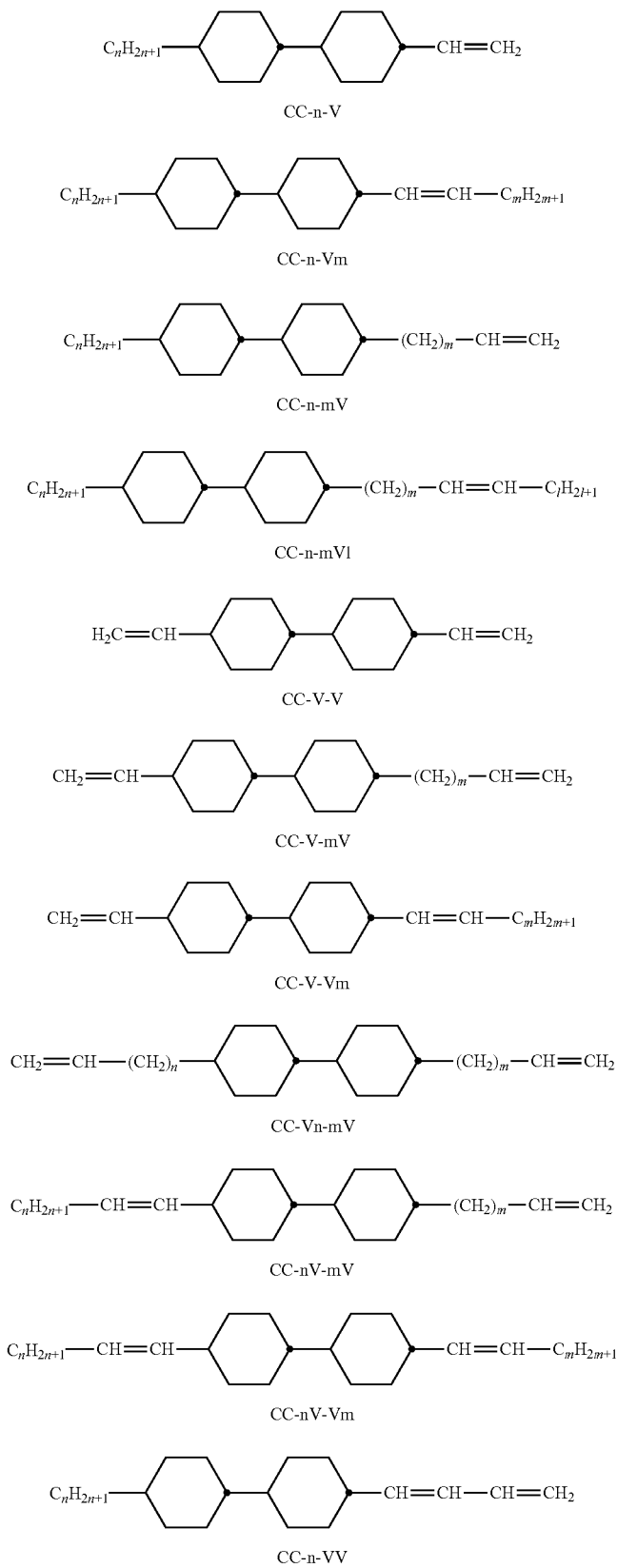

TABLE D-continued
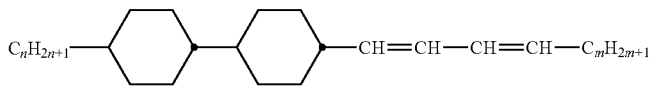
CC-n-VVm
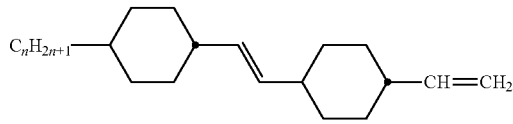
CVC-n-V
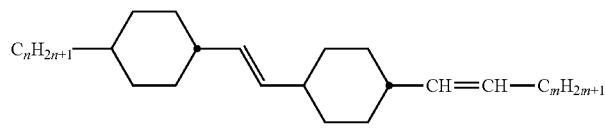
CVC-n-Vm
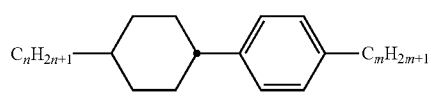
CP-n-m
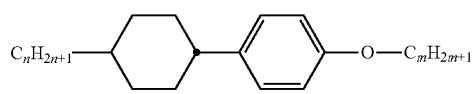
CP-n-Om
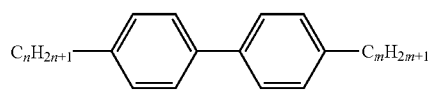
PP-n-m
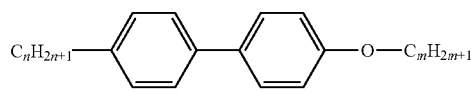
PP-n-Om
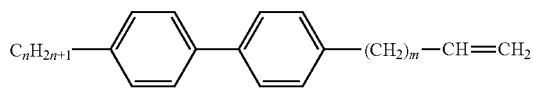
PP-n-mV
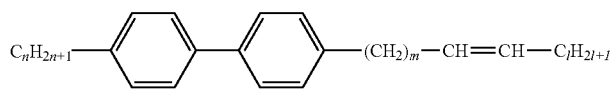
PP-n-mVl
CCP-n-m
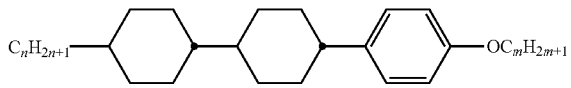
CCP-n-Om TABLE D-continued
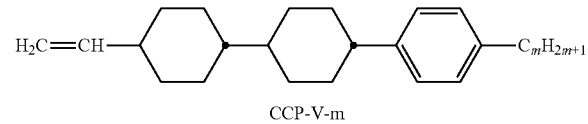
CCP-V-m
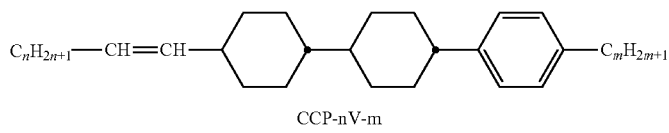
CCP-nV-m
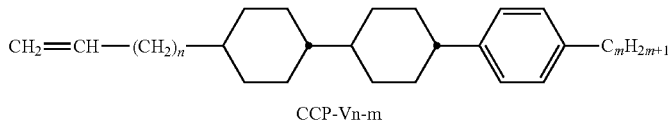
CCP-Vn-m
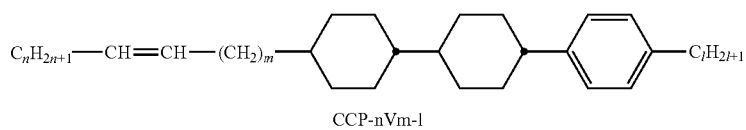
CCP-nVm-l
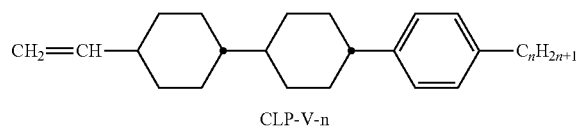
CLP-V-n
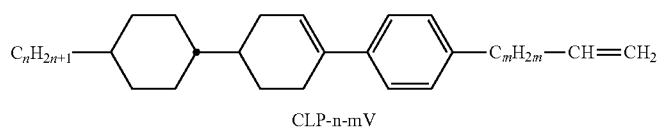
CLP-n-mV
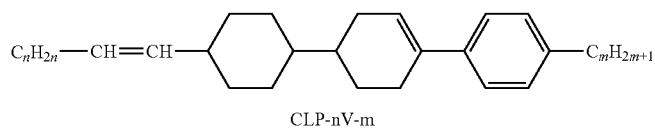
CLP-nV-m
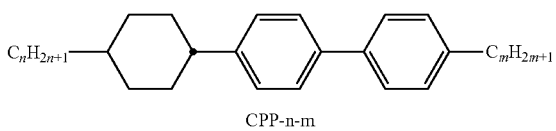
CPP-n-m
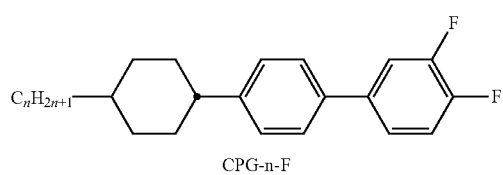
CPG-n-F
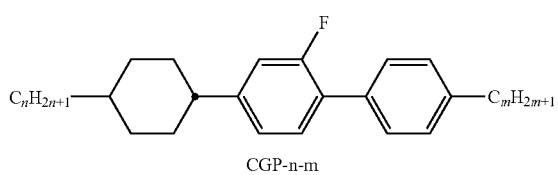
CGP-n-m TABLE D-continued
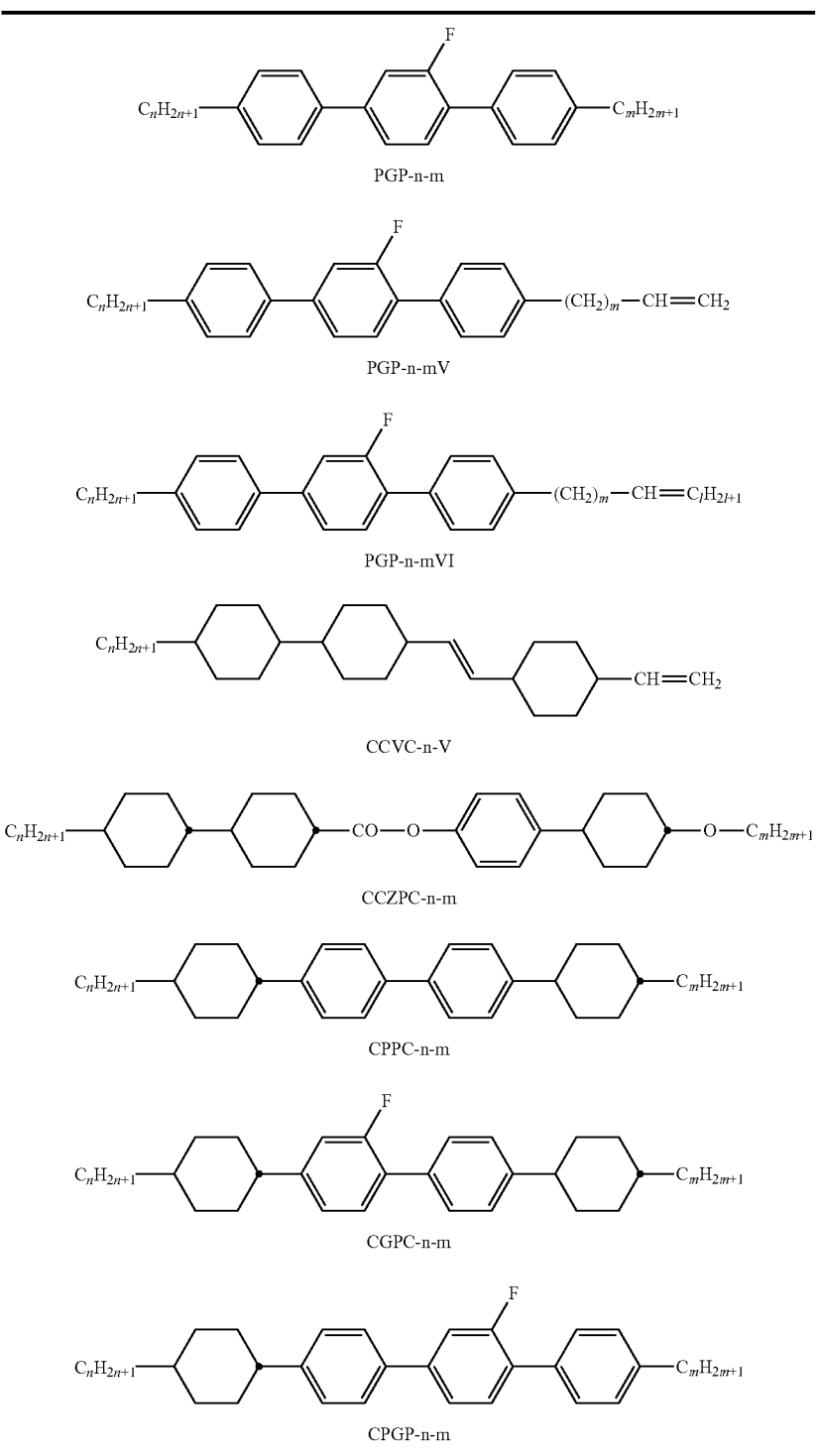
Exemplary, preferred dielectrically negative compounds
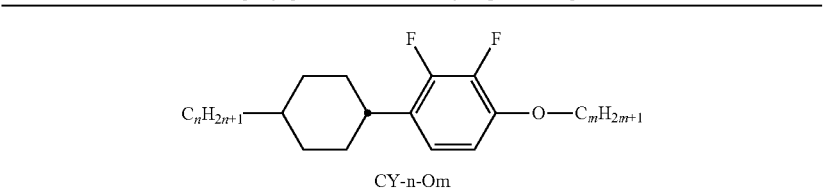

TABLE D-continued
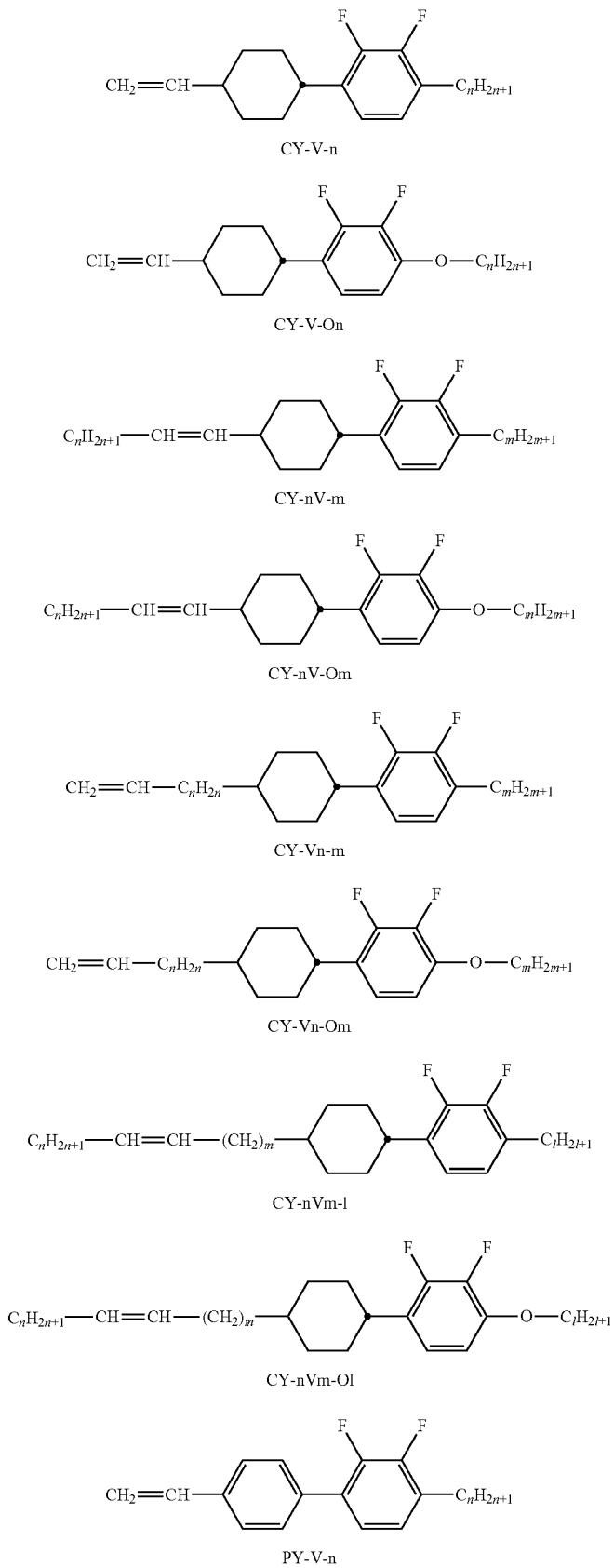

TABLE D-continued
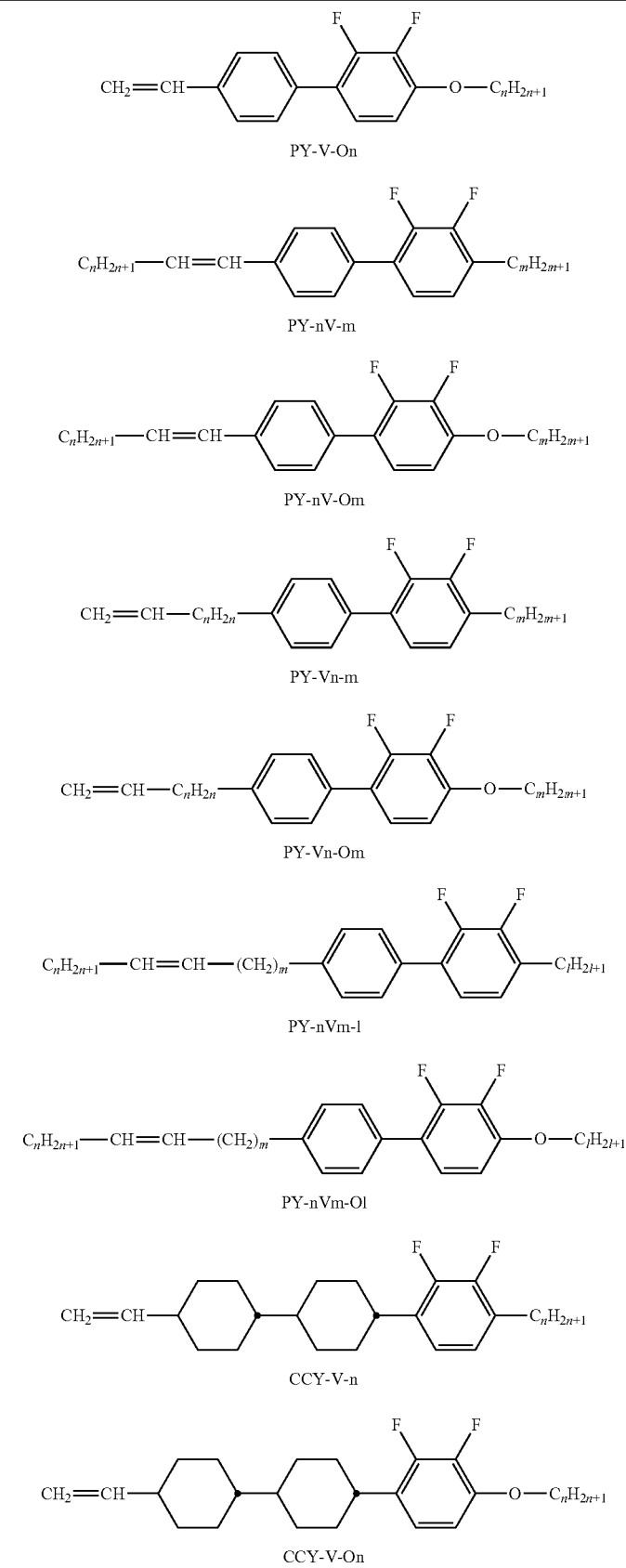

TABLE D-continued
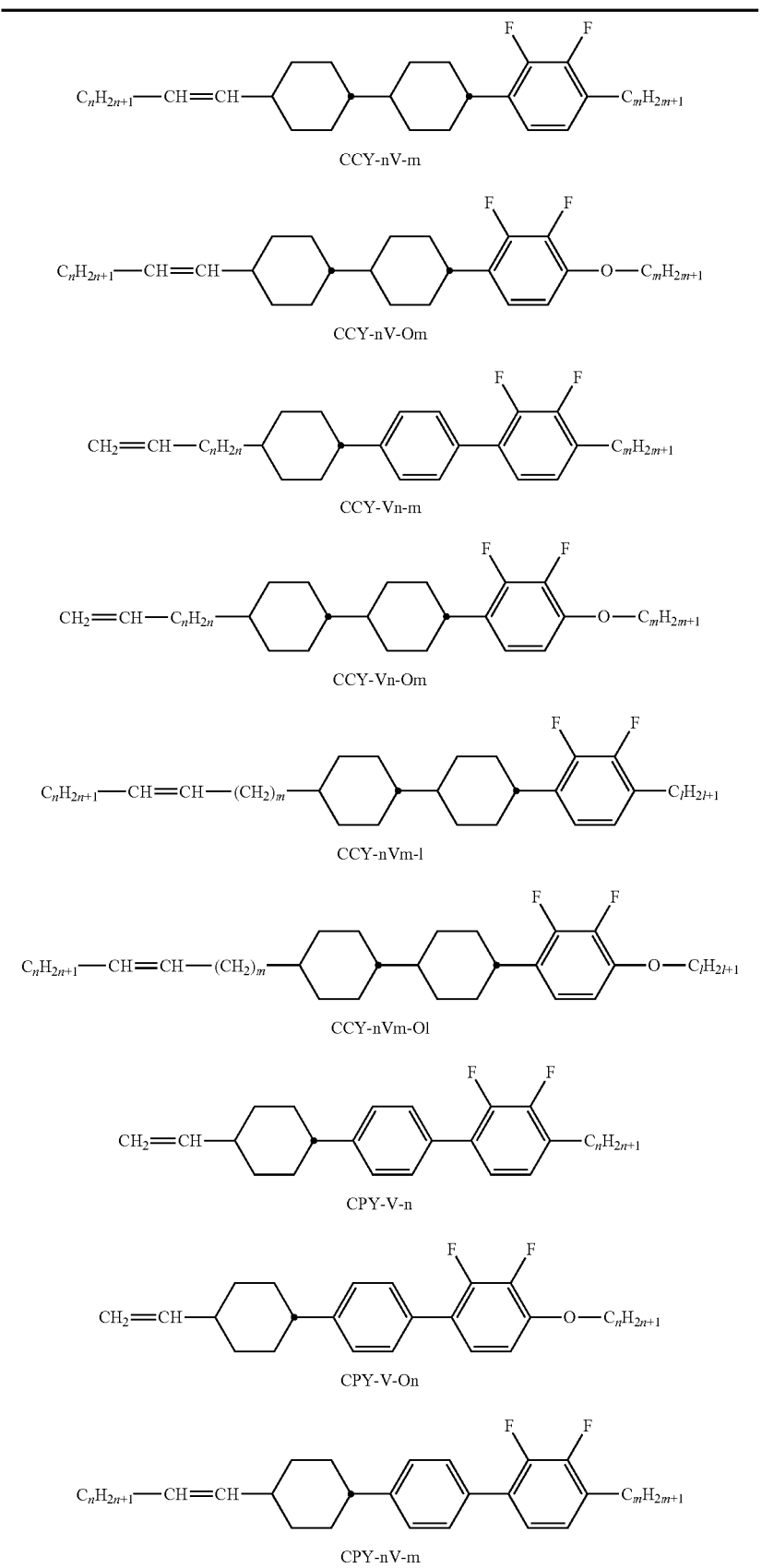

TABLE D-continued
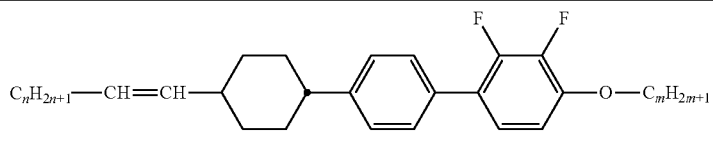
CPY-nV-Om
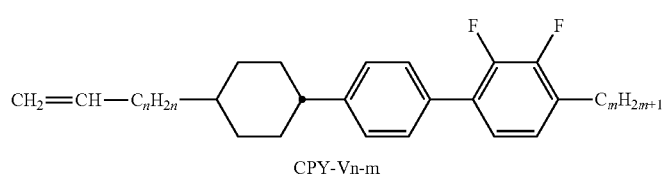
CPY-Vn-m
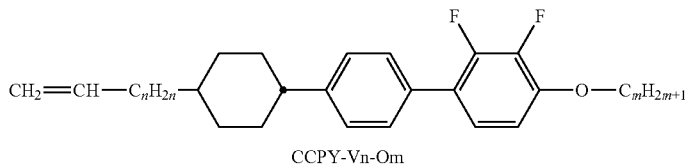
CCPY-Vn-Om
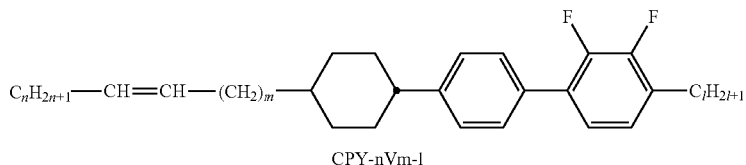
CPY-nVm-l
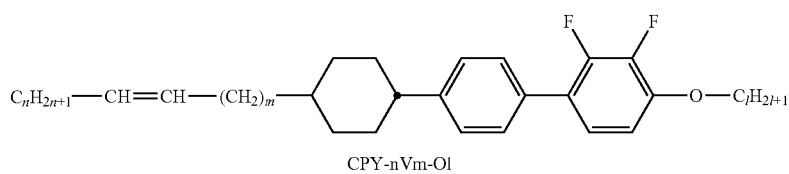
CPY-nVm-Ol
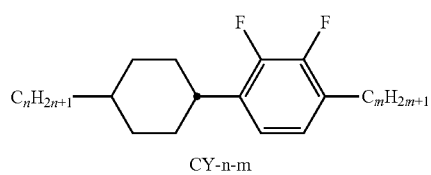
CY-n-m
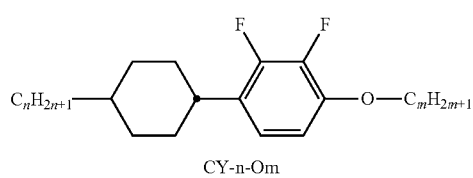
CY-n-Om
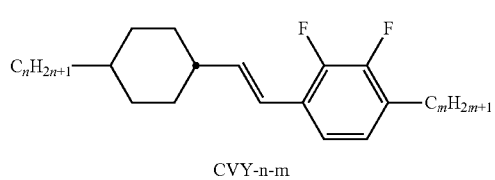
CVY-n-m
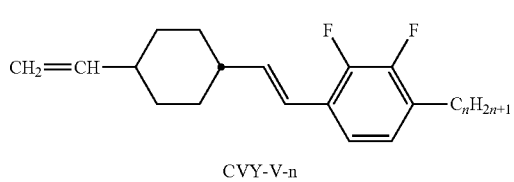
CVY-V-n TABLE D-continued
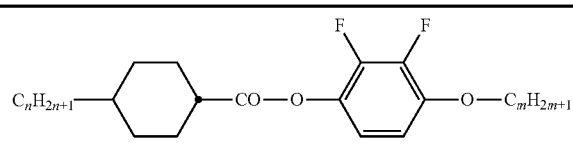
CZY-n-Om
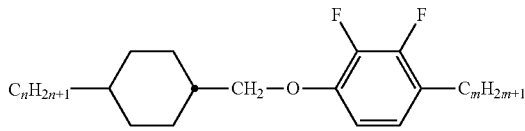
COY-n-m
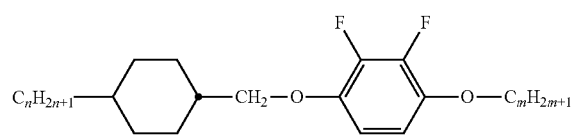
COY-n-Om
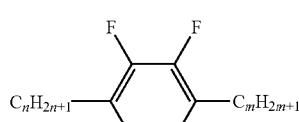
Y-n-m
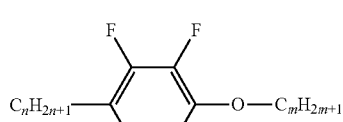
Y-n-Om
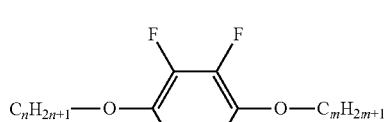
Y-nO-Om
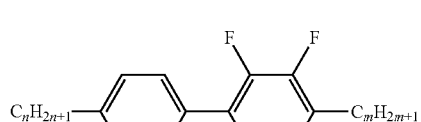
PY-n-m
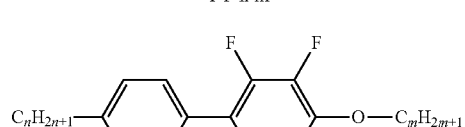
PY-n-Om
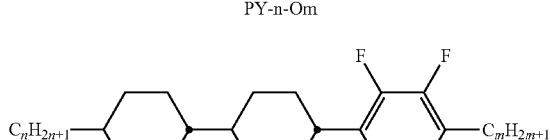
CCY-n-m TABLE D-continued
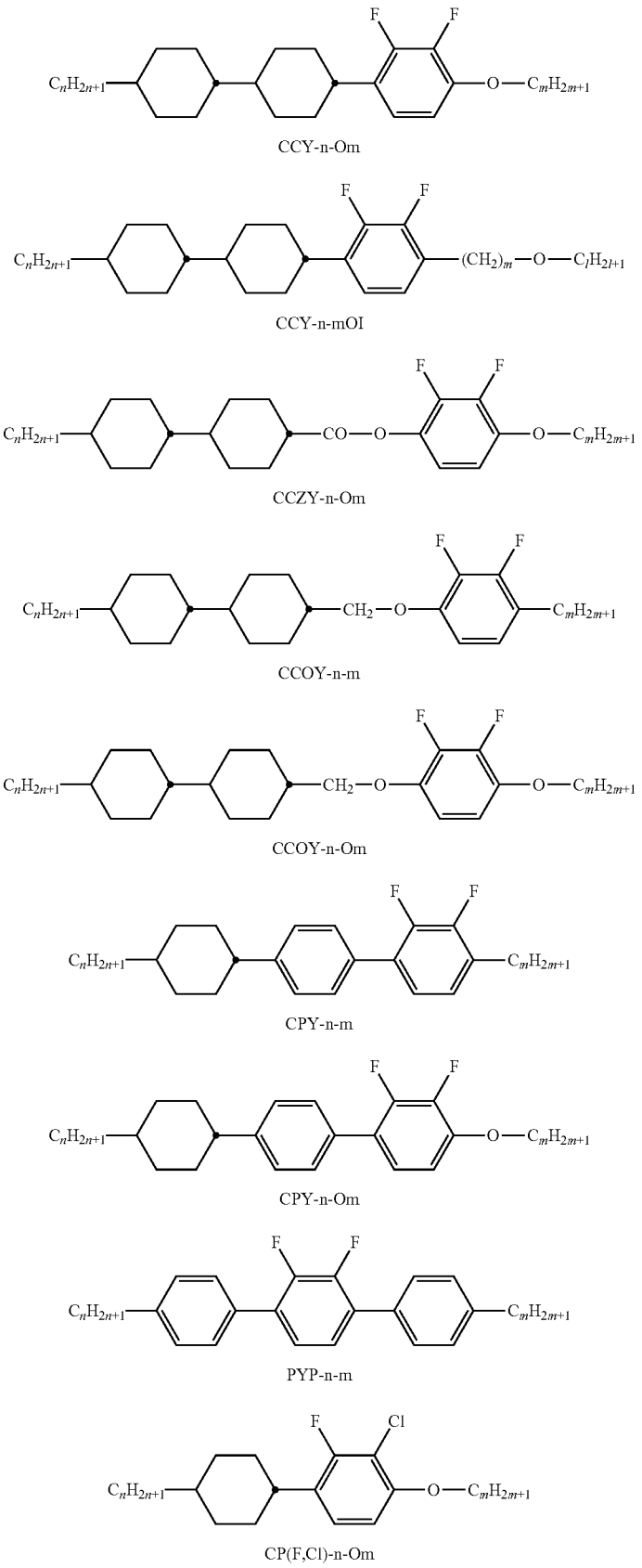

TABLE D-continued
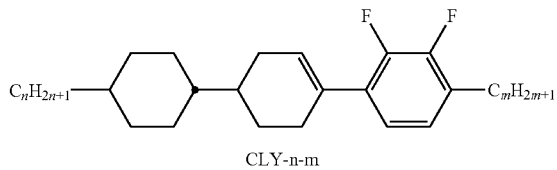
CLY-n-m
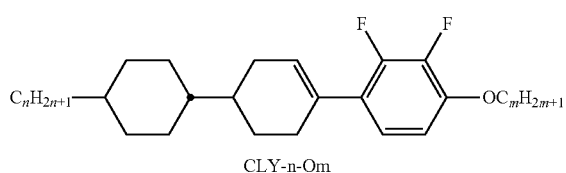
CLY-n-Om
Table E shows chiral dopants which are preferably employed in the mixtures according to the invention.
TABLE E
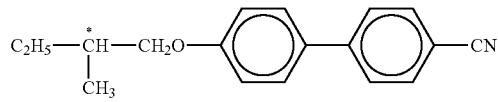
C 15
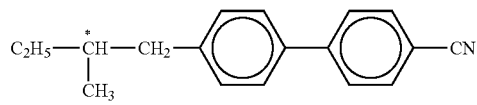
CB 15
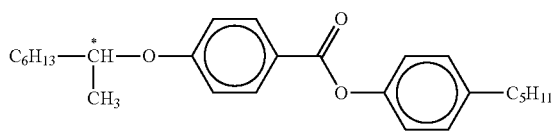
CM 21
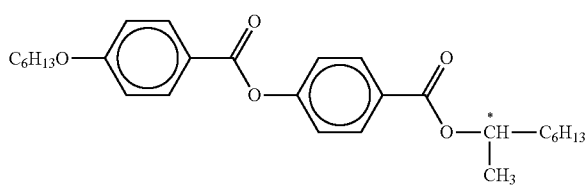
R S-811 / S-811
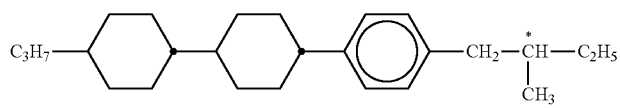
CM 44
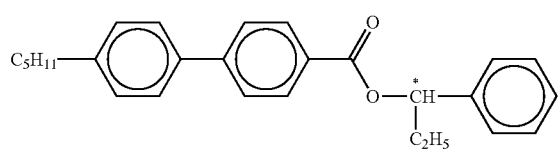
CM 45

TABLE E-continued
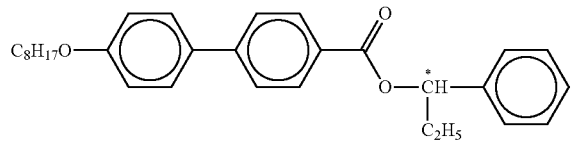
CM 47
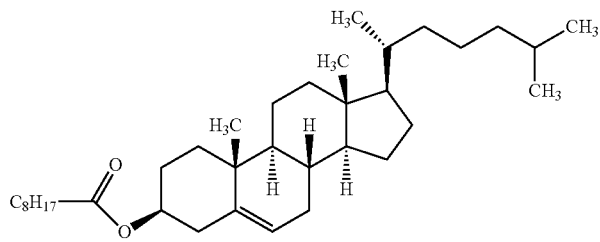
CN
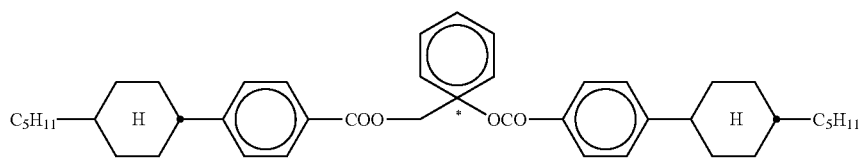
R-1011 / S-1011
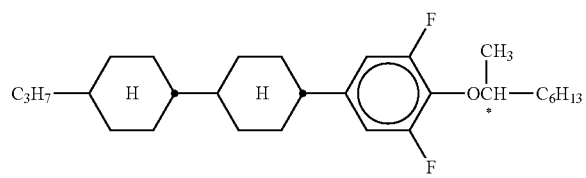
R-2011 / S-2011
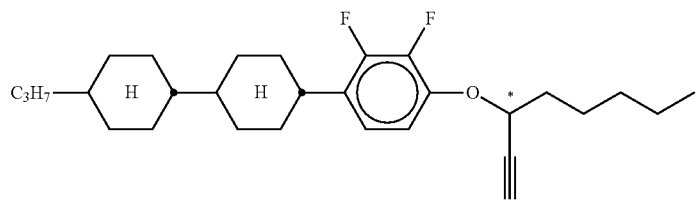
R-3011 / S-3011
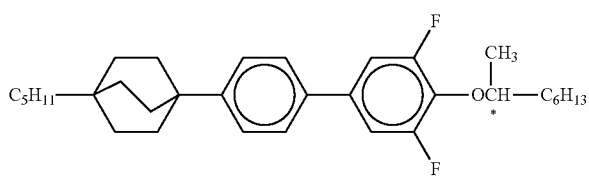
R-4011 / S-4011

TABLE E-continued

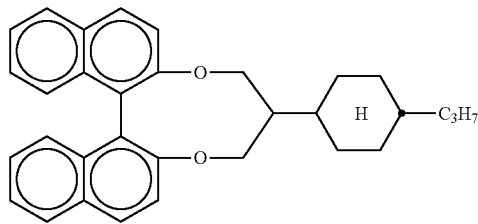

R-5011 / S-5011

In a preferred embodiment of the present invention, the media according to the invention comprise one or more compounds selected from the group of the compounds from Table E.

Table F shows stabilisers which can preferably be employed in the mixtures according to the invention in addition to the compounds of formula I. The parameter n here denotes an integer in the range from 1 to 12. In particular, the phenol derivatives shown can be employed as additional stabilisers since they act as antioxidants.

TABLE F

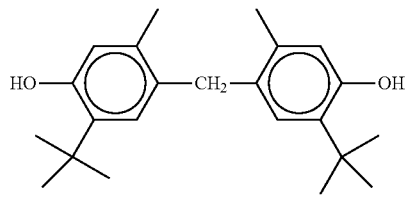

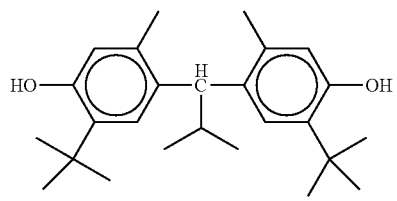

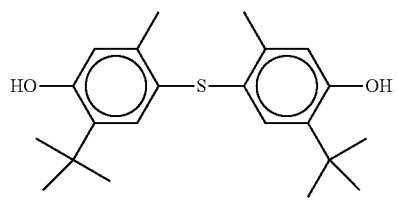

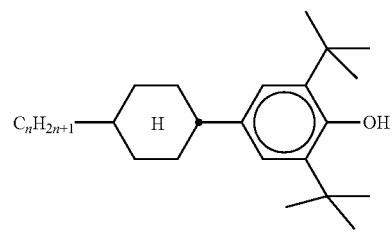

TABLE F-continued
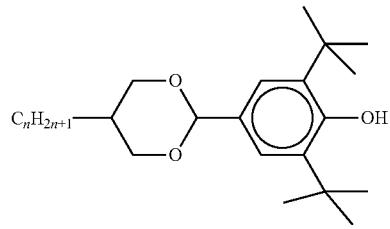
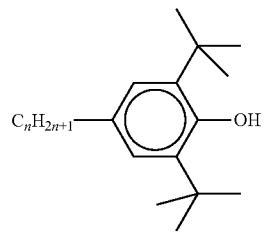
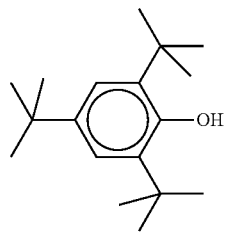
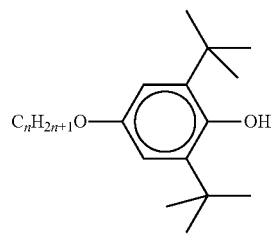
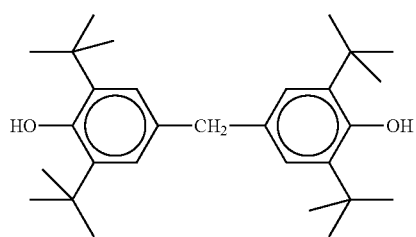
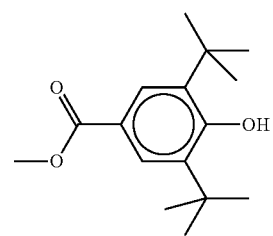

TABLE F-continued
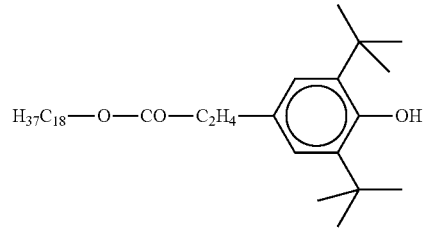
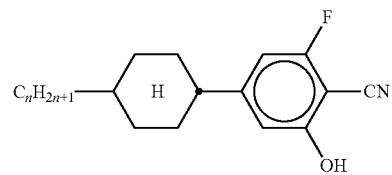
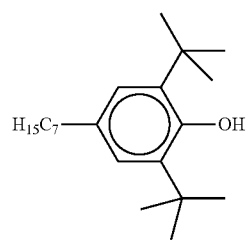
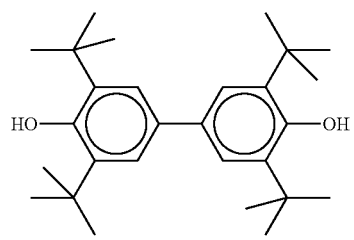
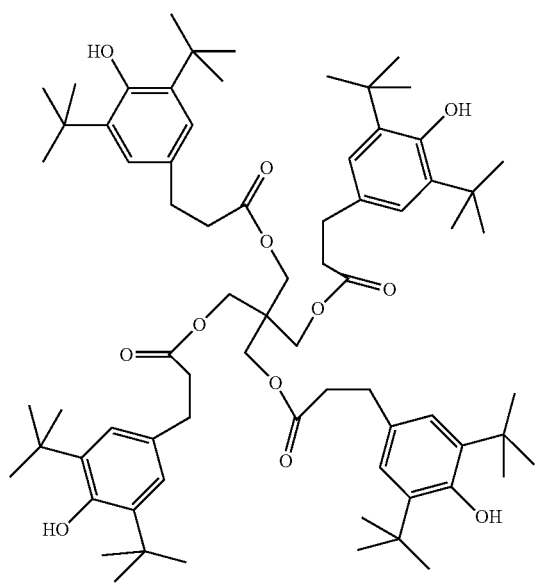 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]

TABLE F-continued
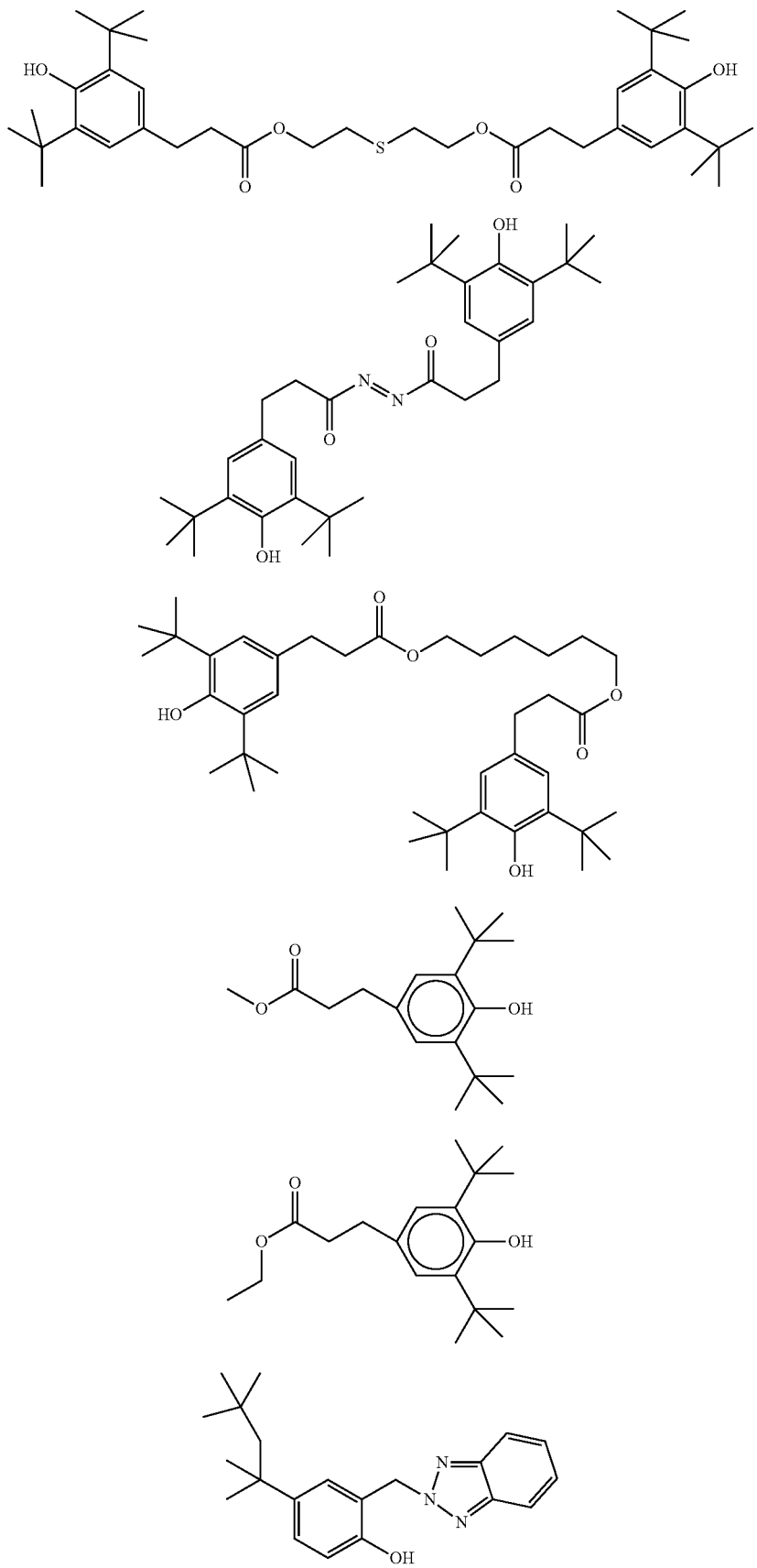

TABLE F-continued
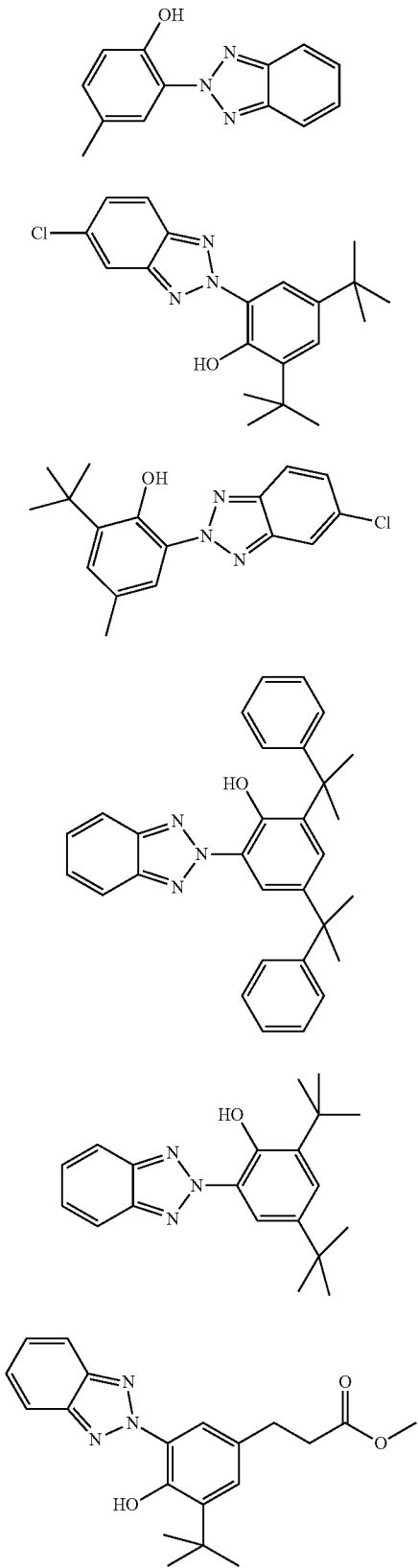

TABLE F-continued
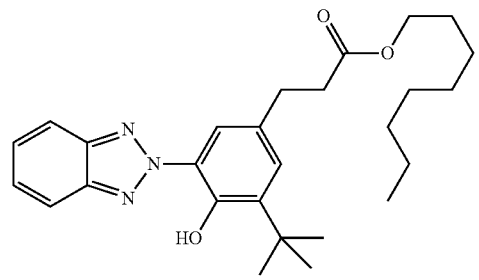 [SMILES: CCCCCCCCOC(=O)CCc1cc(-n2nc3ccccc3n2)c(O)c(C(C)(C)C)c1]
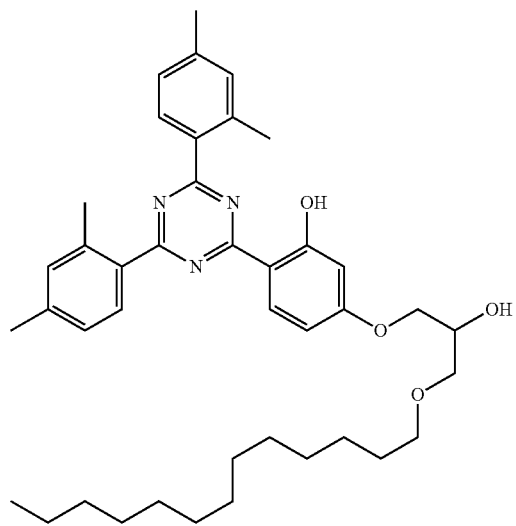 [SMILES: CCCCCCCCCCCCCOCC(O)COc1ccc(-c2nc(-c3ccc(C)cc3C)nc(-c3ccc(C)cc3C)n2)c(O)c1]
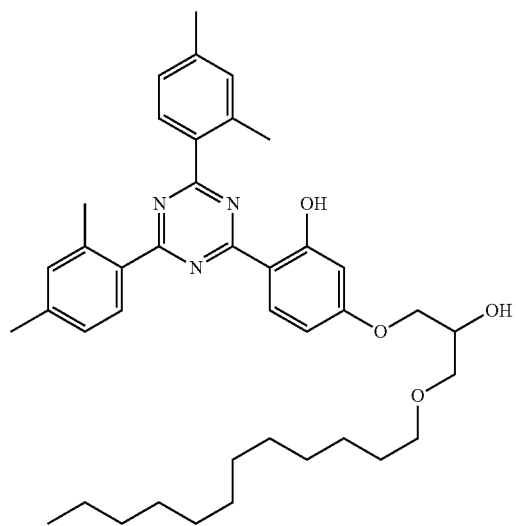 [SMILES: CCCCCCCCCCCCOCC(O)COc1ccc(-c2nc(-c3ccc(C)cc3C)nc(-c3ccc(C)cc3C)n2)c(O)c1]

TABLE F-continued
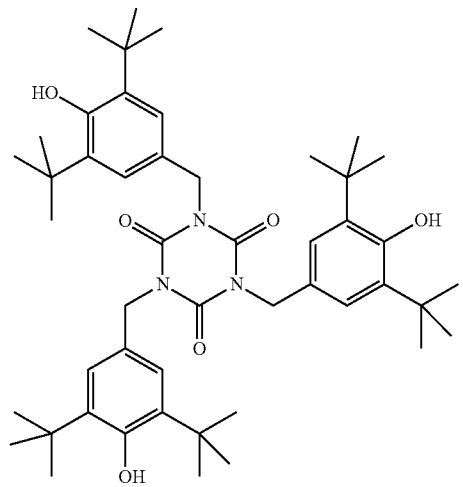 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
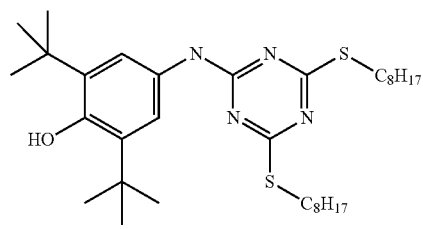
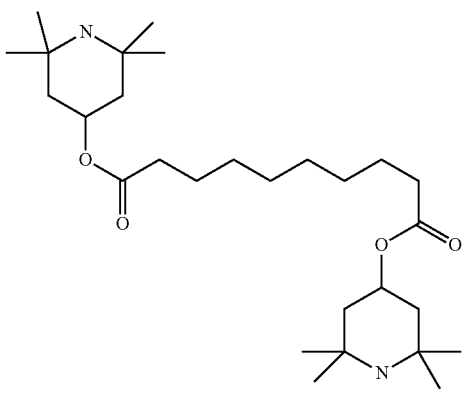
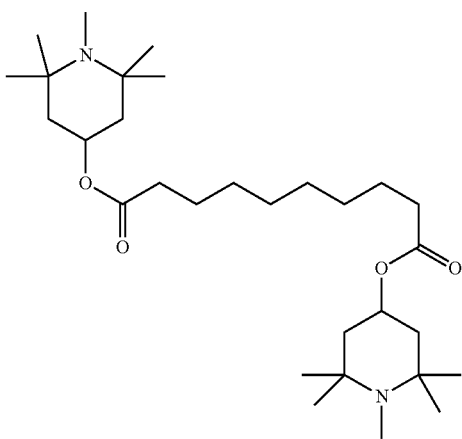

TABLE F-continued
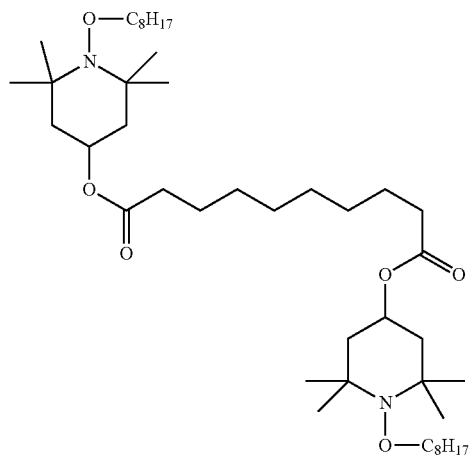
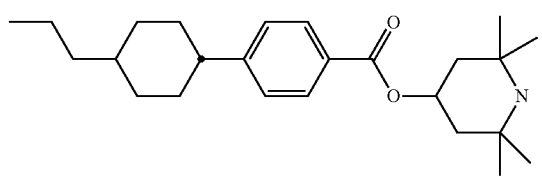
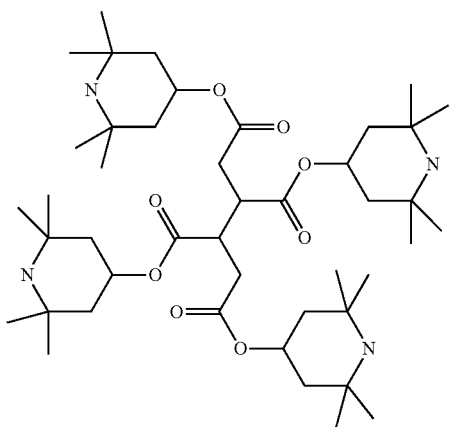
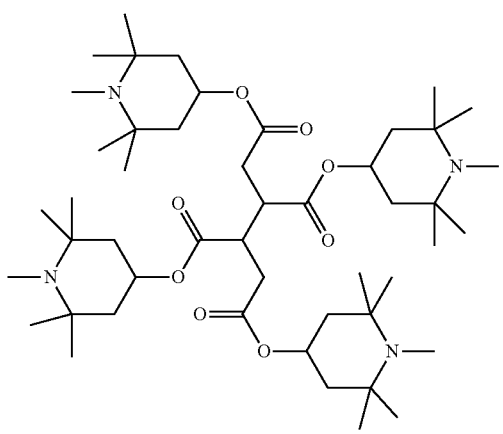

In a preferred embodiment of the present invention, the media according to the invention comprise one or more compounds selected from the group of the compounds from Table F, in particular one or more compounds selected from the group of the compounds of the following two formulae

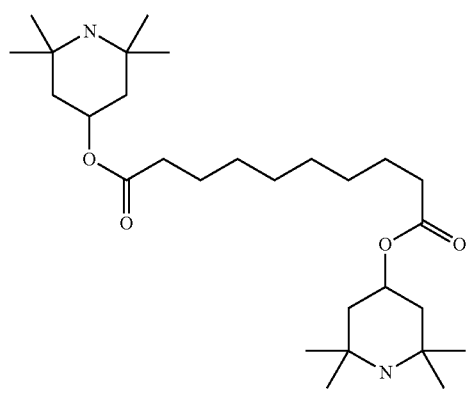

-continued

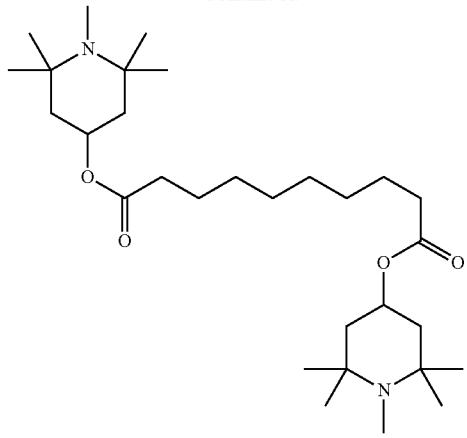

EXAMPLES

The following examples explain the present invention without restricting it in any way. However, the physical properties make it clear to the person skilled in the art what properties can be achieved and in what ranges they can be modified. In particular, the combination of the various properties which can preferably be achieved is thus well defined for the person skilled in the art.

Synthesis Example 1

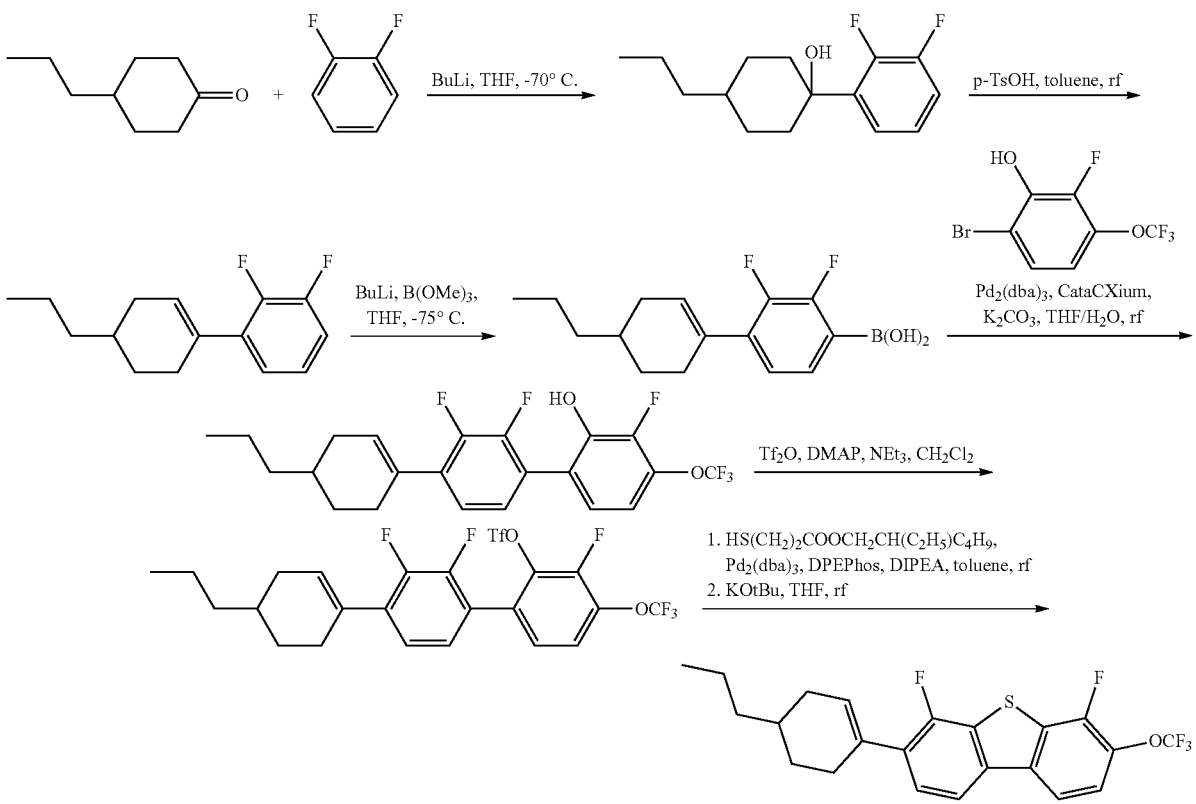

The following abbreviations are used in the synthetic examples.
DMAP 4-(Dimethylamino)pyridine
MTB ether tertButyl methyl ether
TEA Triethylamine
THF Tetrahydrofuran Synthesis Example 1 (LB(S)-3-OT)

Synthesis of 4,6-Difluoro-3-(4-propyl-cyclohex-1-enyl)-7-trifluoromethoxy-dibenzothiophene

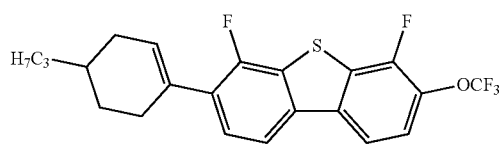

Step 1.1: 3,2',3'-Trifluoro-4'-(4-propyl-cyclohex-1-enyl)-4-trifluoromethoxy-biphenyl-2-ol

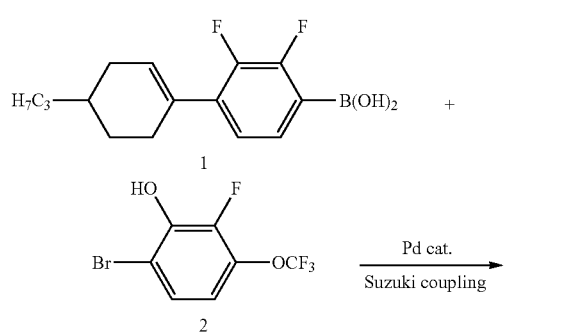

A mixture of 6-bromo-2-fluoro-3-trifluoromethoxyphenol (2, CAS 1805580-01-1) (68.0 g, 0.25 mol), potassium carbonate (50.0 g, 0.36 mol), tris(dibenzylideneacetone)-dipalladium(0) (1.2 g, 1.25 mmol) and CataCXium A (1.4 g, 3.71 mmol) in THF (500 mL) and distilled water (100 mL) is heated to reflux under nitrogen atmosphere, followed by dropwise addition of a solution of 2,3-difluoro-4-(4-propylcyclohex-1-enyl)-phenylboronic acid (1, CAS 947607-78-5) (70.6 g, 0.25 mol) in THF (200 mL). The reaction mixture is heated at reflux temperature overnight. Then it is cooled to room temperature and diluted with MTB ether and distilled water. Throughout this application, unless explicitly stated otherwise, room temperature and ambient temperature are used synonymously and signify a temperature of about 20° C., typically (20±1)° C. The aqueous phase is separated and extracted with MTB ether. The combined organic phases are washed with distilled water and brine, dried (sodium sulphate) and concentrated in vacuo. The residue is purified by silica gel chromatography (solvent 1-chlorobutane/heptane 1:1). 3,2',3'-Trifluoro-4'-(4-propyl-cyclohex-1-enyl)-4-trifluoromethoxy-biphenyl-2-ol (3) is isolated as a brown solid.

Step 1.2: Trifluoromethanesulfonic acid 3,2',3'-trifluoro-4'-(4-propylcyclohex-1-enyl)-4-trifluoromethoxy-biphenyl-2-yl ester

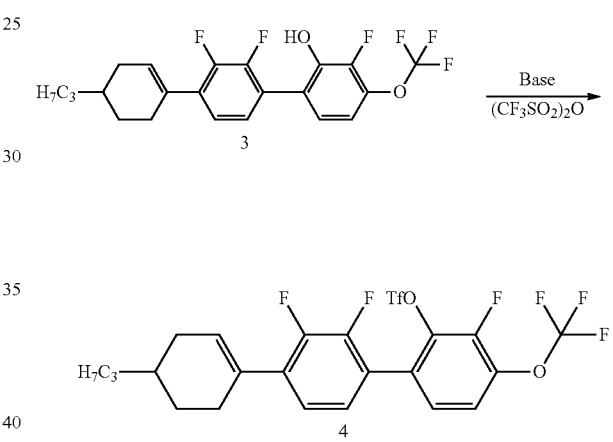

Trifluoromethanesulfonic anhydride (31 mL, 0.19 mol) is slowly added to a solution of 3,2',3'-trifluoro-4'-(4-propyl-cyclohex-1-enyl)-4-trifluoromethoxy-biphenyl-2-ol (3) (66 g, 0.15 mol), TEA (32 mL, 0.23 mol) and DMAP (560 mg, 4.58 mmol) in dichloromethane (500 mL) at 5° C. under nitrogen atmosphere. The solution is stirred at room temperature overnight. The reaction mixture is purified by silica gel chromatography (solvent dichlormethane) to give trifluoromethanesulfonic acid 3,2',3'-trifluoro-4'-(4-propyl-cyclohex-1-enyl)-4-trifluoromethoxy-biphenyl-2-yl ester (4) as a brown oil.

Step 1.3: 4,6-Difluoro-3-(4-propyl-cyclohex-1-enyl)-7-trifluoromethoxy-dibenzothiophene

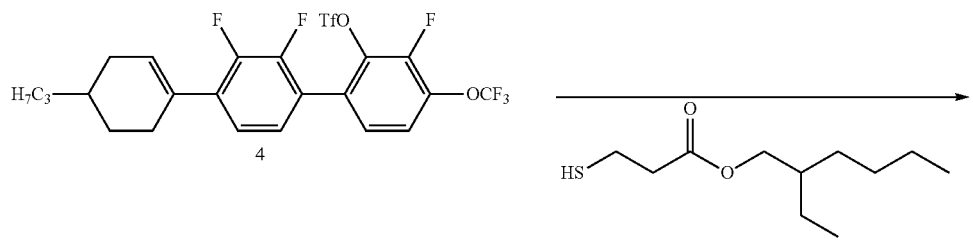

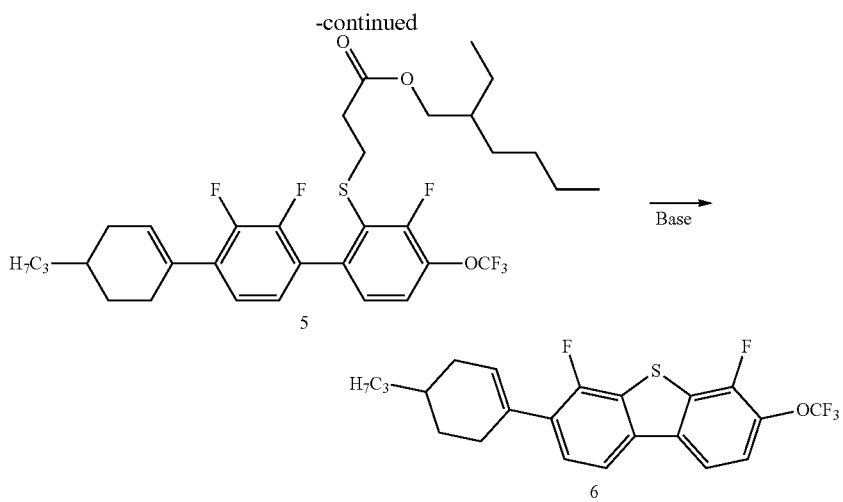

This reaction is performed as a one-pot reaction. In the first step, a solution of trifluoromethanesulfonic acid 3,2',3'-trifluoro-4'-(4-propylcyclohex-1-enyl)-4-trifluoromethoxy-biphenyl-2-yl ester (4) (87 g, 0.15 mol), 3-mercapto-propionic acid 2-ethylhexyl ester (45 mL, 0.19 mol), N-ethyldiisopropylamine (40 mL, 0.24 mol) and toluene (350 mL) is degassed with Argon for 1 h. Tris(dibenzylideneacetone)dipalladium(0) (1.5 g, 1.56 mmol) and (oxydi-2,1-phenylene)bis(diphenylphosphine) (1.6 g, 2.91 mmol) are quickly added to the solution, and the reaction mixture is heated at reflux temperature overnight. Then it is allowed to cool to room temperature. In the second step, a solution of potassium tert-butylate (22 g, 0.20 mol) in THF (200 mL) is added to the reaction mixture containing intermediate (5) in situ. The reaction mixture is heated at reflux temperature overnight, followed by addition of a second portion of a solution of potassium tert-butylate (11 g, 0.1 mol) in THF (100 mL). The reaction mixture is heated again at reflux temperature overnight. Then it is cooled to room temperature, quenched with distilled water and hydrochloric acid (25%) at 0° C. and diluted with MTB ether. The aqueous phase is separated and extracted with MTB ether. The combined organic phases are washed with distilled water and brine, dried (sodium sulphate) and concentrated in vacuo. The residue is purified by silica gel chromatography (solvent heptane) to give 4,6-difluoro-3-(4-propyl-cyclohex-1-enyl)-7-trifluoromethoxy-dibenzothiophene (6) as white crystals.

Compound (6) has the following phase characteristics: K 66° C. SmA 181° C. I.

Synthesis Example 2 (LB(S)-3-T)

Synthesis of 4,6-Difluoro-3-(4-propyl-cyclohex-1-enyl)-7-trifluoromethyl-dibenzothiophene

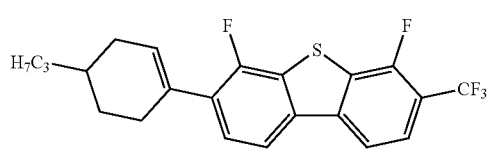

Step 2.1: 3,2',3'-Trifluoro-4-trifluoromethyl-biphenyl-2-ol

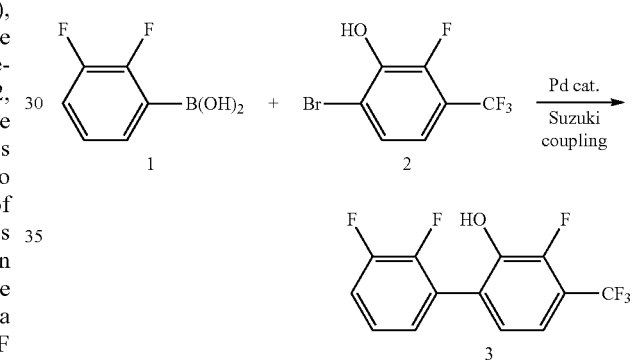

A mixture of 6-bromo-2-fluoro-3-trifluoromethylphenol (2, CAS 1804908-52-8) (100 g, 0.38 mol), potassium carbonate (80 g, 0.58 mol), tris(dibenzylideneacetone)-dipalladium(0) (1.9 g, 2.0 mmol) and CataCXium A (2.2 g, 5.8 mmol) in THF (500 mL) and distilled water (200 mL) is heated to reflux under nitrogen atmosphere, followed by dropwise addition of a solution of 2,3-difluoro-4-phenylboronic acid (1, CAS 121219-16-7) (70 g, 0.43 mol) in THF (300 mL). The reaction mixture is heated at reflux temperature overnight. Then it is cooled to room temperature and diluted with MTB ether and distilled water. Throughout this application, unless explicitly stated otherwise, room temperature and ambient temperature are used synonymously and signify a temperature of about 20° C., typically (20±1)° C. The aqueous phase is separated and extracted with MTB ether. The combined organic phases are washed with distilled water and brine, dried (sodium sulphate) and concentrated in vacuo. The residue is purified by silica gel chromatography (solvent dichloromethane). 3,2',3'-Trifluoro-4-trifluoromethyl-biphenyl-2-ol (3) is isolated as a brown solid.

Step 2.2: Trifluoromethanesulfonic acid 3,2',3'-trifluoro-4-trifluoromethyl-biphenyl-2-yl ester

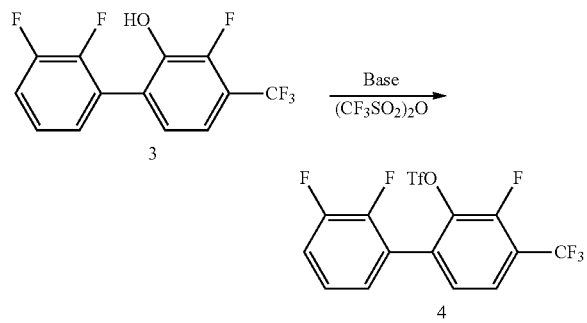

Trifluoromethanesulfonic anhydride (30.0 mL, 0.18 mol) is slowly added to a solution of 3,2',3'-trifluoro-4-trifluoromethyl-biphenyl-2-ol (3) (46.8 g, 0.15 mol), TEA (32 mL, 0.23 mol) and DMAP (600 mg, 4.9 mmol) in dichloromethane (300 mL) at 5° C. under nitrogen atmosphere. The solution is stirred at room temperature overnight. The reaction mixture is purified by silica gel chromatography (solvent dichlormethane) to give trifluoromethanesulfonic acid 3,2',3'-trifluoro-4-trifluoromethyl-biphenyl-2-yl ester (4) as a yellow oil.

Step 2.3: 4,6-Difluoro-3-trifluoromethyl-dibenzothiophene

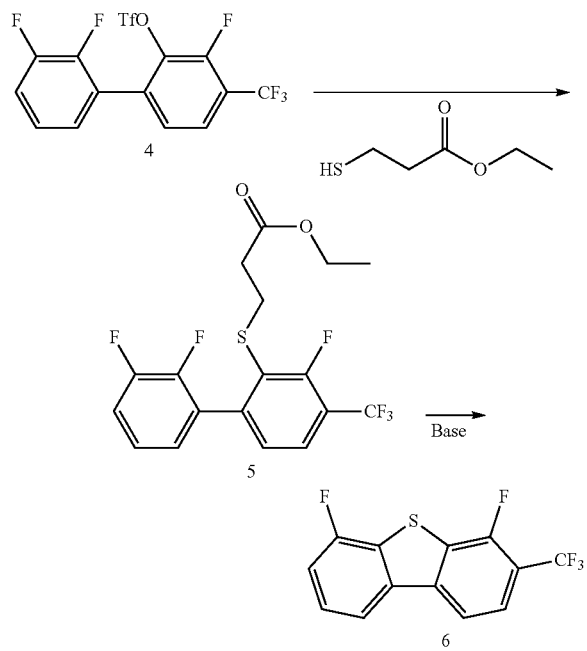

This reaction is performed as a one-pot reaction. In the first step, a solution of trifluoromethanesulfonic acid 3,2',3'-trifluoro-4-trifluoromethyl-biphenyl-2-yl ester (4) (66 g, 0.15 mol) and ethyl 3-mercaptopropionate (24 mL, 0.18 mol) in toluene (500 mL) is heated under nitrogen atmosphere to 80° C. Potassium carbonate (50 g, 0.36 mol), tris(dibenzylideneacetone)dipalladium(0) (7.0 g, 7.3 mmol) and (oxydi-2,1-phenylene)bis(diphenylphosphine) (8.0 g, 14.6 mmol) are quickly added to the solution, and the reaction mixture is heated at reflux temperature overnight. Then it is allowed to cool to room temperature. In the second step, a solution of potassium tert-butylate (18 g, 0.16 mol) in THF (150 mL) is added to the reaction mixture containing intermediate (5) in situ. The reaction mixture is heated at reflux temperature overnight. Then it is cooled to room temperature, quenched with distilled water and hydrochloric acid (25%) at 0° C. and diluted with MTB ether. The aqueous phase is separated and extracted with MTB ether. The combined organic phases are washed with distilled water and brine, dried (sodium sulphate) and concentrated in vacuo. The residue is purified by silica gel chromatography (solvent heptane) to give 4,6-difluoro-3-trifluoromethyl-dibenzothiophene (6) as yellow crystals.

Step 2.4: 1-(4,6-Difluoro-7-trifluoromethyl-dibenzothiophen-3-yl)-4-propyl-cyclohexanol

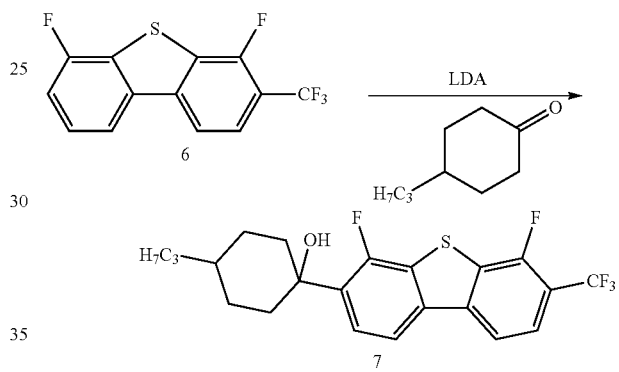

Lithiumdiisopropylamide (6 mL, 2 M in cyclohexane/ethylbenzene/THF, 12 mmol) is added to a solution of 4,6-difluoro-3-trifluoromethyl-dibenzothiophene (6) (3.2 g, 10 mmol) in THF (100 mL) at −70° C. under nitrogen atmosphere. A solution of 4-propylcyclohexanone (1.7 g, 12 mmol) in THF (10 mL) is added after 1 h, and the reaction mixture is stirred for 2 h at −70° C. Then it is allowed to warm to room temperature and is stirred overnight. The reaction is quenched with distilled water and hydrochloric acid (25%) at 0° C. and diluted with MTB ether. The aqueous phase is separated and extracted with MTB ether. The combined organic phases are washed with distilled water and brine, dried (sodium sulphate) and concentrated in vacuo. The residue is purified by silica gel chromatography (solvent dichlormethane) to give 1-(4,6-difluoro-7-trifluoromethyl-dibenzothiophen-3-yl)-4-propyl-cyclohexanol (7) as yellow crystals.

Step 2.5: 4,6-Difluoro-3-(4-propyl-cyclohex-1-enyl)-7-trifluoromethyl-dibenzothiophene

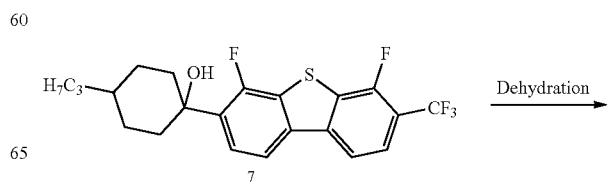

-continued

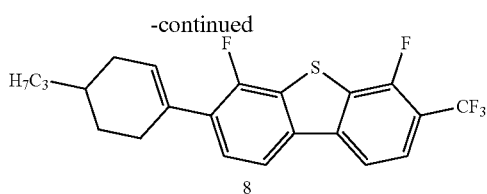

8

A mixture of 1-(4,6-difluoro-7-trifluoromethyl-dibenzothiophen-3-yl)-4-propyl-cyclohexanol (7) (1.2 g, 2.5 mmol) and toluene-4-sulfonic acid monohydrate (50 mg, 0.3 mmol) in toluene (50 mL) is heated in a Dean Stark trap at reflux temperature overnight. Then it is cooled to room temperature and diluted with MTB ether and distilled water. The aqueous phase is separated and extracted with MTB ether. The combined organic phases are washed with distilled water and brine, dried (sodium sulphate) and concentrated in vacuo. The residue is purified by silica gel chromatography (solvent 1-chlorobutane). Subsequent recrystallization of the crude product from heptane results in colorless crystals of 4,6-difluoro-3-(4-propyl-cyclohex-1-enyl)-7-trifluoromethyl-dibenzothiophene.

Compound (7) has the following phase characteristics: K 121° C. SmA 162° C. I.

Synthesis Example 3 (CB(S)-3-T)

Synthesis of 4,6-Difluoro-3-(4-propyl-cyclohexyl)-7-trifluoromethyl-dibenzothiophene

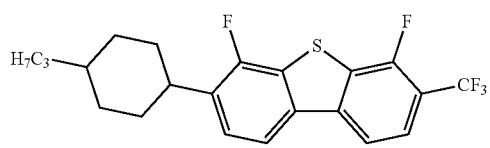

Step 3.1: 3,2',3'-Trifluoro-4'-(4-propyl-cyclohexyl)-4-trifluoromethyl-biphenyl-2-ol

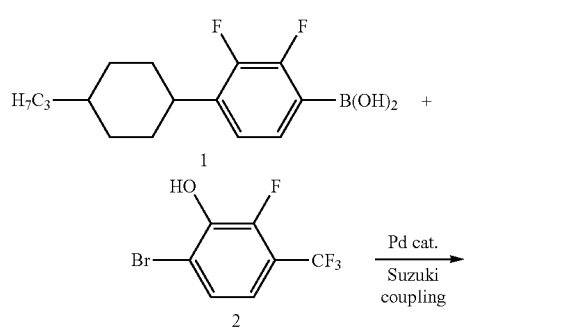

A mixture of 6-bromo-2-fluoro-3-trifluoromethylphenol (2, CAS 1804908-52-8) (7.1 g, 26.9 mmol), potassium carbonate (5.6 g, 40.5 mmol), tris(dibenzylideneacetone)-dipalladium(0) (130 mg, 0.14 mmol) and CataCXium A (150 mg, 0.40 mmol) in THF (50 mL) and distilled water (15 mL) is heated to reflux under nitrogen atmosphere, followed by dropwise addition of a solution of 2,3-difluoro-4-(4-propyl-cyclohexyl)phenylboronic acid (1, CAS 183438-45-1) (7.8 g, 27.2 mmol) in THF (25 mL). The reaction mixture is heated at reflux temperature overnight.

Then it is cooled to room temperature and diluted with MTB ether and distilled water. Throughout this application, unless explicitly stated otherwise, room temperature and ambient temperature are used synonymously and signify a temperature of about 20° C., typically (20±1)° C. The aqueous phase is separated and extracted with MTB ether. The combined organic phases are washed with distilled water and brine, dried (sodium sulphate) and concentrated in vacuo. The residue is purified by silica gel chromatography (solvent 1-chlorobutane/heptane 1:1). 3,2',3'-Trifluoro-4'-(4-propyl-cyclohexyl)-4-trifluoromethyl-biphenyl-2-ol (3) is isolated as a yellow solid.

Step 3.2: Trifluoromethanesulfonic acid 3,2',3'-trifluoro-4'-(4-propyl-cyclohexyl)-4-trifluoromethyl-biphenyl-2-yl ester

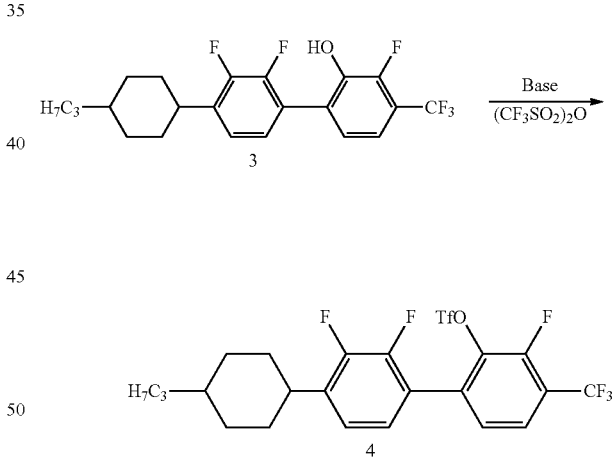

Trifluoromethanesulfonic anhydride (2.8 mL, 17.0 mmol) is slowly added to a solution of 3,2',3'-trifluoro-4'-(4-propyl-cyclohexyl)-4-trifluoromethyl-biphenyl-2-ol (3) (5.5 g, 13.2 mmol), TEA (2.8 mL, 20.2 mmol) and DMAP (50 mg, 0.41 mmol) in dichloromethane (50 mL) at 5° C. under nitrogen atmosphere. The solution is stirred at room temperature overnight. The reaction mixture is purified by silica gel chromatography (solvent dichlormethane) to give trifluoromethanesulfonic acid 3,2',3'-trifluoro-4'-(4-propyl-cyclohexyl)-4-trifluoromethyl-biphenyl-2-yl ester (4) as a yellow oil.

Step 3.3: 4,6-Difluoro-3-(4-propyl-cyclohexyl)-7-trifluoromethyl-dibenzothiophene

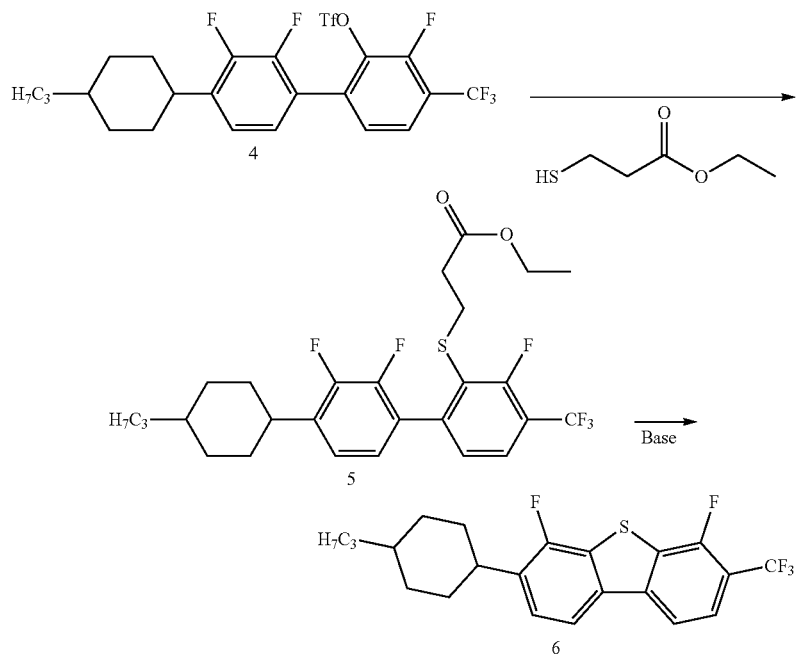

This reaction is performed as a one-pot reaction. In the first step, a solution of trifluoromethanesulfonic acid 3,2',3'-trifluoro-4'-(4-propyl-cyclohexyl)-4-trifluoromethyl-biphenyl-2-yl ester (4) (7.3 g, 13.1 mmol) and ethyl 3-mercaptopropionate (2.2 mL, 16.7 mmol) in toluene (70 mL) is quickly heated under nitrogen atmosphere to 80° C. Potassium carbonate (5.0 g, 36.2 mmol), tris(dibenzylideneacetone)dipalladium(0) (0.7 g, 0.73 mmol) and (oxydi-2,1-phenylene)bis(diphenylphosphine) (0.8 g, 1.46 mmol) are quickly added to the solution, and the reaction mixture is heated at reflux temperature overnight. Then it is allowed to cool to room temperature. In the second step, a solution of potassium tert-butylate (1.8 g, 16.0 mmol) in THF (20 mL) is added to the reaction mixture containing intermediate (5) in situ. The reaction mixture is heated at reflux temperature overnight, followed by addition of a second portion of a solution of potassium tert-butylate (1.8 g, 16.0 mmol) in THF (20 mL). The reaction mixture is heated at reflux temperature overnight. Then it is cooled to room temperature, quenched with distilled water and hydrochloric acid (25%) at 0° C. and diluted with MTB ether. The aqueous phase is separated and extracted with MTB ether. The combined organic phases are washed with distilled water and brine, dried (sodium sulphate) and concentrated in vacuo. The residue is purified by silica gel chromatography (solvent heptane) to give 4,6-difluoro-3-(4-propyl-cyclohexyl)-7-trifluoromethyl-dibenzothiophene (6) as yellowish crystals.

Compound (6) has the following phase characteristics:
K 150° C. N (139° C.) I

Synthesis Example 3a (CB(S)-3-T)

Alternatively, 4,6-Difluoro-3-(4-propyl-cyclohexyl)-7-trifluoromethyl-dibenzothiophene is obtained by hydrogenation of 4,6-Difluoro-3-(4-propyl-cyclohex-1-enyl)-7-trifluoromethyl-dibenzothiophene:

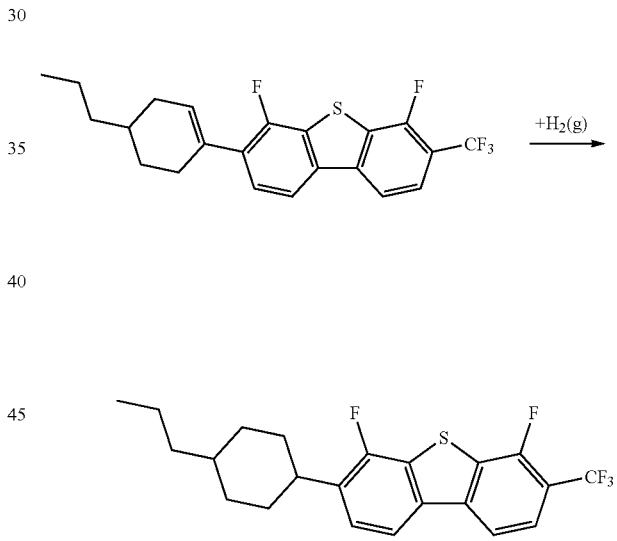

Synthesis Example 4 (CB(S)-3-OT)

Synthesis of 4,6-Difluoro-3-(4-propyl-cyclohexyl)-7-trifluoromethoxy-dibenzothiophene

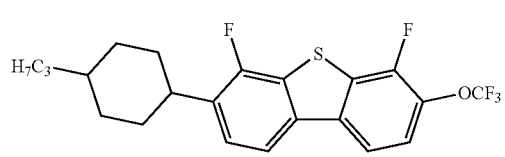

Step 4.1: 3,2',3'-Trifluoro-4'-(4-propyl-cyclohexyl)-4-trifluoromethoxy-biphenyl-2-ol

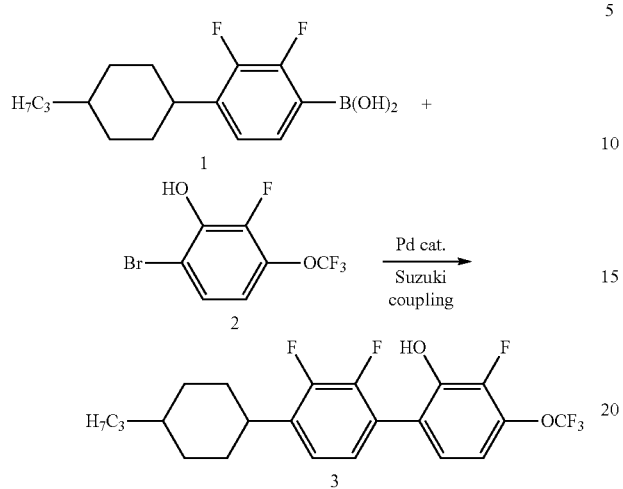

A mixture of 6-bromo-2-fluoro-3-trifluoromethoxyphenol (2, CAS 1805580-01-1) (33.0 g, 0.12 mol), potassium carbonate (25.0 g, 0.18 mol), tris(dibenzylideneacetone)-dipalladium(0) (600 mg, 0.6 mmol) and CataCXium A (700 mg, 1.9 mmol) in THF (250 mL) and distilled water (75 mL) is heated to reflux under nitrogen atmosphere, followed by dropwise addition of a solution of 2,3-difluoro-4-(4-propylcyclohexyl)-phenylboronic acid (1, CAS 183438-45-1) (34.4 g, 0.12 mol) in THF (100 mL). The reaction mixture is heated at reflux temperature overnight. Then it is cooled to room temperature and diluted with MTB ether and distilled water. Throughout this application, unless explicitly stated otherwise, room temperature and ambient temperature are used synonymously and signify a temperature of about 20° C., typically (20±1)° C. The aqueous phase is separated and extracted with MTB ether. The combined organic phases are washed with distilled water and brine, dried (sodium sulphate) and concentrated in vacuo. The residue is purified by silica gel chromatography (solvent 1-chlorobutane/heptane 1:1). 3,2',3'-Trifluoro-4'-(4-propyl-cyclohexyl)-4-trifluoromethoxy-biphenyl-2-ol (3) is isolated as a yellow solid.

Step 4.2: Trifluoromethanesulfonic acid 3,2',3'-trifluoro-4'-(4-propyl-cyclohexyl)-4-trifluoromethoxy-biphenyl-2-yl ester

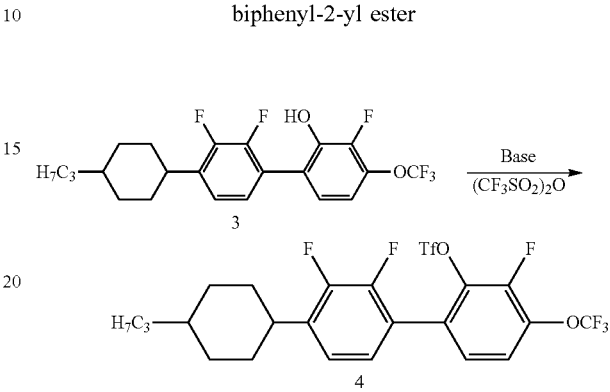

Trifluoromethanesulfonic anhydride (6.0 mL, 36.4 mmol) is slowly added to a solution of 3,2',3'-trifluoro-4'-(4-propyl-cyclohexyl)-4-trifluoromethoxy-biphenyl-2-ol (3) (12.6 g, 29.0 mmol), TEA (6.3 mL, 45.4 mmol) and DMAP (110 mg, 0.9 mmol) in dichloromethane (100 mL) at 5° C. under nitrogen atmosphere. The solution is stirred at room temperature overnight. The reaction mixture is purified by silica gel chromatography (solvent dichlormethane) to give trifluoromethanesulfonic acid 3,2',3'-trifluoro-4'-(4-propyl-cyclohexyl)-4-trifluoromethoxy-biphenyl-2-yl ester (4) as a yellow oil.

Step 4.3: 4,6-Difluoro-3-(4-propyl-cyclohexyl)-7-trifluoromethoxy-dibenzothiophene

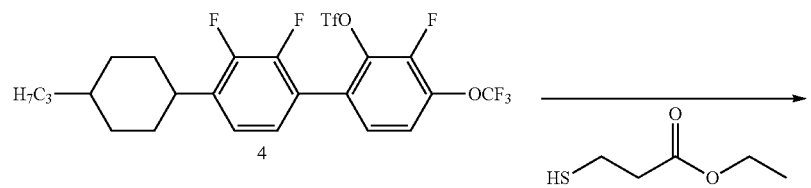

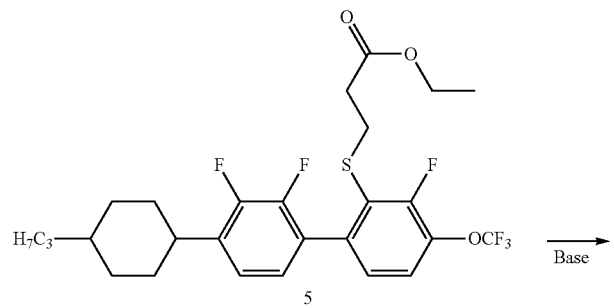

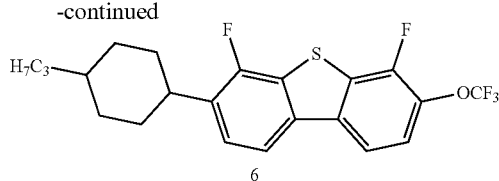

This reaction is performed as a one-pot reaction. In the first step, a solution of trifluoromethanesulfonic acid 3,2',3'-trifluoro-4'-(4-propyl-cyclohexyl)-4-trifluoromethoxy-biphenyl-2-yl ester (4) (16.3 g, 28.1 mmol) and ethyl 3-mercaptopropionate (5.0 mL, 37.9 mmol) in toluene (150 mL) is quickly heated under nitrogen atmosphere to 80° C. Potassium carbonate (10 g, 72.4 mmol), tris(dibenzylideneacetone)dipalladium(0) (1.4 g, 1.5 mmol) and (oxydi-2,1-phenylene)bis(diphenylphosphine) (1.6 g, 2.9 mmol) are quickly added to the solution, and the reaction mixture is heated at reflux temperature overnight. Then it is allowed to cool to room temperature. In the second step, a solution of potassium tert-butylate (3.5 g, 31.2 mmol) in THF (50 mL) is added to the reaction mixture containing intermediate (5) in situ. The reaction mixture is heated at reflux temperature overnight, followed by addition of a second portion of a solution of potassium tert-butylate (3.5 g, 31.2 mmol) in THF (50 mL). The reaction mixture is heated at reflux temperature overnight. Then it is cooled to room temperature, quenched with distilled water and hydrochloric acid (25%) at 0° C. and diluted with MTB ether. The aqueous phase is separated and extracted with MTB ether. The combined organic phases are washed with distilled water and brine, dried (sodium sulphate) and concentrated in vacuo. The residue is purified by silica gel chromatography (solvent heptane) to give 4,6-difluoro-3-(4-propyl-cyclohexyl)-7-trifluoromethoxy-dibenzothiophene (6) as colorless crystals.

Compound (6) has the following phase characteristics:
K 108° C. SmA 141° C. N 169° C. I Synthesis Example 4a (CB(S)-3-OT)

Alternatively, 4,6-Difluoro-3-(4-propyl-cyclohexyl)-7-trifluoromethoxy-dibenzothiophene is obtained by hydrogenation of 4,6-Difluoro-3-(4-propyl-cyclohex-1-enyl)-7-trifluoromethoxy-dibenzothiophene:

COMPOUND EXAMPLES

Exemplary compounds having a high dielectric constant perpendicular to the director ($\varepsilon_\perp$) and a high average dielectric constant ($\varepsilon_{av.}$) are exemplified in the following compound examples.

Compound Examples 1 to 6

Compounds of formula S-1 are e.g.

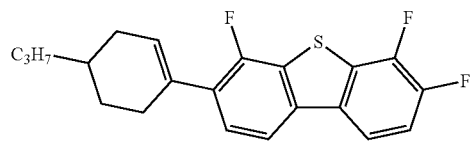

This compound (LB(S)-3-F) has a melting point of 133° C., a clearing point of 155.3° C., a phase range of K 133° C. N 155.3° C. I and a $\Delta\varepsilon$ of +1.3.

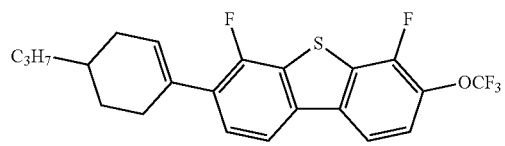

This compound (LB(S)-3-OT), the compound of synthesis example 2, has a melting point of 66° C., a clearing point of 181° C., a phase range of K 66° C. $S_A$ 181° C. I and a $\Delta\varepsilon$ of +4.7.

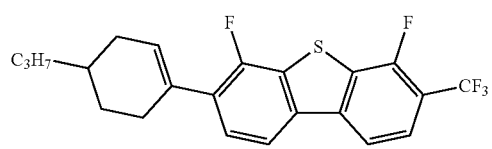

Compounds of formula S-2 are e.g.

This compound (LB(S)-3-T) has a melting point of 121° C., a clearing point of 162° C., a phase range of 121° C. $S_A$ 162° C. I and a $\Delta\varepsilon$ of +7.8.

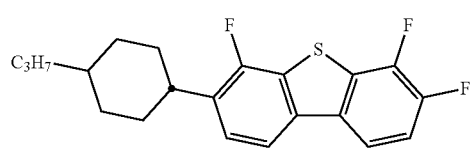

This compound (CB(S)-3-F) has a melting point of 157° C., a clearing point of 170.3° C., a phase range of K 157° C. N 170.3 I.

This compound (CB(S)-3-OT), the compound of synthesis example 2, has a melting point of 108° C., a clearing point of 168.5° C., a phase range of K 108° C. $S_A$ 141° C. N 168.5° C. I and a Δε of +4.5.

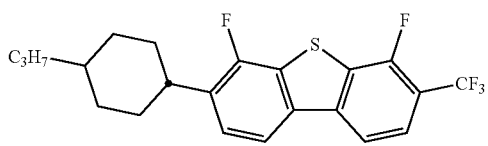

This compound (CB(S)-3-T) has a melting point of 150° C., a (monotropic) clearing point of 138.8° C., a phase range of K 150° C. N (138.8° C.) I and a Δε of +8.1.

Analogously the following compounds of formula S are prepared

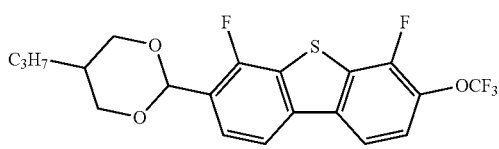

This compound (DB(S)-3-OT) has a melting point of 153° C., a clearing point of 174.1° C. and a phase range of K 153° C. $S_A$ 165° C. N 174.1° C. I.

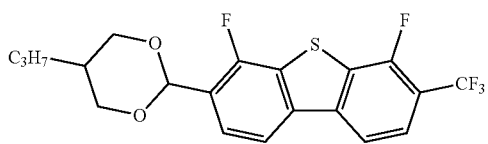

This compound (DB(S)-3-OT) has a melting point of 146° C., a clearing point of 168° C. and a phase range of K 146° C. $S_A$ 168° C. I.

Analogously the following compounds of formula S-1 are prepared

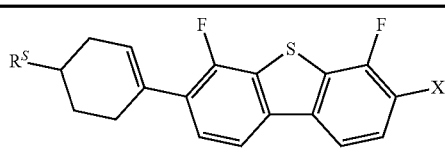

| $R^S$ | $X^S$ | Phase range | Δε |
|---|---|---|---|
| CH$_3$ | F | | |
| C$_2$H$_5$ | F | | |
| C$_3$H$_7$ (see above) | F | K 133 N 155.3 I | 1.5 |
| C$_4$H$_9$ | F | | |
| C$_5$H$_{11}$ | F | | |
| C$_6$H$_{13}$ | F | | |
| C$_7$H$_{15}$ | F | | |
| CH$_2$=CH | F | | |
| CH$_2$=CH—CH$_2$ | F | | |
| CH$_2$=CH—[CH$_2$]$_2$ | F | | |
| CH$_3$—CH$_2$=CH | F | | |
| CH$_3$—CH$_2$=CH—[CH$_2$]$_2$ | F | | |
| CH$_3$ | OCF$_3$ | K 82 SmA 156 I | |
| C$_2$H$_5$ | OCF$_3$ | K 71 SmA 169 I | 4.5 |
| C$_3$H$_7$ (see above) | OCF$_3$ | K 108 SmA 141 N 168.5 I | 4.5 |
| C$_4$H$_9$ | OCF$_3$ | K 64 SmA 177 I | 4.2 |
| C$_5$H$_{11}$ | OCF$_3$ | K 83 SmA 170 I | t.b.d. |
| C$_6$H$_{13}$ | OCF$_3$ | | |
| C$_7$H$_{15}$ | OCF$_3$ | K 80 SmA 167 I | 3.7 |
| CH$_2$=CH | OCF$_3$ | | |
| CH$_2$=CH—CH$_2$ | OCF$_3$ | | |
| CH$_2$=CH—[CH$_2$]$_2$ | OCF$_3$ | | |
| CH$_3$—CH$_2$=CH | OCF$_3$ | | |
| CH$_3$—CH$_2$=CH—[CH$_2$]$_2$ | OCF$_3$ | | |
| CH$_3$ | CF$_3$ | | |
| C$_2$H$_5$ | CF$_3$ | K 121 155 I | 8.8 |
| C$_3$H$_7$ (see above) | CF$_3$ | K 121 $S_A$ 162 I | 7.8 |
| C$_4$H$_9$ | CF$_3$ | | |
| C$_5$H$_{11}$ | CF$_3$ | | |
| C$_6$H$_{13}$ | CF$_3$ | | |
| C$_7$H$_{15}$ | CF$_3$ | | |
| CH$_2$=CH | CF$_3$ | | |
| CH$_2$=CH—CH$_2$ | CF$_3$ | | |
| CH$_2$=CH—[CH$_2$]$_2$ | CF$_3$ | | |
| CH$_3$—CH$_2$=CH | CF$_3$ | | |
| CH$_3$—CH$_2$=CH—[CH$_2$]$_2$ | CF$_3$ | | |

Analogously the following compounds of formula S-2 are prepared

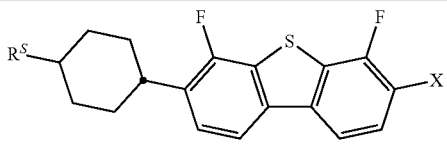

| $R^S$ | $X^S$ | Phase range | Δε |
|---|---|---|---|
| CH$_3$ | F | | |
| C$_2$H$_5$ | F | | |
| C$_3$H$_7$ (see above) | F | K 157 N 170.3 I | |
| C$_4$H$_9$ | F | | |
| C$_5$H$_{11}$ | F | | |
| C$_6$H$_{13}$ | F | | |
| C$_7$H$_{15}$ | F | | |
| CH$_2$=CH | F | | |
| CH$_2$=CH—CH$_2$ | F | | |
| CH$_2$=CH—[CH$_2$]$_2$ | F | | |
| CH$_3$—CH$_2$=CH | F | | |
| CH$_3$—CH$_2$=CH—[CH$_2$]$_2$ | F | | |
| CH$_3$ | OCF$_3$ | | |
| C$_2$H$_5$ | OCF$_3$ | | 4.5 |
| C$_3$H$_7$ (see above) | OCF$_3$ | K 108 $S_A$ 141 N 168.5 I | 4.5 |
| C$_4$H$_9$ | OCF$_3$ | | |
| C$_5$H$_{11}$ | OCF$_3$ | | |
| C$_6$H$_{13}$ | OCF$_3$ | | |
| C$_7$H$_{15}$ | OCF$_3$ | | |
| CH$_2$=CH | OCF$_3$ | | |
| CH$_2$=CH—CH$_2$ | OCF$_3$ | | |
| CH$_2$=CH—[CH$_2$]$_2$ | OCF$_3$ | | |
| CH$_3$—CH$_2$=CH | OCF$_3$ | | |
| CH$_3$—CH$_2$=CH—[CH$_2$]$_2$ | OCF$_3$ | | |

-continued
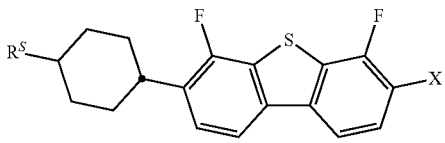
| $R^S$ | $X^S$ | Phase range | Δε |
|---|---|---|---|
| $CH_3$ | $CF_3$ | | |
| $C_2H_5$ | $CF_3$ | | |
| $C_3H_7$ (see above) | $CF_3$ | K 150 N (138.8) I | 8.1 |
| $C_4H_9$ | $CF_3$ | | |
| $C_5H_{11}$ | $CF_3$ | | |
| $C_6H_{13}$ | $CF_3$ | | |
| $C_7H_{15}$ | $CF_3$ | | |
| $CH_2{=}CH$ | $CF_3$ | | |
| $CH_2{=}CH{-}CH_2$ | $CF_3$ | | |
| $CH_2{=}CH{-}[CH_2]_2$ | $CF_3$ | | |
| $CH_3{-}CH{=}CH$ | $CF_3$ | | |
| $CH_3{-}CH_2{=}CH{-}[CH_2]_2$ | $CF_3$ | | |
Further compound examples
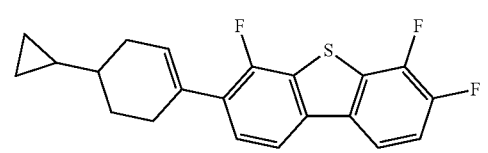
(LB(S)-c3-F)
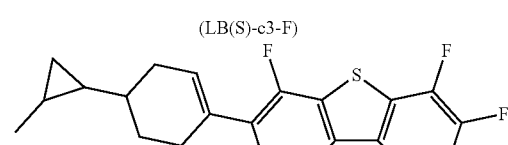
(LB(S)-1c3-F)
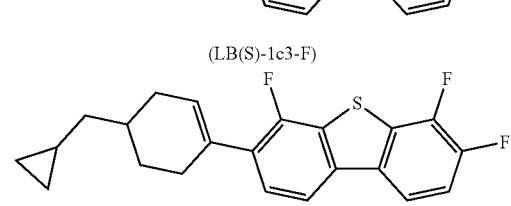
(LB(S)-c3.1-F)
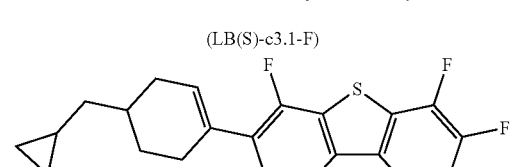
(LB(S)-c3(en)-F)
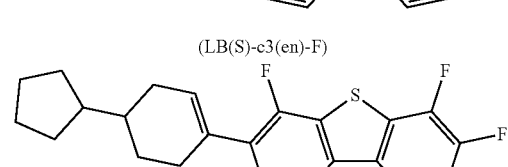
(LB(S)-c5-F)
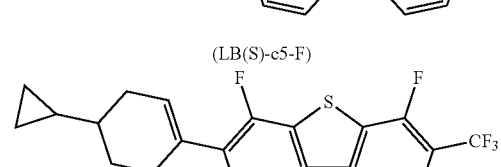
(LB(S)-c3-T)
-continued
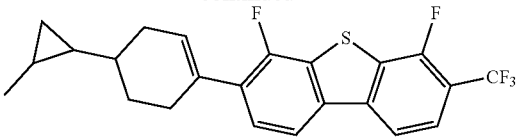
(LB(S)-1c3-T)
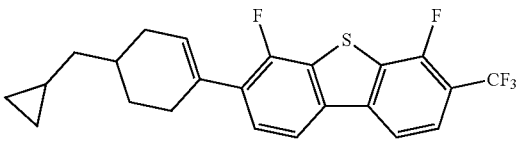
(LB(S)-c3.1-T)
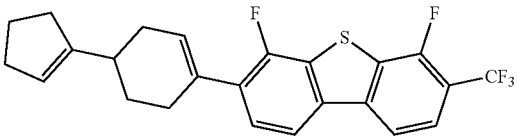
(LB(S)-c5(en)-T)
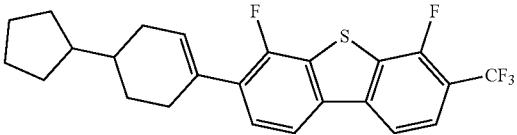
(LB(S)-c5-T)
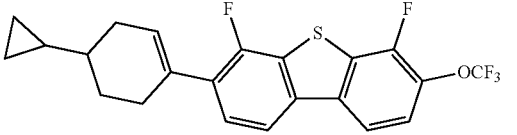
(LB(S)-c3-OT)
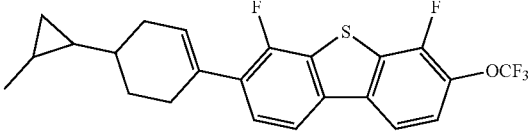
(LB(S)-1c3-OT)
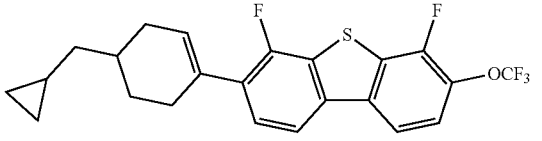
(LB(S)-c3.1-OT)
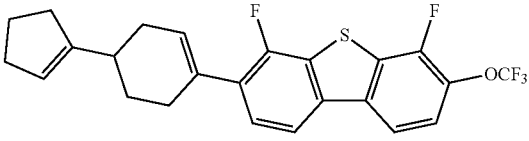
(LB(S)-c5(en)-OT)
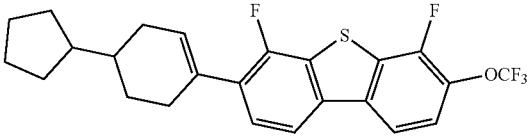
(LB(S)-c5-OT)

MIXTURE EXAMPLES

In the following are exemplary mixtures disclosed.

Example 1

The following mixture (M-1) is prepared and investigated.

Mixture 1

Composition

| No. | Compound Abbreviation | Concentration /% by weight |
|---|---|---|
| 1 | LB(S)-3-OT | 6.0 |
| 2 | CC-3-V | 37.0 |
| 3 | CC-3-V1 | 4.0 |
| 4 | CCP-V-1 | 12.0 |
| 5 | CCP-V2-1 | 1.5 |
| 6 | CLP-V-1 | 7.0 |
| 7 | PP-1-2V1 | 2.5 |
| 8 | PGP-1-2V | 3.0 |
| 9 | PGP-2-2V | 5.0 |
| 10 | CCVC-3-V | 4.0 |
| 11 | CPGP-5-3 | 3.0 |
| 12 | CPGU-3-OT | 4.0 |
| 13 | PPGU-3-F | 0.5 |
| 14 | PUQU-3-F | 6.0 |
| 15 | APUQU-3-F | 2.0 |
| 16 | CDUQU-3-F | 2.5 |
| Σ | | 100.0 |

Physical properties

| | |
|---|---|
| $T(N, I) =$ | 103.5° C. |
| $n_e(20°\ C., 589\ nm) =$ | 1.6096 |
| $\Delta n(20°\ C., 589\ nm) =$ | 0.1186 |
| $\varepsilon_\parallel(20°\ C., 1\ kHz) =$ | 6.7 |
| $\varepsilon_\perp(20°\ C., 1\ kHz) =$ | 3.0 |
| $\Delta\varepsilon(20°\ C., 1\ kHz) =$ | 3.7 |
| $\varepsilon_{av.}(20°\ C., 1\ kHz) =$ | 4.3 |
| $\gamma_1(20°\ C.) =$ | 81 mPa · s |
| $k_{11}(20°\ C.) =$ | 17.3 pN |
| $k_{33}(20°\ C.) =$ | 18.3 pN |
| $V_0(20°\ C.) =$ | 2.28 V |

This mixture, mixture M-1, has a dielectric ratio ($\varepsilon_\perp/\Delta\varepsilon$) of 0.81, a ratio of ($\gamma_1/k_{11}$) of 4.68 mPa·s/pN and is characterized by a very good transmission in an FFS display and shows a very short response time.

Comparative Example A

The following mixture (CE-A) is prepared and investigated.

Mixture CE-A

Composition

| No. | Compound Abbreviation | Concentration /% by weight |
|---|---|---|
| 1 | CC-3-V | 31.5 |
| 2 | CC-3-V1 | 6.5 |
| 3 | CCP-3-3 | 6.0 |
| 4 | CCP-V-1 | 12.0 |
| 5 | CCP-V2-1 | 12.0 |
| 6 | PP-1-2V1 | 5.0 |
| 7 | CPGP-5-2 | 2.0 |
| 8 | PUQU-3-F | 20.0 |
| 9 | APUQU-2-F | 5.0 |
| Σ | | 100.0 |

Physical properties

| | |
|---|---|
| $T(N, I) =$ | 78.5° C. |
| $n_e(20°\ C., 589\ nm) =$ | 1.5876 |
| $\Delta n(20°\ C., 589\ nm) =$ | 0.1001 |
| $\varepsilon_\perp(20°\ C., 1\ kHz) =$ | 3.0 |
| $\Delta\varepsilon(20°\ C., 1\ kHz) =$ | 6.0 |
| $\varepsilon_{av.}(20°\ C., 1\ kHz) =$ | 5.0 |
| $\gamma_1(20°\ C.) =$ | 64 mPa · s |
| $k_{11}(20°\ C.) =$ | 13.3 pN |
| $k_{33}(20°\ C.) =$ | 15.5 pN |
| $V_0(20°\ C.) =$ | 1.58 V |
| $V_{10}(20°\ C.) =$ | 2.13 V |

This comparative mixture, mixture A, has a dielectric ratio ($\varepsilon_\perp/\Delta\varepsilon$) of 0.50, a ratio of ($\gamma_1/k_{11}$) of 4.81 mPa·s/pN and is characterized a moderately good transmission in an FFS display and shows an at best acceptable short response time.

TABLE 1

| Example | CE-A | A-1 | A-2 | A-3 |
|---|---|---|---|---|
| Composition | | | | |
| Cpd. | None | LB(S)-3-F | LB(S)-3-OT | LB(S)-3-T |
| c(Cpd.)/% | 0.0 | 5.0 | 10.0 | 10.0 |
| c(CE-A)/% | 100.0 | 95.0 | 90.0 | 90.0 |
| Properties | | | | |
| $T(N, I)/°\ C.$ | 78.5 | t.b.d. | 84.5 | t.b.d. |
| $n_e(589\ nm)$ | 1.5875 | t.b.d. | 1.5994 | t.b.d. |
| $\Delta n(589\ nm)$ | 0.1001 | t.b.d. | 0.1107 | t.b.d. |
| $\varepsilon_\parallel(1\ kHz)$ | 9.0 | t.b.d. | 9.4 | t.b.d. |
| $\varepsilon_\perp(1\ kHz)$ | 3.0 | t.b.d. | 3.5 | t.b.d. |
| $\Delta\varepsilon(1\ kHz)$ | 6.0 | t.b.d. | 5.9 | t.b.d. |
| $\varepsilon_{av.}(1\ kHz)$ | 5.0 | t.b.d. | 5.5 | t.b.d. |
| $\gamma_1/mPa · s$ | 64 | t.b.d. | 76 | t.b.d. |
| $k_{11}/pN$ | 13.3 | t.b.d. | 14.9 | t.b.d. |
| $k_{33}/pN)$ | 15.5 | t.b.d. | 16.0 | t.b.d. |
| $\gamma_1/k_{11}$ * | 4.81 | t.b.d. | 5.10 | t.b.d. |
| $V_0/V$ | 1.77 | t.b.d. | 1.68 | t.b.d. |

Remarks:
all values (except clearing point) at 20° C.,
* [mPa · s/pN] and
t.b.d.: to be determined.

| Example | CE-A | A-4 | A-5 | A-6 |
|---|---|---|---|---|
| Composition | | | | |
| Cpd. | None | CB(S)-3-F | CB(S)-3-OT | CB(S)-3-T |
| c(Cpd.)/% | 0.0 | 10.0 | 10.0 | 10.0 |
| c(CE-A)/% | 100.0 | 90.0 | 90.0 | 90.0 |
| Properties | | | | |
| $T(N, I)/°\ C.$ | 78.5 | t.b.d. | 85.0 | t.b.d. |
| $n_e(589\ nm)$ | 1.5875 | t.b.d. | 1.5952 | t.b.d. |
| $\Delta n(589\ nm)$ | 0.1001 | t.b.d. | 0.1076 | t.b.d. |
| $\varepsilon_\parallel(1\ kHz)$ | 9.0 | t.b.d. | 9.3 | t.b.d. |
| $\varepsilon_\perp(1\ kHz)$ | 3.0 | t.b.d. | 3.5 | t.b.d. |
| $\Delta\varepsilon(1\ kHz)$ | 6.0 | t.b.d. | 5.8 | t.b.d. |
| $\varepsilon_{av.}(1\ kHz)$ | 5.0 | t.b.d. | 5.4 | t.b.d. |
| $\gamma_1/mPa · s$ | 64 | t.b.d. | 74 | t.b.d. |
| $k_{11}/pN$ | 13.3 | t.b.d. | 14.3 | t.b.d. |
| $k_{33}/pN)$ | 15.5 | t.b.d. | 16.1 | t.b.d. |

TABLE 1-continued

| | | | | |
|---|---|---|---|---|
| $\gamma_1/k_{11}$* | 4.81 | t.b.d. | 5.17 | t.b.d. |
| $V_0$/V | 1.77 | t.b.d. | 1.65 | t.b.d. |

Remarks:
all values (except clearing point) at 20° C.,
* [mPa · s/pN] and
t.b.d.: to be determined.

| Example | A-7 | A-8 | A-9 | A-10 |
|---|---|---|---|---|
| | Composition | | | |
| Cpd. | LB(S)-2-OT | LB(S)-4-OT | LB(S)-5-OT | LB(S)-6-OT |
| c(Cpd.)/% | 10.0 | 10.0 | 10.0 | 10.0 |
| c(Host A)/% | 90.0 | 90.0 | 90.0 | 90.0 |
| | Properties | | | |
| T(N, I)/° C. | 83.0 | 84.5 | 85.0 | 84.5 |
| $n_e$(589 nm) | 1.5991 | 1.5987 | 1.5982 | 1.5972 |
| $\Delta n$(589 nm) | 0.1101 | 0.1100 | 0.1099 | 0.1088 |
| $\varepsilon_\parallel$(1 kHz) | 9.4 | 9.4 | 9.3 | 9.2 |
| $\varepsilon_\perp$(1 kHz) | 3.5 | 3.5 | 3.5 | 3.5 |
| $\Delta\varepsilon$(1 kHz) | 5.9 | 5.9 | 5.8 | 5.8 |
| $\varepsilon_{av.}$(1 kHz) | 5.5 | 5.5 | 5.4 | 5.4 |
| $\gamma_1$/mPa · s | 72 | 74 | 77 | 77 |
| $k_{11}$/pN | 14.8 | 14.5 | 14.8 | 14.5 |
| $k_{33}$/pN | 15.4 | 15.7 | 16.0 | 15.5 |
| $\gamma_1/k_{11}$* | 4.86 | 5.10 | 5.20 | 5.31 |
| $V_0$/V | 1.68 | 1.66 | 1.68 | 1.66 |

Remarks:
all values (except clearing point) at 20° C. and
* [mPa · s/pN].

| Example | A-11 | A-12 | A-13 | A-14 |
|---|---|---|---|---|
| | Composition | | | |
| Cpd. | LB(S)-1-OT | LB(S)-2-T | DB(S)-3-OT | DB(S)-3-T |
| c(Cpd.)/% | 10.0 | 10.0 | 5.0 | 5.0 |
| c(CE-A)/% | 90.0 | 90.0 | 95.0 | 95.0 |
| | Properties | | | |
| T(N, I)/° C. | 81.0 | 83.0 | 83.5 | 81.0 |
| $n_e$(589 nm) | 1.5989 | 1.5991 | t.b.d. | t.b.d. |
| $\Delta n$(589 nm) | 0.1101 | 0.1101 | t.b.d. | t.b.d. |
| $\varepsilon_\parallel$(1 kHz) | 9.5 | 9.4 | t.b.d. | t.b.d. |
| $\varepsilon_\perp$(1 kHz) | 3.6 | 3.5 | t.b.d. | t.b.d. |
| $\Delta\varepsilon$(1 kHz) | 6.0 | 5.9 | t.b.d. | t.b.d. |
| $\varepsilon_{av.}$(1 kHz) | 5.6 | 5.5 | t.b.d. | t.b.d. |
| $\gamma_1$/mPa · s | 71 | 72 | t.b.d. | t.b.d. |
| $k_{11}$/pN | 14.6 | 14.8 | t.b.d. | t.b.d. |
| $k_{33}$/pN | 15.2 | 14.8 | t.b.d. | t.b.d. |
| $\gamma_1/k_{11}$* | 4.86 | 4.86 | t.b.d. | t.b.d. |
| $V_0$/V | 1.64 | 1.68 | t.b.d. | t.b.d. |

Remarks:
all values (except clearing point) at 20° C.,
* [mPa · s/pN] and
t.b.d.: to be determined.

Comparative Example B

The following mixture (CE-B) is prepared and investigated.

| Mixture CE-B | | |
|---|---|---|
| Composition | | |
| | Compound | Concentration |
| No. | Abbreviation | /% by weight |
| 1 | CC-3-5 | 20.0 |
| 2 | CP-5-3 | 10.0 |
| 3 | CCP-3-OT | 10.0 |
| 4 | CCP-5-OT | 10.0 |
| 5 | CCU-2-F | 12.0 |
| 6 | CCU-3-F | 10.0 |
| 7 | CCU-5-F | 8.0 |
| 8 | CCEG-3-F | 10.0 |
| 9 | CCEG-5-F | 10.0 |
| Σ | | 100.0 |
| Physical properties | | |
| T(N, I) = | | 74.0° C. |
| $n_e$(20° C., 589 nm) = | | 1.5484 |
| $\Delta n$(20° C., 589 nm) = | | 0.0730 |
| $\varepsilon_\perp$(20° C., 1 kHz) = | | 3.2 |
| $\Delta\varepsilon$(20° C., 1 kHz) = | | 5.4 |
| $\varepsilon_{av.}$(20° C., 1 kHz) = | | 5.0 |
| $\gamma_1$(20° C.) = | | 114 mPa · s |
| $k_{11}$(20° C.) = | | 12.6 pN |
| $k_{33}$(20° C.) = | | 15.6 pN |
| $V_0$(20° C.) = | | 1.62 V |
| $V_{10}$(20° C.) = | | 1.87 V |

TABLE 2

| Example | CE-B | B-1 | B-2 | B-3 |
|---|---|---|---|---|
| | Composition | | | |
| Cpd. | None | LB(S)-1-OT | LB(S)-3-OT | LB(S)-5-OT |
| c(Cpd.)/% | 0 | 20.0 | 20.0 | 20.0 |
| c(Host A)/% | 100 | 88.0 | 80.0 | 80.0 |
| | Properties | | | |
| T(N, I)/° C. | 74.0 | 83.0 | 86.0 | 85.0 |
| $n_e$(589 nm) | 1.5484 | t.b.d. | t.b.d. | t.b.d. |
| $\Delta n$(589 nm) | 0.0730 | t.b.d. | t.b.d. | t.b.d. |
| $\varepsilon_\perp$(1 kHz) | 3.2 | t.b.d. | t.b.d. | t.b.d. |
| $\Delta\varepsilon$(1 kHz) | 5.4 | t.b.d. | t.b.d. | t.b.d. |
| $\varepsilon_{av.}$(1 kHz) | 5.0 | t.b.d. | t.b.d. | t.b.d. |
| $\varepsilon_\perp/\Delta\varepsilon$(1 kHz) | 0.59 | t.b.d. | t.b.d. | t.b.d. |
| $\gamma_1$/mPa · s | 114 | t.b.d. | t.b.d. | t.b.d. |
| $k_{11}$/pN | 12.6 | t.b.d. | t.b.d. | t.b.d. |
| $k_{33}$/pN | 15.6 | t.b.d. | t.b.d. | t.b.d. |
| $\gamma_1/k_{11}$* | 9.05 | t.b.d. | t.b.d. | t.b.d. |
| $V_0$/V | 1.62 | t.b.d. | t.b.d. | t.b.d. |
| $V_{10}$/V | 1.87 | t.b.d. | t.b.d. | t.b.d. |

Remarks:
all extrapolated values at 20° C.,
* [mPa · s/pN] and
t.b.d.: to be determined.

Example 2

The following mixture (M-2) is prepared and investigated.

| Mixture 2 | | |
|---|---|---|
| Composition | | |
| | Compound | Concentration |
| No. | Abbreviation | /% by weight |
| 1 | LB(S)-3-OT | 4.0 |
| 2 | B-2O-O5 | 1.0 |
| 3 | B(S)-2O-O5 | 3.0 |
| 4 | CC-3-V | 31.5 |
| 5 | CC-3-V1 | 7.0 |
| 6 | CP-3-O2 | 5.0 |
| 7 | CCP-V-1 | 10.0 |
| 8 | CCP-V2-1 | 5.0 |

-continued

| Mixture 2 | | |
|---|---|---|
| 9 | CLP-V-1 | 5.0 |
| 10 | PGP-1-2V | 4.0 |
| 11 | CCVC-3-V | 5.0 |
| 12 | CCP-3-OT | 4.5 |
| 13 | DPGU-4-F | 3.0 |
| 14 | CDUQU-3-F | 2.0 |
| 15 | APUQU-2-F | 2.0 |
| 16 | APUQU-3-F | 3.0 |
| 17 | DGUQU-4-F | 5.0 |
| Σ | | 100.0 |

| Physical properties | |
|---|---|
| T(N, I) = | 104.0° C. |
| $n_e$(20° C., 589 nm) = | 1.5910 |
| Δn(20° C., 589 nm) = | 0.1053 |
| $\varepsilon_\parallel$(20° C., 1 kHz) = | 8.0 |
| $\varepsilon_\perp$(20° C., 1 kHz) = | 3.6 |
| Δε(20° C., 1 kHz) = | 4.4 |
| $\varepsilon_{av.}$(20° C., 1 kHz) = | 5.1 |
| $\gamma_1$(20° C.) = | 85 mPa · s |
| $k_{11}$(20° C.) = | 17.6 pN |
| $k_{33}$(20° C.) = | 18.6 pN |
| $V_0$(20° C.) = | 2.10 V |

This mixture, mixture M-2, has a dielectric ratio ($\varepsilon_\perp/\Delta\varepsilon$) of 0.77, a ratio of ($\gamma_1/k_{11}$) of 4.83 mPa·s/pN and is characterized by a good transmission in an FFS display and shows a short response time.

Example 3

The following mixture (M-3) is prepared and investigated.

| Mixture 3 | | |
|---|---|---|
| Composition | | |
| Compound | | Concentration |
| No. | Abbreviation | /% by weight |
| 1 | LB(S)-3-OT | 5.0 |
| 2 | B(S)-2O-O4 | 1.0 |
| 3 | B(S)-2O-O5 | 2.0 |
| 4 | CC-3-V | 33.0 |
| 5 | CC-3-V1 | 7.5 |
| 6 | CP-3-O2 | 5.0 |
| 7 | CCP-V-1 | 9.0 |
| 8 | CCP-V2-1 | 6.0 |
| 9 | CLP-V-1 | 9.0 |
| 10 | PGP-1-2V | 2.5 |
| 11 | CCVC-3-V | 8.0 |
| 12 | CCP-3-OT | 4.0 |
| 13 | DPGU-4-F | 5.5 |
| 14 | CDUQU-3-F | 2.0 |
| 15 | APUQU-2-F | 1.0 |
| 16 | APUQU-3-F | 3.0 |
| 17 | DGUQU-4-F | 4.0 |
| Σ | | 100.0 |

| Physical properties | |
|---|---|
| T(N, I) = | 103.0° C. |
| $n_e$(20° C., 589 nm) = | 1.5852 |
| Δn(20° C., 589 nm) = | 0.1008 |
| $\varepsilon_\parallel$(20° C., 1 kHz) = | 7.9 |
| $\varepsilon_\perp$(20° C., 1 kHz) = | 3.5 |
| Δε(20° C., 1 kHz) = | 4.4 |
| $\varepsilon_{av.}$(20° C., 1 kHz) = | 5.0 |

-continued

| Mixture 3 | |
|---|---|
| $\gamma_1$(20° C.) = | 83 mPa · s |
| $k_{11}$(20° C.) = | 17.0 pN |
| $k_{33}$(20° C.) = | 18.3 pN |
| $V_0$(20° C.) = | 2.08 V |

This mixture, mixture M-3, has a dielectric ratio ($\varepsilon_\perp/\Delta\varepsilon$) of 0.80, a ratio of ($\gamma_1/k_{11}$) of 4.88 mPa·s/pN and is characterized by a good transmission in an FFS display and shows a short response time.

Example 4

The following mixture (M-4) is prepared and investigated.

| Mixture 4 | | |
|---|---|---|
| Composition | | |
| Compound | | Concentration |
| No. | Abbreviation | /% by weight |
| 1 | LB(S)-3-OT | 10.0 |
| 2 | CC-3-V | 47.5 |
| 3 | CC-3-V1 | 7.0 |
| 4 | CLP-V-1 | 6.0 |
| 5 | PP-1-2V1 | 3.0 |
| 6 | PGP-2-2V | 5.5 |
| 7 | CCVC-3-V | 1.0 |
| 8 | CDU-2-F | 5.0 |
| 9 | PPGU-3-F | 0.5 |
| 10 | PUQU-3-F | 2.5 |
| 11 | APUQU-2-F | 2.0 |
| 12 | APUQU-3-F | 3.0 |
| 13 | PGUQU-3-F | 3.0 |
| 14 | PGUQU-4-F | 4.0 |
| Σ | | 100.0 |

| Physical properties | |
|---|---|
| T(N, I) = | 77.5°C. |
| $n_e$(20° C., 589 nm) = | 1.5910 |
| Δn(20° C., 589 nm) = | 0.1060 |
| $\varepsilon_\parallel$(20° C., 1 kHz) = | 8.6 |
| $\varepsilon_\perp$(20° C., 1 kHz) = | 3.5 |
| Δε(20° C., 1 kHz) = | 5.1 |
| $\varepsilon_{av.}$(20° C., 1 kHz) = | 5.2 |
| $\gamma_1$(20° C.) = | 56 mPa · s |
| $k_{11}$(20° C.) = | 14.0 pN |
| $k_{33}$(20° C.) = | 14.3 pN |
| $V_0$(20° C.) = | 1.75 V |

This mixture, mixture M-4, has a dielectric ratio ($\varepsilon_\perp/\Delta\varepsilon$) of 0.69, a ratio of ($\gamma_1/k_{11}$) of 4.00 mPa·s/pN and is characterized by a good transmission in an FFS display and shows a short response time.

Example 5

The following mixture (M-5) is prepared and investigated.

| Mixture 5 | |
|---|---|
| Composition | |

| No. | Compound Abbreviation | Concentration /% by weight |
|---|---|---|
| 1 | LB(S)-3-OT | 12.0 |
| 2 | CC-3-V | 48.5 |
| 3 | CC-3-V1 | 7.0 |
| 4 | CLP-V-1 | 7.0 |
| 5 | PP-1-2V1 | 3.0 |
| 6 | PGP-2-2V | 5.0 |
| 7 | CDU-2-F | 5.5 |
| 8 | PPGU-3-F | 0.5 |
| 9 | APUQU-2-F | 2.0 |
| 10 | APUQU-3-F | 3.0 |
| 11 | PGUQU-3-F | 2.5 |
| 12 | PGUQU-4-F | 4.0 |
| Σ | | 100.0 |

| Physical properties | |
|---|---|
| T(N, I) = | 78.5° C. |
| $n_e$(20° C., 589 nm) = | 1.5920 |
| Δn(20° C., 589 nm) = | 0.1060 |
| $\varepsilon_\parallel$(20° C., 1 kHz) = | 8.0 |
| $\varepsilon_\perp$(20° C., 1 kHz) = | 3.5 |
| Δε(20° C., 1 kHz) = | 4.5 |
| $\varepsilon_{av.}$(20° C., 1 kHz) = | 5.0 |
| $\gamma_1$(20° C.) = | 55 mPa·s |
| $k_{11}$(20° C.) = | 14.6 pN |
| $k_{33}$(20° C.) = | 14.3 pN |
| $V_0$(20° C.) = | 1.89 V |

This mixture, mixture M-5, has a dielectric ratio ($\varepsilon_\perp/\Delta\varepsilon$) of 0.78, a ratio of ($\gamma_1/k_{11}$) of 3.77 mPa·s/pN and is characterized by a good transmission in an FFS display and shows a short response time.

Example 6

The following mixture (M-6) is prepared and investigated.

| Mixture 6 | |
|---|---|
| Composition | |

| No. | Compound Abbreviation | Concentration /% by weight |
|---|---|---|
| 1 | LB(S)-3-OT | 14.0 |
| 2 | CC-3-V | 50.0 |
| 3 | CC-3-V1 | 7.0 |
| 4 | CLP-V-1 | 6.5 |
| 5 | PP-1-2V1 | 1.5 |
| 6 | PGP-2-2V | 4.0 |
| 7 | CDU-2-F | 5.0 |
| 8 | PPGU-3-F | 0.5 |
| 9 | APUQU-2-F | 2.0 |
| 10 | APUQU-3-F | 3.0 |
| 11 | PGUQU-3-F | 2.5 |
| 12 | PGUQU-4-F | 4.0 |
| Σ | | 100.0 |

| Physical properties | |
|---|---|
| T(N, I) = | 79.5° C. |
| $n_e$(20° C., 589 nm) = | 1.5884 |
| Δn(20° C., 589 nm) = | 0.1043 |
| $\varepsilon_\parallel$(20° C., 1 kHz) = | 7.9 |
| $\varepsilon_\perp$(20° C., 1 kHz) = | 3.6 |
| Δε(20° C., 1 kHz) = | 4.4 |
| $\varepsilon_{av.}$(20° C., 1 kHz) = | 5.1 |
| $\gamma_1$(20° C.) = | 55 mPa·s |
| $k_{11}$(20° C.) = | 14.5 pN |
| $k_{33}$(20° C.) = | 14.7 pN |
| $V_0$(20° C.) = | 1.92 V |

This mixture, mixture M-6, has a dielectric ratio ($\varepsilon_\perp/\Delta\varepsilon$) of 0.82, a ratio of ($\gamma_1/k_{11}$) of 3.79 mPa·s/pN and is characterized by a good transmission in an FFS display and shows a short response time.

Example 7

The following mixture (M-7) is prepared and investigated.

| Mixture 7 | |
|---|---|
| Composition | |

| No. | Compound Abbreviation | Concentration /% by weight |
|---|---|---|
| 1 | LB(S)-3-OT | 16.0 |
| 2 | CC-3-V | 49.5 |
| 3 | CC-3-V1 | 7.0 |
| 4 | CLP-V-1 | 6.5 |
| 5 | PP-1-2V1 | 2.0 |
| 6 | PGU-3-F | 4.5 |
| 7 | CLP-3-T | 4.0 |
| 8 | PPGU-3-F | 0.5 |
| 9 | APUQU-3-F | 3.0 |
| 10 | DGUQU-4-F | 3.0 |
| 11 | PGUQU-4-F | 4.0 |
| Σ | | 100.0 |

| Physical properties | |
|---|---|
| T(N, I) = | 80.0° C. |
| $n_e$(20° C., 589 nm) = | 1.5885 |
| Δn(20° C., 589 nm) = | 0.1047 |
| $\varepsilon_\parallel$(20° C., 1 kHz) = | 8.0 |
| $\varepsilon_\perp$(20° C., 1 kHz) = | 3.6 |
| Δε(20° C., 1 kHz) = | 4.5 |
| $\varepsilon_{av.}$(20° C., 1 kHz) = | 5.1 |
| $\gamma_1$(20° C.) = | 57 mPa·s |
| $k_{11}$(20° C.) = | 15.4 pN |
| $k_{33}$(20° C.) = | 15.3 pN |
| $V_0$(20° C.) = | 1.96 V |

This mixture, mixture M-7, has a dielectric ratio ($\varepsilon_\perp/\Delta\varepsilon$) of 0.80, a ratio of ($\gamma_1/k_{11}$) of 3.75 mPa·s/pN and is characterized by a good transmission in an FFS display and shows a short response time.

Example 8

The following mixture (M-8) is prepared and investigated.

| Mixture 8 | | |
|---|---|---|
| Composition | | |
| Compound | | Concentration |
| No. | Abbreviation | /% by weight |
| 1 | LB(S)-3-OT | 16.0 |
| 2 | CC-3-V | 48.0 |
| 3 | CC-3-V1 | 7.0 |
| 4 | CLP-V-1 | 7.0 |
| 5 | PP-1-2V1 | 2.0 |
| 6 | PGU-3-F | 4.5 |
| 7 | CLP-3-T | 4.0 |
| 8 | PPGU-3-F | 0.5 |
| 9 | APUQU-2-F | 3.0 |
| 10 | DGUQU-4-F | 4.0 |
| 11 | PGUQU-4-F | 4.0 |
| Σ | | 100.0 |

| Physical properties | |
|---|---|
| T(N, I) = | 80.0° C. |
| $n_e$(20° C., 589 nm) = | t.b.d. |
| $\Delta n$(20° C., 589 nm) = | t.b.d. |
| $\varepsilon_{\parallel}$(20° C., 1 kHz) = | t.b.d. |
| $\varepsilon_{\perp}$(20° C., 1 kHz) = | t.b.d. |
| $\Delta\varepsilon$(20° C., 1 kHz) = | t.b.d. |
| $\varepsilon_{av.}$(20° C., 1 kHz) = | t.b.d. |
| $\gamma_1$(20° C.) = | t.b.d. mPa · s |
| $k_{11}$(20° C.) = | t.b.d. pN |
| $k_{33}$(20° C.) = | t.b.d. pN |
| $V_0$(20° C.) = | t.b.d. V |
| $\varepsilon_{\perp}/\Delta\varepsilon$(20° C.) = | t.b.d. |
| $\gamma_1/k_{11}$(20° C.) = | t.b.d. * |

Remark:
t.b.d.: to be determined and
* [mPa · s/pN].

This mixture, mixture M-8, is characterized by a good transmission in an FFS display and shows a short response time.

Example 9

The following mixture (M-9) is prepared and investigated.

| Mixture 9 | | |
|---|---|---|
| Composition | | |
| Compound | | Concentration |
| No. | Abbreviation | /% by weight |
| 1 | LB(S)-3-OT | 10.0 |
| 2 | CC-3-V | 47.5 |
| 3 | CC-3-V1 | 7.0 |
| 4 | CLP-V-1 | 6.0 |
| 5 | CCVC-3-V | 1.0 |
| 6 | PP-1-2V1 | 3.0 |
| 7 | PGP-2-2V | 5.5 |
| 8 | CDU-2-F | 5.0 |
| 9 | PPGU-3-F | 0.5 |
| 10 | PUQU-3-F | 2.5 |
| 11 | APUQU-2-F | 2.0 |
| 12 | APUQU-3-F | 3.0 |
| 13 | PGUQU-3-F | 3.0 |
| 14 | PGUQU-4-F | 4.0 |
| Σ | | 100.0 |

| Mixture 9 | |
|---|---|
| Physical properties | |
| T(N, I) = | 77.5° C. |
| $n_e$(20° C., 589 nm) = | 1.5910 |
| $\Delta n$(20° C., 589 nm) = | 0.1060 |
| $\varepsilon_{\parallel}$(20° C., 1 kHz) = | 8.6 |
| $\varepsilon_{\perp}$(20° C., 1 kHz) = | 3.5 |
| $\Delta\varepsilon$(20° C., 1 kHz) = | 5.1 |
| $\varepsilon_{av.}$(20° C., 1 kHz) = | 5.2 |
| $\gamma_1$(20° C.) = | 56 mPa · s |
| $k_{11}$(20° C.) = | 14.0 pN |
| $k_{33}$(20° C.) = | 14.3 pN |
| $V_0$(20° C.) = | 1.75 V |
| $\varepsilon_{\perp}/\Delta\varepsilon$(20° C.) = | 0.69 |
| $\gamma_1/k_{11}$(20° C.) = | 4.0 * |

Remark:
* [mPa · s/pN].

This mixture, mixture M-9, is characterized by a good transmission in an FFS display and shows a short response time.

Example 10

The following mixture (M-10) is prepared and investigated.

| Mixture 10 | | |
|---|---|---|
| Composition | | |
| Compound | | Concentration |
| No. | Abbreviation | /% by weight |
| 1 | LB(S)-3-OT | 3.5 |
| 2 | B(S)-2O-O4 | 1.0 |
| 3 | B(S)-2O-O5 | 0.8 |
| 4 | CC-3-V | 32.8 |
| 5 | CC-3-V1 | 9.0 |
| 6 | CP-3-O2 | 8.3 |
| 7 | CCP-V-1 | 7.0 |
| 8 | CCP-V2-1 | 4.5 |
| 9 | CLP-1V-1 | 3.0 |
| 10 | CCVC-3-V | 8.4 |
| 11 | PGP-1-2V | 2.5 |
| 12 | CCP-3-OT | 2.7 |
| 13 | DPGU-4-F | 9.0 |
| 14 | CDUQU-3-F | 0.8 |
| 15 | APUQU-2-F | 0.2 |
| 16 | APUQU-3-F | 1.8 |
| 17 | DGUQU-4-F | 4.7 |
| Σ | | 100.0 |

| Physical properties | |
|---|---|
| T(N, I) = | 105.0° C. |
| $n_e$(20° C., 589 nm) = | 1.5852 |
| $\Delta n$(20° C., 589 nm) = | 0.1011 |
| $\varepsilon_{\parallel}$(20° C., 1 kHz) = | 7.9 |
| $\varepsilon_{\perp}$(20° C., 1 kHz) = | 3.3 |
| $\Delta\varepsilon$(20° C., 1 kHz) = | 4.6 |
| $\varepsilon_{av.}$(20° C., 1 kHz) = | 4.8 |
| $\gamma_1$(20° C.) = | 85 mPa · s |
| $k_{11}$(20° C.) = | 17.4 pN |
| $k_{33}$(20° C.) = | 18.7 pN |
| $V_0$(20° C.) = | 2.06 V |
| $\varepsilon_{\perp}/\Delta\varepsilon$(20° C.) = | 0.72 |
| $\gamma_1/k_{11}$(20° C.) = | 4.89 * |

Remark:
* [mPa · s/pN].

This mixture, mixture M-10, is characterized by a good transmission in an FFS display and shows a short response time.

Example 11

The following mixture (M-11) is prepared and investigated.

| Mixture 11 | | |
|---|---|---|
| Composition | | |
| Compound | | Concentration |
| No. | Abbreviation | /% by weight |
| 1 | LB(S)-3-OT | 3.5 |
| 2 | B(S)-2O-O4 | 1.0 |
| 3 | B(S)-2O-O5 | 0.8 |
| 4 | CC-3-V | 32.3 |
| 5 | CC-3-V1 | 9.0 |
| 6 | CP-3-O2 | 8.3 |
| 7 | CCP-V-1 | 7.0 |
| 8 | CCP-V2-1 | 4.5 |
| 9 | CLP-1V-1 | 3.9 |
| 10 | CCVC-3-V | 8.2 |
| 11 | PGP-1-2V | 2.5 |
| 12 | CCP-3-OT | 2.5 |
| 13 | DPGU-4-F | 9.0 |
| 14 | CDUQU-3-F | 0.8 |
| 15 | APUQU-3-F | 2.0 |
| 16 | DGUQU-4-F | 4.7 |
| Σ | | 100.0 |
| Physical properties | | |
| $T(N, I) =$ | | 106.0° C. |
| $n_e(20° C., 589\ nm) =$ | | t.b.d. |
| $\Delta n(20° C., 589\ nm) =$ | | t.b.d. |
| $\varepsilon_\parallel(20° C., 1\ kHz) =$ | | t.b.d. |
| $\varepsilon_\perp(20° C., 1\ kHz) =$ | | t.b.d. |
| $\Delta\varepsilon(20° C., 1\ kHz) =$ | | t.b.d. |
| $\varepsilon_{av.}(20° C., 1\ kHz) =$ | | t.b.d. |
| $\gamma_1(20° C.) =$ | | t.b.d. mPa·s |
| $k_{11}(20° C.) =$ | | t.b.d. pN |
| $k_{33}(20° C.) =$ | | t.b.d. pN |
| $V_0(20° C.) =$ | | t.b.d. V |
| $\varepsilon_\perp/\Delta\varepsilon(20° C.) =$ | | t.b.d. |
| $\gamma_1/k_{11}(20° C.) =$ | | t.b.d. * |

Remark:
t.b.d.: to be determined and
* [mPa·s/pN].

This mixture, mixture M-11, is characterized by a good transmission in an FFS display and shows a short response time.

Example 12

The following mixture (M-12) is prepared and investigated.

| Mixture 12 | | |
|---|---|---|
| Composition | | |
| Compound | | Concentration |
| No. | Abbreviation | /% by weight |
| 1 | LB(S)-3-OT | 3.5 |
| 2 | B(S)-2O-O4 | 1.0 |
| 3 | B(S)-2O-O5 | 0.8 |
| 4 | CC-3-V | 32.5 |
| 5 | CC-3-V1 | 9.0 |
| 6 | CP-3-O2 | 8.3 |
| 7 | CCP-V-1 | 7.0 |
| 8 | CCP-V2-1 | 4.5 |
| 9 | CLP-1V-1 | 3.9 |
| 10 | CCVC-3-V | 8.2 |
| 11 | PGP-1-2V | 2.5 |
| 12 | CCP-3-OT | 2.3 |
| 13 | DPGU-4-F | 9.0 |
| 14 | CDUQU-3-F | 0.8 |
| 15 | APUQU-3-F | 2.0 |
| 16 | DGUQU-4-F | 4.7 |
| Σ | | 100.0 |
| Physical properties | | |
| $T(N, I) =$ | | 106.0° C. |
| $n_e(20° C., 589\ nm) =$ | | 1.5872 |
| $\Delta n(20° C., 589\ nm) =$ | | 0.1027 |
| $\varepsilon_\parallel(20° C., 1\ kHz) =$ | | 7.8 |
| $\varepsilon_\perp(20° C., 1\ kHz) =$ | | 3.3 |
| $\Delta\varepsilon(20° C., 1\ kHz) =$ | | 4.5 |
| $\varepsilon_{av.}(20° C., 1\ kHz) =$ | | 4.8 |
| $\gamma_1(20° C.) =$ | | 86 mPa·s |
| $k_{11}(20° C.) =$ | | 17.6 pN |
| $k_{33}(20° C.) =$ | | 19.2 pN |
| $V_0(20° C.) =$ | | 2.07 V |
| $\varepsilon_\perp/\Delta\varepsilon(20° C.) =$ | | 0.73 |
| $\gamma_1/k_{11}(20° C.) =$ | | 4.89 * |

Remark:
* [mPa·s/pN].

This mixture, mixture M-12, is characterized by a good transmission in an FFS display and shows a short response time.

Example 13

The following mixture (M-13) is prepared and investigated.

| Mixture 13 | | |
|---|---|---|
| Composition | | |
| Compound | | Concentration |
| No. | Abbreviation | /% by weight |
| 1 | LB(S)-3-OT | 6.0 |
| 2 | CC-3-V | 45.0 |
| 3 | CC-3-V1 | 12.0 |
| 4 | CCP-V-1 | 11.0 |
| 5 | CCP-V2-1 | 5.0 |
| 6 | PP-1-2V1 | 7.0 |
| 7 | PGP-2-3 | 4.0 |
| 8 | PPGU-3-F | 0.5 |
| 9 | APUQU-3-F | 4.0 |
| 10 | PGUQU-3-F | 5.5 |
| Σ | | 100.0 |
| Physical properties | | |
| $T(N, I) =$ | | 79.0° C. |
| $n_e(20° C., 589\ nm) =$ | | 1.5865 |
| $\Delta n(20° C., 589\ nm) =$ | | 0.1003 |
| $\varepsilon_\parallel(20° C., 1\ kHz) =$ | | 5.4 |
| $\varepsilon_\perp(20° C., 1\ kHz) =$ | | 2.9 |
| $\Delta\varepsilon(20° C., 1\ kHz) =$ | | 2.6 |
| $\varepsilon_{av.}(20° C., 1\ kHz) =$ | | 3.8 |
| $\gamma_1(20° C.) =$ | | 51 mPa·s |

-continued

| Mixture 13 | |
|---|---|
| $k_{11}(20° C.) =$ | 14.5 pN |
| $k_{33}(20° C.) =$ | 16.2 pN |
| $V_0(20° C.) =$ | 2.50 V |
| $\varepsilon_\perp/\Delta\varepsilon(20° C.) =$ | 1.12 |
| $\gamma_1/k_{11}(20° C.) =$ | 3.52 * |

Remark:
* [mPa · s/pN].

This mixture, mixture M-13, is characterized by a good transmission in an FFS display and shows a short response time.

Example 14

The following mixture (M-14) is prepared and investigated.

| Mixture 14 | | |
|---|---|---|
| Composition | | |
| Compound | | Concentration |
| No. | Abbreviation | /% by weight |
| 1 | LB(S)-3-OT | 6.0 |
| 2 | CC-3-V | 46.0 |
| 3 | CC-3-V1 | 11.0 |
| 4 | CCP-V-1 | 8.0 |
| 5 | CLP-V-1 | 8.0 |
| 6 | PP-1-2V1 | 5.5 |
| 7 | PGP-2-3 | 3.0 |
| 8 | CLP-3-T | 4.0 |
| 9 | PPGU-3-F | 0.5 |
| 10 | APUQU-3-F | 3.0 |
| 11 | PGUQU-3-F | 5.0 |
| Σ | | 100.0 |
| Physical properties | | |
| $T(N, I) =$ | | 82.0° C. |
| $n_e(20° C., 589\ nm) =$ | | 1.5867 |
| $\Delta n(20° C., 589\ nm) =$ | | 0.1005 |
| $\varepsilon_\parallel(20° C., 1\ kHz) =$ | | 5.5 |
| $\varepsilon_\perp(20° C., 1\ kHz) =$ | | 2.8 |
| $\Delta\varepsilon(20° C., 1\ kHz) =$ | | 2.7 |
| $\varepsilon_{av.}(20° C., 1\ kHz) =$ | | 3.7 |
| $\gamma_1(20° C.) =$ | | 54 mPa · s |
| $k_{11}(20° C.) =$ | | 15.9 pN |
| $k_{33}(20° C.) =$ | | 16.5 pN |
| $V_0(20° C.) =$ | | 2.59 V |
| $\varepsilon_\perp/\Delta\varepsilon(20° C.) =$ | | 1.04 |
| $\gamma_1/k_{11}(20° C.) =$ | | 3.40 * |

Remark:
* [mPa · s/pN].

This mixture, mixture M-14, is characterized by a good transmission in an FFS display and shows a short response time.

Example 15

The following mixture (M-15) is prepared and investigated.

| Mixture 15 | | |
|---|---|---|
| Composition | | |
| Compound | | Concentration |
| No. | Abbreviation | /% by weight |
| 1 | LB(S)-3-OT | 6.0 |
| 2 | CC-3-V | 49.5 |
| 3 | CC-3-V1 | 11.0 |
| 4 | CLP-V-1 | 8.0 |
| 5 | CLP-1V-1 | 5.0 |
| 6 | PP-1-2V1 | 6.0 |
| 7 | PGP-2-3 | 2.0 |
| 8 | CLP-3-T | 4.0 |
| 9 | PPGU-3-F | 0.5 |
| 10 | APUQU-3-F | 3.0 |
| 11 | PGUQU-3-F | 5.0 |
| Σ | | 100.0 |
| Physical properties | | |
| $T(N, I) =$ | | 80.5° C. |
| $n_e(20° C., 589\ nm) =$ | | 1.5850 |
| $\Delta n(20° C., 589\ nm) =$ | | 0.1000 |
| $\varepsilon_\parallel(20° C., 1\ kHz) =$ | | 5.5 |
| $\varepsilon_\perp(20° C., 1\ kHz) =$ | | 2.8 |
| $\Delta\varepsilon(20° C., 1\ kHz) =$ | | 2.7 |
| $\varepsilon_{av.}(20° C., 1\ kHz) =$ | | 3.7 |
| $\gamma_1(20° C.) =$ | | 52 mPa · s |
| $k_{11}(20° C.) =$ | | 16.2 pN |
| $k_{33}(20° C.) =$ | | 16.9 pN |
| $V_0(20° C.) =$ | | 2.62 V |
| $\varepsilon_\perp/\Delta\varepsilon(20° C.) =$ | | 1.04 |
| $\gamma_1/k_{11}(20° C.) =$ | | 3.21 * |

Remark:
* [mPa · s/pN].

This mixture, mixture M-15, is characterized by a good transmission in an FFS display and shows a short response time.

Example 16

The following mixture (M-16) is prepared and investigated.

| Mixture 16 | | |
|---|---|---|
| Composition | | |
| Compound | | Concentration |
| No. | Abbreviation | /% by weight |
| 1 | LB(S)-3-OT | 10.0 |
| 2 | CC-3-V | 46.0 |
| 3 | CC-3-V1 | 11.0 |
| 4 | CCP-V-1 | 8.5 |
| 5 | CLP-V-1 | 6.0 |
| 6 | PP-1-2V1 | 6.5 |
| 7 | CLP-3-T | 4.0 |
| 8 | PPGU-3-F | 0.5 |
| 9 | APUQU-3-F | 2.0 |
| 10 | PGUQU-3-F | 5.0 |
| Σ | | 100.0 |
| Physical properties | | |
| $T(N, I) =$ | | 81.0° C. |
| $n_e(20° C., 589\ nm) =$ | | 1.5847 |
| $\Delta n(20° C., 589\ nm) =$ | | 0.0991 |
| $\varepsilon_\parallel(20° C., 1\ kHz) =$ | | 5.6 |
| $\varepsilon_\perp(20° C., 1\ kHz) =$ | | 3.0 |

-continued

| Mixture 16 | |
|---|---|
| Δε(20° C., 1 kHz) = | 2.6 |
| $\varepsilon_{av.}$(20° C., 1 kHz) = | 3.9 |
| $\gamma_1$(20° C.) = | 52 mPa · s |
| $k_{11}$(20° C.) = | 15.9 pN |
| $k_{33}$(20° C.) = | 16.6 pN |
| $V_0$(20° C.) = | 2.59 V |
| $\varepsilon_\perp/\Delta\varepsilon$(20° C.) = | 1.15 |
| $\gamma_1/k_{11}$(20° C.) = | 3.27 * |

Remark:
* [mPa · s/pN].

This mixture, mixture M-16, is characterized by a good transmission in an FFS display and shows a short response time.

Example 17

The following mixture (M-17) is prepared and investigated.

| Mixture 17 | | |
|---|---|---|
| Composition | | |
| Compound | | Concentration |
| No. | Abbreviation | /% by weight |
| 1 | LB(S)-3-OT | 3.0 |
| 2 | CC-3-V | 49.5 |
| 3 | CC-3-V1 | 10.5 |
| 4 | CLP-V-1 | 9.0 |
| 5 | CLP-1V-1 | 6.0 |
| 6 | PP-1-2V1 | 7.0 |
| 7 | PGP-2-3 | 2.0 |
| 8 | CLP-3-T | 4.0 |
| 9 | PPGU-3-F | 0.5 |
| 10 | APUQU-3-F | 2.5 |
| 11 | PGUQU-3-F | 6.0 |
| Σ | | 100.0 |

| Physical properties | |
|---|---|
| T(N, I) = | 81.0° C. |
| $n_e$(20° C., 589 nm) = | 1.5850 |
| Δn(20° C., 589 nm) = | 0.1004 |
| $\varepsilon_\parallel$(20° C., 1 kHz) = | 5.4 |
| $\varepsilon_\perp$(20° C., 1 kHz) = | 2.7 |
| Δε(20° C., 1 kHz) = | 2.7 |
| $\varepsilon_{av.}$(20° C., 1 kHz) = | 3.6 |
| $\gamma_1$(20° C.) = | 52 mPa · s |
| $k_{11}$(20° C.) = | 16.3 pN |
| $k_{33}$(20° C.) = | 17.4 pN |
| $V_0$(20° C.) = | 2.62 V |
| $\varepsilon_\perp/\Delta\varepsilon$(20° C.) = | 1.00 |
| $\gamma_1/k_{11}$(20° C.) = | 3.19 * |

Remark:
* [mPa · s/pN].

This mixture, mixture M-17, is characterized by a good transmission in an FFS display and shows a short response time.

Example 18

The following mixture (M-18) is prepared and investigated.

| Mixture 18 | | |
|---|---|---|
| Composition | | |
| Compound | | Concentration |
| No. | Abbreviation | /% by weight |
| 1 | LB(S)-3-OT | 3.0 |
| 2 | CC-3-V | 49.5 |
| 3 | CC-3-V1 | 10.5 |
| 4 | CLP-V-1 | 9.0 |
| 5 | CLP-1V-1 | 5.5 |
| 6 | PP-1-2V1 | 7.0 |
| 7 | PGP-2-3 | 3.0 |
| 8 | CLP-3-T | 3.5 |
| 9 | PPGU-3-F | 0.5 |
| 10 | APUQU-3-F | 3.5 |
| 11 | PGUQU-3-F | 5.0 |
| Σ | | 100.0 |

| Physical properties | |
|---|---|
| T(N, I) = | 80.5° C. |
| $n_e$(20° C., 589 nm) = | 1.5870 |
| Δn(20° C., 589 nm) = | 0.1008 |
| $\varepsilon_\parallel$(20° C., 1 kHz) = | 5.3 |
| $\varepsilon_\perp$(20° C., 1 kHz) = | 2.7 |
| Δε(20° C., 1 kHz) = | 2.7 |
| $\varepsilon_{av.}$(20° C., 1 kHz) = | 3.6 |
| $\gamma_1$(20° C.) = | 51 mPa · s |
| $k_{11}$(20° C.) = | 16.2 pN |
| $k_{33}$(20° C.) = | 17.8 pN |
| $V_0$(20° C.) = | 2.60 V |
| $\varepsilon_\perp/\Delta\varepsilon$(20° C.) = | 1.00 |
| $\gamma_1/k_{11}$(20° C.) = | 3.15 * |

Remark:
* [mPa · s/pN].

This mixture, mixture M-18, is characterized by a good transmission in an FFS display and shows a short response time.

Example 19

The following mixture (M-19) is prepared and investigated.

| Mixture 19 | | |
|---|---|---|
| Composition | | |
| Compound | | Concentration |
| No. | Abbreviation | /% by weight |
| 1 | LB(S)-3-OT | 3.0 |
| 2 | CC-3-V | 49.5 |
| 3 | CC-3-V1 | 10.5 |
| 4 | CLP-V-1 | 9.0 |
| 5 | CLP-1V-1 | 5.0 |
| 6 | PP-1-2V1 | 6.5 |
| 7 | PGP-2-3 | 2.0 |
| 8 | CLP-3-T | 4.5 |
| 9 | PPGU-3-F | 0.5 |
| 10 | APUQU-3-F | 3.0 |
| 11 | PGUQU-3-F | 6.5 |
| Σ | | 100.0 |

| Physical properties | |
|---|---|
| T(N, I) = | 80.5° C. |
| $n_e$(20° C., 589 nm) = | 1.5854 |
| Δn(20° C., 589 nm) = | 0.0996 |
| $\varepsilon_\parallel$(20° C., 1 kHz) = | 5.7 |

Mixture 19 -continued

| | |
|---|---|
| $\varepsilon_\perp(20°\ C., 1\ kHz) =$ | 2.7 |
| $\Delta\varepsilon(20°\ C., 1\ kHz) =$ | 3.0 |
| $\varepsilon_{av.}(20°\ C., 1\ kHz) =$ | 3.7 |
| $\gamma_1(20°\ C.) =$ | 51 mPa·s |
| $k_{11}(20°\ C.) =$ | 16.2 pN |
| $k_{33}(20°\ C.) =$ | 16.9 pN |
| $V_0(20°\ C.) =$ | 2.45 V |
| $\varepsilon_\perp/\Delta\varepsilon(20°\ C.) =$ | 0.90 |
| $\gamma_1/k_{11}(20°\ C.) =$ | 3.15 * |

Remark:
* [mPa·s/pN].

This mixture, mixture M-19, is characterized by a good transmission in an FFS display and shows a short response time.

Example 20

The following mixture (M-20) is prepared and investigated.

Mixture 20

Composition

| Compound | | Concentration |
|---|---|---|
| No. | Abbreviation | /% by weight |
| 1 | LB(S)-3-OT | 6.0 |
| 2 | CC-3-V | 25.0 |
| 3 | CC-3-V1 | 9.0 |
| 4 | CC-3-2V1 | 6.0 |
| 5 | CCP-V-1 | 12.0 |
| 6 | CCP-V2-1 | 2.0 |
| 7 | PP-1-2V1 | 2.0 |
| 8 | PGP-1-2V | 5.0 |
| 9 | CCVC-3-V | 6.0 |
| 10 | CPGP-4-3 | 3.0 |
| 11 | CCP-3-OT | 2.0 |
| 12 | CCG-V-F | 3.0 |
| 13 | CLP-3-T | 3.0 |
| 14 | CCGU-3-F | 4.0 |
| 15 | CDUQU-3-F | 9.0 |
| 16 | DGUQU-4-F | 4.5 |
| Σ | | 100.0 |

Physical properties

| | |
|---|---|
| T(N, I) = | 114.0° C. |
| $n_e(20°\ C., 589\ nm) =$ | t.b.d. |
| $\Delta n(20°\ C., 589\ nm) =$ | t.b.d. |
| $\varepsilon_\parallel(20°\ C., 1\ kHz) =$ | t.b.d. |
| $\varepsilon_\perp(20°\ C., 1\ kHz) =$ | t.b.d. |
| $\Delta\varepsilon(20°\ C., 1\ kHz) =$ | t.b.d. |
| $\varepsilon_{av.}(20°\ C., 1\ kHz) =$ | t.b.d. |
| $\gamma_1(20°\ C.) =$ | t.b.d. mPa·s |
| $k_{11}(20°\ C.) =$ | t.b.d. pN |
| $k_{33}(20°\ C.) =$ | t.b.d. pN |
| $V_0(20°\ C.) =$ | t.b.d. V |
| $\varepsilon_\perp/\Delta\varepsilon(20°\ C.) =$ | t.b.d. |
| $\gamma_1/k_{11}(20°\ C.) =$ | t.b.d. * |

Remark:
* [mPa·s/pN].

This mixture, mixture M-20, is characterized by a very good transmission in an FFS display and shows a short response time.

Example 21

The following mixture (M-21) is prepared and investigated.

Mixture 21

Composition

| Compound | | Concentration |
|---|---|---|
| No. | Abbreviation | /% by weight |
| 1 | LB(S)-3-OT | 6.0 |
| 2 | CC-3-V | 25.0 |
| 3 | CC-3-V1 | 9.0 |
| 4 | CC-3-2V1 | 9.0 |
| 5 | CCP-V-1 | 10.5 |
| 6 | CCP-V2-1 | 1.0 |
| 7 | PP-1-2V1 | 1.5 |
| 8 | PGP-1-2V | 5.0 |
| 9 | CCVC-3-V | 6.0 |
| 10 | CPGP-4-3 | 1.5 |
| 11 | CCP-3-OT | 4.5 |
| 12 | CCG-V-F | 1.5 |
| 13 | CLP-3-T | 4.0 |
| 14 | CCGU-3-F | 2.0 |
| 15 | CDUQU-3-F | 9.0 |
| 16 | DGUQU-4-F | 4.5 |
| Σ | | 100.0 |

Physical properties

| | |
|---|---|
| T(N, I) = | 112.0° C. |
| $n_e(20°\ C., 589\ nm) =$ | 1.5853 |
| $\Delta n(20°\ C., 589\ nm) =$ | 0.1014 |
| $\varepsilon_\parallel(20°\ C., 1\ kHz) =$ | 8.2 |
| $\varepsilon_\perp(20°\ C., 1\ kHz) =$ | 3.2 |
| $\Delta\varepsilon(20°\ C., 1\ kHz) =$ | 5.1 |
| $\varepsilon_{av.}(20°\ C., 1\ kHz) =$ | 4.9 |
| $\gamma_1(20°\ C.) =$ | 100 mPa·s |
| $k_{11}(20°\ C.) =$ | 20.1 pN |
| $k_{33}(20°\ C.) =$ | 21.2 pN |
| $V_0(20°\ C.) =$ | 2.09 V |
| $\varepsilon_\perp/\Delta\varepsilon(20°\ C.) =$ | 0.63 |
| $\gamma_1/k_{11}(20°\ C.) =$ | 4.98 * |

Remark:
* [mPa·s/pN].

This mixture, mixture M-21, is characterized by a very good transmission in an FFS display and shows a short response time.

Example 22

The following mixture (M-22) is prepared and investigated.

Mixture 22

Composition

| Compound | | Concentration |
|---|---|---|
| No. | Abbreviation | /% by weight |
| 1 | LB(S)-3-OT | 10.0 |
| 2 | CC-3-V | 30.0 |
| 3 | CC-3-V1 | 8.0 |
| 4 | CC-3-2V1 | 4.5 |
| 5 | CCP-V-1 | 13.5 |
| 6 | CCVC-3-V | 6.0 |
| 7 | CCP-3-OT | 8.0 |
| 8 | CLP-3-T | 10.0 |
| 9 | DGUQU-2-F | 2.0 |
| 10 | DGUQU-4-F | 8.0 |
| Σ | | 100.0 |

-continued

Mixture 22

Physical properties

| | |
|---|---|
| T(N, I) = | 104.0° C. |
| $n_e$(20° C., 589 nm) = | t.b.d. |
| $\Delta n$(20° C., 589 nm) = | t.b.d. |
| $\varepsilon_\parallel$(20° C., 1 kHz) = | t.b.d. |
| $\varepsilon_\perp$(20° C., 1 kHz) = | t.b.d. |
| $\Delta\varepsilon$(20° C., 1 kHz) = | t.b.d. |
| $\varepsilon_{av.}$(20° C., 1 kHz) = | t.b.d. |
| $\gamma_1$(20° C.) = | t.b.d. mPa · s |
| $k_{11}$(20° C.) = | t.b.d. pN |
| $k_{33}$(20° C.) = | t.b.d. pN |
| $V_0$(20° C.) = | t.b.d. V |
| $\varepsilon_\perp/\Delta\varepsilon$(20° C.) = | t.b.d. |
| $\gamma_1/k_{11}$(20° C.) = | t.b.d. * |

Remark:
* [mPa · s/pN].

This mixture, mixture M-22, is characterized by a very good transmission in an FFS display and shows a short response time.

Example 23

The following mixture (M-23) is prepared and investigated.

Mixture 23

Composition

| No. | Compound Abbreviation | Concentration /% by weight |
|---|---|---|
| 1 | LB(S)-3-OT | 5.0 |
| 2 | CC-3-V | 27.0 |
| 3 | CC-3-V1 | 7.0 |
| 4 | CC-3-2V1 | 8.0 |
| 5 | CCP-V-1 | 15.0 |
| 6 | CCP-V2-1 | 4.0 |
| 7 | PP-1-2V1 | 3.5 |
| 8 | CCVC-3-V | 6.0 |
| 9 | CCP-3-OT | 5.0 |
| 10 | CLP-3-T | 4.0 |
| 11 | CCGU-3-F | 1.5 |
| 12 | CDUQU-3-F | 8.0 |
| 13 | DGUQU-2-F | 2.0 |
| 14 | DGUQU-4-F | 4.0 |
| Σ | | 100.0 |

Physical properties

| | |
|---|---|
| T(N, I) = | 107.0° C. |
| $n_e$(20° C., 589 nm) = | 1.5756 |
| $\Delta n$(20° C., 589 nm) = | 0.0932 |
| $\varepsilon_\parallel$(20° C., 1 kHz) = | 8.2 |
| $\varepsilon_\perp$(20° C., 1 kHz) = | 3.0 |
| $\Delta\varepsilon$(20° C., 1 kHz) = | 5.1 |
| $\varepsilon_{av.}$(20° C., 1 kHz) = | 4.7 |
| $\gamma_1$(20° C.) = | 92 mPa · s |
| $k_{11}$(20° C.) = | 19.1 pN |
| $k_{33}$(20° C.) = | 21.2 pN |
| $V_0$(20° C.) = | 2.03 V |
| $\varepsilon_\perp/\Delta\varepsilon$(20° C.) = | 0.59 |
| $\gamma_1/k_{11}$(20° C.) = | 4.82 * |

Remark:
* [mPa · s/pN].

This mixture, mixture M-23, is characterized by a very good transmission in an FFS display and shows a short response time.

Example 24

The following mixture (M-24) is prepared and investigated.

Mixture 24

Composition

| No. | Compound Abbreviation | Concentration /% by weight |
|---|---|---|
| 1 | LB(S)-3-OT | 6.0 |
| 2 | CC-3-V | 22.0 |
| 3 | CC-3-V1 | 8.0 |
| 4 | CC-3-2V1 | 8.0 |
| 5 | CCP-V-1 | 15.0 |
| 6 | CCP-V2-1 | 5.0 |
| 7 | PP-1-2V1 | 4.0 |
| 8 | CCVC-3-V | 4.0 |
| 9 | CCP-3-OT | 5.0 |
| 10 | CCP-5-OT | 2.0 |
| 11 | CLP-3-T | 5.0 |
| 12 | CCGU-3-F | 5.0 |
| 13 | CDUQU-3-F | 5.0 |
| 14 | DGUQU-2-F | 2.0 |
| 15 | DGUQU-4-F | 4.0 |
| Σ | | 100.0 |

Physical properties

| | |
|---|---|
| T(N, I) = | 112.0° C. |
| $n_e$(20° C., 589 nm) = | 1.5827 |
| $\Delta n$(20° C., 589 nm) = | 0.0990 |
| $\varepsilon_\parallel$(20° C., 1 kHz) = | 8.3 |
| $\varepsilon_\perp$(20° C., 1 kHz) = | 3.1 |
| $\Delta\varepsilon$(20° C., 1 kHz) = | 5.2 |
| $\varepsilon_{av.}$(20° C., 1 kHz) = | 4.8 |
| $\gamma_1$(20° C.) = | 104 mPa · s |
| $k_{11}$(20° C.) = | 20.4 pN |
| $k_{33}$(20° C.) = | 22.1 pN |
| $V_0$(20° C.) = | 2.09 V |
| $\varepsilon_\perp/\Delta\varepsilon$(20° C.) = | 0.50 |
| $\gamma_1/k_{11}$(20° C.) = | 5.10 * |

Remark:
* [mPa · s/pN].

This mixture, mixture M-24, is characterized by a very good transmission in an FFS display and shows a short response time.

Example 25

The following mixture (M-25) is prepared and investigated.

Mixture 25

Composition

| No. | Compound Abbreviation | Concentration /% by weight |
|---|---|---|
| 1 | LB(S)-3-OT | 10.0 |
| 2 | CC-3-V | 26.0 |
| 3 | CC-3-V1 | 9.0 |
| 4 | CC-3-2V1 | 9.0 |
| 5 | CCP-V-1 | 6.0 |
| 6 | CCP-V2-1 | 1.0 |
| 7 | PP-1-2V1 | 2.0 |
| 8 | PGP-1-2V | 5.0 |
| 9 | CCVC-3-V | 6.0 |
| 10 | CPGP-4-3 | 2.5 |

Mixture 25 -continued

| | | |
|---|---|---|
| 11 | CCP-3-OT | 4.0 |
| 12 | CLP-3-T | 2.0 |
| 13 | CCGU-3-F | 4.0 |
| 14 | CDUQU-3-F | 9.0 |
| 15 | DGUQU-4-F | 4.5 |
| Σ | | 100.0 |

Physical properties

| | |
|---|---|
| T(N, I) = | 113.0° C. |
| $n_e$(20° C., 589 nm) = | 1.5892 |
| Δn(20° C., 589 nm) = | 0.1080 |
| $\varepsilon_\parallel$(20° C., 1 kHz) = | 8.6 |
| $\varepsilon_\perp$(20° C., 1 kHz) = | 3.4 |
| Δε(20° C., 1 kHz) = | 5.2 |
| $\varepsilon_{av.}$(20° C., 1 kHz) = | 5.2 |
| $\gamma_1$(20° C.) = | 105 mPa · s |
| $k_{11}$(20° C.) = | 20.5 pN |
| $k_{33}$(20° C.) = | 20.9 pN |
| $V_0$(20° C.) = | 2.09 V |
| $\varepsilon_\perp/\Delta\varepsilon$(20° C.) = | 0.65 |
| $\gamma_1/k_{11}$(20° C.) = | 5.12 * |

Remark:
* [mPa · s/pN].

This mixture, mixture M-25, is characterized by a very good transmission in an FFS display and shows a short response time.

Example 26

The following mixture (M-26) is prepared and investigated.

Mixture 26
Composition

| No. | Compound Abbreviation | Concentration /% by weight |
|---|---|---|
| 1 | LB(S)-3-OT | 5.0 |
| 2 | CC-3-V | 28.5 |
| 3 | CC-3-V1 | 7.0 |
| 4 | CC-3-2V1 | 8.5 |
| 5 | CCP-V-1 | 8.0 |
| 6 | CCP-V2-1 | 4.5 |
| 7 | CLP-V-1 | 7.0 |
| 8 | CCVC-3-V | 5.0 |
| 9 | CCP-3-OT | 5.0 |
| 10 | CLP-3-T | 4.0 |
| 11 | CCGU-3-F | 4.0 |
| 12 | CDUQU-3-F | 8.0 |
| 13 | DGUQU-2-F | 1.5 |
| 14 | DGUQU-4-F | 4.0 |
| Σ | | 100.0 |

Physical properties

| | |
|---|---|
| T(N, I) = | 112.5° C. |
| $n_e$(20° C., 589 nm) = | 1.5750 |
| Δn(20° C., 589 nm) = | 0.0928 |
| $\varepsilon_\parallel$(20° C., 1 kHz) = | 8.5 |
| $\varepsilon_\perp$(20° C., 1 kHz) = | 3.1 |
| Δε(20° C., 1 kHz) = | 5.4 |
| $\varepsilon_{av.}$(20° C., 1 kHz) = | 4.9 |
| $\gamma_1$(20° C.) = | 101 mPa · s |
| $k_{11}$(20° C.) = | 20.1 pN |
| $k_{33}$(20° C.) = | 22.0 pN |
| $V_0$(20° C.) = | 2.03 V |

Mixture 26 -continued

| | |
|---|---|
| $\varepsilon_\perp/\Delta\varepsilon$(20° C.) = | 0.57 |
| $\gamma_1/k_{11}$(20° C.) = | 5.02 * |

Remark:
* [mPa · s/pN].

This mixture, mixture M-26, is characterized by a very good transmission in an FFS display and shows a short response time.

Example 27

The following mixture (M-27) is prepared and investigated.

Mixture 27
Composition

| No. | Compound Abbreviation | Concentration /% by weight |
|---|---|---|
| 1 | LB(S)-3-OT | 5.0 |
| 2 | CC-3-V | 28.5 |
| 3 | CC-3-V1 | 7.0 |
| 4 | CC-3-2V1 | 8.5 |
| 5 | CCP-V-1 | 8.0 |
| 6 | CCP-V2-1 | 4.5 |
| 7 | CLP-V-1 | 7.0 |
| 8 | CCVC-3-V | 7.0 |
| 9 | CCP-3-OT | 5.0 |
| 10 | CLP-3-T | 4.0 |
| 11 | PUQU-3-F | 2.0 |
| 12 | CDUQU-3-F | 8.0 |
| 13 | DGUQU-2-F | 1.5 |
| 14 | DGUQU-4-F | 4.0 |
| Σ | | 100.0 |

Physical properties

| | |
|---|---|
| T(N, I) = | 109.0° C. |
| $n_e$(20° C., 589 nm) = | 1.5733 |
| Δn(20° C., 589 nm) = | 0.0916 |
| $\varepsilon_\parallel$(20° C., 1 kHz) = | 8.3 |
| $\varepsilon_\perp$(20° C., 1 kHz) = | 3.0 |
| Δε(20° C., 1 kHz) = | 5.3 |
| $\varepsilon_{av.}$(20° C., 1 kHz) = | 4.8 |
| $\gamma_1$(20° C.) = | 93 mPa · s |
| $k_{11}$(20° C.) = | 19.8 pN |
| $k_{33}$(20° C.) = | 21.5 pN |
| $V_0$(20° C.) = | 2.03 V |
| $\varepsilon_\perp/\Delta\varepsilon$(20° C.) = | 0.57 |
| $\gamma_1/k_{11}$(20° C.) = | 4.70 * |

Remark:
* [mPa · s/pN].

This mixture, mixture M-27, is characterized by a very good transmission in an FFS display and shows a short response time.

Example 28

The following mixture (M-28) is prepared and investigated.

Mixture 28

Composition

| No. | Compound Abbreviation | Concentration /% by weight |
|---|---|---|
| 1 | LB-3-T | 3.5 |
| 2 | LB(S)-3-OT | 7.5 |
| 3 | CC-3-V | 31.0 |
| 4 | CC-3-V1 | 8.5 |
| 5 | CC-3-2V1 | 10.0 |
| 6 | CCP-V-1 | 5.0 |
| 7 | CCVC-3-V | 4.0 |
| 8 | CLP-V-1 | 4.0 |
| 9 | CCP-3-OT | 5.0 |
| 10 | CLP-3-T | 8.0 |
| 11 | CDUQU-3-F | 8.0 |
| 12 | DGUQU-2-F | 1.5 |
| 13 | DGUQU-4-F | 4.0 |
| Σ | | 100.0 |

Physical properties

| | |
|---|---|
| T(N, I) = | 99.5° C. |
| $n_e$(20° C., 589 nm) = | 1.5695 |
| $\Delta n$(20° C., 589 nm) = | 0.0913 |
| $\varepsilon_{\parallel}$(20° C., 1 kHz) = | 8.7 |
| $\varepsilon_{\perp}$(20° C., 1 kHz) = | 3.5 |
| $\Delta\varepsilon$(20° C., 1 kHz) = | 5.2 |
| $\varepsilon_{av.}$(20° C., 1 kHz) = | 5.2 |
| $k_{11}$(20° C.) = | 19.8 pN |
| $k_{33}$(20° C.) = | 20.2 pN |
| $V_0$(20° C.) = | 2.07 V |
| $\varepsilon_{\perp}/\Delta\varepsilon$(20° C.) = | 0.67 |

Remark:
* [mPa · s/pN].

This mixture, mixture M-28, is characterized by a very good transmission in an FFS display and shows a short response time.

Example 29

The following mixture (M-29) is prepared and investigated.

Mixture 29

Composition

| No. | Compound Abbreviation | Concentration /% by weight |
|---|---|---|
| 1 | LB-3-T | 2.0 |
| 2 | LB(S)-3-OT | 5.5 |
| 3 | CC-3-V | 31.5 |
| 4 | CC-3-V1 | 8.0 |
| 5 | CC-3-2V1 | 8.0 |
| 6 | CCP-V-1 | 8.0 |
| 7 | CCVC-3-V | 4.0 |
| 8 | CLP-V-1 | 6.0 |
| 9 | CCP-3-OT | 5.0 |
| 10 | CLP-3-T | 6.0 |
| 11 | CCGU-3-F | 3.0 |
| 12 | CDUQU-3-F | 8.0 |
| 13 | DGUQU-2-F | 1.0 |
| 14 | DGUQU-4-F | 4.0 |
| Σ | | 100.0 |

Physical properties

| | |
|---|---|
| T(N, I) = | 104.5° C. |
| $n_e$(20° C., 589 nm) = | 1.5722 |
| $\Delta n$(20° C., 589 nm) = | 0.0923 |
| $\varepsilon_{\parallel}$(20° C., 1 kHz) = | 8.4 |
| $\varepsilon_{\perp}$(20° C., 1 kHz) = | 3.2 |
| $\Delta\varepsilon$(20° C., 1 kHz) = | 5.2 |
| $\varepsilon_{av.}$(20° C., 1 kHz) = | 4.9 |
| $k_{11}$(20° C.) = | 19.2 pN |
| $k_{33}$(20° C.) = | 20.9 pN |
| $V_0$(20° C.) = | 2.03 V |
| $\varepsilon_{\perp}/\Delta\varepsilon$(20° C.) = | 0.62 |

Remark:
* [mPa · s/pN].

This mixture, mixture M-29, is characterized by a very good transmission in an FFS display and shows a short response time.

Example 30

The following mixture (M-30) is prepared and investigated.

Mixture 30

Composition

| No. | Compound Abbreviation | Concentration /% by weight |
|---|---|---|
| 1 | LB-3-T | 7.0 |
| 2 | LB(S)-3-OT | 9.0 |
| 3 | CC-3-V | 43.0 |
| 4 | CC-3-V1 | 12.0 |
| 5 | CCP-V-1 | 10.5 |
| 6 | PGP-2-2V | 4.0 |
| 7 | CY-3-O2 | 4.0 |
| 8 | PPGU-3-F | 0.5 |
| 9 | APUQU-2-F | 4.0 |
| 10 | APUQU-3-F | 6.0 |
| Σ | | 100.0 |

Physical properties

| | |
|---|---|
| T(N, I) = | 79.2° C. |
| $n_e$(20° C., 589 nm) = | 1.5820 |
| $\Delta n$(20° C., 589 nm) = | 0.0994 |
| $\varepsilon_{\parallel}$(20° C., 1 kHz) = | 6.7 |
| $\varepsilon_{\perp}$(20° C., 1 kHz) = | 4.1 |
| $\Delta\varepsilon$(20° C., 1 kHz) = | 2.6 |
| $\varepsilon_{av.}$(20° C., 1 kHz) = | 5.0 |
| $\gamma_1$(20° C.) = | 63 mPa · s |
| $k_{11}$(20° C.) = | 14.5 pN |
| $k_{33}$(20° C.) = | 14.4 pN |
| $V_0$(20° C.) = | 2.48 V |
| $\varepsilon_{\perp}/\Delta\varepsilon$(20° C.) = | 1.58 |
| $\gamma_1/k_{11}$(20° C.) = | 4.34 * |

Remark:
* [mPa · s/pN].

This mixture, mixture M-30, is characterized by a very good transmission in an FFS display and shows a short response time.

Example 31

The following mixture (M-31) is prepared and investigated.

| Mixture 31 | |
|---|---|
| Composition | |
| Compound | Concentration |
| No. | Abbreviation | /% by weight |

| No. | Abbreviation | /% by weight |
|---|---|---|
| 1 | LB-3-T | 10.0 |
| 2 | LB(S)-3-OT | 10.0 |
| 3 | CC-3-V | 47.5 |
| 4 | CC-3-V1 | 5.0 |
| 5 | CCP-V-1 | 4.0 |
| 6 | CCP-V2-1 | 10.0 |
| 7 | PP-1-2V1 | 4.0 |
| 8 | PPGU-3-F | 0.5 |
| 9 | APUQU-2-F | 3.0 |
| 10 | APUQU-3-F | 6.0 |
| Σ | | 100.0 |

| Physical properties | |
|---|---|
| $T(N, I) =$ | 81.2° C. |
| $n_e(20° C., 589\ nm) =$ | 1.5849 |
| $\Delta n(20° C., 589\ nm) =$ | 0.1013 |
| $\varepsilon_\parallel(20° C., 1\ kHz) =$ | 6.7 |
| $\varepsilon_\perp(20° C., 1\ kHz) =$ | 4.1 |
| $\Delta\varepsilon(20° C., 1\ kHz) =$ | 2.6 |
| $\varepsilon_{av.}(20° C., 1\ kHz) =$ | 5.0 |
| $\gamma_1(20° C.) =$ | 64 mPa·s |
| $k_{11}(20° C.) =$ | 15.6 pN |
| $k_{33}(20° C.) =$ | 14.5 pN |
| $V_0(20° C.) =$ | 2.55 V |
| $\varepsilon_\perp/\Delta\varepsilon(20° C.) =$ | 1.58 |
| $\gamma_1/k_{11}(20° C.) =$ | 4.10 * |

Remark:
* [mPa·s/pN].

This mixture, mixture M-31, is characterized by a very good transmission in an FFS display and shows a short response time.

Example 32

The following mixture (M-32) is prepared and investigated.

| Mixture 32 | | |
|---|---|---|
| Composition | | |
| Compound | | Concentration |
| No. | Abbreviation | /% by weight |
| 1 | LB-4-T | 3.0 |
| 2 | LB(S)-3-OT | 3.0 |
| 3 | CC-3-V | 37.0 |
| 4 | CC-3-V1 | 4.0 |
| 5 | CCP-V-1 | 11.0 |
| 6 | CCP-V2-1 | 3.0 |
| 7 | CLP-V-1 | 6.0 |
| 8 | CCVC-3-V | 5.0 |
| 9 | CPGP-5-2 | 2.5 |
| 10 | PGP-1-2V | 5.0 |
| 11 | PGP-2-2V | 7.0 |
| 12 | PPGU-3-F | 0.5 |
| 13 | DPGU-4-F | 2.0 |
| 14 | PUQU-3-F | 6.0 |
| 15 | APUQU-2-F | 3.0 |
| 16 | DGUQU-4-F | 2.0 |
| Σ | | 100.0 |

| Mixture 32 | |
|---|---|
| Physical properties | |
| $T(N, I) =$ | 103.0° C. |
| $n_e(20° C., 589\ nm) =$ | 1.6117 |
| $\Delta n(20° C., 589\ nm) =$ | 0.1198 |
| $\varepsilon_\parallel(20° C., 1\ kHz) =$ | 7.0 |
| $\varepsilon_\perp(20° C., 1\ kHz) =$ | 3.2 |
| $\Delta\varepsilon(20° C., 1\ kHz) =$ | 3.8 |
| $\varepsilon_{av.}(20° C., 1\ kHz) =$ | 4.0 |
| $k_{11}(20° C.) =$ | 17.0 pN |
| $k_{33}(20° C.) =$ | 17.3 pN |
| $V_0(20° C.) =$ | 2.24 V |
| $\varepsilon_\perp/\Delta\varepsilon(20° C.) =$ | 0.82 |

This mixture, mixture M-32, is characterized by a very good transmission in an FFS display and shows a short response time.

Example 33

The following mixture (M-33) is prepared and investigated.

| Mixture 33 | | |
|---|---|---|
| Composition | | |
| Compound | | Concentration |
| No. | Abbreviation | /% by weight |
| 1 | LB(S)-3-OT | 3.0 |
| 2 | CC-3-V | 49.5 |
| 3 | CC-3-V1 | 10.5 |
| 4 | CLP-V-1 | 9.0 |
| 5 | CLP-1V-1 | 6.0 |
| 6 | PPGU-3-F | 0.5 |
| 7 | PP-1-2V1 | 7.0 |
| 8 | PGP-2-3 | 2.0 |
| 9 | CLP-3-T | 4.0 |
| 10 | APUQU-3-F | 2.5 |
| 11 | PGUQU-3-F | 6.0 |
| Σ | | 100.0 |

| Physical properties | |
|---|---|
| $T(N, I) =$ | 81.0° C. |
| $n_e(20° C., 589\ nm) =$ | 1.5865 |
| $\Delta n(20° C., 589\ nm) =$ | 0.1004 |
| $\varepsilon_\parallel(20° C., 1\ kHz) =$ | 5.4 |
| $\varepsilon_\perp(20° C., 1\ kHz) =$ | 2.7 |
| $\Delta\varepsilon(20° C., 1\ kHz) =$ | 2.7 |
| $\varepsilon_{av.}(20° C., 1\ kHz) =$ | 3.6 |
| $\gamma_1(20° C.) =$ | 52 mPa·s |
| $k_{11}(20° C.) =$ | 16.3 pN |
| $k_{33}(20° C.) =$ | 17.4 pN |
| $V_0(20° C.) =$ | 2.59 V |
| $\varepsilon_\perp/\Delta\varepsilon(20° C.) =$ | 1.00 |
| $\gamma_1/k_{11}(20° C.) =$ | 3.19 * |

Remark:
* [mPa·s/pN].

This mixture, mixture M-33, is characterized by a very good transmission in an FFS display and shows a short response time.

Example 34

The following mixture (M-34) is prepared and investigated.

Mixture 34

Composition

| No. | Compound Abbreviation | Concentration /% by weight |
|---|---|---|
| 1 | LB-4-T | 6.0 |
| 2 | LB(S)-3-OT | 8.0 |
| 3 | LB(S)-4-OT | 8.0 |
| 4 | CC-3-V | 46.0 |
| 5 | CC-3-V1 | 7.0 |
| 6 | CC-3-2V1 | 5.5 |
| 7 | CLP-V-1 | 4.0 |
| 8 | CLP-1V-1 | 4.0 |
| 9 | PP-1-2V1 | 2.5 |
| 10 | PGU-3-F | 2.5 |
| 11 | APUQU-2-F | 2.0 |
| 12 | DGUQU-4-F | 4.5 |
| Σ | | 100.0 |

Physical properties

| | |
|---|---|
| T(N, I) = | 81.0° C. |
| $n_e$(20° C., 589 nm) = | 1.5851 |
| $\Delta n$(20° C., 589 nm) = | 0.1020 |
| $\varepsilon_{\parallel}$(20° C., 1 kHz) = | 6.8 |
| $\varepsilon_{\perp}$(20° C., 1 kHz) = | 4.0 |
| $\Delta\varepsilon$(20° C., 1 kHz) = | 2.8 |
| $\varepsilon_{av.}$(20° C., 1 kHz) = | 4.9 |
| $\gamma_1$(20° C.) = | 62 mPa · s |
| $k_{11}$(20° C.) = | 16.2 pN |
| $k_{33}$(20° C.) = | 15.3 pN |
| $V_0$(20° C.) = | 2.55 V |
| $\varepsilon_{\perp}/\Delta\varepsilon$(20° C.) = | 1.48 |
| $\gamma_1/k_{11}$(20° C.) = | 3.83 * |

Remark:
* [mPa · s/pN].

This mixture, mixture M-34, is characterized by a very good transmission in an FFS display and shows a short response time.

Example 35

The following mixture (M-35) is prepared and investigated.

Mixture 35

Composition

| No. | Compound Abbreviation | Concentration /% by weight |
|---|---|---|
| 1 | LB-4-T | 4.0 |
| 2 | LB(S)-3-OT | 7.0 |
| 3 | LB(S)-4-OT | 7.0 |
| 4 | CC-3-V | 43.5 |
| 5 | CC-3-V1 | 6.0 |
| 6 | CC-3-2V1 | 5.0 |
| 7 | CLP-V-1 | 2.0 |
| 8 | PP-1-2V1 | 7.5 |
| 9 | PGP-2-2V | 10.0 |
| 10 | PGU-3-F | 3.5 |
| 11 | DGUQU-4-F | 4.5 |
| Σ | | 100.0 |

Physical properties

| | |
|---|---|
| T(N, I) = | 75.0° C. |
| $n_e$(20° C., 589 nm) = | 1.6065 |
| $\Delta n$(20° C., 589 nm) = | 0.1180 |
| $\varepsilon_{\parallel}$(20° C., 1 kHz) = | 6.3 |
| $\varepsilon_{\perp}$(20° C., 1 kHz) = | 3.7 |
| $\Delta\varepsilon$(20° C., 1 kHz) = | 2.6 |
| $\varepsilon_{av.}$(20° C., 1 kHz) = | 4.6 |
| $\gamma_1$(20° C.) = | 55 mPa · s |
| $k_{11}$(20° C.) = | 16.2 pN |
| $k_{33}$(20° C.) = | 14.8 pN |
| $V_0$(20° C.) = | 2.65 V |
| $\varepsilon_{\perp}/\Delta\varepsilon$(20° C.) = | 1.42 |
| $\gamma_1/k_{11}$(20° C.) = | 3.40 * |

Remark:
* [mPa · s/pN].

This mixture, mixture M-35, is characterized by a very good transmission in an FFS display and shows a short response time.

Example 36

The following mixture (M-36) is prepared and investigated.

Mixture 36

Composition

| No. | Compound Abbreviation | Concentration /% by weight |
|---|---|---|
| 1 | LB-4-T | 6.0 |
| 2 | LB(S)-3-OT | 8.0 |
| 3 | LB(S)-4-OT | 8.0 |
| 4 | CC-3-V | 46.5 |
| 5 | CC-3-V1 | 7.0 |
| 6 | CC-3-2V1 | 6.0 |
| 7 | CLP-V-1 | 3.0 |
| 8 | CLP-1V-1 | 4.0 |
| 9 | PP-1-2V1 | 2.0 |
| 10 | PGU-3-F | 2.5 |
| 11 | APUQU-2-F | 2.5 |
| 12 | DGUQU-4-F | 4.5 |
| Σ | | 100.0 |

Physical properties

| | |
|---|---|
| T(N, I) = | 80.5° C. |
| $n_e$(20° C., 589 nm) = | 1.5840 |
| $\Delta n$(20° C., 589 nm) = | 0.1014 |
| $\varepsilon_{\parallel}$(20° C., 1 kHz) = | 6.9 |
| $\varepsilon_{\perp}$(20° C., 1 kHz) = | 4.0 |
| $\Delta\varepsilon$(20° C., 1 kHz) = | 3.0 |
| $\varepsilon_{av.}$(20° C., 1 kHz) = | 5.0 |
| $\gamma_1$(20° C.) = | 61 mPa · s |
| $k_{11}$(20° C.) = | 16.0 pN |
| $k_{33}$(20° C.) = | 15.2 pN |
| $V_0$(20° C.) = | 2.46 V |
| $\varepsilon_{\perp}/\Delta\varepsilon$(20° C.) = | 1.33 |
| $\gamma_1/k_{11}$(20° C.) = | 3.81 * |

Remark:
* [mPa · s/pN].

This mixture, mixture M-36, is characterized by a very good transmission in an FFS display and shows a short response time.

Example 37

The following mixture (M-37) is prepared and investigated.

| Mixture 37 | | |
|---|---|---|
| Composition | | |
| Compound | | Concentration |
| No. | Abbreviation | /% by weight |
| 1 | LB(S)-3-OT | 2.0 |
| 2 | CC-3-V | 29.0 |
| 3 | CC-3-V1 | 7.0 |
| 4 | CC-3-2V1 | 8.5 |
| 5 | CCP-V-1 | 8.0 |
| 6 | CCP-V2-1 | 4.5 |
| 7 | CLP-V-1 | 7.0 |
| 8 | CCVC-3-V | 4.0 |
| 9 | PP-1-2V1 | 3.5 |
| 10 | CCP-3-OT | 5.0 |
| 11 | CLP-3-T | 4.0 |
| 12 | CCGU-3-F | 4.0 |
| 13 | CDUQU-3-F | 8.0 |
| 14 | DGUQU-2-F | 1.5 |
| 15 | DGUQU-4-F | 4.0 |
| Σ | | 100.0 |

| Physical properties | |
|---|---|
| T(N, I) = | 106.0° C. |
| $n_e$(20° C., 589 nm) = | 1.5761 |
| Δn(20° C., 589 nm) = | 0.0932 |
| $\varepsilon_\parallel$(20° C., 1 kHz) = | 8.2 |
| $\varepsilon_\perp$(20° C., 1 kHz) = | 2.9 |
| Δε(20° C., 1 kHz) = | 5.3 |
| $\varepsilon_{av.}$(20° C., 1 kHz) = | 4.7 |
| $\gamma_1$(20° C.) = | 92 mPa · s |
| $k_{11}$(20° C.) = | 19.5 pN |
| $k_{33}$(20° C.) = | 21.1 pN |
| $V_0$(20° C.) = | 2.02 V |
| $\varepsilon_\perp/\Delta\varepsilon$(20° C.) = | 0.53 |
| $\gamma_1/k_{11}$(20° C.) = | 4.72 * |

Remark:
* [mPa · s/pN].

This mixture, mixture M-37, is characterized by a very good transmission in an FFS display and shows a short response time.

Example 38

The following mixture (M-38) is prepared and investigated.

| Mixture 38 | | |
|---|---|---|
| Composition | | |
| Compound | | Concentration |
| No. | Abbreviation | /% by weight |
| 1 | LB(S)-3-OT | 2.5 |
| 2 | CC-3-V | 29.0 |
| 3 | CC-3-V1 | 9.0 |
| 4 | CCP-V-1 | 13.0 |
| 5 | CCP-V2-1 | 2.0 |
| 6 | CLP-1V-1 | 6.0 |
| 7 | CCVC-3-V | 3.0 |
| 8 | CP-3-O2 | 3.0 |
| 9 | PP-1-2V1 | 3.0 |
| 10 | PGP-1-2V | 3.0 |
| 11 | PGP-2-2V | 7.0 |
| 12 | CCP-3-OT | 3.0 |
| 13 | CCP-5-OT | 2.0 |
| 14 | DPGU-4-F | 1.5 |
| 15 | APUQU-2-F | 2.5 |
| 16 | APUQU-3-F | 3.5 |
| 17 | PGUQU-3-F | 3.0 |
| 18 | DGUQU-4-F | 4.0 |
| Σ | | 100.0 |

| Physical properties | |
|---|---|
| T(N, I) = | 108.0° C. |

Remark:
t.b.d.: to be determined.

This mixture, mixture M-38, is characterized by a very good transmission in an FFS display and shows a short response time.

Example 39

The following mixture (M-39) is prepared and investigated.

| Mixture 39 | | |
|---|---|---|
| Composition | | |
| Compound | | Concentration |
| No. | Abbreviation | /% by weight |
| 1 | LB-4-T | 1.5 |
| 2 | LB(S)-3-OT | 2.5 |
| 3 | CC-3-V | 29.0 |
| 4 | CC-3-V1 | 7.5 |
| 5 | CC-3-2V1 | 8.5 |
| 6 | CCP-V-1 | 9.5 |
| 7 | CCP-V2-1 | 2.5 |
| 8 | CLP-V-1 | 7.0 |
| 9 | CCVC-3-V | 4.0 |
| 10 | PP-1-2V1 | 2.0 |
| 11 | CCP-3-OT | 5.0 |
| 12 | CLP-3-T | 4.0 |
| 13 | CCGU-3-F | 3.5 |
| 14 | CDUQU-3-F | 8.0 |
| 15 | DGUQU-2-F | 1.5 |
| 16 | DGUQU-4-F | 4.0 |
| Σ | | 100.0 |

| Physical properties | |
|---|---|
| T(N, I) = | 106.0° C. |
| $n_e$(20° C., 589 nm) = | 1.5746 |
| Δn(20° C., 589 nm) = | 0.0926 |
| $\varepsilon_\parallel$(20° C., 1 kHz) = | 8.3 |
| $\varepsilon_\perp$(20° C., 1 kHz) = | 3.0 |
| Δε(20° C., 1 kHz) = | 5.3 |
| $\varepsilon_{av.}$(20° C., 1 kHz) = | 4.8 |
| $\gamma_1$(20° C.) = | 92 mPa · s |
| $k_{11}$(20° C.) = | 19.4 pN |
| $k_{33}$(20° C.) = | 20.8 pN |
| $V_0$(20° C.) = | 2.03 V |
| $\varepsilon_\perp/\Delta\varepsilon$(20° C.) = | 0.57 |
| $\gamma_1/k_{11}$(20° C.) = | 4.74 * |

Remark:
* [mPa · s/pN].

This mixture, mixture M-39, is characterized by a very good transmission in an FFS display and shows a short response time.

Example 40

The following mixture (M-40) is prepared and investigated.

| Mixture 340 | | |
|---|---|---|
| Composition | | |
| Compound | | Concentration |
| No. | Abbreviation | /% by weight |
| 1 | LB-4-T | 2.0 |
| 2 | LB(S)-3-OT | 2.0 |
| 3 | CC-3-V | 28.0 |
| 4 | CC-3-V1 | 7.5 |
| 5 | CC-3-2V1 | 8.5 |
| 6 | CCP-V-1 | 10.5 |
| 7 | CCP-V2-1 | 1.5 |
| 8 | CLP-V-1 | 7.0 |
| 9 | CCVC-3-V | 4.5 |
| 10 | PP-1-2V1 | 2.0 |
| 11 | CCP-3-OT | 5.0 |
| 12 | CLP-3-T | 5.5 |
| 13 | CCGU-3-F | 2.0 |
| 14 | PUQU-3-F | 1.5 |
| 15 | CDUQU-3-F | 7.0 |
| 16 | DGUQU-2-F | 1.5 |
| 17 | DGUQU-4-F | 4.0 |
| Σ | | 100.0 |
| Physical properties | | |
| $T(N, I) =$ | | 104.5° C. |
| $n_e(20° C., 589\ nm) =$ | | 1.5756 |
| $\Delta n(20° C., 589\ nm) =$ | | 0.0936 |
| $\varepsilon_{\parallel}(20° C., 1\ kHz) =$ | | 8.4 |
| $\varepsilon_{\perp}(20° C., 1\ kHz) =$ | | 3.1 |
| $\Delta\varepsilon(20° C., 1\ kHz) =$ | | 5.3 |
| $\varepsilon_{av.}(20° C., 1\ kHz) =$ | | 4.9 |
| $\gamma_1(20° C.) =$ | | 91 mPa·s |
| $k_{11}(20° C.) =$ | | 19.5 pN |
| $k_{33}(20° C.) =$ | | 20.4 pN |
| $V_0(20° C.) =$ | | 2.03 V |
| $\varepsilon_{\perp}/\Delta\varepsilon(20° C.) =$ | | 0.58 |
| $\gamma_1/k_{11}(20° C.) =$ | | 4.67 * |

Remark:
* [mPa·s/pN].

This mixture, mixture M-40, is characterized by a very good transmission in an FFS display and shows a short response time.

Example 41

The following mixture (M-41) is prepared and investigated.

| Mixture 41 | | |
|---|---|---|
| Composition | | |
| Compound | | Concentration |
| No. | Abbreviation | /% by weight |
| 1 | LB-4-T | 2.0 |
| 2 | LB(S)-3-OT | 1.5 |
| 3 | CC-3-V | 30.0 |
| 4 | CC-3-V1 | 7.5 |
| 5 | CC-3-2V1 | 8.5 |
| 6 | CCP-V-1 | 8.0 |
| 7 | CCP-V2-1 | 4.5 |
| 8 | CLP-V-1 | 6.5 |
| 9 | CCVC-3-V | 4.0 |
| 10 | PP-1-2V1 | 1.5 |
| 11 | CCP-3-OT | 5.0 |
| 12 | CLP-3-T | 4.0 |
| 13 | CCGU-3-F | 3.5 |
| 14 | CDUQU-3-F | 8.0 |
| 15 | DGUQU-2-F | 1.5 |
| 16 | DGUQU-4-F | 4.0 |
| Σ | | 100.0 |
| Physical properties | | |
| $T(N, I) =$ | | 106.0° C. |
| $n_e(20° C., 589\ nm) =$ | | 1.5725 |
| $\Delta n(20° C., 589\ nm) =$ | | 0.0910 |
| $\varepsilon_{\parallel}(20° C., 1\ kHz) =$ | | 8.2 |
| $\varepsilon_{\perp}(20° C., 1\ kHz) =$ | | 3.0 |
| $\Delta\varepsilon(20° C., 1\ kHz) =$ | | 5.2 |
| $\varepsilon_{av.}(20° C., 1\ kHz) =$ | | 4.7 |
| $\gamma_1(20° C.) =$ | | 91 mPa·s |
| $k_{11}(20° C.) =$ | | 19.2 pN |
| $k_{33}(20° C.) =$ | | 21.1 pN |
| $V_0(20° C.) =$ | | 2.02 V |
| $\varepsilon_{\perp}/\Delta\varepsilon(20° C.) =$ | | 0.58 |
| $\gamma_1/k_{11}(20° C.) =$ | | 4.74 * |

Remark:
* [mPa·s/pN].

This mixture, mixture M-41, is characterized by a very good transmission in an FFS display and shows a short response time.

Example 42

The following mixture (M-42) is prepared and investigated.

| Mixture 42 | | |
|---|---|---|
| Composition | | |
| Compound | | Concentration |
| No. | Abbreviation | /% by weight |
| 1 | LB(S)-3-OT | 3.0 |
| 2 | B(S)-2O-O4 | 4.0 |
| 3 | B(S)-2O-O5 | 4.0 |
| 4 | CC-3-V | 45.0 |
| 5 | CC-3-V1 | 11.0 |
| 6 | CCP-V-1 | 16.0 |
| 7 | CLP-3-T | 1.0 |
| 8 | PPGU-3-F | 0.5 |
| 9 | PGUQU-3-F | 7.5 |
| 10 | PGUQU-5-F | 3.0 |
| 11 | DGUQU-4-F | 5.0 |
| Σ | | 100.0 |
| Physical properties | | |
| $T(N, I) =$ | | 79.0° C. |
| $n_e(20° C., 589\ nm) =$ | | 1.5824 |
| $\Delta n(20° C., 589\ nm) =$ | | 0.0978 |
| $\varepsilon_{\parallel}(20° C., 1\ kHz) =$ | | 7.9 |
| $\varepsilon_{\perp}(20° C., 1\ kHz) =$ | | 3.9 |
| $\Delta\varepsilon(20° C., 1\ kHz) =$ | | 4.0 |
| $\varepsilon_{av.}(20° C., 1\ kHz) =$ | | 5.2 |
| $\gamma_1(20° C.) =$ | | 56 mPa·s |
| $k_{11}(20° C.) =$ | | 13.1 pN |
| $k_{33}(20° C.) =$ | | 15.3 pN |
| $V_0(20° C.) =$ | | 1.91 V |
| $\varepsilon_{\perp}/\Delta\varepsilon(20° C.) =$ | | 0.98 |
| $\gamma_1/k_{11}(20° C.) =$ | | 4.27 * |

Remark:
* [mPa·s/pN].

This mixture, mixture M-42, is characterized by a very good transmission in an FFS display and shows a short response time.

Example 43

The following mixture (M-43) is prepared and investigated.

| Mixture 43 | | |
|---|---|---|
| Composition | | |
| Compound | | Concentration |
| No. | Abbreviation | /% by weight |
| 1 | LB-3-T | 1.0 |
| 2 | LB(S)-3-OT | 3.0 |
| 3 | CC-3-V | 43.0 |
| 4 | CC-3-V1 | 5.5 |
| 5 | CCP-V-1 | 6.5 |
| 6 | PP-1-2V1 | 10.0 |
| 7 | PGP-1-2V | 3.0 |
| 8 | PGP-2-2V | 7.5 |
| 9 | CLP-3-T | 5.0 |
| 10 | PGU-3-F | 4.5 |
| 11 | DPGU-4-F | 4.0 |
| 12 | PPGU-3-F | 0.5 |
| 13 | APUQU-3-F | 1.5 |
| 14 | DGUQU-2-F | 1.5 |
| 15 | DGUQU-4-F | 3.5 |
| Σ | | 100.0 |

| Physical properties | |
|---|---|
| T(N, I) = | 77.0° C. |
| $n_e$(20° C., 589 nm) = | 1.6106 |
| Δn(20° C., 589 nm) = | 0.1198 |
| $ε_∥$(20° C., 1 kHz) = | 7.7 |
| $ε_⊥$(20° C., 1 kHz) = | 3.1 |
| Δε(20° C., 1 kHz) = | 4.6 |
| $ε_{av.}$(20° C., 1 kHz) = | 4.6 |
| $γ_1$(20° C.) = | 56 mPa · s |
| $k_{11}$(20° C.) = | 15.7 pN |
| $k_{33}$(20° C.) = | 14.2 pN |
| $V_0$(20° C.) = | 1.95 V |
| $ε_⊥/Δε$(20° C.) = | 0.67 |
| $γ_1/k_{11}$(20° C.) = | 3.57 * |

Remark:
* [mPa · s/pN].

This mixture, mixture M-43, is characterized by a very good transmission in an FFS display and shows a short response time.

Example 44

The following mixture (M-44) is prepared and investigated.

| Mixture 44 | | |
|---|---|---|
| Composition | | |
| Compound | | Concentration |
| No. | Abbreviation | /% by weight |
| 1 | LB-3-T | 4.0 |
| 2 | LB(S)-3-OT | 6.0 |
| 3 | CC-3-V | 41.5 |
| 4 | CC-3-V1 | 4.0 |
| 5 | CCP-V-1 | 10.0 |
| 6 | PGP-1-2V | 5.0 |
| 7 | PGP-2-2V | 7.0 |
| 8 | PGP-3-2V | 2.0 |
| 9 | PPGU-3-F | 0.5 |
| 10 | PUQU-3-F | 5.0 |
| 11 | APUQU-3-F | 4.0 |
| 12 | PGUQU-3-F | 4.0 |
| 13 | PGUQU-4-F | 4.0 |
| 14 | PGUQU-5-F | 3.0 |
| Σ | | 100.0 |

| Physical properties | |
|---|---|
| T(N, I) = | 85.5° C. |
| $n_e$(20° C., 589 nm) = | 1.6167 |
| Δn(20° C., 589 nm) = | 0.1269 |
| $ε_∥$(20° C., 1 kHz) = | 9.4 |
| $ε_⊥$(20° C., 1 kHz) = | 3.7 |
| Δε(20° C., 1 kHz) = | 5.8 |
| $ε_{av.}$(20° C., 1 kHz) = | 4.9 |
| $γ_1$(20° C.) = | 70 mPa · s |
| $k_{11}$(20° C.) = | 14.7 pN |
| $k_{33}$(20° C.) = | 14.8 pN |
| $V_0$(20° C.) = | 1.68 V |
| $ε_⊥/Δε$(20° C.) = | 0.64 |
| $γ_1/k_{11}$(20° C.) = | 4.76 * |

Remark:
* [mPa · s/pN].

This mixture, mixture M-44, is characterized by a very good transmission in an FFS display and shows a short response time.

Example 45

The following mixture (M-45) is prepared and investigated.

| Mixture 45 | | |
|---|---|---|
| Composition | | |
| Compound | | Concentration |
| No. | Abbreviation | /% by weight |
| 1 | LB-3-T | 7.0 |
| 2 | LB(S)-3-OT | 9.5 |
| 3 | CPY-3-O2 | 7.0 |
| 4 | CC-3-V | 50.0 |
| 5 | CCP-V-1 | 15.0 |
| 6 | CCGU-3-F | 2.0 |
| 7 | PPGU-3-F | 0.5 |
| 8 | PUQU-3-F | 9.0 |
| Σ | | 100.0 |

| Physical properties | |
|---|---|
| T(N, I) = | 79.5° C. |
| $n_e$(20° C., 589 nm) = | 1.5839 |
| Δn(20° C., 589 nm) = | 0.1000 |
| $ε_∥$(20° C., 1 kHz) = | 6.6 |
| $ε_⊥$(20° C., 1 kHz) = | 4.3 |
| Δε(20° C., 1 kHz) = | 2.3 |
| $ε_{av.}$(20° C., 1 kHz) = | 5.1 |
| $γ_1$(20° C.) = | 60 mPa · s |
| $k_{11}$(20° C.) = | 13.6 pN |
| $k_{33}$(20° C.) = | 14.8 pN |
| $V_0$(20° C.) = | 2.55 V |

-continued

| Mixture 45 | |
|---|---|
| $\varepsilon_\perp/\Delta\varepsilon(20°\text{ C.}) =$ | 1.87 |
| $\gamma_1/k_{11}(20°\text{ C.}) =$ | 4.41 * |

Remark:

* [mPa · s/pN].

This mixture, mixture M-45, is characterized by a very good transmission in an FFS display and shows a short response time.

Example 46

The following mixture (M-46) is prepared and investigated.

Mixture 46

Composition

| Compound | | Concentration |
|---|---|---|
| No. | Abbreviation | /% by weight |
| 1 | LB-3-T | 6.5 |
| 2 | LB(S)-3-OT | 10.0 |
| 3 | CY-3-O4 | 5.0 |
| 4 | CCY-3-O2 | 2.0 |
| 5 | CC-3-V | 49.5 |
| 6 | CCP-V-1 | 13.5 |
| 7 | PGU-3-F | 8.0 |
| 8 | CCGU-3-F | 5.0 |
| 9 | PPGU-3-F | 0.5 |
| Σ | | 100.0 |

Physical properties

| | |
|---|---|
| T(N, I) = | 78.0° C. |
| $n_e(20°\text{ C., }589\text{ nm}) =$ | 1.5851 |
| $\Delta n(20°\text{ C., }589\text{ nm}) =$ | 0.1003 |
| $\varepsilon_\parallel(20°\text{ C., }1\text{ kHz}) =$ | 6.3 |
| $\varepsilon_\perp(20°\text{ C., }1\text{ kHz}) =$ | 4.3 |
| $\Delta\varepsilon(20°\text{ C., }1\text{ kHz}) =$ | 2.1 |
| $\varepsilon_{av.}(20°\text{ C., }1\text{ kHz}) =$ | 5.0 |
| $\gamma_1(20°\text{ C.}) =$ | 62 mPa · s |
| $k_{11}(20°\text{ C.}) =$ | 13.3 pN |
| $k_{33}(20°\text{ C.}) =$ | 14.3 pN |
| $V_0(20°\text{ C.}) =$ | 2.67 V |
| $\varepsilon_\perp/\Delta\varepsilon(20°\text{ C.}) =$ | 2.05 |
| $\gamma_1/k_{11}(20°\text{ C.}) =$ | 4.66 * |

Remark:

* [mPa · s/pN].

This mixture, mixture M-46, is characterized by a very good transmission in an FFS display and shows a short response time.

Example 47

The following mixture (M-47) is prepared and investigated.

Mixture 47

Composition

| Compound | | Concentration |
|---|---|---|
| No. | Abbreviation | /% by weight |
| 1 | LB(S)-3-OT | 7.0 |
| 2 | CC-3-V | 44.0 |
| 3 | CC-3-V1 | 6.5 |
| 4 | CCP-V-1 | 5.5 |
| 5 | PP-1-2V1 | 1.5 |
| 6 | PGP-1-2V | 6.0 |
| 7 | PGP-2-2V | 6.0 |
| 8 | PGP-3-2V | 3.0 |
| 9 | PPGU-3-F | 0.5 |
| 10 | APUQU-2-F | 4.5 |
| 11 | APUQU-2-F | 4.0 |
| 12 | PGUQU-3-F | 4.0 |
| 13 | PGUQU-4-F | 4.5 |
| 14 | PGUQU-5-F | 3.0 |
| Σ | | 100.0 |

Physical properties

| | |
|---|---|
| T(N, I) = | 86.0° C. |
| $n_e(20°\text{ C., }589\text{ nm}) =$ | 1.6144 |
| $\Delta n(20°\text{ C., }589\text{ nm}) =$ | 0.1250 |
| $\varepsilon_\parallel(20°\text{ C., }1\text{ kHz}) =$ | 9.2 |
| $\varepsilon_\perp(20°\text{ C., }1\text{ kHz}) =$ | 3.4 |
| $\Delta\varepsilon(20°\text{ C., }1\text{ kHz}) =$ | 5.8 |
| $\varepsilon_{av.}(20°\text{ C., }1\text{ kHz}) =$ | 5.3 |
| $\gamma_1(20°\text{ C.}) =$ | 66 mPa · s |
| $k_{11}(20°\text{ C.}) =$ | 15.1 pN |
| $k_{33}(20°\text{ C.}) =$ | 16.2 pN |
| $V_0(20°\text{ C.}) =$ | 1.68 V |
| $\varepsilon_\perp/\Delta\varepsilon(20°\text{ C.}) =$ | 0.59 |
| $\gamma_1/k_{11}(20°\text{ C.}) =$ | 4.37 * |

Remark:

* [mPa · s/pN].

This mixture, mixture M-47, is characterized by a very good transmission in an FFS display and shows a short response time.

Example 48

The following mixture (M-48) is prepared and investigated.

Mixture 48

Composition

| Compound | | Concentration |
|---|---|---|
| No. | Abbreviation | /% by weight |
| 1 | LB(S)-3-OT | 5.0 |
| 2 | B(S)-2O-O4 | 2.0 |
| 3 | CC-3-V | 44.0 |
| 4 | CC-3-V1 | 6.5 |
| 5 | CCP-V-1 | 5.5 |
| 6 | PP-1-2V1 | 1.5 |
| 7 | PGP-1-2V | 5.5 |
| 8 | PGP-2-2V | 6.0 |
| 9 | PGP-3-2V | 3.0 |
| 10 | PPGU-3-F | 0.5 |
| 11 | APUQU-2-F | 4.5 |
| 12 | APUQU-3-F | 4.5 |
| 13 | PGUQU-3-F | 4.0 |

-continued

| Mixture 48 | | |
|---|---|---|
| 14 | PGUQU-4-F | 4.5 |
| 15 | PGUQU-5-F | 3.0 |
| Σ | | 100.0 |

| Physical properties | |
|---|---|
| T(N, I) = | 85.0° C. |
| $n_e$(20° C., 589 nm) = | 1.6138 |
| Δn(20° C., 589 nm) = | 0.1248 |
| $\varepsilon_\parallel$(20° C., 1 kHz) = | 9.3 |
| $\varepsilon_\perp$(20° C., 1 kHz) = | 3.5 |
| Δε(20° C., 1 kHz) = | 5.8 |
| $\varepsilon_{av.}$(20° C., 1 kHz) = | 5.4 |
| $\gamma_1$(20° C.) = | 66 mPa · s |
| $k_{11}$(20° C.) = | 15.0 pN |
| $k_{33}$(20° C.) = | 15.7 pN |
| $V_0$(20° C.) = | 1.69 V |
| $\varepsilon_\perp/\Delta\varepsilon$(20° C.) = | 0.60 |
| $\gamma_1/k_{11}$(20° C.) = | 4.40 * |

Remark:
* [mPa · s/pN].

This mixture, mixture M-48, is characterized by a very good transmission in an FFS display and shows a short response time.

Example 49

The following mixture (M-49) is prepared and investigated.

| Mixture 49 | | |
|---|---|---|
| Composition | | |
| Compound | | Concentration |
| No. | Abbreviation | /% by weight |
| 1 | LB-3-T | 2.0 |
| 2 | LB(S)-3-OT | 5.0 |
| 3 | CC-3-V | 30.0 |
| 4 | CC-3-V1 | 8.0 |
| 5 | CC-3-2V1 | 8.5 |
| 6 | CCP-V-1 | 9.5 |
| 7 | CLP-V-1 | 6.0 |
| 8 | CCVC-3-V | 4.0 |
| 9 | CCP-3-OT | 5.5 |
| 10 | CLP-3-T | 6.0 |
| 11 | CCGU-3-F | 2.5 |
| 12 | CDUQU-3-F | 7.5 |
| 13 | DGUQU-2-F | 1.5 |
| 14 | DGUQU-4-F | 4.0 |
| Σ | | 100.0 |

| Physical properties | |
|---|---|
| T(N, I) = | 105.5° C. |
| $n_e$(20° C., 589 nm) = | 1.5728 |
| Δn(20° C., 589 nm) = | 0.0923 |
| $\varepsilon_\parallel$(20° C., 1 kHz) = | 8.5 |
| $\varepsilon_\perp$(20° C., 1 kHz) = | 3.2 |
| Δε(20° C., 1 kHz) = | 5.2 |
| $\varepsilon_{av.}$(20° C., 1 kHz) = | 4.9 |
| $\gamma_1$(20° C.) = | 94 mPa · s |
| $k_{11}$(20° C.) = | 19.8 pN |
| $k_{33}$(20° C.) = | 21.9 pN |
| $V_0$(20° C.) = | 2.04 V |
| $\varepsilon_\perp/\Delta\varepsilon$(20° C.) = | 0.62 |
| $\gamma_1/k_{11}$(20° C.) = | 4.75 * |

Remark:
* [mPa · s/pN].

This mixture, mixture M-49, is characterized by a very good transmission in an FFS display and shows a short response time.

Example 50

The following mixture (M-50) is prepared and investigated.

| Mixture 50 | | |
|---|---|---|
| Composition | | |
| Compound | | Concentration |
| No. | Abbreviation | /% by weight |
| 1 | LB-3-T | 3.0 |
| 2 | LB(S)-3-OT | 7.5 |
| 3 | CC-3-V | 40.0 |
| 4 | CC-3-V1 | 8.0 |
| 5 | CCP-V-1 | 6.0 |
| 6 | PGP-1-2V | 4.0 |
| 7 | PGP-2-2V | 7.5 |
| 8 | PGP-3-2V | 3.0 |
| 9 | PPGU-3-F | 0.5 |
| 10 | PUQU-3-F | 4.5 |
| 11 | APUQU-2-F | 4.5 |
| 12 | APUQU-3-F | 4.0 |
| 13 | PGUQU-3-F | 2.5 |
| 14 | PGUQU-4-F | 3.0 |
| 15 | PGUQU-5-F | 2.0 |
| Σ | | 100.0 |

| Physical properties | |
|---|---|
| T(N, I) = | 84.5° C. |
| $n_e$(20° C., 589 nm) = | 1.6146 |
| Δn(20° C., 589 nm) = | 0.1257 |
| $\varepsilon_\parallel$(20° C., 1 kHz) = | 9.7 |
| $\varepsilon_\perp$(20° C., 1 kHz) = | 3.7 |
| Δε(20° C., 1 kHz) = | 6.0 |
| $\varepsilon_{av.}$(20° C., 1 kHz) = | 5.7 |
| $\gamma_1$(20° C.) = | 69 mPa · s |
| $k_{11}$(20° C.) = | 15.1 pN |
| $k_{33}$(20° C.) = | 14.8 pN |
| $V_0$(20° C.) = | 1.67 V |
| $\varepsilon_\perp/\Delta\varepsilon$(20° C.) = | 0.62 |
| $\gamma_1/k_{11}$(20° C.) = | 4.57 * |

Remark:
* [mPa · s/pN].

This mixture, mixture M-50, is characterized by a very good transmission in an FFS display and shows a short response time.

Example 51

The following mixture (M-51) is prepared and investigated.

| Mixture 51 | |
|---|---|
| Composition | |
| Compound | Concentration |
| No.    Abbreviation | /% by weight |
| 1    LB(S)-3-OT | 8.0 |
| 2    CC-3-V | 31.0 |
| 3    CC-3-V1 | 8.0 |
| 4    CC-3-2V1 | 8.0 |
| 5    CCP-V-1 | 3.5 |
| 6    CLP-V-1 | 7.0 |
| 7    CCVC-3-V | 5.0 |
| 8    CCP-3-OT | 5.0 |
| 9    CLP-3-T | 7.0 |
| 10    CCGU-3-F | 2.0 |
| 11    CCQU-3-F | 6.0 |
| 12    CDUQU-3-F | 1.5 |
| 13    DGUQU-2-F | 4.0 |
| 14    DGUQU-4-F | 4.0 |
| Σ | 100.0 |
| Physical properties | |
| T(N, I) = | 103.5° C. |
| $n_e$(20° C., 589 nm) = | 1.5713 |
| Δn(20° C., 589 nm) = | 0.0922 |
| $\varepsilon_{\parallel}$(20° C., 1 kHz) = | 8.5 |
| $\varepsilon_{\perp}$(20° C., 1 kHz) = | 3.2 |
| Δε(20° C., 1 kHz) = | 5.4 |
| $\varepsilon_{av.}$(20° C., 1 kHz) = | 5.1 |
| $\gamma_1$(20° C.) = | 90 mPa·s |
| $k_{11}$(20° C.) = | 19.7 pN |
| $k_{33}$(20° C.) = | 20.1 pN |
| $V_0$(20° C.) = | 2.02 V |
| $\varepsilon_{\perp}/\Delta\varepsilon$(20° C.) = | 0.61 |
| $\gamma_1/k_{11}$(20° C.) = | 4.57 * |

Remark:
* [mPa·s/pN].

This mixture, mixture M-51, is characterized by a very good transmission in an FFS display and shows a short response time.

Example 52

The following mixture (M-52) is prepared and investigated.

| Mixture 52 | |
|---|---|
| Composition | |
| Compound | Concentration |
| No.    Abbreviation | /% by weight |
| 1    LB(S)-3-OT | 3.0 |
| 2    B(S)-2O-O4 | 4.0 |
| 3    B(S)-2O-O5 | 4.0 |
| 4    CPY-3-O2 | 9.0 |
| 5    CC-3-V | 49.5 |
| 6    CCP-V-1 | 13.0 |
| 7    CCGU-3-F | 6.0 |
| 8    PPGU-3-F | 0.5 |
| 9    PUQU-3-F | 11.0 |
| Σ | 100.0 |
| Physical properties | |
| T(N, I) = | 79.5° C. |
| $n_e$(20° C., 589 nm) = | 1.5847 |
| Δn(20° C., 589 nm) = | 0.0996 |
| $\varepsilon_{\parallel}$(20° C., 1 kHz) = | 6.9 |
| $\varepsilon_{\perp}$(20° C., 1 kHz) = | 4.5 |
| Δε(20° C., 1 kHz) = | 2.4 |
| $\varepsilon_{av.}$(20° C., 1 kHz) = | 5.3 |
| $\gamma_1$(20° C.) = | 61 mPa·s |
| $k_{11}$(20° C.) = | 13.5 pN |
| $k_{33}$(20° C.) = | 14.7 pN |
| $V_0$(20° C.) = | 2.51 V |
| $\varepsilon_{\perp}/\Delta\varepsilon$(20° C.) = | 1.88 |
| $\gamma_1/k_{11}$(20° C.) = | 4.52 * |

Remark:
* [mPa·s/pN].

This mixture, mixture M-52, is characterized by a very good transmission in an FFS display and shows a short response time.

Example 53

The following mixture (M-53) is prepared and investigated.

| Mixture 53 | |
|---|---|
| Composition | |
| Compound | Concentration |
| No.    Abbreviation | /% by weight |
| 1    LB-3-T | 6.5 |
| 2    LB(S)-3-OT | 10.0 |
| 3    CPY-3-O2 | 7.0 |
| 4    CC-3-V | 49.5 |
| 5    CCP-V-1 | 13.0 |
| 6    CCGU-3-F | 3.5 |
| 7    PPGU-3-F | 0.5 |
| 8    PUQU-3-F | 10.0 |
| Σ | 100.0 |
| Physical properties | |
| T(N, I) = | 79.5° C. |
| $n_e$(20° C., 589 nm) = | 1.5849 |
| Δn(20° C., 589 nm) = | 0.1012 |
| $\varepsilon_{\parallel}$(20° C., 1 kHz) = | 7.1 |
| $\varepsilon_{\perp}$(20° C., 1 kHz) = | 4.3 |
| Δε(20° C., 1 kHz) = | 2.8 |
| $\varepsilon_{av.}$(20° C., 1 kHz) = | 5.2 |
| $\gamma_1$(20° C.) = | 62 mPa·s |
| $k_{11}$(20° C.) = | 13.5 pN |
| $k_{33}$(20° C.) = | 14.7 pN |
| $V_0$(20° C.) = | 2.32 V |
| $\varepsilon_{\perp}/\Delta\varepsilon$(20° C.) = | 1.54 |
| $\gamma_1/k_{11}$(20° C.) = | 4.59 * |

Remark:
* [mPa·s/pN].

This mixture, mixture M-53, is characterized by a very good transmission in an FFS display and shows a short response time.

Example 54

The following mixture (M-54) is prepared and investigated.

| Mixture 54 | |
|---|---|
| Composition | |
| Compound | Concentration |
| No. | Abbreviation | /% by weight |

| No. | Abbreviation | Concentration /% by weight |
|---|---|---|
| 1 | LB-3-T | 3.0 |
| 2 | LB(S)-3-OT | 5.5 |
| 3 | CC-3-V | 29.0 |
| 4 | CC-3-V1 | 8.0 |
| 5 | CCP-V-1 | 12.0 |
| 6 | CCP-V2-1 | 5.0 |
| 7 | CLP-V-1 | 5.0 |
| 8 | CCVC-3-V | 5.0 |
| 9 | PP-1-2V1 | 5.0 |
| 10 | PGP-1-2V | 8.0 |
| 11 | PGP-2-2V | 0.5 |
| 12 | PPGU-3-F | 0.5 |
| 13 | CDUQU-3-F | 4.0 |
| 14 | PGUQU-3-F | 3.0 |
| 15 | PGUQU-4-F | 2.5 |
| 16 | DGUQU-4-F | 4.0 |
| Σ | | 100.0 |

| Physical properties | |
|---|---|
| T(N, I) = | 105.0° C. |
| $n_e$(25° C., 589 nm) = | 1.610 |
| Δn(25° C., 589 nm) = | 0.120 |
| $\varepsilon_{\parallel}$(25° C., 1 kHz) = | 7.5 |
| $\varepsilon_{\perp}$(25° C., 1 kHz) = | 3.3 |
| Δε(25° C., 1 kHz) = | 4.2 |
| $\varepsilon_{av.}$(25° C., 1 kHz) = | 4.7 |
| $\gamma_1$(25° C.) = | 83 mPa · s |
| $k_{11}$(25° C.) = | 17.8 pN |
| $k_{33}$(25° C.) = | 18.5 pN |
| $V_0$(25° C.) = | 2.19 V |
| $\varepsilon_{\perp}/\Delta\varepsilon$(25° C.) = | 0.79 |
| $\gamma_1/k_{11}$(25° C.) = | 4.66 |

Remarks:
physical data determined at 25° C.

This mixture, mixture M-54, is characterized by a very good transmission in an FFS display and shows a short response time.

The preceding examples can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. From the description, one skilled in the art can easily ascertain the essential characteristics of this invention and, without departing from the spirit and scope thereof, can make various changes and modifications of the invention to adapt it to various usages and conditions.

The entire disclosures of all applications, patents and publications, cited herein and of corresponding European application No. EP 17001126.6, filed Jun. 30, 2017, and of European application No. EP 17201168.6, filed Nov. 10, 2017, are incorporated by reference herein.

The invention claimed is:

1. A liquid-crystalline medium comprising one or more compounds of formula S

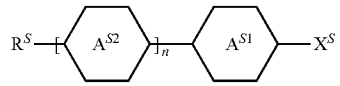

in which

denotes

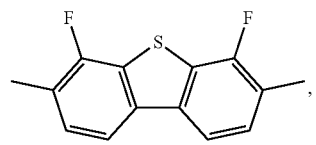

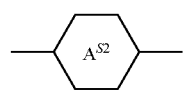

denotes, in each occurrence independently of each other,

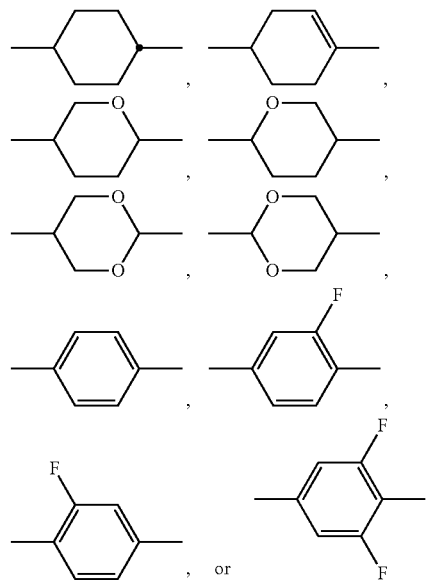

n denotes 1 or 2, $R^S$ denotes alkyl, alkoxy, fluorinated alkyl or fluorinated alkoxy, wherein one —CH$_2$— group may be replaced by cyclopropylene, 1,3-cyclobutylene, 1,3-cyclopentylene, or 1,3-cyclo-pentenylene, or denotes alkenyl, alkenyloxy, alkoxyalkyl or fluorinated alkenyl having 2 to 7 C atoms, wherein one —CH$_2$— group may be replaced by cyclopropylene, 1,3-cyclobutylene, 1,3-cyclopentylene, or 1,3-cyclo-pentenylene, and $X^S$ denotes F, Cl, CN, NCS, fluorinated alkyl, fluorinated alkenyl, fluorinated alkoxy or fluorinated alkenyloxy.

2. The medium according to claim 1, wherein the one or more compounds of formula S are selected from the group consisting of compounds of formulae S-1 and S-2:

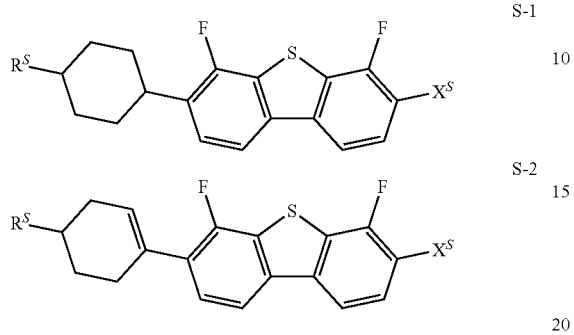

in which $R^S$ denotes alkyl, alkoxy, fluorinated alkyl or fluorinated alkoxy, or alkenyl, alkenyloxy, alkoxyalkyl or fluorinated alkenyl having 2 to 7 C atoms, and $X^S$ denotes F, Cl, CN, NCS, fluorinated alkyl, fluorinated alkenyl, fluorinated alkoxy or fluorinated alkenyloxy.

3. The medium according to claim 2, comprising one or more compounds of formula formulae S-1 and one or more compounds of formula S-2.

4. The medium according to claim 1, further comprising one or more compounds of formulae II and/or III:

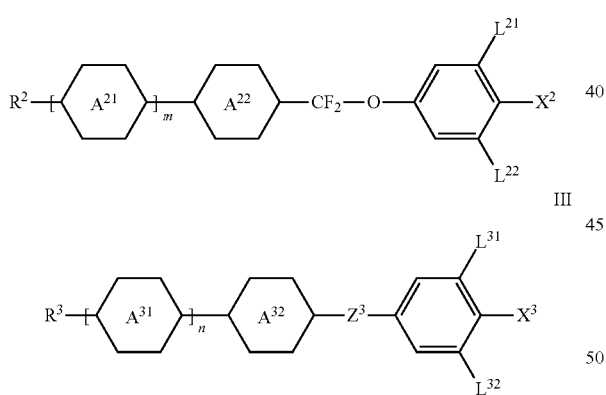

in which $R^2$ denotes alkyl, alkoxy, fluorinated alkyl or fluorinated alkoxy having 1 to 7 C atoms, or alkenyl, alkenyloxy, alkoxyalkyl or fluorinated alkenyl having 2 to 7 C atoms,

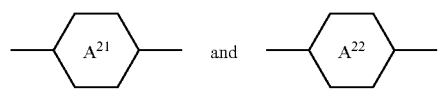

on each appearance, independently of one another, denote

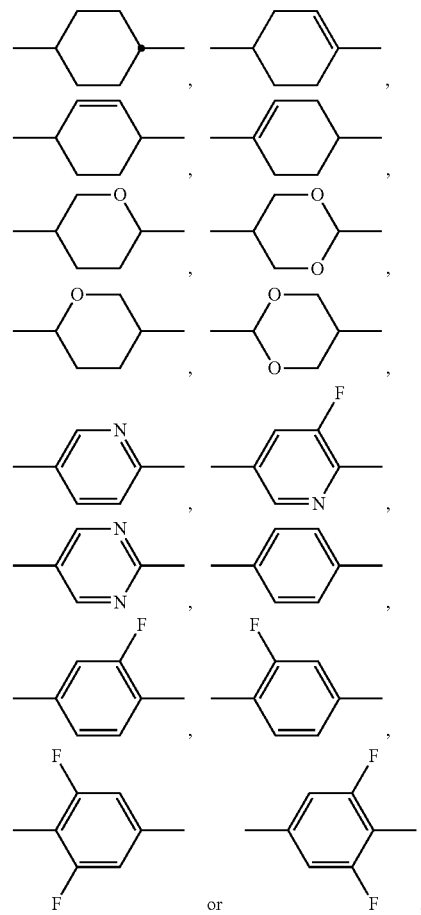

$L^{21}$ and $L^{22}$ denote H or F, $X^2$ denotes halogen, halogenated alkyl or alkoxy having 1 to 3 C atoms or halogenated alkenyl or alkenyloxy having 2 or 3 C atoms, m denotes 0, 1, 2 or 3, $R^3$ denotes alkyl, alkoxy, fluorinated alkyl or fluorinated alkoxy having 1 to 7 C atoms, or alkenyl, alkenyloxy, alkoxyalkyl or fluorinated alkenyl having 2 to 7 C atoms

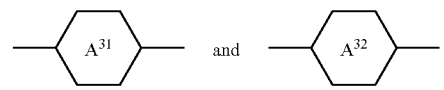

on each appearance, independently of one another, are

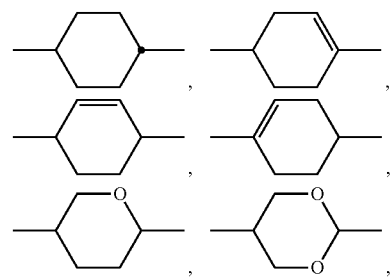

187

-continued

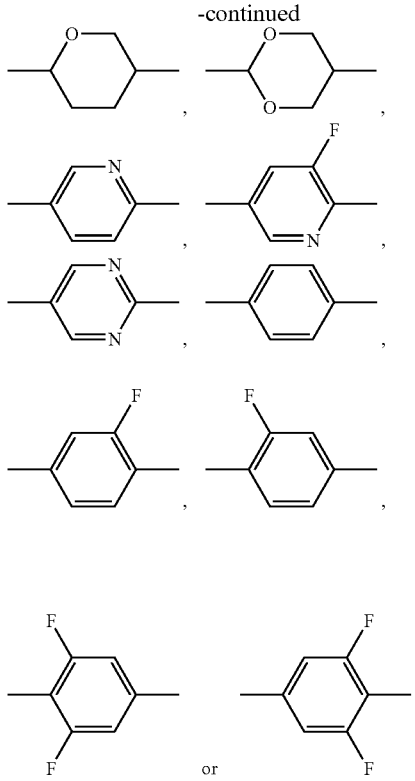

L³¹ and L³², independently of one another, denote H or F,
X³ denotes halogen, halogenated alkyl or alkoxy having 1 to 3 C atoms or halogenated alkenyl or alkenyloxy having 2 or 3 C atoms, F, Cl, —OCF₃, —OCHF₂, O—CH₂CF₃, —O—CH=CF₂, —O—CH=CH₂ or —CF₃,
Z³ denotes —CH₂CH₂—, —CF₂CF₂—, —COO—, trans-CH=CH—, trans-CF=CF—, —CH₂O— or a single bond, and
n denotes 0, 1, 2 or 3.

5. The medium according to claim 1, further comprising one or more compounds of formulae IV and/or V:

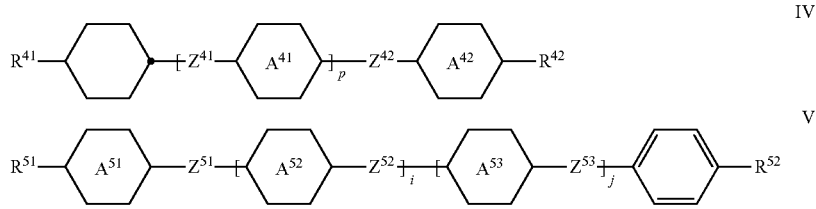

in which
R⁴¹ and R⁴² each, independently of one another, denotes alkyl, alkoxy, fluorinated alkyl or fluorinated alkoxy having 1 to 7 C atoms, or alkenyl, alkenyloxy, alkoxyalkyl or fluorinated alkenyl having 2 to 7 C atoms,

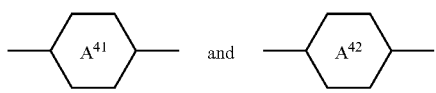

188 independently of one another and, if

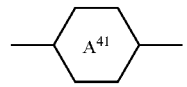

occurs twice,
also these independently of one another, denote

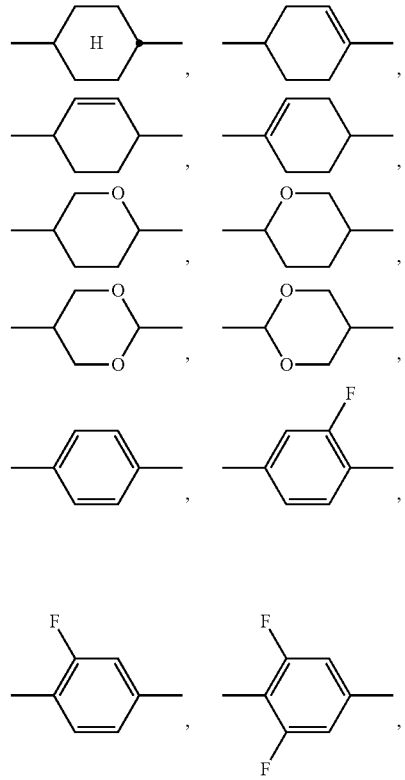

-continued

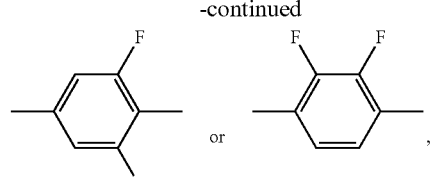

Z⁴¹ and Z⁴², independently of one another and, if Z⁴¹ occurs twice, also these independently of one another, denote —CH$_2$CH$_2$—, —COO—, trans-CH=CH—, trans-CF=CF—, —CH$_2$O—, —CF$_2$O—, —C≡C— or a single bond, p denotes 0, 1 or 2, R$^{51}$ and R$^{52}$ each, independently of one another, denotes alkyl, alkoxy, fluorinated alkyl or fluorinated alkoxy having 1 to 7 C atoms, or alkenyl, alkenyloxy, alkoxyalkyl or fluorinated alkenyl having 2 to 7 C atoms,

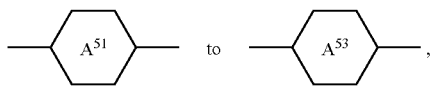

if present, each, independently of one another, denote

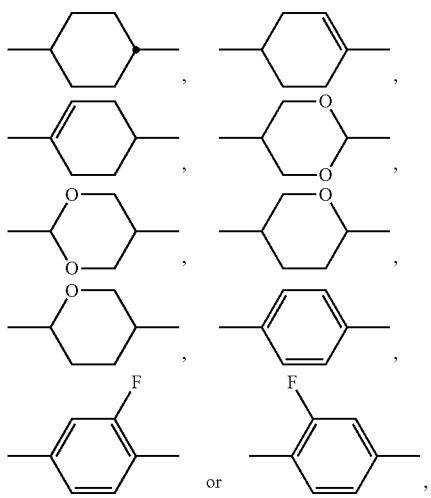

Z$^{51}$ to Z$^{53}$ each, independently of one another, denote —CH$_2$—CH$_2$—, —CH$_2$—O—, —CH=CH—, —C≡C—, —COO— or a single bond, and i and j each, independently of one another, denotes 0 or 1.

6. The medium according to claim 5, further comprising one or more compounds of formulae VI to IX:

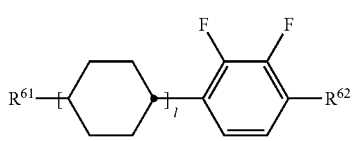
VI

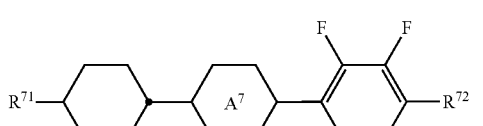
VII

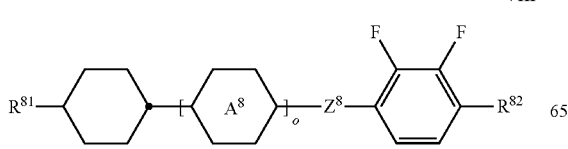
VIII

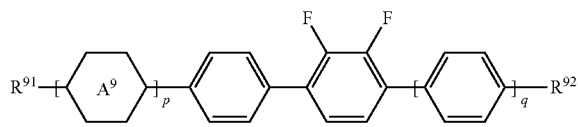
IX wherein

R$^{61}$ denotes an unsubstituted alkyl radical having 1 to 7 C atoms, an unsubstituted alkenyl radical having 2 to 7 C atoms, an unsubstituted alkoxy radical having 1 to 6 C atoms or an unsubstituted alkenyloxy radical having 2 to 6 C atoms, R$^{62}$ denotes an unsubstituted alkyl radical having 1 to 7 C atoms, an unsubstituted alkoxy radical having 1 to 6 C atoms or an unsubstituted alkenyloxy radical having 2 to 6 C atoms, and l denotes 0 or 1, R$^{71}$ denotes an unsubstituted alkyl radical having 1 to 7 C atoms, or an unsubstituted alkenyl radical having 2 to 7 C atoms, R$^{72}$ denotes an unsubstituted alkyl radical having 1 to 7 C atoms, an unsubstituted alkoxy radical having 1 to 6 C atoms or an unsubstituted alkenyloxy radical having 2 to 6 C atoms,

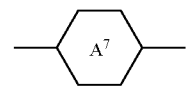

denotes

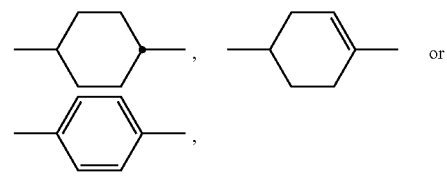

R$^{81}$ denotes an unsubstituted alkyl radical having 1 to 7 C atoms, or an unsubstituted alkenyl radical having 2 to 7 C atoms, R$^{82}$ denotes an unsubstituted alkyl radical having 1 to 7 C atoms, an unsubstituted alkoxy radical having 1 to 6 C atoms or an unsubstituted alkenyloxy radical having 2 to 6 C atoms,

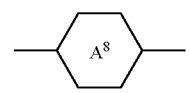

denotes

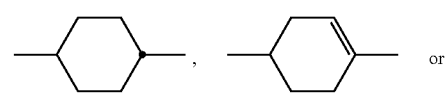

-continued

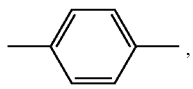, $Z^8$ denotes —(C=O)—O—, —CH$_2$—O—, —CF$_2$—O— or —CH$_2$—CH$_2$—, o denotes 0 or 1, $R^{91}$ and $R^{92}$ each, independently of one another denotes an unsubstituted alkyl radical having 1 to 7 C atoms, an unsubstituted alkoxy radical having 1 to 6 C atoms or an unsubstituted alkenyloxy radical having 2 to 6 C atoms,

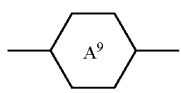

denotes

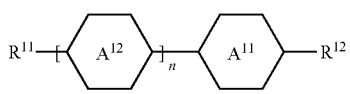, p and q independently of each other denote 0 or 1.

7. The medium according to claim 1, further comprising one or more compounds of formula I

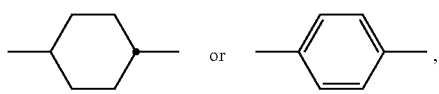 I in which

denotes

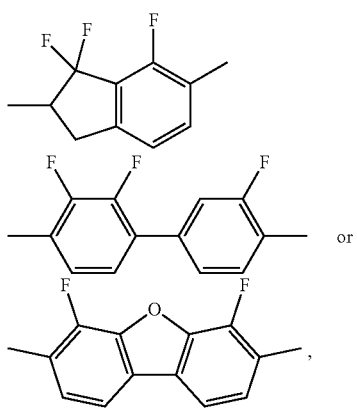,

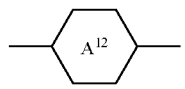

denotes

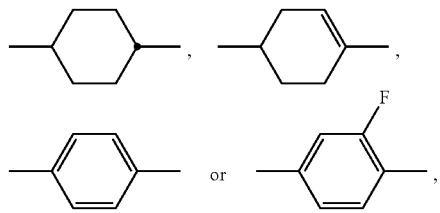

n denotes 0 or 1, $R^{11}$ and $R^{12}$ independently of each other denote alkyl, alkoxy, fluorinated alkyl or fluorinated alkoxy, wherein one —CH$_2$— group may be replaced by cyclopropylene, 1,3-cyclobutylene, 1,3-cyclopentylene, or 1,3-cyclo-pentenylene, or denote alkenyl, alkenyloxy, alkoxyalkyl or fluorinated alkenyl having 2 to 7 C atoms, wherein one —CH$_2$— group may be replaced by cyclo-propylene, 1,3-cyclobutylene, 1,3-cyclopentylene, or 1,3-cyclo-pentenylene, and $R^{11}$ alternatively denotes $R^1$ and $R^{12}$ alternatively denotes $X^1$, $R^1$ denotes alkyl, alkoxy, fluorinated alkyl or fluorinated alkoxy, wherein one —CH$_2$— group may be replaced by cyclo-propylene, 1,3-cyclobutylene, 1,3-cyclopentylene, 1,3-cyclo-pentenylene, or denotes alkenyl, alkenyloxy, alkoxyalkyl or fluorinated alkenyl having 2 to 7 C atoms, wherein one —CH$_2$— group may be replaced by cyclo-propylene, 1,3-cyclobutylene, 1,3-cyclopentylene, or 1,3-cyclo-pentenylene, and $X^1$ denotes F, Cl, fluorinated alkyl, fluorinated alkenyl, fluorinated alkoxy or fluorinated alkenyloxy.

8. The medium according to claim 7, wherein the total concentration of the compounds of formula S in the medium as a whole is 1% or more to 60% or less.

9. The medium according to claim 1, additionally comprising one or more chiral compounds.

10. An electro-optical display or electro-optical component, comprising a liquid-crystalline medium according to claim 1.

11. The display according to claim 10, which is based on the IPS- or FFS mode.

12. The display according to claim 10, which contains an active-matrix addressing device.

13. The medium according to claim 1, which has a nematic phase and a dielectric anisotropy of 0.5 or more.

14. The display according to claim 10, which is a mobile display.

15. A process for the preparation of a liquid-crystalline medium according to claim 1, comprising mixing together one or more compounds of formula S with one or more mesogenic compounds that are not of formula S.

16. A compound of formula S

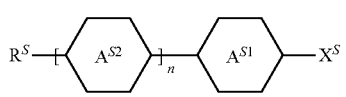 S in which

denotes

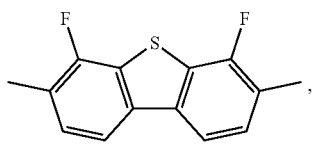,

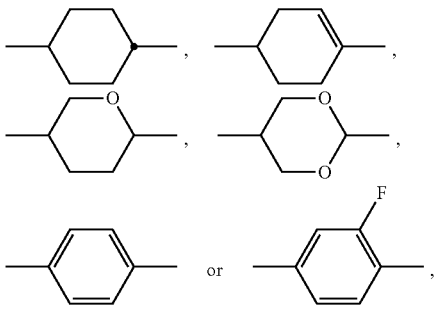

denotes, in each occurrence independently of each other, n denotes 1 or 2,
R$^S$ denotes alkyl, alkoxy, fluorinated alkyl or fluorinated alkoxy, wherein one —CH$_2$— group may be replaced by cyclopropylene, 1,3-cyclobutylene, 1,3-cyclopentylene, or 1,3-cyclo-pentenylene, or denotes alkenyl, alkenyloxy, alkoxyalkyl or fluorinated alkenyl having 2 to 7 C atoms, wherein one —CH$_2$— group may be replaced by cyclopropylene, 1,3-cyclobutylene, 1,3-cyclopentylene, or 1,3-cyclo-pentenylene, and
X$^S$ denotes F, Cl, CN, NCS fluorinated alkyl, fluorinated alkenyl, fluorinated alkoxy or fluorinated alkenyloxy.

17. A process for the preparation of a compound of formula S according to claim 16, comprising forming an S-heterocyclic ring system of the following formula

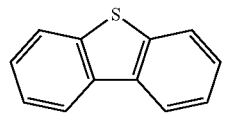 [SMILES: c1ccc2c(c1)sc1ccccc12]

via successive Migita coupling and closure of the ring induced by a base, which may be performed as a single pot reaction.

18. A compound of formula S according to claim 16, which is selected from the group consisting of compounds of formulae S-1 and S-2:

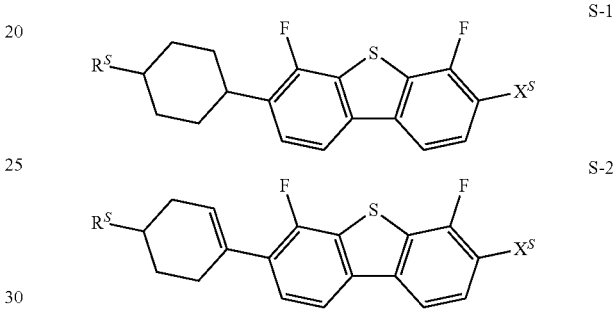

in which
R$^S$ denotes alkyl, alkoxy, fluorinated alkyl or fluorinated alkoxy, or alkenyl, alkenyloxy, alkoxyalkyl or fluorinated alkenyl having 2 to 7 C atoms, and
X$^S$ denotes F, Cl, CN, NCS, fluorinated alkyl, fluorinated alkenyl, fluorinated alkoxy or fluorinated alkenyloxy.

19. A compound of formula S according to claim 16, wherein
R$^S$ denotes alkyl, alkoxy, fluorinated alkyl or fluorinated alkoxy having 1 to 7 C atoms, wherein one —CH$_2$— group may be replaced by cyclopropylene or 1,3-cyclopentylene, or denotes alkenyl, alkenyloxy, alkoxyalkyl or fluorinated alkenyl having 2 to 7 C atoms, wherein one —CH$_2$— group may be replaced by cyclopropylene or 1,3-cyclopentylene, and
X$^S$ denotes F, CF$_3$ or OCF$_3$.

20. A compound of formula S according to claim 16, wherein
X$^S$ denotes F, CF$_3$ or OCF$_3$.

* * * * *